US009879094B2

(12) United States Patent
Atwal et al.

(10) Patent No.: US 9,879,094 B2
(45) Date of Patent: Jan. 30, 2018

(54) NUCLEIC ACID MOLECULES ENCODING FOR BACE1 ANTIBODIES

(71) Applicant: Genentech, Inc., South San Francisco, CA (US)

(72) Inventors: Jasvinder Atwal, San Carlos, CA (US); Yongmei Chen, Millbrae, CA (US); Cecilia Pui Chi Chiu, San Carlos, CA (US); Robert A. Lazarus, Millbrae, CA (US); Weiru Wang, Lafayette, CA (US); Ryan J. Watts, San Mateo, CA (US); Yan Wu, Foster City, CA (US); Yingnan Zhang, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/234,649

(22) Filed: Aug. 11, 2016

(65) Prior Publication Data
US 2017/0058049 A1 Mar. 2, 2017

Related U.S. Application Data

(62) Division of application No. 14/292,461, filed on May 30, 2014, now Pat. No. 9,453,079, which is a division of application No. 13/292,633, filed on Nov. 9, 2011, now Pat. No. 8,772,457.

(60) Provisional application No. 61/426,425, filed on Dec. 22, 2010, provisional application No. 61/148,850, filed on Dec. 1, 2010, provisional application No. 61/418,310, filed on Nov. 30, 2010, provisional application No. 61/456,642, filed on Nov. 10, 2010.

(51) Int. Cl.
*C07H 21/04* (2006.01)
*C07K 16/18* (2006.01)
*C12P 21/08* (2006.01)
*C07K 16/40* (2006.01)
*A61K 39/395* (2006.01)
*G01N 33/573* (2006.01)
*C12P 21/00* (2006.01)
*A61K 47/68* (2017.01)
*A61K 39/00* (2006.01)

(52) U.S. Cl.
CPC .......... *C07K 16/40* (2013.01); *A61K 39/3955* (2013.01); *A61K 47/6871* (2017.08); *C12P 21/005* (2013.01); *G01N 33/573* (2013.01); *A61K 2039/505* (2013.01); *C07K 2317/51* (2013.01); *C07K 2317/515* (2013.01); *C07K 2317/56* (2013.01); *C07K 2317/565* (2013.01); *C07K 2317/76* (2013.01); *C07K 2317/92* (2013.01)

(58) Field of Classification Search
CPC .... C07K 16/18; C07K 16/40; C07K 2317/56; C07K 2317/565; C07K 2317/76; C07K 2317/51; C07K 2317/515; C07K 2317/92; A61K 2039/505; A61K 39/3955; C12P 21/005; C07H 21/04
See application file for complete search history.

(56) References Cited

U.S. PATENT DOCUMENTS

| | | |
|---|---|---|
| 5,200,339 A | 4/1993 | Abraham |
| 5,744,346 A | 4/1998 | Chrysler et al. |
| 5,849,560 A | 12/1998 | Abraham |
| 5,942,400 A | 8/1999 | Anderson et al. |
| 6,221,645 B1 | 4/2001 | Chrysler et al. |
| 6,319,689 B1 | 11/2001 | Powell et al. |
| 6,329,163 B1 | 12/2001 | Anderson et al. |
| 6,545,127 B1 | 4/2003 | Tang et al. |
| 6,627,739 B1 | 9/2003 | Anderson et al. |
| 6,706,485 B1 | 3/2004 | Gurney et al. |
| 6,727,074 B2 | 4/2004 | Gurney et al. |
| 6,852,482 B1 | 2/2005 | Chrysler et al. |
| 7,067,271 B1 | 6/2006 | Anderson et al. |
| 7,109,017 B1 | 9/2006 | Anderson et al. |
| 7,115,410 B1 | 10/2006 | Anderson et al. |
| 7,244,708 B2 | 7/2007 | Tang et al. |
| 7,252,963 B2 | 8/2007 | Anderson et al. |
| 7,262,043 B2 | 8/2007 | Anderson et al. |
| 7,276,349 B2 | 10/2007 | Anderson et al. |
| 7,314,726 B2 | 1/2008 | Kornacker et al. |
| 7,413,737 B2 | 8/2008 | Wittrup et al. |
| 7,456,007 B1 | 11/2008 | Anderson et al. |
| 7,479,372 B2 | 1/2009 | Brady et al. |
| 7,514,408 B1 | 4/2009 | John et al. |
| 7,569,391 B2 | 8/2009 | Beyer et al. |
| 7,579,180 B2 | 8/2009 | Citron et al. |
| 7,582,465 B2 | 9/2009 | Citron et al. |
| 7,601,528 B1 | 10/2009 | Benson et al. |
| 7,630,838 B2 | 12/2009 | Chopra et al. |

(Continued)

FOREIGN PATENT DOCUMENTS

| | | |
|---|---|---|
| WO | WO 92/03542 | 3/1992 |
| WO | WO 96/40885 | 12/1996 |

(Continued)

OTHER PUBLICATIONS

Tabrizi et al., "Biodistribution Mechanisms of Therapeutic Monoclonal Antibodies in Health and Disease," The AAPS Journal, vol. 12 (2010) 33-43.
Frank et al., "Strategies for enhancing antibody delivery to the brain," Biochimica et Biophysica Acta 1816 (2011) 191-198.
European Search Report for European Application No. 16194064.8, dated Apr. 24, 2017, 11 pages.
Arbel et al., "Immunotherapy for Alzheimer's Disease: Attacking Amyloid-β from the Inside" Trends in Immunology 28(12):511-513 (2007).
Atwal et al., "A Therapeutic Antibody Targeting BACE1 Inhibits Amyloid-β Production in Vivo" Science Translational Medicine 3(84):1-12 (May 2011).

(Continued)

Primary Examiner — Kimberly A. Ballard
(74) Attorney, Agent, or Firm — McNeill Baur PLLC

(57) ABSTRACT

The invention provides antibodies to specific neural proteins and methods of using the same.

27 Claims, 39 Drawing Sheets

(56) References Cited

U.S. PATENT DOCUMENTS

| | | | |
|---|---|---|---|
| 7,678,760 B2 | 3/2010 | Tang et al. | |
| 7,691,977 B2 | 4/2010 | Fuh et al. | |
| 7,696,330 B2 | 4/2010 | Meulen et al. | |
| 7,758,859 B2 | 7/2010 | Fuh et al. | |
| 7,790,864 B2 | 9/2010 | Desire | |
| 7,799,899 B2 * | 9/2010 | Ackerly | C07K 16/22 424/130.1 |
| 7,825,221 B2 | 11/2010 | Kirchhofer et al. | |
| 7,829,669 B2 | 11/2010 | Koelsch et al. | |
| 7,834,154 B2 * | 11/2010 | Koch | C07K 16/2803 424/130.1 |
| 7,989,597 B2 | 8/2011 | Chang et al. | |
| 8,414,890 B2 | 4/2013 | Martin et al. | |
| 9,453,079 B2 | 9/2016 | Atwal et al. | |
| 2002/0055459 A1 | 5/2002 | Chopra et al. | |
| 2007/0149763 A1 | 6/2007 | Kornacker et al. | |
| 2008/0215249 A1 | 9/2008 | Benson et al. | |
| 2008/0247951 A1 | 10/2008 | Koch et al. | |
| 2009/0125289 A1 | 5/2009 | Benson et al. | |
| 2010/0047232 A1 | 2/2010 | Atwal et al. | |
| 2010/0055103 A1 | 3/2010 | Chen et al. | |
| 2010/0233156 A1 | 9/2010 | Burns et al. | |
| 2012/0171120 A1 | 7/2012 | Dennis et al. | |
| 2012/0237526 A1 | 9/2012 | De Strooper et al. | |
| 2012/0282176 A1 | 11/2012 | Bohrmann et al. | |

FOREIGN PATENT DOCUMENTS

| | | |
|---|---|---|
| WO | WO 98/26059 | 6/1998 |
| WO | WO 01/00663 | 1/2001 |
| WO | WO 01/00665 | 1/2001 |
| WO | WO 01/29563 | 4/2001 |
| WO | WO 02/06306 | 1/2002 |
| WO | WO 02/47466 | 6/2002 |
| WO | WO 02/053594 | 11/2002 |
| WO | WO 03/039454 | 5/2003 |
| WO | WO 03/102244 | 12/2003 |
| WO | WO 2004/035606 | 4/2004 |
| WO | WO 2004/099402 | 11/2004 |
| WO | WO 2005/014815 | 2/2005 |
| WO | WO 2006/038684 | 4/2006 |
| WO | WO 2007/021886 | 2/2007 |
| WO | WO 2007/056470 | 5/2007 |
| WO | WO 2007/127506 | 11/2007 |
| WO | WO 2007/130697 | 11/2007 |
| WO | WO 2007/140371 | 12/2007 |
| WO | WO 2008/052187 | 5/2008 |
| WO | WO 2008/129023 | 10/2008 |
| WO | WO 2009/121948 | 8/2009 |
| WO | WO 2009/155609 | 12/2009 |
| WO | WO 2010/146058 | 12/2010 |
| WO | WO 2012/064836 | 5/2012 |
| WO | WO 2012/075037 | 6/2012 |
| WO | WO 2013/177062 | 11/2013 |

OTHER PUBLICATIONS

Bigott-Hennkens et al., "In vitro receptor binding assay: general methods and considerations," Quarterly J. Nucl. Med. Mol. Imaging, 52(3): 245-253 (2008).

Birtalan et al., "The Functional Capacity of the Natural Amino Acids for Molecular Recognition" Molecular BioSystems 6:1186-1194 (2010).

Cai et al., "BACE1 is the Major β-Secretase for Generation of Aβ Peptides by Neurons" Nature Neuroscience 4(3):233-234 (2001).

Carter et al., "Humanization of an anti-p185 HER2 antibody for human cancer therapy" P Natl Acad Sci USA 89:4285-4289 (May 1992).

Chang et al., "In Vivo Inhibition of Aβ Production by Memapsin 2 (β-Secretase) Inhibitors" Journal of Neurochemistry 89:1409-1416 (2004).

Chang et al., "Amyloid-beta reduction by memapsin 2 (beta-secretase) immunization" The FASEB Journal 21:3184-3196 (2007).

Chang et al., "P2-323: Memapsin 2 (beta-secretase, BACE) immunization as specific and safe therapy for Alzheimer's disease" Alzheimer's & Dementia 4(3): T467 (Jul. 2008).

Charrier et al., "Second Generation of Hydroxyethylamine BACE-1 Inhibitors: Optimizing Potency and Oral Bioavailability" Journal Med. Chem. 51:3313-3317 (2008).

Chezal et al., "Evaluation of Radiolabeled (Hetero) Armatic Analogues of N-(2-diethylaminoethyl)-4-Iodobenzamide for Imaging and Targeted Radionuclide Therapy of Melanoma" Journal of Med. Chem. 51:3133-3144 (2008).

Citron, "β-Secretase as a Target for the Treatment of Alzheimer's Disease" Journal of Neuroscience Research 70:373-379 (2002).

Clackson et al., "Making antibody fragments using phage display libraries" Nature 352:624-628 (Aug. 1991).

Cole et al., "BACE1 Structure and Function in Health and Alzheimer's Disease" Current Alzheimer Research 5:100-120 (2008).

Dominguez et al., "Phenotypic and Biochemical Analyses of BACE1- and BACE2-Deficient Mice" Journal of Biological Chemistry 280(35):30797-30806 (2005).

Fellouse et al., "High-throughput generation of synthetic antibodies from highly functional minimalist phage-displayed libraries" J Mol Biol. 373(4):924-40 (Nov. 2007).

Gallop et al. et al., "Applications of combinatorial technologies to drug discovery. 1. background and peptide combinatorial libraries" J Med Chem 37(9):1233-1251 (1994).

Ghosh et al., "β-Secretase as a Therapeutic Target for Alzheimer's Disease" Neurotherapeutics 5:399-408 ( 2008).

Haniu et al., "Characterization of Alzheimer's β-Secretase Protein BACE" Journal of Biological Chemistry 257:21099-21106 (2000).

Hong et al., "Structure of the Protease Domain of Memapsin 2 (β-Secretase) Complexed with Inhibitor" Science 290:150-153 ( 2000).

Hoogenboom, "Overview of Antibody Phage-Display Technology and Its Applications" Methods in Molecular Biology 178:1-37 (2001).

Howlett et al., "In Search of an Enzyme: The β-Secretase of Alzheimer's Disease is an Aspartic Proteinase" Trends in Neuroscience 23(11):565-570 ( 2000).

Hu et al., "Genetic deletion of BACE1 in mice affects remyelination of sciatic nerves," FASEB J., 22: 2970-2980 (2008).

Hussain et al., "Identification of a Novel Aspartic Protease (Asp 2) as β-Secretase" Molecular and Cellular Neuroscience 14(6):419-427 (1999).

"International Search Report for PCT/US2011/059964" (dated May 2013).

International Search Report and Written Opinion for PCT/US2015/061401, dated May 3, 2016 (29 pages).

Kornacker et al., "An Inhibitor Binding Pocket Distinct from the Catalytic Active Site on Human β-APP Cleaving Enzyme" Biochemistry 44:11567-11573 (2005).

Kunkel et al., "Rapid and Efficient Site-specific Mutagenesis Without Phenotypic Selection" Method Enzymol 154:367-382 (1987).

Laird et al., "BACE1, Major Determinant of Selective Vulnerability of the Brain to Amyloid-β Amyloidogenesis, is Essential for Cognitive, Emotional, and Synaptic Functions" Journal of Neuroscience 25(50):11693-11709 (2005).

Lee et al., "High-affinity human antibodies from phage-displayed synthetic Fab libraries with a single framework scaffold" J Mol Biol 340(5):1073-1093 (2004).

Lemere et al., "Can Alzheimer Disease Be Prevented by Amyloid-β Immunotherapy" Nature Rev. Neurol. 6:108-119 (2010).

Lin et al., "Human Aspartic Protease memapsin 2 Cleaves the β Secretase Site of β-Amyloid Precursor Protein" PNAS 97(4):1456-1460 (2000).

Liu et al., "Amyloid βpeptide alters intracellular vesicle trafficking and cholesterol homeostasis," Proc. Natl. Acad. Sci. USA, 95: 13266-13271 (1998).

Liu et al., "Glu 1 Site Cleavage and N-Terminally Aβ Production upon BACE Overexpression" Biochemistry 41:3128-3136 (2002).

(56) References Cited

OTHER PUBLICATIONS

Luo et al., "Mice Deficent in BACE1, the Alzheimer's βSecretase, have Normal Phenotype and Abolished β-Amyloid Generation" Nature Neuroscience 4(3):231-232 (2001).
Marks et al., "By-passing Immunization Human Antibodies from V-gene Libraries Displayed on Phage" J. Mol. Biol. 222:581-597 (1991).
Marks et al., "Selection of Human Antibodies from Phage Display Libraries" Methods in Molecular Biology 248:161-176 (2003).
McCafferty et al., "Phage antibodies: filamentous phage displaying antibody variable domains" Nature 348:552-554 (Dec. 6, 1990).
McConlogue et al., "Partial Reduction of BACE1 Has Dramatic Effects on Alzheimer Plaque and Synaptic Pathology in APP Transgenic Mice" Journal of Biological Chemistry 282(36):26326-26334 ( 2007).
McGuaghey et al., "Structure-Guided Design of β-Secretase (BACE-1) Inhibitors" Expert Opinion Drug Discov. 2(8):1129-1138 (2007).
Morris, "96: Epitope Mapping of Protein Antigens by Competition ELISA," from *The Protein Protocols Handbook*, Ed. J.M. Walker, Humana Press Inc., NJ, pp. 595-600 (1996).
Nikolaev et al., "APP binds DR6 to trigger axon pruning and neuron death via distinct caspases" NATURE 457:981-990 (Feb. 19, 2009).
Ohno et al., "BACE1 Deficiency Rescues Memory Deficits and Cholinergic Dysfunction in a Mouse Model of Alzheimer's Disease" Neuron 41:27-33 (2008).
Pajoohesh-Ganji et al., "Inhibition of amyloid precursor protein secretases reduces recovery after spinal cord injury," Brain Res., 1560: 73-82 (2014).
Paul, "Therapeutic Antibodies for Brain Disorders" Alzheimer's Disease 3(84):1-5 (May 2011).
Pluckthun, "Antibodies from *Escherichia coli*" The Pharmacology of Monoclonal Antibodies 11 (1994).
Polson et al., "Antibody-drug conjugates targeted to CD79 for the treatment of non-Hodgkin lymphoma," Blood, vol. 10, No. 2, pp. 616-623 (2007).
Rajendran et al., "Efficient Inhibition of the Alzheimer's Disease β-Secretase by Membrane Targeting" Science 320:520-523 (2008).
Richards et al., "PS2APP Transgenic Mice, Coexpressing hPS2mut and hAPPswe, Show Age-Related Cognitive Deficits Associated with Discrete Brain Amyloid Deposition and Inflammation" Journal of Neuroscience 23(26):8989-9003 (2003).
Roberds et al., "BACE Knockout Mie are Healthy Despite Lacking the Primary β-Secretase Activity in Brain: Implications for Alzheimer's Disease Therapeutics" Human Molecular Genetics 10(12):1317-1324 (2001).
Saldanha, "6" Molecular Engineering 1: Humanization," from *Handbook of Therapeutic Antibodies*, Ed. E. Dübel, Wiley-VCH, Weinheim, pp. 119-144 (2007).
Salum et al., "Fragment-Guided Approach to Incorporating Structural Information into a CoMFA Study: BACE-1 as an Example" Journal Comput. Aided Mol. Des. 24:803-817 (2010).
Shimizu et al., "Crystal Structure of an Active Form of BACE1, an Enzyme Responsible for Amyloid β Protein Production" Molecular and Cellular Biology 28(11):3663-3671 (Jun. 2008).
Sidhu et al., "Phage Display for Selection of Novel Binding Peptides" Method Enzymol 328:333-363 (2000).
Sidhu et al., "Phage-displayed Antibody Libraries of Synthetic Heavy Chain Complementarity Determining Regions" J. Mol. Bol 338:299-310 (2004).
Singer et al., "Targeting BACE1 with siRNAs Ameliorates Alzheimer Disease Neuropathology in a Transgenic Model" Nature Neuroscience 8(10):1343 (2005).
Sinha et al., "Purification and Cloning of Amyloid Precursor Protein β-Secretase from Human Brain" Nature 402:537-540 (1999).
Stachel et al., "Progress Toward the Development of a Viable BACE-1 Inhibitor" Drug Development Research 70:101-110 (2009).
Strooper et al., "The Secretases: Enzymes with Therapeutic Potential in Alzheimer Disease" Nature Reviews Neurology 6:99-107 (2010).
Turner et al., "Structural Locations and Functional Roles of New Subsites S5, S6, and S7 in Memapsin 2 (β-Secretase)" Biochemistry 44:105-112 (2005).
van Dijk et al., "Human antibodies as next generation therapeutics" Current Opinion in Chemical Biology 5:368-374 (2001).
Varghese et al., "Human β-Secretase (BACE) and BACE Inhibitors: Progess Report" Current Topics in Medicinal Chemistry 6:569-578 (2006).
Vassar et al., "β-Secretase Cleavage of Alzheimer's Amyloid Precursor Protein by the Transmembrane Aspartic Protease BACE" Science 286:735-741 (1999).
Vassar, "The β-Secretase, BACE" Journal of Molecular Neuroscience 17:157-170 (2001).
Vassar, "β-Secretase (BACE) as a Drug Target for Alzheimer's Disease" Advanced Drug Delivery Reviews 54:1589-1602 (2002).
Vassar et al., "The β-Secretase Enzyme BACE in Health and Alzheimer's Disease: Regulation, Cell Biology, Function, and Therapeutic Potential" Journal of Neuroscience 29:12787-12794 (2009).
Wang et al., "Allosteric inhibition of BACE1 by an exosite-binding antibody," Curr. Opin. Structural Biol., 23: 797-805 (2013).
Yan et al., "Membrane-Anchored Aspartyl Protease with Alzheimer's Disease β-Secretase Activity" Nature 402:533-537 ( 1999).
Yu et al., "Boosting Brain Uptake of a Therapeutic Antibody by Reducing Its Affinity for a Transcytosis Targer" Science Translational Medicine 3(84):1-8 (May 2011).
Zhou et al., "Inhibition of β-Secretase in Vivo via Antibody Binding to Unique loops (D and F) of BACE1" Journal of Biological Chemistry 286(10):8677-8687 (2011).

* cited by examiner

| Kabat# | | |
|---|---|---|
| Fab12 | | (SEQ ID NO: 31) |
| LC6 IgG | | (SEQ ID NO: 32) |
| LC9 IgG | | (SEQ ID NO: 33) |
| LC10 IgG | | (SEQ ID NO: 34) |

Kabat positions 1–37 (with insertions A B C D E F after 27):
Kabat – CDR L1 / Chothia – CDR L1 / Contact – CDR L1

| Kabat# | 1 2 3 4 5 6 7 8 9 10 11 12 13 14 15 16 17 18 19 20 21 22 23 | 24 25 26 27 A B C D E F 28 29 30 31 32 33 34 35 36 37 |
|---|---|---|
| Fab12    | D I Q M T Q S P S S L S A S V G D R V T I T C | R A S Q       S V S S A V A W Y Q |
| LC6 IgG  | D I Q M T Q S P S S L S A S V G D R V T I T C | R A S Q       S V S S A V A W Y Q |
| LC9 IgG  | D I Q M T Q S P S S L S A S V G D R V T I T C | R A S Q       S V S S A V A W Y Q |
| LC10 IgG | D I Q M T Q S P S S L S A S V G D R V T I T C | R A S Q       S V S S A V A W N Y Q |

Kabat positions 38–80:
Kabat – CDR L2 / Chothia – CDR L2 / Contact – CDR L2

| Kabat# | 38 39 40 41 42 43 44 45 46 47 48 49 | 50 51 52 53 54 55 56 | 57 58 59 60 61 62 63 64 65 66 67 68 69 70 71 72 73 74 75 76 77 78 79 80 |
|---|---|---|---|
| Fab12    | Q K P G K A P K L L I Y | S A S S L Y S | G V P S R F S G S G S G T D F T L T I S S |
| LC6 IgG  | Q K P G K A P K L L I Y | S A S S W Y S | G V P S R F S G S G S G T D F T L T I S S |
| LC9 IgG  | Q K P G K A P K L L I Y | N A S W L Y S | G V P D R F T G S G S G T E F T L T I S S |
| LC10 IgG | Q K P G R A P K L L I Y | W A S S L Y S | G V P D R F T G S G S G T E F T L T I S S |

Kabat positions 81–109:
Kabat – CDR L3 / Chothia – CDR L3 / Contact – CDR L3

| Kabat# | 81 82 83 84 85 86 87 | 88 89 90 91 92 93 94 95 96 97 | 98 99 100 101 102 103 104 105 106 107 109 |
|---|---|---|---|
| Fab12    | E D F A T Y Y | C Q Q Y S S P F T | F G Q G T K V E I K R |
| LC6 IgG  | E D F A T Y Y | C Q Q Y S S P F T | F G Q G T K V E I K R |
| LC9 IgG  | E D F A V Y Y | C Q Q Y S S P F T | F G Q G T K V E I K R |
| LC10 IgG | E D F A V Y Y | C Q Q Y S S P F T | F G Q G T K V E I K R |

| | | Competition ELISA Ratio | Fab ID | Parent |
|---|---|---|---|---|
| | | | LC4 | Fab5 |
| | | 6.3 | LC11 | Fab5 |
| | | 4.4 | LC6 | Fab12 |
| | | 4 | LC9 | Fab12 |
| | | 11.7 | LC10 | Fab12 |
| | | 7.8 | LC40 | Fab14 |
| | | 3 | | |

(Figure 6 — table of CDR sequences for Fab variants LC4, LC11, LC6, LC9, LC10, LC40 with parent Fabs Fab5, Fab5, Fab12, Fab12, Fab12, Fab14)

FIG. 6

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 27A | 27B | 27C | 27D | 27E | 27F | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
|  |  |  |  |  |  |  |  |  |  |  |  |  |  |  |  |  |  |  |  |  |  |  |  | Kabat – CDR L1 | | | | | | | | | | | | | | | | | | |
|  |  |  |  |  |  |  |  |  |  |  |  |  |  |  |  |  |  |  |  |  |  |  |  | | | | Chothia – CDR L1 | | | | | | | | | | | | | | |
|  |  |  |  |  |  |  |  |  |  |  |  |  |  |  |  |  |  |  |  |  |  |  |  | | | | | | | | | Contact – CDR L1 | | | | | | | | | |
| YW412.8.31 | D | I | Q | M | T | Q | S | P | S | S | L | S | A | S | V | G | D | R | V | T | I | T | C | R | A | S | Q | | | | | | | D | V | S | T | A | V | A | W | Y | Q |
| YW412.8.31.41S | D | I | Q | M | T | Q | S | P | S | S | L | S | A | S | V | G | D | R | V | T | I | T | C | R | A | S | Q | | | | | | | D | V | S | T | A | V | A | W | Y | Q |
| YW412.8.31.25BS | D | I | Q | M | T | Q | S | P | S | S | L | S | A | S | V | G | D | R | V | T | I | T | C | R | A | S | Q | | | | | | | D | V | S | T | A | V | A | W | Y | Q |
| YW412.8.31.81S | D | I | Q | M | T | Q | S | P | S | S | L | S | A | S | V | G | D | R | V | T | I | T | C | R | A | S | Q | | | | | | | D | V | S | T | A | V | A | W | Y | Q |
| YW412.8.31.6S | D | I | Q | M | T | Q | S | P | S | S | L | S | A | S | V | G | D | R | V | T | I | T | C | R | A | S | Q | | | | | | | D | V | S | T | A | V | A | W | Y | Q |
| YW412.8.31.75S | D | I | Q | M | T | Q | S | P | S | S | L | S | A | S | V | G | D | R | V | T | I | T | C | R | A | S | Q | | | | | | | D | V | S | T | A | V | A | W | Y | Q |
| YW412.8.31.9S | D | I | Q | M | T | Q | S | P | S | S | L | S | A | S | V | G | D | R | V | T | I | T | C | R | A | S | Q | | | | | | | D | V | S | T | A | V | A | W | Y | Q |
| YW412.8.31.65S | D | I | Q | M | T | Q | S | P | S | S | L | S | A | S | V | G | D | R | V | T | I | T | C | R | A | S | Q | | | | | | | D | V | S | T | A | V | A | W | Y | Q |
| YW412.8.31.86S | D | I | Q | M | T | Q | S | P | S | S | L | S | A | S | V | G | D | R | V | T | I | T | C | R | A | S | Q | | | | | | | D | V | S | T | A | V | A | W | Y | Q |
| YW412.8.31.55S | D | I | Q | M | T | Q | S | P | S | S | L | S | A | S | V | G | D | R | V | T | I | T | C | R | A | S | Q | | | | | | | D | V | S | T | A | V | A | W | Y | Q |
| YW412.8.31.58S | D | I | Q | M | T | Q | S | P | S | S | L | S | A | S | V | G | D | R | V | T | I | T | C | R | A | S | Q | | | | | | | D | V | S | T | A | V | A | W | Y | Q |
| YW412.8.31.25S | D | I | Q | M | T | Q | S | P | S | S | L | S | A | S | V | G | D | R | V | T | I | T | C | R | A | S | Q | | | | | | | D | V | S | T | A | V | A | W | Y | Q |
| YW412.8.31.3S | D | I | Q | M | T | Q | S | P | S | S | L | S | A | S | V | G | D | R | V | T | I | T | C | R | A | S | Q | | | | | | | D | V | S | T | A | V | A | W | Y | Q |
| YW412.8.31.89S | D | I | Q | M | T | Q | S | P | S | S | L | S | A | S | V | G | D | R | V | T | I | T | C | R | A | S | Q | | | | | | | D | V | S | T | A | V | A | W | Y | Q |
| YW412.8.31.54S | D | I | Q | M | T | Q | S | P | S | S | L | S | A | S | V | G | D | R | V | T | I | T | C | R | A | S | Q | | | | | | | D | V | S | T | A | V | A | W | Y | Q |
| YW412.8.31.71S | D | I | Q | M | T | Q | S | P | S | S | L | S | A | S | V | G | D | R | V | T | I | T | C | R | A | S | Q | | | | | | | D | V | S | T | A | V | A | W | Y | Q |
| YW412.8.31.51 | D | I | Q | M | T | Q | S | P | S | S | L | S | A | S | V | G | D | R | V | T | I | T | C | R | A | S | Q | | | | | | | D | V | S | T | A | V | A | W | Y | Q |
| YW412.8.31.53 | D | I | Q | M | T | Q | S | P | S | S | L | S | A | S | V | G | D | R | V | T | I | T | C | R | A | S | Q | | | | | | | D | V | S | T | A | V | A | W | Y | Q |
| YW412.8.31.69 | D | I | Q | M | T | Q | S | P | S | S | L | S | A | S | V | G | D | R | V | T | I | T | C | R | A | S | Q | | | | | | | D | V | S | T | A | V | A | W | Y | Q |
| YW412.8.31.77 | D | I | Q | M | T | Q | S | P | S | S | L | S | A | S | V | G | D | R | V | T | I | T | C | R | A | S | Q | | | | | | | D | V | S | T | A | V | A | W | Y | Q |

| Kabat## | 79 80 81 82 A B C 83 84 85 86 87 88 89 90 91 92 93 94 95 96 97 98 99 100 A B C D E F G H I J K 101 102 103 104 105 106 107 108 109 110 111 112 113 | SEQ ID NO: |
|---|---|---|
| | | Kabat - CDR H3 |
| | | Chothia - CDR H3 |
| | | Contact - CDR H3 |
| YW412.8.31 | Y Q M S R S R A E D T A V Y Y C A R G P F G S P W V R W G Q G T L V T V S S | 21 |
| YW412.8.31.41S | Y Q M S R S R A E D T A V Y Y C A R G P F G S P W M H D Y W G Q G T L V T V S S | 80 |
| YW412.8.31.25ES | Y Q M S R S R A E D T A V Y Y C A R G P F G S P W M H D Y W G Q G T L V T V S S | 81 |
| YW412.8.31.81S | Y Q M S R S R A E D T A V Y Y C A R G P F G S P W M H D Y W G Q G T L V T V S S | 82 |
| YW412.8.31.6S | Y Q M S R S R A E D T A V Y Y C A R G P F G S P W M H D Y W G Q G T L V T V S S | 83 |
| YW412.8.31.75S | Y Q M S R S R A E D T A V Y Y C A R G P F G S P W M H D Y W G Q G T L V T V S S | 84 |
| YW412.8.31.9S | Y Q M S R S R A E D T A V Y Y C A R G P F G S P W M H D Y W G Q G T L V T V S S | 85 |
| YW412.8.31.65S | Y Q M S R S R A E D T A V Y Y C A R G P F G S P W M H D Y W G Q G T L V T V S S | 86 |
| YW412.8.31.86S | Y Q M S R S R A E D T A V Y Y C A R G P F G S P W M H D Y W G Q G T L V T V S S | 87 |
| YW412.8.31.55S | Y Q M S R S R A E D T A V Y Y C A R G P F G S P W M H D Y W G Q G T L V T V S S | 88 |
| YW412.8.31.58S | Y Q M S R S R A E D T A V Y Y C A R G P F G S P W M H D Y W G Q G T L V T V S S | 89 |
| YW412.8.31.25S | Y Q M S R S R A E D T A V Y Y C A R G P F G S P W M H D Y W G Q G T L V T V S S | 90 |
| YW412.8.31.3S | Y Q M S R S R A E D T A V Y Y C A R G P F G S P W M H D Y W G Q G T L V T V S S | 91 |
| YW412.8.31.69S | Y Q M S R S R A E D T A V Y Y C A R G P F G S P W M H D Y W G Q G T L V T V S S | 92 |
| YW412.8.31.54S | Y Q M S R S R A E D T A V Y Y C A R G P F G S P W M H D Y W G Q G T L V T V S S | 93 |
| YW412.8.31.71S | Y Q M S R S R A E D T A V Y Y C A R G P F T S P W M H D Y W G Q G T L V T V S S | 94 |
| YW412.8.31.51 | Y Q M S R S R A E D T A V Y Y C A R G P F G S P W M H D Y W G Q G T L V T V S S | 95 |
| YW412.8.31.53 | Y Q M S R S R A E D T A V Y Y C A R G P F G S P W M H D Y W G Q G T L V T V S S | 96 |
| YW412.8.31.69 | Y Q M S R S R A E D T A V Y Y C A R G P F G S P W M H D Y W G Q G T L V T V S S | 97 |
| YW412.8.31.77 | Y Q M S R S R A E D T A V Y Y C A R G P F G S P W M H D Y W G Q G T L V T V S S | 98 |

NUCLEIC ACID MOLECULES ENCODING FOR BACE1 ANTIBODIES

RELATED APPLICATIONS

This is a divisional application of U.S. patent application Ser. No. 14/292,461, filed May 30, 2014, which is a divisional application of U.S. application Ser. No. 13/292,633, filed Nov. 9, 2011, now U.S. Pat. No. 8,772,457; which claims the benefit of U.S. Provisional Application No. 61/456,642 filed on Nov. 10, 2010, U.S. Provisional Application No. 61/418,310, filed Nov. 30, 2010, U.S. Provisional Application No. 61/418,850, filed Dec. 1, 2010 and U.S. Provisional Application No. 61/426,425, filed Dec. 22, 2010, all of which are incorporated by reference herein in their entireties.

FIELD OF THE INVENTION

The present invention relates generally to antibodies which are BACE1 antagonists that, for example, inhibit or decrease BACE1 activity and to compositions comprising such antibodies. Additional embodiments include methods for treating and diagnosing various neurological diseases or disorders, as well as methods of reducing APP and/or Aβ polypeptides in a patient.

REFERENCE TO SEQUENCE LISTING SUBMITTED AS A TEXT FILE VIA EFS-WEB

A sequence listing is submitted concurrently with the specification as an ASCII formatted text file via EFS-Web, with a file name of "2016-08-09_01146-0047-02US_SeqList_ST25.txt," a creation date of Aug. 9, 2016, and a size of 117,228 bytes. The sequence listing filed via EFS-Web is part of the specification an is hereby incorporated by reference in its entirety.

BACKGROUND

Amyloidosis is not a single disease entity but rather a diverse group of progressive disease processes characterized by extracellular tissue deposits of a waxy, starch-like protein called amyloid, which accumulates in one or more organs or body systems. As the amyloid deposits accumulate, they begin to interfere with the normal function of the organ or body system. There are at least 15 different types of amyloidosis. The major forms are primary amyloidosis without known antecedent, secondary amyloidosis following some other condition, and hereditary amyloidosis.

Many diseases of aging are based on or associated with amyloid-like proteins and are characterized, in part, by the buildup of extracellular deposits of amyloid or amyloid-like material that contribute to the pathogenesis, as well as the progression of the disease. These diseases include, but are not limited to, neurological disorders such as Alzheimer's Disease (AD), Lewy body dementia, Down's syndrome, hereditary cerebral hemorrhage with amyloidosis (Dutch type); the Guam Parkinson-Dementia complex. Other diseases which are based on or associated with amyloid-like proteins are progressive supranuclear palsy, multiple sclerosis, Creutzfeld Jacob disease, Parkinson's disease, HIV-related dementia, ALS (amyotropic lateral sclerosis), Adult Onset Diabetes, senile cardiac amyloidosis, endocrine tumors, and others, including macular degeneration.

The polypeptide β-amyloid (Aβ) is likely to play a central role in the pathogenesis of Alzheimer's disease (AD). Vassar et al., *J. Neurosci.* 29:12787-12794 (2009). Aβ polypeptide accumulation in the CNS results in synaptic dysfunction, axon degeneration and neuronal death. The brains of AD patients show a characteristic pathology of prominent neuropathologic lesions, such as neurofibrillary tangles (NFTs), and amyloid-rich senile plaques. The major component of amyloid plaques is Aβ. These lesions are associated with massive loss of populations of central nervous system (CNS) neurons and their progression accompanies the clinical dementia associated with AD.

Aβ is the proteolytic product of the precursor protein, beta amyloid precursor protein (β-APP or APP). APP is a type-I trans-membrane protein which is sequentially cleaved by two proteases, a β- and γ-secretase. The β-secretase, known as β-site amyloid precursor protein cleaving enzyme 1 (BACE1), first cleaves APP to expose the N-terminus of Aβ, thereby producing a membrane bound fragment known as C99. Vassar et al., *J. Neurosci.*, 29:12787-12794 (2009) and UniProtKB/Swiss-Prot Entry P56817 (BACE1 HUMAN). The γ-secretase then is able to cleave C99 to produce the mature Aβ polypeptide. Aβ is produced with heterogenous C termini ranging in length from 38 amino acids to 43 amino acids. The 42 amino acid form of Aβ ($A\beta_{42}$) is the fibrillogenic form of Aβ and is over produced in patients with Down's syndrome and has been suggested to play a role in the early pathogenesis of AD. Vassar et al., *J. Neurosci.* 29:12787-12794 (2009). BACE1 has thus become a therapeutic target as its inhibition would presumably inhibit APP and Aβ production.

Indeed, BACE1 knock-out mice ($BACE1^{-/-}$) do not produce cerebral Aβ, confirming that BACE1 is the major, if not only, enzyme responsible for producing Aβ in the brain. Roberds et al., *Human Mol. Genetics* 10:1317-1324 (2001). Moreover, BACE1 knockout mice in AD models do not form amyloid plaques; cognitive defects and cholinergic dysfunction are rescued as well. McConlogue et al., *J. Biol. Chem.* 282: 26326-26334 (2007); Ohno et al., *Neuron* 41: 27-33 (2004); and Laird et al., *J. Neurosci.* 25:11693-11709 (2005). Additionally, BACE1 heterozygous knock-out mice have reduced plaque formation indicating the complete inhibition of BACE1 activity is not necessary for plaque reduction. McConlogue et al., *J. Biol. Chem.* 282: 26326-26334 (2007).

Recently, APP has been shown to be a ligand for Death Receptor 6 (DR6) which triggers caspase-dependent neuronal cell body death and axon pruning Nikolaev et al., *Nature* 457: 981-989 (2009). In addition, a BACE1 compound inhibitor impaired degeneration of axons and cell bodies. Id. These results point to a model in which APP, via DR6 binding may contribute to AD.

It would be beneficial to have an effective therapeutic inhibitor of BACE1 to reduce APP and Aβ production in patients with neurological diseases and disorders, such as AD. The invention provided herein relates to such inhibitors, including their use in a variety of methods.

All references cited herein, including patent applications and publications, are incorporated by reference in their entirety.

SUMMARY

The invention provides BACE1 antagonist antibodies and methods of using the same. Specifically, the antibodies inhibit or reduce the activity of BACE1.

In one embodiment, an isolated antibody that binds to BACE1, wherein the antibody reduces or inhibits the activity of the BACE1 polypeptide is provided. In particular, the antibody binds to the active site of BACE1 or to an exosite of BACE1.

In another embodiment, an isolated antibody that binds to BACE1 is provided wherein the antibody reduces or inhibits the activity of the BACE1 polypeptide and comprises at least one hypervariable region (HVR) sequence selected from the group consisting of SEQ ID NOs: 7-19, 22-26, 28-30, 35-47, 56-79 and 118-122.

In an additional embodiment, an isolated antibody that binds to BACE1 is provided wherein the antibody reduces or inhibits the activity of the BACE1 polypeptide and comprises at least one sequence selected from the group consisting of HVR-H1, HVR-H2 and HVR-H3, wherein HVR-H1 comprises the amino acid sequence GFX$_{30}$FX$_{31}$X$_{32}$X$_{33}$X$_{34}$IH (SEQ ID NO:45), wherein X$_{30}$=N or T; X$_{31}$=S, L or Y; X$_{32}$=G or Y; X$_{33}$=Y or S; and X$_{34}$=A, G or S; HVR-H2 comprises the amino acid sequence X$_{35}$X$_{36}$ISPX$_{37}$X$_{38}$GX$_{39}$TX$_{40}$YADSVKG (SEQ ID NO:46), wherein X$_{35}$=A or G; X$_{36}$=W or S; X$_{37}$=A or Y; X$_{38}$=G or S; X$_{39}$=S or Y; and X$_{40}$=D or S; and HVR-H3 comprises the amino acid sequence X$_{41}$PX$_{42}$X$_{43}$X$_{44}$X$_{45}$X$_{46}$X$_{47}$MDY (SEQ ID NO:47), wherein X$_{41}$=Q or G; X$_{42}$=T or F; X$_{43}$=H or S; X$_{44}$=Y or P; X$_{45}$=Y or W; X$_{46}$=Y or V and wherein X$_{47}$ optionally includes the sequence YAKGYKA (SEQ ID NO:48). Alternatively, the antibody comprises an HVR-H1 sequence comprising the amino acid sequence GFTFX$_{13}$GYX$_{14}$IH (SEQ ID NO:26), wherein X$_{13}$=S or L and X$_{14}$=A or G; or an amino acid sequence selected from the group consisting of SEQ ID NO:22; SEQ ID NO:23; and SEQ ID NO:28.

In an additional embodiment, an isolated antibody that binds to BACE1 is provided wherein the antibody reduces or inhibits the activity of the BACE1 polypeptide and comprises at least one sequence selected from the group consisting of HVR-H1, HVR-H2 and HVR-H3, wherein HVR-H1 comprises the amino acid sequence GX$_{71}$X$_{72}$X$_{73}$X$_{74}$X$_{75}$X$_{76}$X$_{77}$IH (SEQ ID NO:120), wherein X$_{71}$=F or Y; X$_{72}$=F, N or T; X$_{73}$=F or Y; X$_{74}$=L, Q, I, S or Y; X$_{75}$=G or Y; X$_{76}$=Y or S; and X$_{77}$=A, G or S; HVR-H2 comprises the amino acid sequence X$_{78}$X$_{79}$ISPX$_{80}$X$_{81}$GX$_{82}$X$_{83}$X$_{84}$YADSVKG (SEQ ID NO:121), wherein X$_{78}$=A or G; X$_{79}$=W or S; X$_{80}$=A, S, Q or Y; X$_{81}$=G or S; X$_{82}$=S, K, L or Y; X$_{83}$=T or Y; and X$_{84}$=D or S; and HVR-H3 comprises the amino acid sequence X$_{85}$PX$_{86}$X$_{87}$X$_{88}$X$_{89}$X$_{90}$X$_{91}$MDY (SEQ ID NO:122), wherein X$_{85}$=Q or G; X$_{86}$=T or F; X$_{87}$=H, Y or S; X$_{88}$=Y or P; X$_{89}$=Y or W; X$_{90}$=Y or V and wherein X$_{91}$ optionally includes the sequence YAKGYKA (SEQ ID NO:48). Alternatively, the antibody comprises an HVR-H1 sequence comprising the amino acid sequence GX$_{53}$X$_{54}$X$_{55}$X$_{56}$GYGIH (SEQ ID NO:68), wherein X$_{53}$=F or Y; X$_{54}$=T or F; X$_{55}$=F or Y; X$_{56}$=L, Q or I; or an amino acid sequence selected from the group consisting of SEQ ID NOs:71-73. Alternatively, the antibody comprises an HVR-H2 sequence comprising the amino acid sequence GWISPX$_{57}$X$_{58}$GX$_{59}$X$_{60}$DYADSVKG (SEQ ID NO:69), wherein X$_{57}$=A, S or Q; X$_{58}$=G or S; X$_{59}$=S, K or L; X$_{60}$=T or Y; or an amino acid sequence selected from the group consisting of SEQ ID NOs:74-78. Alternatively, the antibody comprises an HVR-H3 sequence comprising the amino acid sequence GPFX$_{61}$PWVMDY (SEQ ID NO:70), wherein X$_{61}$=S or Y; or an amino acid sequence of SEQ ID NO:79.

In one embodiment, an isolated antibody that binds to BACE1 is provided wherein the antibody reduces or inhibits the activity of the BACE1 polypeptide and comprises an HVR-H1 sequence comprising an amino acid sequence selected from SEQ ID NO:22, SEQ ID NO:23, SEQ ID NO:28 and SEQ ID NOs:71-73.

In one embodiment, an isolated antibody that binds to BACE1 is provided wherein the antibody reduces or inhibits the activity of the BACE1 polypeptide and comprises an HVR-H2 sequence comprising an amino acid sequence selected from SEQ ID NO:24, SEQ ID NO:29 and SEQ ID NOs:74-78.

In another embodiment, an isolated antibody that binds to BACE1 is provided wherein the antibody reduces or inhibits the activity of the BACE1 polypeptide and comprises an HVR-H3 sequence comprising an amino acid sequence selected from SEQ ID NO:25, SEQ ID NO:30 and SEQ ID NO:79.

In one embodiment, an isolated antibody that binds to BACE1 is provided wherein the antibody reduces or inhibits the activity of the BACE1 polypeptide and comprises HVR-H1, HVR-H2, and HVR-H3 sequences corresponding to those set forth for clones YW412.8, YW412.8.31, YW412.8.30, YW412.8.2, YW412.8.29 and YW412.8.51 in FIG. 1(B) or those set forth for clones Fab12, LC6, LC9 and LC10 in FIG. 2(B) or those clones set forth in FIGS. 24A-C.

In one embodiment, an isolated antibody that binds to BACE1 is provided wherein the antibody reduces or inhibits the activity of the BACE1 polypeptide and comprises an HVR-H1 sequence of SEQ ID NO:22 or 23, an HVR-H2 sequence of SEQ ID NO:24 and an HVR-H3 sequence of SEQ ID NO:25. In another embodiment, an isolated antibody that binds to BACE1 is provided wherein the antibody reduces or inhibits the activity of the BACE1 polypeptide and comprises an HVR-H1 sequence of SEQ ID NO:23, an HVR-H2 sequence of SEQ ID NO:24 and an HVR-H3 sequence of SEQ ID NO:25. In yet another embodiment, an isolated antibody that binds to BACE1 is provided wherein the antibody reduces or inhibits the activity of the BACE1 polypeptide and comprises an HVR-H1 sequence of SEQ ID NO:28, an HVR-H2 sequence of SEQ ID NO:29, and an HVR-H3 sequence of SEQ ID NO:30.

In one embodiment, an isolated antibody that binds to BACE1 is provided wherein the antibody reduces or inhibits the activity of the BACE1 polypeptide and comprises an HVR-H1 sequence selected from SEQ ID NOs:71-73, an HVR-H2 sequence selected from SEQ ID NOs:74-78 and an HVR-H3 sequence selected from SEQ ID NO:79.

In one embodiment, an isolated antibody that binds to BACE1 is provided wherein the antibody reduces or inhibits the activity of the BACE1 polypeptide and comprises a variable heavy (VH) chain having an amino acid sequence selected from the group consisting of SEQ ID NOs: 20, 21, 27 and 80-98. In one aspect, the antibody comprises the VH chain amino acid sequence of SEQ ID NO:21.

In another embodiment, an isolated antibody that binds to BACE1 is provided wherein the antibody reduces or inhibits the activity of the BACE1 polypeptide and comprises at least one sequence selected from the group of HVR-L1, HVR-L2 and HVR-L3, wherein HVR-L1 comprises the amino acid sequence RASQX$_{17}$VX$_{18}$X$_{19}$X$_{20}$X$_{21}$A (SEQ ID NO:42), wherein X$_{17}$=S, D or V; X$_{18}$=S or A; X$_{19}$=S, T or N; X$_{20}$=A or S; X$_{21}$=V or L, HVR-L2 comprises the amino acid sequence X$_{22}$ASX$_{23}$LYS (SEQ ID NO:43), wherein X$_{22}$=S, W, Y or L; X$_{23}$=F, S or W, and HVR-L3 comprises the amino acid sequence QQX$_{24}$X$_{25}$X$_{26}$X$_{27}$X$_{28}$X$_{29}$T (SEQ ID NO:44), wherein X$_{24}$=S, F, G, D or Y; X$_{25}$=Y, P, S or A; X$_{26}$=Y, T or N; X$_{27}$=T, Y, D or S; X$_{28}$=P or L; and X$_{29}$=F, P or T.

In another embodiment, an isolated antibody that binds to BACE1 is provided wherein the antibody reduces or inhibits the activity of the BACE1 polypeptide and comprises at least one sequence selected from the group of HVR-L1, HVR-L2 and HVR-L3, wherein HVR-L1 comprises the amino acid sequence RASQX$_{17}$VX$_{18}$X$_{19}$X$_{20}$X$_{21}$A (SEQ ID NO:42), wherein X$_{17}$=S, D or V; X$_{18}$=S or A; X$_{19}$=S, T or N; X$_{20}$=A or S; X$_{21}$=V or L, HVR-L2 comprises the amino acid sequence X$_{62}$ASX$_{63}$X$_{64}$YX$_{65}$ (SEQ ID NO:118), wherein X$_{62}$=S, W, Y, F or L; X$_{63}$=F, S, Y or W; X$_{64}$=L or R; X$_{65}$=S, P, R, K or W, and HVR-L3 comprises the amino acid sequence QQX$_{66}$X$_{67}$X$_{68}$X$_{69}$X$_{70}$X$_{71}$T (SEQ ID NO:119), wherein X$_{66}$=S, F, G, D or Y; X$_{67}$=Y, P, S or A; X$_{68}$=Y, T or N; X$_{69}$=T, Y, D or S; X$_{70}$=P, Q, S, K or L; and X$_{71}$=F, P or T.

In certain embodiments, an isolated antibody that binds to BACE1 is provided wherein the antibody reduces or inhibits the activity of the BACE1 polypeptide and comprises an HVR-L1 sequence comprising the amino acid sequence RASQX$_1$VX$_2$X$_3$X$_4$X$_5$A (SEQ ID NO:17), wherein X$_1$=D or V; X$_2$=S or A; X$_3$=T or N; X$_4$=S or A; X$_5$=V or L or an amino acid sequence selected from the group consisting of SEQ ID NO:7, SEQ ID NO:8 or SEQ ID NO:35.

In one embodiment, an isolated antibody that binds to BACE1 is provided wherein the antibody reduces or inhibits the activity of the BACE1 polypeptide and comprises an HVR-L2 sequence comprising the amino acid sequence X$_6$ASFLYS (SEQ ID NO:18), wherein X$_6$=S or L or X$_{15}$ASX$_{16}$LYS (SEQ ID NO:41), wherein X$_{15}$=S, W or Y and X$_{16}$=S or W or an amino acid sequence selected from the group consisting of SEQ ID NO:9, SEQ ID NO:10, and SEQ ID NOs:36-39.

In one embodiment, an isolated antibody that binds to BACE1 is provided wherein the antibody reduces or inhibits the activity of the BACE1 polypeptide and comprises an HVR-L3 sequence comprising the amino acid sequence QQX$_7$X$_8$X$_9$X$_{10}$X$_{11}$X$_{12}$T (SEQ ID NO:19), wherein X$_7$=S, F, G, D or Y; X$_8$=Y, P, S, or A; X$_9$=T or N; X$_{10}$=T, Y, D or S; X$_{11}$=P or L; X$_{12}$=P or T or an amino acid sequence selected from the group consisting of SEQ ID NOs:11-16 and SEQ ID NO:40.

In certain embodiments, an isolated antibody that binds to BACE1 is provided wherein the antibody reduces or inhibits the activity of the BACE1 polypeptide and comprises an HVR-L1 sequence comprising the amino acid sequence RASQX$_1$VX$_2$X$_3$X$_4$X$_5$A (SEQ ID NO:17), wherein X$_1$=D or V; X$_2$=S or A; X$_3$=T or N; X$_4$=S or A; X$_5$=V or L or an amino acid sequence selected from the group consisting of SEQ ID NO:7.

In one embodiment, an isolated antibody that binds to BACE1 is provided wherein the antibody reduces or inhibits the activity of the BACE1 polypeptide and comprises an HVR-L2 sequence comprising the amino acid sequence X$_{48}$ASX$_{49}$X$_{50}$YX$_{51}$ (SEQ ID NO:56), wherein X$_{48}$=S or F; X$_{49}$=F or Y; X$_{50}$=L or R; X$_{51}$=S, P, R, K or W or an amino acid sequence selected from the group consisting of SEQ ID NOs:58-64.

In one embodiment, an isolated antibody that binds to BACE1 is provided wherein the antibody reduces or inhibits the activity of the BACE1 polypeptide and comprises an HVR-L3 sequence comprising the amino acid sequence QQFPTYX$_{52}$PT (SEQ ID NO:57), wherein X$_{52}$=L, Q, S or K or an amino acid sequence selected from the group consisting of SEQ ID NOs:65-67.

In one embodiment, an isolated antibody that binds to BACE1 is provided wherein the antibody reduces or inhibits the activity of the BACE1 polypeptide and comprises HVR-L1, HVR-L2 and HVR-L3 sequences corresponding to those set forth for clones YW412.8, YW412.8.31, YW412.8.30, YW412.8.2, YW412.8.29 and YW412.8.51 in FIG. 1(A) or those set forth for clones Fab12, LC6, LC9 and LC10 in FIG. 2(A) or those set forth for clones in FIG. 23A-C.

In one embodiment, an isolated antibody that binds to BACE1 is provided wherein the antibody reduces or inhibits the activity of the BACE1 polypeptide and comprises an HVR-L1 sequence of SEQ ID NO:7 or SEQ ID NO:8; an HVR-L2 sequence selected from the group consisting of SEQ ID NO:9, SEQ ID NO:10 or SEQ ID NOs: 58-64; and an HVR-L3 sequence selected from the group consisting of: SEQ ID NOs:11-16 and 65-67. In another aspect, an isolated antibody that binds to BACE1 is provided wherein the antibody reduces or inhibits the activity of the BACE1 polypeptide and comprises an HVR-L1 sequence of SEQ ID NO:7, an HVR-L2 sequence of SEQ ID NO:9 and an HVR-L3 sequence of SEQ ID NO:12.

In an additional embodiment, an isolated antibody that binds to BACE1 is provided wherein the antibody reduces or inhibits the activity of the BACE1 polypeptide and comprises an HVR-L1 sequence of SEQ ID NO:7, SEQ ID NO:8 or SEQ ID NO:35.

In an additional embodiment, an isolated antibody that binds to BACE1 is provided wherein the antibody reduces or inhibits the activity of the BACE1 polypeptide and comprises an HVR-L2 sequence of SEQ ID NOs:9-10, 36-39 or 58-64.

In an additional embodiment, an isolated antibody that binds to BACE1 is provided wherein the antibody reduces or inhibits the activity of the BACE1 polypeptide and comprises an HVR-L3 sequence of SEQ ID NOs: 11-16, 40 or 65-67.

In another embodiment, an isolated antibody that binds to BACE1 is provided wherein the antibody reduces or inhibits the activity of the BACE1 polypeptide and comprises a variable light (VL) chain sequence having an amino acid sequence selected from the group consisting of: SEQ ID NOs: 1-6, 31-34 and 99-117. In one aspect, the VL chain amino acid sequence is SEQ ID NO:2.

In an additional embodiment, an isolated antibody that binds to BACE1 is provided wherein the antibody reduces or inhibits the activity of the BACE1 polypeptide and comprises an HVR-H1 sequence of SEQ ID NO:23, an HVR-H2 sequence of SEQ ID NO:24, an HVR-H3 sequence of SEQ ID NO:25, an HVR-L1 of SEQ ID NO:7, an HVR-L2 of SEQ ID NO:9 and an HVR-L3 of SEQ ID NO:12.

In one embodiment, an isolated antibody that binds to BACE1 is provided wherein the antibody reduces or inhibits the activity of the BACE1 polypeptide and comprises a VL chain comprising the amino acid sequence of SEQ ID NO:2 and a VH chain comprising the amino acid sequence of SEQ ID NO:21.

In another embodiment, an isolated antibody which binds to an epitope comprising at least one of the amino acid residues of BACE1 selected from the group consisting of: 314 SER; 316 GLU; 317 LYS; 327 GLN; 330 CYS; 331 TRP; 332 GLN; 335 THR; and 378 ASP of SEQ ID NO:49 is provided. In certain embodiments, the antibody binds to an epitope of BACE1 comprising the amino acids: 314 SER; 316 GLU; 317 LYS; 327 GLN; 330 CYS; 331 TRP; 332 GLN; 335 THR; and 378 ASP of SEQ ID NO:49.

In other embodiments, the antibody binds to an epitope of BACE1 comprising at least one amino acid region of BACE1 selected from the group consisting of: amino acids 315-318 of SEQ ID NO:49; amino acids 331-335 of SEQ ID NO:49; amino acids 370-381 of SEQ ID NO:49; and any combination thereof. In one embodiment, the antibody binds to an epitope of BACE1 comprising amino acids 315-318, 331-335 and 370-381 of SEQ ID NO:49.

In another embodiment the antibody binds to an epitope of BACE1 which results in a conformational change in the structure of the P6 and P7 sites of BACE1 upon binding. In an additional embodiment, the antibody binds to an epitope of BACE1 which induces amino acids 218-231 of SEQ ID NO:49 to adopt a random loop structure.

An antibody of the invention can be in any number of forms. For example, an antibody of the invention can be a human antibody, humanized antibody or chimeric antibody. In other aspects the antibody of the invention is a full length antibody or a fragment thereof (e.g., a fragment comprising an antigen binding component). In other aspects of the invention, the antibody is a monoclonal antibody. In another aspect, an antibody of the invention can be linked or conjugated to an agent or moiety, e.g. a cytotoxic agent, to create an immunoconjugate.

In one embodiment, a pharmaceutical formulation is provided which comprises an antibody of the invention and a pharmaceutically acceptable carrier. In additional embodiments an isolated nucleic acid encoding an antibody of the invention is provided, as well as vector that comprises the nucleic acid encoding an antibody of the invention. In another aspect, a host cell comprising the nucleic acid encoding an antibody of the invention is provided as well as methods for producing an antibody of the invention comprising culturing the host cell comprising the nucleic acid encoding an antibody of the invention under conditions suitable for production of the antibody.

In another embodiment, a method of treating an individual having a neurological disease or disorder comprising administering to the individual an effective amount of an antibody of the invention is provided.

In an additional embodiment, a method of reducing amyloid plaques, or inhibiting amyloid plaque formation, in a patient suffering from, or at risk of contracting, a neurological disease or disorder comprising administering to the individual an effective amount of an antibody of the invention is provided.

In one embodiment, a method of reducing Aβ protein in a patient comprising administering to the patient an effective amount of an antibody of the invention. In one aspect, the patient is suffering from, or at risk of contracting, a neurological disease or disorder.

In another embodiment, a method of inhibiting axon degeneration in a patient comprising administering to the patient an effective amount of an antibody of the invention is provided.

In an additional embodiment, a method of diagnosing a neurological disease or disorder in patient comprising contacting a biological sample isolated from the patient with an antibody of the invention under conditions suitable for binding of the antibody to a BACE1 polypeptide, and detecting whether a complex is formed between the antibody and the BACE1 polypeptide.

In one embodiment, a method of determining whether a patient is eligible for therapy with an anti-BACE1 antibody, comprising contacting a biological sample isolated from the patient with an antibody of the invention under conditions suitable for binding of the antibody to a BACE1 polypeptide, and detecting whether a complex is formed between the antibody and the BACE1 polypeptide, wherein the presence of a complex between the antibody and BACE1 is indicative of a patient eligible for therapy with an anti-BACE1 antibody. In one aspect the patient is suffering from, or at risk of contracting, a neurological disease or disorder.

In one aspect, biological samples that may be used in the diagnosis of a neurological disease or condition; or for predicting responsiveness, or determining eligibility, of a patient to a treatment with a BACE1 antibody include, but are not limited to, fluids such as serum, plasma, saliva, gastric secretions, mucus, cerebrospinal fluid, lymphatic fluid and the like or tissue or cell samples obtained from an organism such as neuronal, brain, cardiac or vascular tissue.

In one aspect of the methods of the invention, the patient is mammalian. In another aspect, the patient is human. In another aspect, the neurological disease or disorder is selected from the group consisting of Alzheimer's disease (AD), traumatic brain injury, stroke, glaucoma, dementia, muscular dystrophy (MD), multiple sclerosis (MS), amyotrophic lateral sclerosis (ALS), cystic fibrosis, Angelman's syndrome, Liddle syndrome, Paget's disease, traumatic brain injury, Lewy body disease, postpoliomyelitis syndrome, Shy-Draeger syndrome, olivopontocerebellar atrophy, Parkinson's disease, multiple system atrophy, striatonigral degeneration, supranuclear palsy, bovine spongiform encephalopathy, scrapie, Creutzfeldt-Jakob syndrome, kuru, Gerstmann-Straussler-Scheinker disease, chronic wasting disease, fatal familial insomnia, bulbar palsy, motor neuron disease, Canavan disease, Huntington's disease, neuronal ceroid-lipofuscinosis, Alexander's disease, Tourette's syndrome, Menkes kinky hair syndrome, Cockayne syndrome, Halervorden-Spatz syndrome, lafora disease, Rett syndrome, hepatolenticular degeneration, Lesch-Nyhan syndrome, and Unverricht-Lundborg syndrome, dementia (including, but not limited to, Pick's disease, and spinocerebellar ataxia). In one aspect, the neurological disease or disorder is Alzheimer's disease.

In one embodiment, a BACE1 epitope which is specifically recognized by an antibody, or fragment thereof, comprising at least one of the amino acid residues of BACE1 which correspond to the amino acids selected from the group consisting of: 314 SER; 316 GLU; 317 LYS; 327 GLN; 330 CYS; 331 TRY; 332 GLN; 335 THR; and 378 ASP of SEQ ID NO:49 is provided. In one aspect, the BACE1 epitope comprises amino acids which correspond to 314 SER; 316 GLU; 317 LYS; 327 GLN; 330 CYS; 331 TRY; 332 GLN; 335 THR; and 378 ASP of SEQ ID NO:49. In one embodiment, a BACE1 epitope which is specifically recognized by an antibody, or fragment thereof, comprising at least one amino acid region of BACE1 selected from the group consisting of: amino acids 315-318 of SEQ ID NO:49; amino acids 331-335 of SEQ ID NO:49; amino acids 370-381 of SEQ ID NO:49; and any combination thereof. In one aspect, the BACE1 epitope comprises amino acids 315-318, 331-335 and 370-381 of SEQ ID NO:49.

BRIEF DESCRIPTION OF THE FIGURES

FIGS. 1A-1B depict the light and heavy chain amino acid sequences of clone YW412.8 obtained from a naïve sort of the natural diversity phage display library and affinity-matured forms of YW412.8 as described in Example 1(A). FIG. 1A depicts the light chain sequence alignments. FIG. 1B depicts the heavy chain sequence alignments. In both FIGS. 1A and 1B, the HVR sequences for each clone are indicated by the boxed regions, with the first box indicating HVR-L1 (SEQ ID NOs:7 and 8—FIG. 1A) or HVR-H1 (SEQ ID NOs:22 and 23—FIG. 1B), the second box indicating HVR-L2 (SEQ ID NOs:9 and 10—FIG. 1A) or HVR-H2 (SEQ ID NO:24—FIG. 1B), and the third box indicating HVR-L3 (SEQ ID NOs:11-16—FIG. 1A) or HVR-H3 (SEQ ID NO:25—FIG. 1B).

FIGS. 2A-2B depict the light and heavy chain amino acid sequences of clone Fab 12 obtained from a naïve sort of a synthetic diversity phage display library and affinity-matured forms of Fab 12, as described in Example 1(B). FIG. 2A depicts the light chain sequence alignments. FIG. 2B depicts the heavy chain sequence alignments. In both FIGS. 2A and 2B, the HVR sequences for each clone are indicated by the boxed regions, with the first box indicating HVR-L1 (SEQ ID NO:35—FIG. 2A) or HVR-H1 (SEQ ID NO:28—FIG. 2B), the second box indicating HVR-L2 (SEQ ID NOs:36-39—FIG. 2A) or HVR-H2 (SEQ ID NO:29—FIG. 2B), and the third box indicating HVR-L3 (SEQ ID NO:40—FIG. 2A) or HVR-H3 (SEQ ID NO:30—FIG. 2B).

FIGS. 3A and 3B depict the HVR or CDR sequences from the light and heavy chain Fabs isolated from the synthetic diversity phage display library as described in Example 1(B). The numbering is according to the nomenclature of Kabat et al. FIG. 3A discloses the "CDRL1" sequences as SEQ ID NO: 133, the "CDRL2" sequences as SEQ ID NO: 134, the "CDRL3" sequences as SEQ ID NOS 135-144, 141, and 145-152 and the "CDRH1" sequences as SEQ ID NOS 153-159, 158, 160-161, 159, 158, 162, 161, and 163-167 all, respectively, in order of appearance. FIG. 3B discloses the "CDRH2" sequences as SEQ ID NOS 168-177, 174, 171, 178-182, 177, and 183, and the "CDRH3" sequences as SEQ ID NOS 184-202, all, respectively, in order of appearance.

FIG. 6 depicts the CDR or HVR sequences of affinity matured anti-BACE1 Fabs as described in Example 1(B). The numbering is according to the nomenclature of Kabat et al. The competition ELISA ratio is the ratio of ELISA signal in the absence or presence of 20 nM BACE1 as competitor in solution in one-point competition ELISA assays as described in Example 1(B). FIG. 6 discloses the "CDRL1" sequences as SEQ ID NOS 133, 133, 133, 133, 133, and 203, the "CDRL2" sequences as SEQ ID NOS 134, 134, and 204-207, the "CDRL3" sequences as SEQ ID NOS 208-209, 145, 145, and 145-146, the "CDRH1" sequences as SEQ ID NOS 157, 157, 158, 158, 158, and 162, the "CDRH2" sequences as SEQ ID NOS 172, 172, 171, 171, 171, and 178, and the "CDRH3" sequences as SEQ ID NOS 188, 188, 195, 195, and 195-196, all, respectively, in order of appearance.

FIGS. 7A, 7B and 7C depict competition curves for the parent and corresponding affinity matured antibodies.

FIGS. 8A, 8B and 8C are inhibition curves for the parent and corresponding affinity matured derivatives. The $IC_{50}$ for OM99-2 was 11 nM in this assay.

FIG. 11A shows results from experiments using 293-HEK cells stably expressing wild-type human APP. BACE1 SMI is a small molecule BACE1 inhibitor which was used as a control (Compound 8e—Charrier et al., J. Med. Chem. 51:3313-3317 (2008). FIG. 11B shows results from experiments using E13.5 dorsal root ganglia neurons cultured from wild-type CD1 mice. Additional experiments were performed using cultures of E16.5 cortical neurons (FIG. 11C) and E16.5 cultured hippocampal neurons (FIG. 11D) from wild-type CD1 mice.

FIG. 12A shows internalization of YW412.8.31 anti-BACE1 antibody into intracellular vesicles in neurons. Embryonic cortical neurons were incubated at 37° C. for the times indicated. Bound YW412.8.31 was detected on surface (non-permeabilized) or internal (permeabilized) cellular compartments with α-human-Alexa 568. The majority of signal was internalized. Internalized YW412.8.31 was localized to subcellular compartments by co-staining with the indicated markers for vascular compartments: early endosomes (TfR); trans-golgi network (VAMP4) and lysosome (LAMP1). Scale bar=65 µm (top) and 20 µm (bottom). FIG. 12B shows uptake of anti-BACE1 antibody into E13.5 dorsal root ganglion (DRG) neurons at two different temperatures and three different time points, as indicated in the figure. Cells were permeabilized to allow for labeling of intracellular BACE1 antibody. Only externally bound YW412.8.31 anti-BACE1 antibody is labeled in the non-permeabilized cells. FIG. 12(C) shows uptake into E16.5 cortical neurons of YW412.8.31 anti-BACE1 antibody from BACE1-expressing or BACE1 knockout mice.

FIG. 16A shows the results of genetic studies examining the contribution of BACE1 to $A\beta_{1-40}$ production in mice. Levels of $A\beta_{1-40}$ observed in BACE1 knockout mice (BACE1−/−) provide a control for how specific inhibitors of BACE1 alter $A\beta_{1-40}$ production in wild-type mice. FIG. 16B shows effects of dosing control IgG or anti-BACE1 YW412.8.31 (50 mg/kg) on $A\beta_{1-40}$ production in plasma and CNS (cortex) 24 or 48 hours after dosing. A single dose of control IgG or anti-BACE1 antibody (50 mg/kg) was delivered by IV injection to C57Bl/6 mice. 24 or 48 hours later, plasma and brain samples were harvested to analyze $A\beta_{1-40}$. Plasma $A\beta_{1-40}$ is reduced by 35% (at 24 hr) and cortical $A\beta_{1-40}$ by ~20%. Values plotted are mean (±SEM) * $p<0.01$; ** $p<0.001$.

FIG. 17A shows plots of $A\beta_{1-40}$ levels observed in the plasma and the hippocampus of mice treated with the YW412.8.31 anti-BACE1 antibody at two different concentrations in comparison to vehicle control treatment. FIG. 17B is a plot of individual pharmacokinetic versus pharmacodynamic readouts, indicating that a PK/PD relationship exists in this mouse model for the YW412.8.31 anti-BACE1 antibody.

In FIG. 18A, Animals received vehicle or anti-BACE1 antibody (30 or 100 mg/kg) by IP injection (3 doses @ Q4D). 2 hours after the last dose, plasma and brain samples were harvested to analyze $A\beta_{1-40}$ and $A\beta_{1-42}$. Plasma $A\beta_{1-40}$ and $A\beta_{1-42}$ were reduced to ~30% control levels at both 30 and 100 mg/kg anti-BACE1 antibody. Hippocampal $A\beta_{1-40}$ and $A\beta_{1-42}$ were reduced (13-22%) by the high dose of anti-BACE1 (100 mg/kg), and cortical $A\beta_{1-40}$ and $A\beta_{1-42}$ showed a trend toward reduction (12-18%). In FIG. 18B, Control IgG or anti-BACE1 antibody was delivered by unilateral ICV infusion for 7 days. Consistent reductions were seen in $A\beta_{1-40}$ and $A\beta_{1-42}$ at both doses in cortex (15-23%) and in hippocampus (15-20%). Panel C shows the levels of anti-BACE1 antibody in the brain following systemic vs. ICV delivery. Values plotted are mean (±SEM) * $p<0.05$; ** $p<0.001$

FIG. 22A is a graph showing $A\beta_{1-40}$ production following a single dose of control IgG or YW412.8.31 (100 mg/kg) administered by IP injection to C57Bl/6J mice. 4 hours later, plasma and brain samples were harvested to analyze $A\beta_{1-40}$. Plasma $A\beta_{1-40}$ is reduced by 48%, but forebrain $A\beta_{1-40}$ is not reduced in this paradigm. FIG. 22B is a graph showing $A\beta_{1-40}$ production following control IgG or YW412.8.31 (30 or 100 mg/kg) administration by 3 IP injections, each 4 days apart. 4 hours after the last dose, plasma and brain samples were harvested to analyze $A\beta_{1-40}$. Plasma $A\beta_{1-40}$ is reduced by 50-53%, whereas forebrain $A\beta_{1-40}$ is not reduced by dosing at 30 mg/kg, but is reduced by 42% when dosed at 100 mg/kg. Values plotted are mean (±SEM) * $p<0.0001$ FIGS. 23A-23C depict the light chain amino acid sequences of clone YW412.8.31 and affinity-matured forms of YW412.8.31. FIGS. 23A-23C depict the complete light chain sequence alignments. The HVR sequences for each clone are indicated by the boxed regions, with the first box indicating HVR-L1 (SEQ ID NO:7—FIG. 23A), the second box indicating HVR-L2 (SEQ ID NOs:9 and 58-64—FIG. 23B), and the third box indicating HVR-L3 (SEQ ID NOs: 12 and 66-67—FIG. 23C).

FIGS. 24A-24C depict the heavy chain amino acid sequences of clone YW412.8.31 and affinity-matured forms of YW412.8.31. FIGS. 24A-24C depict the complete heavy chain sequence alignments. The HVR sequences for each clone are indicated by the boxed regions, with the first box indicating HVR-H1 (SEQ ID NOs:24 and 71-73—FIG. 24A), the second box indicating HVR-H2 (SEQ ID NOs:24 and 74-78—FIG. 24B), and the third box indicating HVR-H3 (SEQ ID NOs:25 and 79—FIG. 24C).

DETAILED DESCRIPTION OF EMBODIMENTS OF THE INVENTION

I. Definitions

Figure 4:
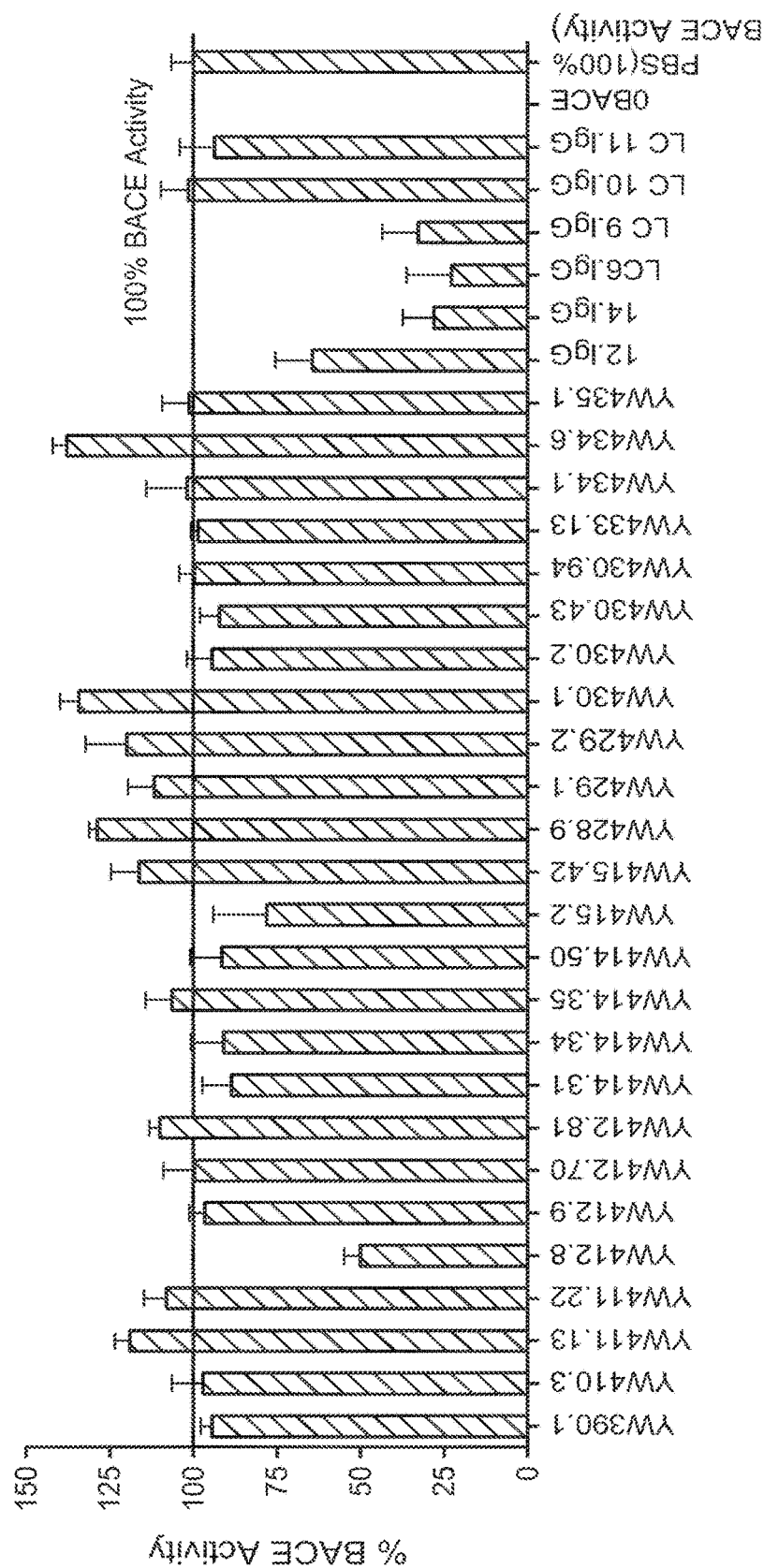
FIG. 4 provides a graph showing the inhibition of BACE1 by the various clones identified from the natural diversity and synthetic diversity phage display libraries. The clones were tested for BACE1 inhibition in a homogenous time-resolved fluorescence (HTRF) assay, as described in Example 1(A). All YW series antibodies were used at a concentration of 500 nM except for the YW 434.6 antibody, which was tested at a concentration of 320 nM. Antibodies 12.IgG, 14.IgG LC6.IgG, LC9.IgG, LC10.IgG and LC11.IgG were tested at 1 µM concentration.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-beta-secretase antibody", "anti-BACE1 antibody", "an antibody that binds to beta-secretase" and "an antibody that binds to BACE1" refer to an antibody that is capable of binding BACE1 with sufficient affinity such that the antibody is useful as a diagnostic and/or therapeutic agent in targeting BACE1. In one embodiment, the extent of binding of an anti-BACE1 antibody to an unrelated, non-BACE1 protein is less than about 10% of the binding of the antibody to BACE1 as measured, e.g., by a radioimmunoassay (RIA). In certain embodiments, an antibody that binds to BACE1 has a dissociation constant (Kd) of ≤10 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-BACE1 antibody binds to an epitope of BACE1 that is conserved among BACE1 from different species and isoforms.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and µ, respectively.

The term "cytotoxic agent" as used herein refers to a substance that inhibits or prevents a cellular function and/or causes cell death or destruction. Cytotoxic agents include, but are not limited to radioactive isotopes (e.g., $A^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, *vinca* alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anti-cancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest,* Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest,* 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-BACE1 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative. The term "BACE1," as used herein, refers to any native beta-secretase 1 (also called β-site amyloid precursor protein cleaving enzyme 1, membrane-associated aspartic protease 2, memapsin 2, aspartyl protease 2 or Asp2) from any vertebrate source, including mammals such as primates (e.g. humans) and rodents (e.g., mice and rats), unless otherwise indicated. The term encompasses "full-length," unprocessed BACE1 as well as any form of BACE1 that results from processing in the cell. The term also encompasses naturally occurring variants of BACE1, e.g., splice variants or allelic variants. The amino acid sequence of an exemplary BACE1 polypeptide is shown in SEQ ID NO:49 below, and is the sequence for human BACE1, isoform A as reported in Vassar et al., *Science* 286:735-741 (1999), which is incorporated herein by reference in its entirety.

(SEQ ID NO: 49)
MAQALPWLLLWMGAGVLPAHGTQHGIRLPLRSGLGGAPLGLRLPRETDEE

PEEPGRRGSFVEMVDNLRGKSGQGYYVEMTVGSPPQTLNILVDTGSSNFA

VGAAPHPFLHRYYQRQLSSTYRDLRKGVYVPYTQGKWEGELGTDLVSIPH

GPNVTVRANIAAITESDKFFINGSNWEGILGLAYAEIARPDDSLEPFFDS

LVKQTHVPNLFSLQLCGAGFPLNQSEVLASVGGSMIIGGIDHSLYTGSLW

YTPIRREWYYEVIIVRVEINGQDLKMDCKEYNYDKSIVDSGTTNLRLPKK

VFEAAVKSIKAASSTEKFPDGFWLGEQLVCWQAGTTPWNIFPVISLYLMG

EVTNQSFRITILPQQYLRPVEDVATSQDDCYKFAISQSSTGTVMGAVIME

GFYVVFDRARKRIGFAVSACHVHDEFRTAAVEGPFVTLDMEDCGYNIPQT

DESTLMTIAYVMAAICALFMLPLCLMVCQWCCLRCLRQQHDDFADDISLL

K

Several other isoforms of human BACE1 exist including isoforms B, C and D. See UniProtKB/Swiss-Prot Entry P56817, which is incorporated herein by reference in its entirety. Isoform B is shown in SEQ ID NO:50 and differs from isoform A (SEQ ID NO:49) in that it is missing amino acids 190-214 (i.e. deletion of amino acids 190-214 of SEQ ID NO:49). Isoform C is shown in SEQ ID NO:51 and differs from isoform A (SEQ ID NO:49) in that it is missing amino acids 146-189 (i.e. deletion of amino acids 146-189 of (SEQ ID NO:49). Isoform D is shown in SEQ ID NO:52 and differs from isoform A (SEQ ID NO:49) in that it is missing amino acids 146-189 and 190-214 (i.e. deletion of amino acids 146-189 and 190-214 of SEQ ID NO:49).

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6*th* ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "neurological disorder" or "neurological disease" refer to or describe a disease or disorder of the central and/or peripheral nervous system in mammals. Examples of neurological disorders include, but are not limited to the following list of disease and disorders.

Neuropathy disorders are diseases or abnormalities of the nervous system characterized by inappropriate or uncontrolled nerve signaling or lack thereof, and include, but are not limited to, chronic pain (including nociceptive pain (pain caused by an injury to body tissues, including cancer-related pain), neuropathic pain (pain caused by abnormalities in the nerves, spinal cord, or brain), and psychogenic pain (entirely or mostly related to a psychological disorder), headache, migraine, neuropathy, and symptoms and syndromes often accompanying such neuropathy disorders such as vertigo or nausea. Amyloidoses are a group of diseases and disorders associated with extracellular proteinaceous deposits in the CNS, including, but not limited to, secondary amyloidosis, age-related amyloidosis, Alzheimer's Disease (AD), mild cognitive impairment (MCI), Lewy body dementia, Down's syndrome, hereditary cerebral hemorrhage with amyloidosis (Dutch type); the Guam Parkinson-Dementia complex, cerebral amyloid angiopathy, Huntington's disease, progressive supranuclear palsy, multiple sclerosis; Creutzfeld Jacob disease, Parkinson's disease, transmissible spongiform encephalopathy, HIV-related dementia, amyotropic lateral sclerosis (ALS), inclusion-body myositis (IBM), and ocular diseases relating to beta-amyloid deposition (i.e., macular degeneration, drusen-related optic neuropathy, and cataract). Cancers of the CNS are characterized by aberrant proliferation of one or more CNS cell (i.e., a neural cell) and include, but are not limited to, glioma, glioblastoma multiforme, meningioma, astrocytoma, acoustic neuroma, chondroma, oligodendroglioma, medulloblastomas, ganglioglioma, Schwannoma, neurofibroma, neuroblastoma, and extradural, intramedullary or intradural tumors. Ocular diseases or disorders are diseases or disorders of the eye, which for the purposes herein is considered a CNS organ subject to the BBB. Ocular diseases or disorders include, but are not limited to, disorders of sclera, cornea, iris and ciliary body (i.e., scleritis, keratitis, corneal ulcer, corneal abrasion, snow blindness, arc eye, Thygeson's superficial punctate keratopathy, corneal neovascularisation, Fuchs' dystrophy, keratoconus, keratoconjunctivitis sicca, iritis and uveitis), disorders of the lens (i.e., cataract), disorders of choroid and retina (i.e., retinal detachment, retinoschisis, hypertensive retinopathy, diabetic retinopathy, retinopathy, retinopathy of prematurity, age-related macular degeneration, macular degeneration (wet or dry), epiretinal membrane, retinitis pigmentosa and macular edema), glaucoma, floaters, disorders of optic nerve and visual pathways (i.e., Leber's hereditary optic neuropathy and optic disc drusen), disorders of ocular muscles/binocular movement accommodation/refraction (i.e., strabismus, ophthalmoparesis, progressive external opthalmoplegia, esotropia, exotropia, hypermetropia, myopia, astigmatism, anisometropia, presbyopia and ophthalmoplegia), visual disturbances and blindness (i.e., amblyopia, Lever's congenital amaurosis, scotoma, color blindness, achromatopsia, nyctalopia, blindness, river blindness and micro-opthalmia/coloboma), red eye, Argyll Robertson pupil, keratomycosis, xerophthalmia and andaniridia. Viral or microbial infections of the CNS include, but are not limited to, infections by viruses (i.e., influenza, HIV, poliovirus, rubella), bacteria (i.e., *Neisseria* sp., *Streptococcus* sp., *Pseudomonas* sp., *Proteus* sp., *E. coli, S. aureus, Pneumococcus* sp., *Meningococcus* sp., *Haemophilus* sp., and *Mycobacterium tuberculosis*) and other microorganisms such as fungi (i.e., yeast, *Cryptococcus neoformans*), parasites (i.e., *toxoplasma gondii*) or amoebas resulting in CNS pathophysiologies including, but not limited to, meningitis, encephalitis, myelitis, vasculitis and abscess, which can be acute or chronic. Inflammation of the CNS is inflammation that is caused by an injury to the CNS, which can be a physical injury (i.e., due to accident, surgery, brain trauma, spinal cord injury, concussion) or an injury due to or related to one or more other diseases or disorders of the CNS (i.e., abscess, cancer, viral or microbial infection). Ischemia of the CNS, as used herein, refers to a group of disorders relating to aberrant blood flow or vascular behavior in the brain or the causes therefor, and includes, but is not limited to, focal brain ischemia, global brain ischemia, stroke (i.e., subarachnoid hemorrhage and intracerebral hemorrhage), and aneurysm. Neurodegenerative diseases are a group of diseases and disorders associated with neural cell loss of function or death in the CNS, and include, but are not limited to, adrenoleukodystrophy, Alexander's disease, Alper's disease, amyotrophic lateral sclerosis, ataxia telangiectasia, Batten disease, cockayne syndrome, corticobasal degeneration, degeneration caused by or associated with an amyloidosis, Friedreich's ataxia, frontotemporal lobar degeneration, Kennedy's disease, multiple system atrophy, multiple sclerosis, primary lateral sclerosis, progressive supranuclear palsy, spinal muscular atrophy, transverse myelitis, Refsum's disease, and spinocerebellar ataxia. Seizure diseases and disorders of the CNS involve inappropriate and/or abnormal electrical conduction in the CNS, and include, but are not limited to, epilepsy (i.e., absence seizures, atonic seizures, benign Rolandic epilepsy, childhood absence, clonic seizures, complex partial seizures, frontal lobe epilepsy, febrile seizures, infantile spasms, juvenile myoclonic epilepsy, juvenile absence epilepsy, Lennox-Gastaut syndrome, Landau-Kleffner Syndrome, Dravet's syndrome, Otahara syndrome, West syndrome, myoclonic seizures, mitochondrial disorders, progressive myoclonic epilepsies, psychogenic seizures, reflex epilepsy, Rasmussen's Syndrome, simple partial seizures, secondarily generalized seizures, temporal lobe epilepsy, toniclonic seizures, tonic seizures, psychomotor seizures, limbic epilepsy, partial-onset seizures, generalized-onset seizures, status epilepticus, abdominal epilepsy, akinetic seizures, autonomic seizures, massive bilateral myoclonus, catamenial epilepsy, drop seizures, emotional seizures, focal seizures, gelastic seizures, Jacksonian March, Lafora Disease, motor seizures, multifocal seizures, nocturnal seizures, photosensitive seizure, pseudo seizures, sensory seizures, subtle seizures, sylvan seizures, withdrawal seizures, and visual reflex seizures) Behavioral disorders are disorders of the CNS characterized by aberrant behavior on the part of the afflicted subject and include, but are not limited to, sleep disorders (i.e., insomnia, parasomnias, night terrors, circadian rhythm sleep disorders, and narcolepsy), mood disorders (i.e., depression, suicidal depression, anxiety, chronic affective disorders, phobias, panic attacks, obsessive-compulsive disorder, attention deficit hyperactivity disorder (ADHD), attention deficit disorder (ADD), chronic fatigue syndrome, agoraphobia, post-traumatic stress disorder, bipolar disorder), eating disorders (i.e., anorexia or bulimia), psychoses, developmental behavioral disorders (i.e., autism, Rett's syndrome, Aspberger's syndrome), personality disorders and psychotic disorders (i.e., schizophrenia, delusional disorder, and the like). Lysosomal storage disorders are metabolic disorders which are in some cases associated with the CNS or have CNS-specific symptoms; such disorders include, but are not limited to Tay-Sachs disease, Gaucher's disease, Fabry disease, mucopolysaccharidosis (types I, II, III, IV, V, VI and VII), glycogen storage disease, GM1-gangliosidosis, metachromatic leukodystrophy, Farber's disease, Canavan's leukodystrophy, and neuronal ceroid lipofuscinoses types 1 and 2, Niemann-Pick disease, Pompe disease, and Krabbe's disease.

II. Compositions and Methods

In one aspect, the invention is based, in part, on antibodies which bind BACE1 and reduce and/or inhibit BACE1 activity. In certain embodiments, antibodies that bind to the active site or an exosite of BACE1 are provided.

A. Exemplary Anti-BACE1 Antibodies

In one aspect, the invention provides an anti-BACE1 antibody comprising at least one, two, three, four, five, or six HVRs selected from (a) HVR-H1 comprising the amino acid sequence of SEQ ID NO:22, 23, 26, 28, 45, 68, 71, 72, 73 or 120; (b) HVR-H2 comprising the amino acid sequence of SEQ ID NO:24, 29, 46, 69, 74, 75, 76, 77, 78 or 121; (c) HVR-H3 comprising the amino acid sequence of SEQ ID NO:25, 30, 47, 70, 79 or 122; (d) HVR-L1 comprising the amino acid sequence of SEQ ID NO:7, 8, 17, 35 or 42; (e) HVR-L2 comprising the amino acid sequence of SEQ ID NO:9, 10, 18, 36-39, 41, 43, 56, 58, 59, 60, 61, 62, 63, 64 or 118; and (f) HVR-L3 comprising the amino acid sequence of SEQ ID NO:11-16, 19, 40, 44, 57, 65, 66, 67 or 119.

In one aspect, the invention provides an antibody comprising at least one, at least two, or all three VH HVR sequences selected from (a) HVR-H1 comprising the amino acid sequence of SEQ ID NO: 22, 23, 26, 28, 45, 68, 71-73 or 120; (b) HVR-H2 comprising the amino acid sequence of SEQ ID NO: 24, 29, 46, 69, 74-78 or 121; and (c) HVR-H3 comprising the amino acid sequence of SEQ ID NO: 25, 30, 47, 70, 79 or 122.

In one embodiment, the antibody comprises HVR-H1 comprising the amino acid sequence SEQ ID NO:22 or SEQ ID NO:23 or SEQ ID NO:28 or SEQ ID NO:71 or SEQ ID NO:72 or SEQ ID NO:73. In another embodiment, the antibody comprises HVR-H2 comprising the amino acid sequence SEQ ID NO:24 or SEQ ID NO:29 or SEQ ID NO:74 or SEQ ID NO:75 or SEQ ID NO:76 or SEQ ID NO:77 or SEQ ID NO:78. In an additional embodiment, the antibody comprises HVR-H3 comprising the amino acid sequence SEQ ID NO:25 or SEQ ID NO:30 or SEQ ID NO:79. In one embodiment, the antibody comprises HVR-H1 comprising the amino acid sequence SEQ ID NO:28. In another embodiment, the antibody comprises HVR-H2 comprising the amino acid sequence SEQ ID NO:29. In an additional embodiment, the antibody comprises HVR-H3 comprising the amino acid sequence SEQ ID NO:30.

In another embodiment, the antibody comprises (a) HVR-H1 comprising the amino acid sequence of SEQ ID NO:22; (b) HVR-H2 comprising the amino acid sequence of SEQ ID NO:24; and (c) HVR-H3 comprising the amino acid sequence of SEQ ID NO:25 or the antibody comprises (a) HVR-H1 comprising the amino acid sequence of SEQ ID NO:23; (b) HVR-H2 comprising the amino acid sequence of SEQ ID NO:24; and (c) HVR-H3 comprising the amino acid sequence of SEQ ID NO:25. In an additional embodiment, the antibody comprises (a) HVR-H1 comprising the amino acid sequence of SEQ ID NO:28; (b) HVR-H2 comprising the amino acid sequence of SEQ ID NO:29; and (c) HVR-H3 comprising the amino acid sequence of SEQ ID NO:30. In an additional embodiment, the antibody comprises (a) HVR-H1 comprising the amino acid sequence of SEQ ID NO:23; (b) HVR-H2 comprising the amino acid sequence of SEQ ID NO:74; and (c) HVR-H3 comprising the amino acid sequence of SEQ ID NO:25 or the antibody comprises (a) HVR-H1 comprising the amino acid sequence of SEQ ID NO:23; (b) HVR-H2 comprising the amino acid sequence of SEQ ID NO:75; and (c) HVR-H3 comprising the amino acid sequence of SEQ ID NO:25 or the antibody comprises (a) HVR-H1 comprising the amino acid sequence of SEQ ID NO:71; (b) HVR-H2 comprising the amino acid sequence of SEQ ID NO:24; and (c) HVR-H3 comprising the amino acid sequence of SEQ ID NO:25 or the antibody comprises (a) HVR-H1 comprising the amino acid sequence of SEQ ID NO:72; (b) HVR-H2 comprising the amino acid sequence of SEQ ID NO:24; and (c) HVR-H3 comprising the amino acid sequence of SEQ ID NO:25 or the antibody comprises (a) HVR-H1 comprising the amino acid sequence of SEQ ID NO:23; (b) HVR-H2 comprising the amino acid sequence of SEQ ID NO:76; and (c) HVR-H3 comprising the amino acid sequence of SEQ ID NO:25 or the antibody comprises (a) HVR-H1 comprising the amino acid sequence of SEQ ID NO:23; (b) HVR-H2 comprising the amino acid sequence of SEQ ID NO:77; and (c) HVR-H3 comprising the amino acid sequence of SEQ ID NO:79 or the antibody comprises (a) HVR-H1 comprising the amino acid sequence of SEQ ID NO:73; (b) HVR-H2 comprising the amino acid sequence of SEQ ID NO:78; and (c) HVR-H3 comprising the amino acid sequence of SEQ ID NO:25.

In another aspect, the invention provides an antibody comprising at least one, at least two, or all three VL HVR sequences selected from (a) HVR-L1 comprising the amino acid sequence of SEQ ID NO: 7, 8, 17, 35 and 42; (b) HVR-L2 comprising the amino acid sequence of SEQ ID NO: 9, 10, 18, 36-39, 41, 43, 56, 58-64 or 118; and (c) HVR-L3 comprising the amino acid sequence of SEQ ID NO: 11-16, 19, 40, 44, 57, 65-67 or 119.

In one embodiment, the antibody comprises HVR-L1 comprising the amino acid sequence SEQ ID NO:7 or SEQ ID NO:8. In another embodiment, the antibody comprises HVR-L2 comprising the amino acid sequence SEQ ID NO:9 or SEQ ID NO:10 or SEQ ID NO:58 or SEQ ID NO:59 or SEQ ID NO:60 or SEQ ID NO:61 or SEQ ID NO:62 or SEQ ID NO:63 or SEQ ID NO:64. In an additional embodiment, the antibody comprises HVR-L3 comprising the amino acid sequence of SEQ ID NO:11 or SEQ ID NO:12 or SEQ ID NO:13 or SEQ ID NO:14 or SEQ ID NO:15 or SEQ ID NO:16 or SEQ ID NO:65 or SEQ ID NO:66 or SEQ ID NO:67. In another embodiment, the antibody comprises HVR-L1 comprising the amino acid sequence SEQ ID NO:35. In another embodiment, the antibody comprises HVR-L2 comprising the amino acid sequence selected from the group consisting of SEQ ID NO:36-39. In an additional embodiment, the antibody comprises HVR-L3 comprising the amino acid sequence SEQ ID NO:40.

In another embodiment, the antibody comprises (a) HVR-L1 comprising the amino acid sequence of SEQ ID NO:7; (b) HVR-L2 comprising the amino acid sequence of SEQ ID NO:9; and (c) HVR-L3 comprising the amino acid sequence of SEQ ID NO:11 or the antibody comprises (a) HVR-L1 comprising the amino acid sequence of SEQ ID NO:7; (b) HVR-L2 comprising the amino acid sequence of SEQ ID NO:9; and (c) HVR-L3 comprising the amino acid sequence of SEQ ID NO:12 or the antibody comprises (a) HVR-L1 comprising the amino acid sequence of SEQ ID NO:7; (b) HVR-L2 comprising the amino acid sequence of SEQ ID NO:9; and (c) HVR-L3 comprising the amino acid sequence of SEQ ID NO:13 or the antibody comprises (a) HVR-L1 comprising the amino acid sequence of SEQ ID NO:7; (b) HVR-L2 comprising the amino acid sequence of SEQ ID NO:9; and (c) HVR-L3 comprising the amino acid sequence of SEQ ID NO:14 or the antibody comprises (a) HVR-L1 comprising the amino acid sequence of SEQ ID NO:7; (b) HVR-L2 comprising the amino acid sequence of SEQ ID NO:9; and (c) HVR-L3 comprising the amino acid sequence of SEQ ID NO:16 or the antibody comprises (a) HVR-L1 comprising the amino acid sequence of SEQ ID NO:8; (b) HVR-L2 comprising the amino acid sequence of SEQ ID NO:10; and (c) HVR-L3 comprising the amino acid sequence of SEQ ID NO:15. In an additional embodiment, the antibody comprises (a) HVR-L1 comprising the amino acid sequence of SEQ ID NO:35; (b) HVR-L2 comprising the amino acid sequence of SEQ ID NO:36; and (c) HVR-L3 comprising the amino acid sequence of SEQ ID NO:40 or the antibody comprises (a) HVR-L1 comprising the amino acid sequence of SEQ ID NO:35; (b) HVR-L2 comprising the amino acid sequence of SEQ ID NO:37; and (c) HVR-L3 comprising the amino acid sequence of SEQ ID NO:40 or the antibody comprises (a) HVR-L1 comprising the amino acid sequence of SEQ ID NO:35; (b) HVR-L2 comprising the amino acid sequence of SEQ ID NO:38; and (c) HVR-L3 comprising the amino acid sequence of SEQ ID NO:40 or the antibody comprises (a) HVR-L1 comprising the amino acid sequence of SEQ ID NO:35; (b) HVR-L2 comprising the amino acid sequence of SEQ ID NO:39; and (c) HVR-L3 comprising the amino acid sequence of SEQ ID NO:40.

In another embodiment, the antibody comprises (a) HVR-L1 comprising the amino acid sequence of SEQ ID NO:7; (b) HVR-L2 comprising the amino acid sequence of SEQ ID NO:58; and (c) HVR-L3 comprising the amino acid sequence of SEQ ID NO:12 or the antibody comprises (a) HVR-L1 comprising the amino acid sequence of SEQ ID NO:7; (b) HVR-L2 comprising the amino acid sequence of SEQ ID NO:9; and (c) HVR-L3 comprising the amino acid sequence of SEQ ID NO:65 or the antibody comprises (a) HVR-L1 comprising the amino acid sequence of SEQ ID NO:7; (b) HVR-L2 comprising the amino acid sequence of SEQ ID NO:59; and (c) HVR-L3 comprising the amino acid sequence of SEQ ID NO:12 or the antibody comprises (a) HVR-L1 comprising the amino acid sequence of SEQ ID NO:7; (b) HVR-L2 comprising the amino acid sequence of SEQ ID NO:9; and (c) HVR-L3 comprising the amino acid sequence of SEQ ID NO:66 or the antibody comprises (a) HVR-L1 comprising the amino acid sequence of SEQ ID NO:7; (b) HVR-L2 comprising the amino acid sequence of SEQ ID NO:9; and (c) HVR-L3 comprising the amino acid sequence of SEQ ID NO:67 or the antibody comprises (a) HVR-L1 comprising the amino acid sequence of SEQ ID NO:7; (b) HVR-L2 comprising the amino acid sequence of SEQ ID NO:60; and (c) HVR-L3 comprising the amino acid sequence of SEQ ID NO:67 or the antibody comprises (a) HVR-L1 comprising the amino acid sequence of SEQ ID NO:7; (b) HVR-L2 comprising the amino acid sequence of SEQ ID NO:61; and (c) HVR-L3 comprising the amino acid sequence of SEQ ID NO:65 or the antibody comprises (a) HVR-L1 comprising the amino acid sequence of SEQ ID NO:7; (b) HVR-L2 comprising the amino acid sequence of SEQ ID NO:59; and (c) HVR-L3 comprising the amino acid sequence of SEQ ID NO:66 or the antibody comprises (a) HVR-L1 comprising the amino acid sequence of SEQ ID NO:7; (b) HVR-L2 comprising the amino acid sequence of SEQ ID NO:62; and (c) HVR-L3 comprising the amino acid sequence of SEQ ID NO:67 or the antibody comprises (a) HVR-L1 comprising the amino acid sequence of SEQ ID NO:7; (b) HVR-L2 comprising the amino acid sequence of SEQ ID NO:63; and (c) HVR-L3 comprising the amino acid sequence of SEQ ID NO:12 or the antibody comprises (a) HVR-L1 comprising the amino acid sequence of SEQ ID NO:7; (b) HVR-L2 comprising the amino acid sequence of SEQ ID NO:64; and (c) HVR-L3 comprising the amino acid sequence of SEQ ID NO:12.

In another aspect, an antibody of the invention comprises (a) a VH domain comprising at least one, at least two, or all three VH HVR sequences selected from (i) HVR-H1 comprising the amino acid sequence selected from SEQ ID NO:22, 23, 26, 28, 45, 68, 71-73 or 120 (ii) HVR-H2 comprising the amino acid sequence selected from SEQ ID NO: 24, 29, 46, 69, 74-78 or 121 and (iii) HVR-H3 comprising an amino acid sequence selected from SEQ ID NO: 25, 30, 47, 70, 79 or 122; and (b) a VL domain comprising at least one, at least two, or all three VL HVR sequences selected from (i) HVR-L1 comprising the amino acid sequence selected from SEQ ID NO: 7, 8, 17, 35 or 42, (ii) HVR-L2 comprising the amino acid sequence selected from SEQ ID NO: 9, 10, 18, 36-39, 41, 43, 56, 58-64 or 118, and (c) HVR-L3 comprising the amino acid sequence selected from SEQ ID NO: 11-16, 19, 40, 44, 57, 65-67 or 119.

In another aspect, the invention provides an antibody comprising (a) HVR-H1 comprising the amino acid sequence of SEQ ID NO:23; (b) HVR-H2 comprising the amino acid sequence of SEQ ID NO:24; (c) HVR-H3 comprising the amino acid sequence of SEQ ID NO:25; (d) HVR-L1 comprising the amino acid sequence of SEQ ID NO:7; (e) HVR-L2 comprising the amino acid sequence of SEQ ID NO:9; and (f) HVR-L3 comprising an amino acid sequence selected from SEQ ID NO:12.

In certain embodiments, the antibody comprises at least one sequence selected from HVR-H1, HVR-H2, HVR-H3, wherein HVR-H1 comprises the amino acid sequence GFX$_{30}$FX$_{31}$X$_{32}$X$_{33}$X$_{34}$IH (SEQ ID NO:45), wherein X$_{30}$=N or T; X$_{31}$=S, L or Y; X$_{32}$=G or Y; X$_{33}$=Y or S; and X$_{34}$=A, G or S; wherein HVR-H2 comprises the amino acid sequence X$_{35}$X$_{36}$ISPX$_{37}$X$_{38}$GX$_{39}$TX$_{40}$YADSVKG (SEQ ID NO:46), wherein X$_{35}$=A or G; X$_{36}$=W or S; X$_{37}$=A or Y; X$_{38}$=G or S; X$_{39}$=S or Y; and X$_{40}$=D or S; and wherein HVR-H3 comprises the sequence X$_{41}$PX$_{42}$X$_{43}$X$_{44}$X$_{45}$X$_{46}$X$_{47}$MDY (SEQ ID NO:47), wherein X$_{41}$=Q or G; X$_{42}$=T or F; X$_{43}$=H or S; X$_{44}$=Y or P; X$_{45}$=Y or W; X$_{46}$=Y or V and wherein X$_{47}$ optionally includes the sequence YAKGYKA (SEQ ID NO:48).

In certain embodiments, the antibody comprises at least one sequence selected from HVR-H1, HVR-H2 and HVR-H3, wherein HVR-H1 comprises the amino acid sequence GX$_{71}$X$_{72}$X$_{73}$X$_{74}$X$_{75}$X$_{76}$X$_{77}$IH (SEQ ID NO:120), wherein X$_{71}$=F or Y; X$_{72}$=F, N or T; X$_{73}$=F or Y; X$_{74}$=L, Q, I, S or Y; X$_{75}$=G or Y; X$_{76}$=Y or S; and X$_{77}$=A, G or S; HVR-H2 comprises the amino acid sequence X$_{78}$X$_{79}$ISPX$_{80}$X$_{81}$GX$_{82}$X$_{83}$X$_{84}$YADSVKG (SEQ ID NO:121), wherein X$_{78}$=A or G; X$_{79}$=W or S; X$_{80}$=A, S, Q or Y; X$_{81}$=G or S; X$_{82}$=S, K, L or Y; X$_{83}$=T or Y; and X$_{84}$=D or S; and HVR-H3 comprises the amino acid sequence X$_{85}$PX$_{86}$X$_{87}$X$_{88}$X$_{89}$X$_{90}$X$_{91}$MDY (SEQ ID NO:122), wherein X$_{85}$=Q or G; X$_{86}$=T or F; X$_{87}$=H, Y or S; X$_{88}$=Y or P; X$_{89}$=Y or W; X$_{90}$=Y or V and wherein X$_{91}$ optionally includes the sequence YAKGYKA (SEQ ID NO:48).

In certain embodiments, the antibody comprises at least one sequence selected from HVR-L1, HVR-L2, HVR-L3, wherein HVR-L1 comprises the amino acid sequence RASQX$_{17}$VX$_{18}$X$_{19}$X$_{20}$X$_{21}$A, (SEQ ID NO:42) wherein X$_{17}$=S, D or V; X$_{18}$=S or A; X$_{19}$=S, T or N; X$_{20}$=A or S; X$_{21}$=V or L, wherein HVR-L2 comprises the amino acid sequence X$_{22}$ASX$_{23}$LYS (SEQ ID NO:43), wherein X$_{22}$=S, W, Y or L; X$_{23}$=F, S or W, and wherein HVR-L3 comprises the amino acid sequence QQX$_{24}$X$_{25}$X$_{26}$X$_{27}$X$_{28}$X$_{29}$T (SEQ ID NO:44), wherein X$_{24}$=S, F, G, D or Y; X$_{25}$=Y, P, S or A; X$_{26}$=Y, T or N; X$_{27}$=T, Y, D or S; X$_{28}$=P or L; and X$_{29}$=F, P or T.

In certain embodiments, the antibody comprises at least one sequence selected from the group of HVR-L1, HVR-L2 and HVR-L3, wherein HVR-L1 comprises the amino acid sequence RASQX$_{17}$VX$_{18}$X$_{19}$X$_{20}$X$_{21}$A (SEQ ID NO:42), wherein X$_{17}$=S, D or V; X$_{18}$=S or A; X$_{19}$=S, T or N; X$_{20}$=A or S; X$_{21}$=V or L, wherein HVR-L2 comprises the amino acid sequence X$_{62}$ASX$_{63}$X$_{64}$YX$_{65}$ (SEQ ID NO:118), wherein X$_{62}$=S, W, Y, F or L; X$_{63}$=F, S, Y or W; X$_{64}$=L or R; X$_{65}$=S, P, R, K or W, and HVR-L3 comprises the amino acid sequence QQX$_{66}$X$_{67}$X$_{68}$X$_{69}$X$_{70}$X$_{71}$T (SEQ ID NO:119), wherein X$_{66}$=S, F, G, D or Y; X$_{67}$=Y, P, S or A; X$_{68}$=Y, T or N; X$_{69}$=T, Y, D or S; X$_{70}$=P, Q, S, K or L; and X$_{71}$=F, P or T.

In certain embodiments, the antibody comprises at least one sequence selected from HVR-L1, HVR-L2, HVR-L3, wherein HVR-L1 comprises the amino acid sequence RASQX$_1$VX$_2$X$_3$X$_4$X$_5$A (SEQ ID NO:17), wherein X$_1$=D or V; X$_2$=S or A; X$_3$=T or N; X$_4$=S or A; X$_5$=V or L, wherein HVR-L2 comprises the amino acid sequence X$_6$ASFLYS (SEQ ID NO:18), wherein X$_6$=S or L, and wherein the HVR-L3 comprises the amino acid sequence QQX$_7$X$_8$X$_9$X$_{10}$X$_{11}$X$_{12}$T (SEQ ID NO:19), wherein X$_7$=S, F, G, D or Y; X$_8$=Y, P, S, or A; X$_9$=T or N; X$_{10}$=T, Y, D or S; X$_{11}$=P or L; X$_{12}$=P or T.

In certain embodiments, the antibody comprises at least one sequence selected from HVR-L1, HVR-L2, HVR-L3, wherein HVR-L1 comprises the amino acid sequence RASQX$_1$VX$_2$X$_3$X$_4$X$_5$A (SEQ ID NO:17), wherein X$_1$=D or V; X$_2$=S or A; X$_3$=T or N; X$_4$=S or A; X$_5$=V or L, wherein HVR-L2 comprises the amino acid sequence X$_{48}$ASX$_{49}$X$_{50}$YX$_{51}$ (SEQ ID NO:56), wherein X$_{48}$=S or F; X$_{49}$=F or Y; X$_{50}$=L or R; X$_{51}$=S, P, R, K or W, wherein HVR-L3 comprises the amino acid sequence QQFPTYX$_{52}$PT (SEQ ID NO:57), wherein X$_{52}$=L, Q, S or K.

In certain embodiments, the antibody comprises at least one sequence selected from HVR-H1, HVR-H2, HVR-H3, wherein HVR-H1 comprises the amino acid sequence GFTFX$_{13}$GYX$_{14}$IH (SEQ ID NO:26), wherein X$_{13}$=S or L and X$_{14}$=A or G, wherein the HVR-H2 comprises the amino acid sequence GWISPAGGSTDYADSVKG (SEQ ID NO:24), and wherein the HVR-H3 comprises the amino acid sequence GPFSPWVMDY (SEQ ID NO:25).

In certain embodiments, the antibody comprises at least one sequence selected from HVR-H1, HVR-H2, HVR-H3, wherein HVR-H1 comprises the amino acid sequence GX$_{53}$X$_{54}$X$_{55}$X$_{56}$GYGIH (SEQ ID NO:68), wherein X$_{53}$=F or Y; X$_{54}$=T or F; X$_{55}$=F or Y; X$_{56}$=L, Q or I, wherein HVR-H2 comprises the amino acid sequence GWISPX$_{57}$X$_{58}$GX$_{59}$X$_{60}$DYADSVKG (SEQ ID NO:69), wherein X$_{57}$=A, S or Q; X$_{58}$=G or S; X$_{59}$=S, K or L; X$_{60}$=T or Y, and wherein the HVR-H3 sequence comprises the amino acid sequence GPFX$_{61}$PWVMDY (SEQ ID NO:70), wherein X$_{61}$=S or Y.

In certain embodiments, the antibody comprises at least one sequence selected from HVR-L1, HVR-L2, HVR-L3, wherein HVR-L1 comprises the amino acid sequence RASQSVSSAVA (SEQ ID NO:35), wherein HVR-L2 comprises the amino acid sequence X$_{15}$ASX$_{16}$LYS (SEQ ID NO:41), wherein X$_{15}$=S, W or Y and X$_{16}$=S or W, and wherein HVR-L3 comprises the amino acid sequence QQYSYSPFT (SEQ ID NO:40).

In certain embodiments, any one or more amino acids of an anti-BACE1 antibody, as provided, above are substituted at the following HVR positions:
  in HVR-H1 (SEQ ID NO:26): positions 5 and 8;
  in HVR-L1 (SEQ ID NO:17): positions 5, 7, 8, 9 and 10;
  in HVR-L2 (SEQ ID NO:18): position 1 or HVR-L2 (SEQ ID NO:41) positions 1 and 4; and
  in HVR-L3 (SEQ ID NO:19): positions 3, 4, 5, 6, 7 and 8.

In certain embodiments, the substitutions are conservative substitutions, as provided herein. In certain embodiments, any one or more of the following substitutions may be made in any combination:
  in HVR-H1 (SEQ ID NO:26): serine or leucine at position 5 and alanine or glycine at position 8;
  in HVR-L1 (SEQ ID NO:17): aspartic acid or valine at position 5; serine or alanine at position 7; threonine or asparagine at position 8; serine or alanine at position 9 and valine or leucine at position 10;

in HVR-L2 (SEQ ID NO:18): serine or leucine at position 1 or HVR-L2 (SEQ ID NO:41) serine, tyrosine or tryptophan at position 1 or tyrosine, serine or tryptophan at position 4; and in HVR-L3 (SEQ ID NO:19): serine, phenylalanine, glycine, aspartic acid or tyrosine at position 3; tyrosine or proline at position 4, serine, alanine, threonine or asparagine at position 5; tyrosine, threonine, aspartic acid or serine at position 6, aspartic acid, serine, proline or leucine at position 7 and proline or threonine at position 8.

In certain embodiments, the substitutions are conservative substitutions, as provided herein. In certain embodiments, any one or more of the following substitutions may be made in any combination:

in HVR-H1 (SEQ ID NO:26): S5L and A8G;
in HVR-L1 (SEQ ID NO:17): D5V; S7A; T8N; S9A and V10L;
in HVR-L2 (SEQ ID NO:18): S1L or HVR-L2 (SEQ ID NO:41) positions S1W or Y and S4W; and
in HVR-L3 (SEQ ID NO:19): positions S3F, G, D or Y1; Y4P, S or A; T5N; T6Y, D or S; P7L and P8T.

In certain embodiments, any one or more amino acids of an anti-BACE1 antibody, as provided, above are substituted at the following HVR positions:

in HVR-H1 (SEQ ID NO:120): positions 2, 3, 5, 6, 7 and 8;
in HVR-H2 (SEQ ID NO:121): positions 1, 2, 6, 7, 9, 10, and 11;
in HVR-H3 (SEQ ID NO:122) positions 1, 3, 4, 5, 6, 7, and 8 in HVR-L1 (SEQ ID NO:42): positions 5, 7, 8, 9 and 10;
in HVR-L2 (SEQ ID NO:118): position 1, 4, 5 and 7; and
in HVR-L3 (SEQ ID NO:119): positions 3, 4, 5, 6, 7 and 8.

In certain embodiments, the substitutions are conservative substitutions, as provided herein.

Possible combinations of the above substitutions are encompassed by the consensus sequences of SEQ ID NO:42-47 and 118-122 as described above.

In any of the above embodiments, an anti-BACE1 antibody is humanized. In one embodiment, an anti-BACE1 antibody comprises HVRs as in any of the above embodiments, and further comprises an acceptor human framework, e.g. a human immunoglobulin framework or a human consensus framework. In another embodiment, an anti-BACE1 antibody comprises HVRs as in any of the above embodiments, and further comprises a VH or VL comprising an FR1, FR2, FR3, or FR4 sequence of SEQ ID NO:1-6, 20, 21, 27, 31-34, 80-98 and 99-117.

In another aspect, an anti-BACE1 antibody comprises a heavy chain variable domain (VH) sequence having at least 90%, 91%, 92%, 93%, 94%, 95%, 96%, 97%, 98%, 99%, or 100% sequence identity to the amino acid sequence selected from SEQ ID NO:20, 21, 27 and 80-98. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-BACE1 antibody comprising that sequence retains the ability to bind to BACE1 and/or inhibit or reduce BACE1 activity. In certain embodiments, a total of 1 to 10 amino acids have been substituted, inserted and/or deleted in SEQ ID NO:20, 21, 27 and 80-98. In certain embodiments, substitutions, insertions, or deletions occur in regions outside the HVRs (i.e., in the FRs). Optionally, the anti-BACE1 antibody comprises the VH sequence in SEQ ID NO:20, 21, 27 or 80-98, including post-translational modifications of that sequence. In a particular embodiment, the VH comprises one, two or three HVRs selected from: (a) HVR-H1 comprising the amino acid sequence of SEQ ID NO:22, 23, 26, 28, 45, 68, 71, 72, 73 or 120, (b) HVR-H2 comprising the amino acid sequence of SEQ ID NO:24, 29, 46, 69, 74, 75, 76, 77, 78 or 121, and (c) HVR-H3 comprising the amino acid sequence of SEQ ID NO:25, 30, 47, 70, 79 or 122.

Figure 1A:
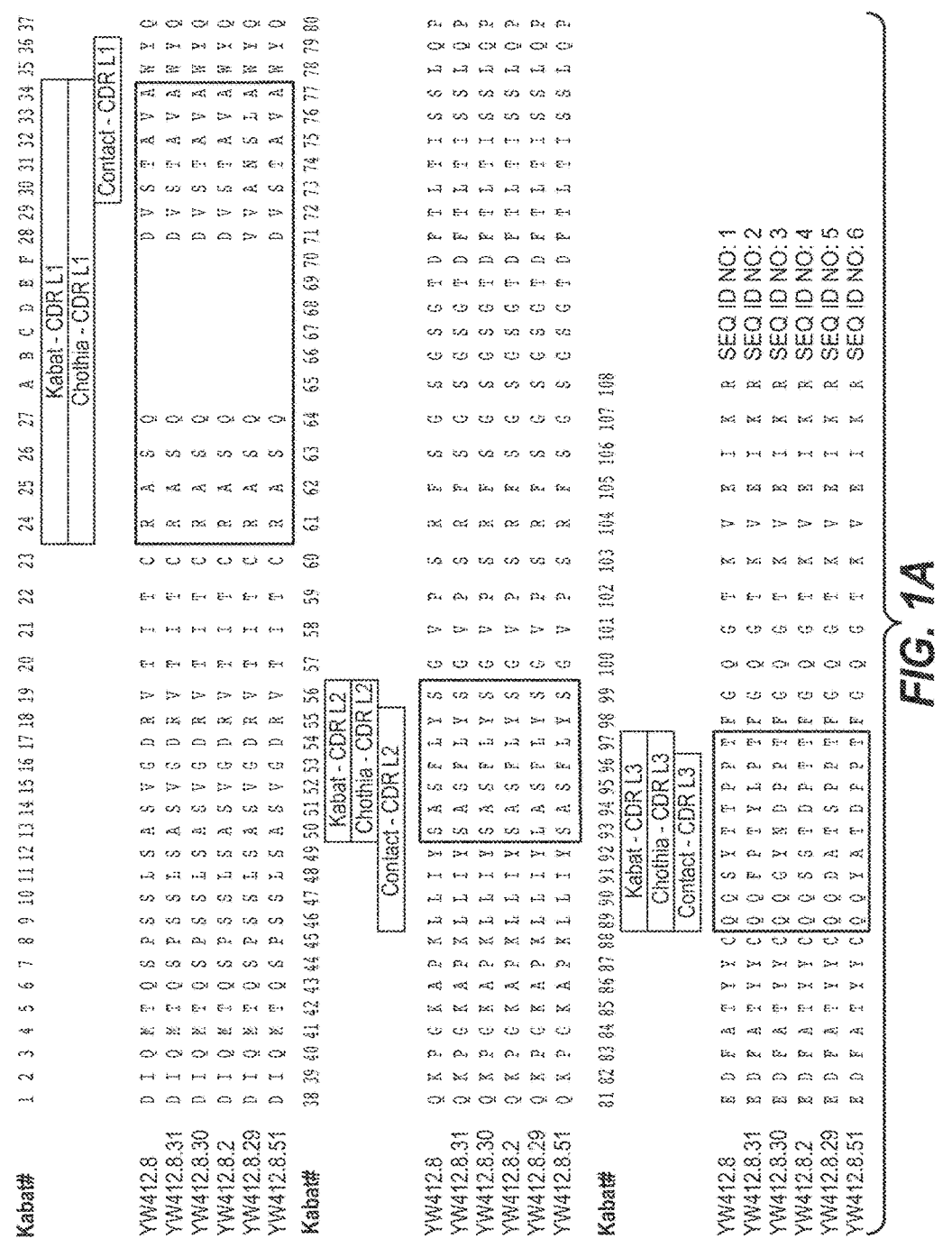
Figure 1B:
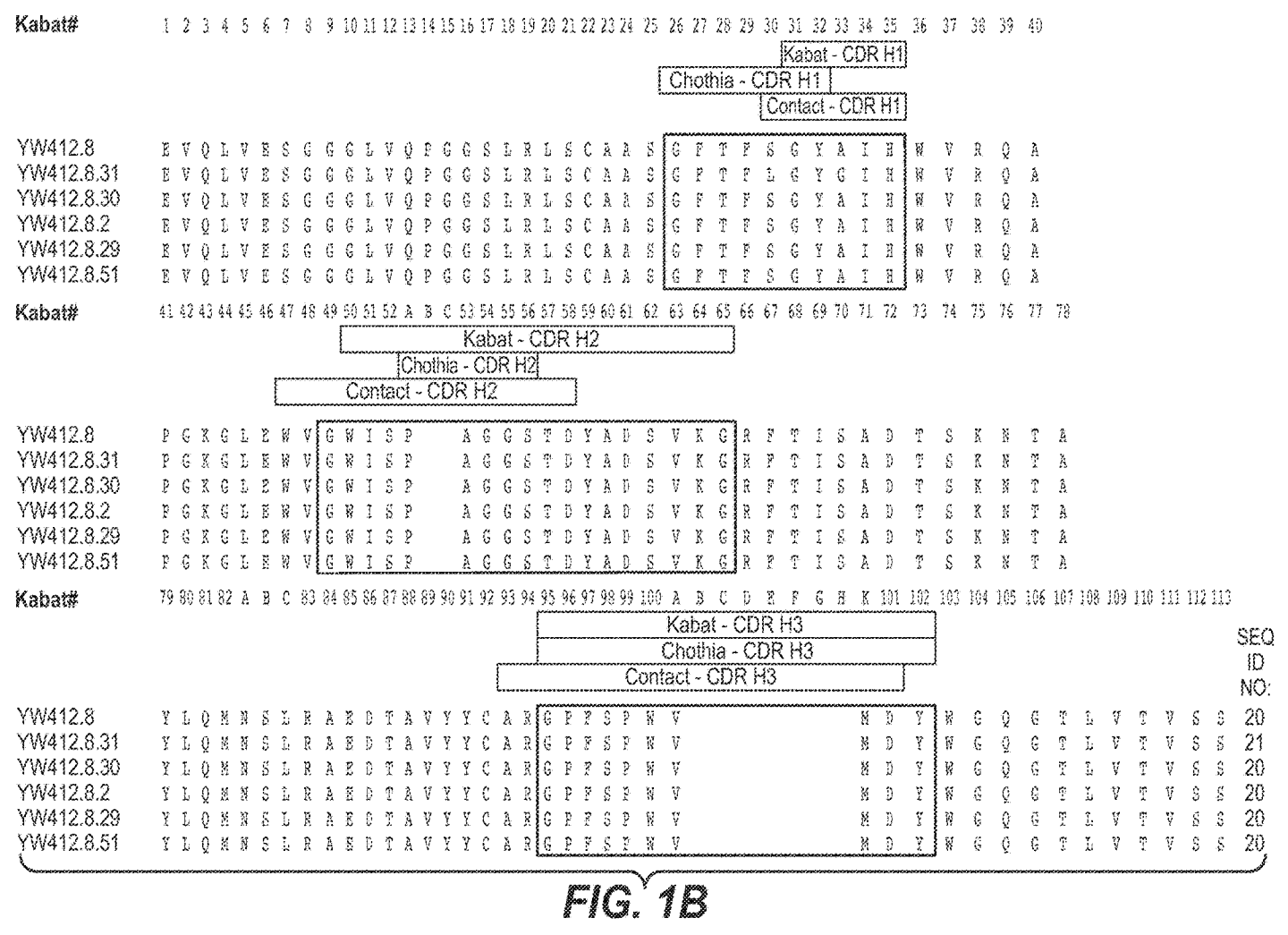
Figure 2B:
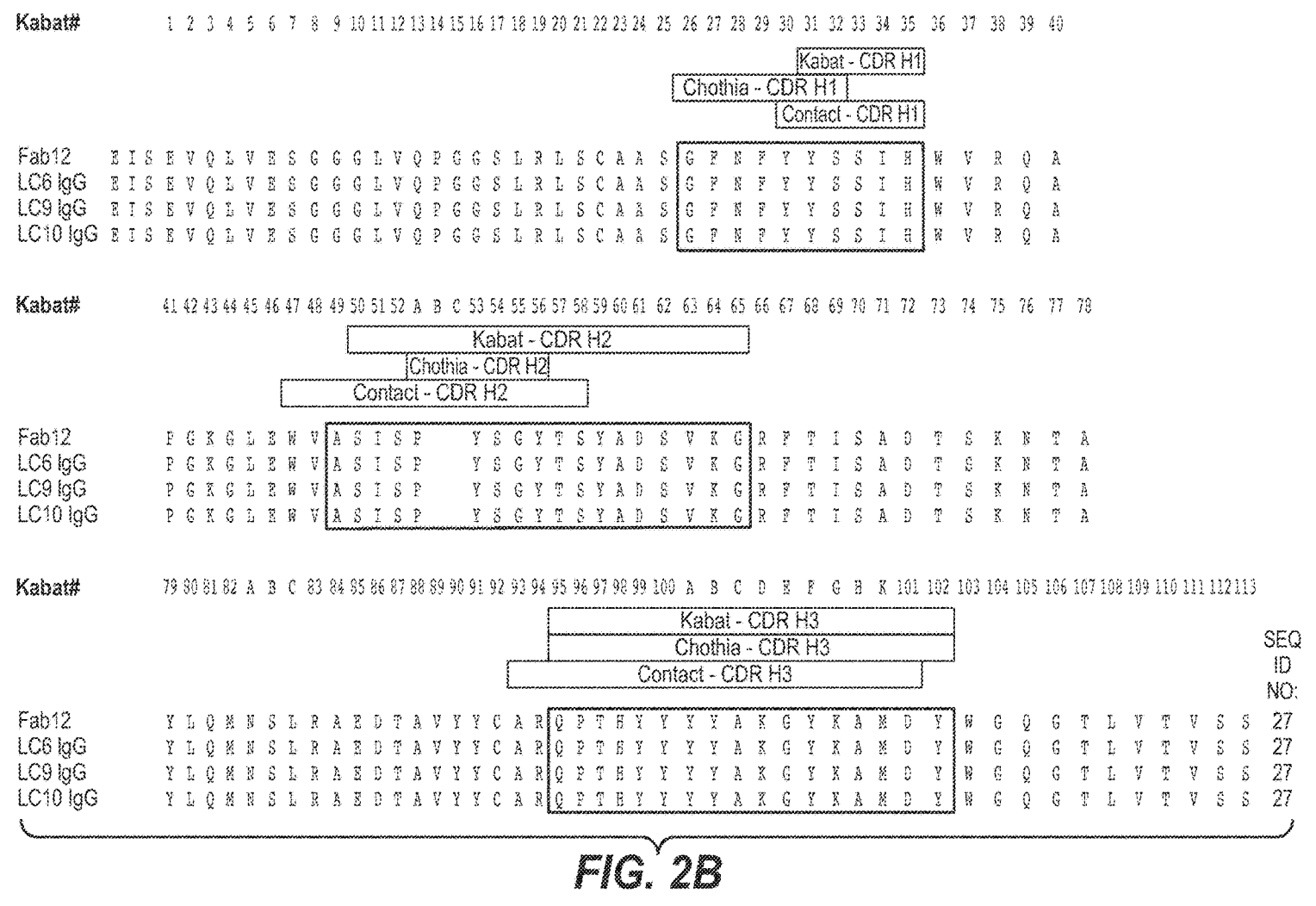
Figure 23B:
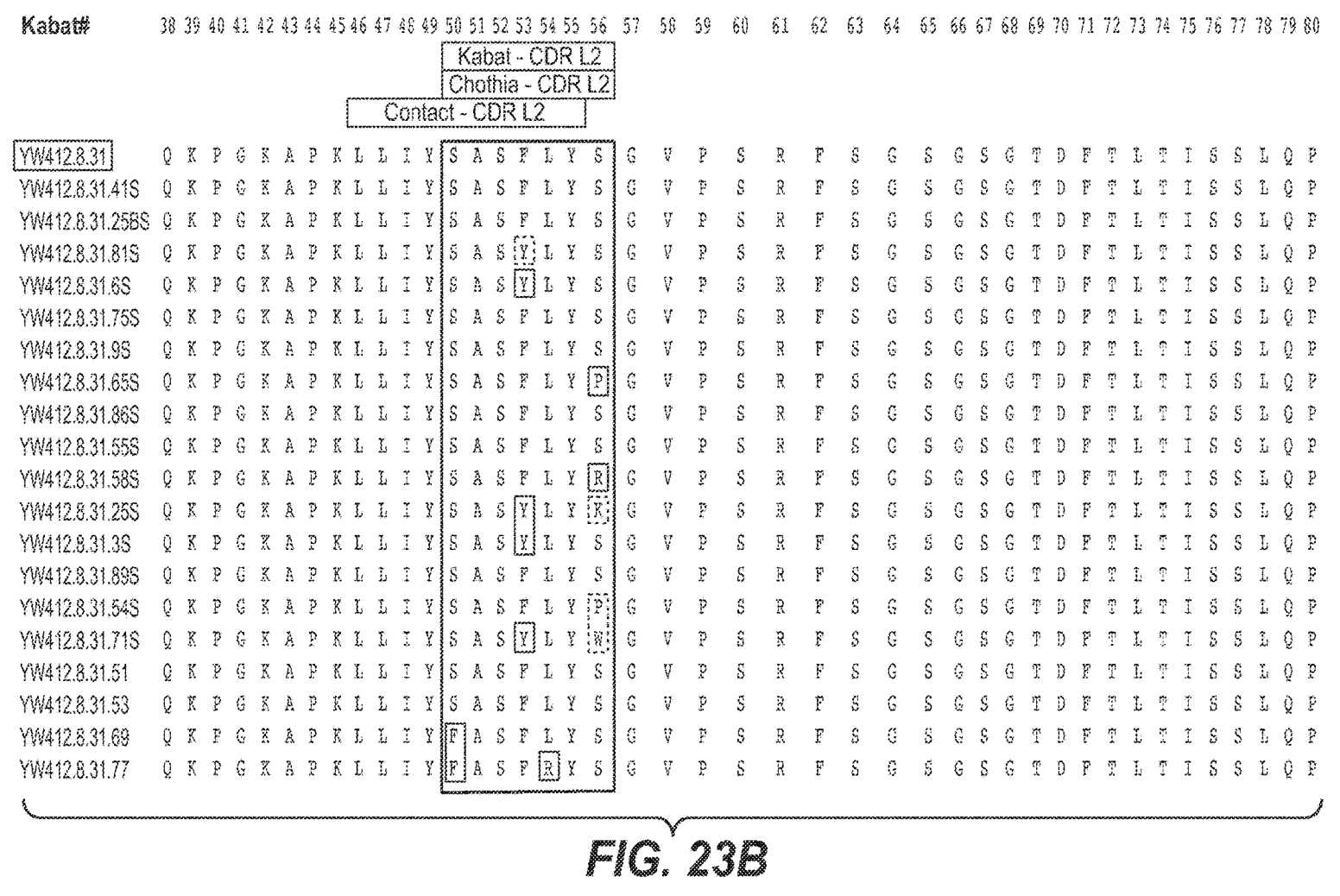
Figure 23C:
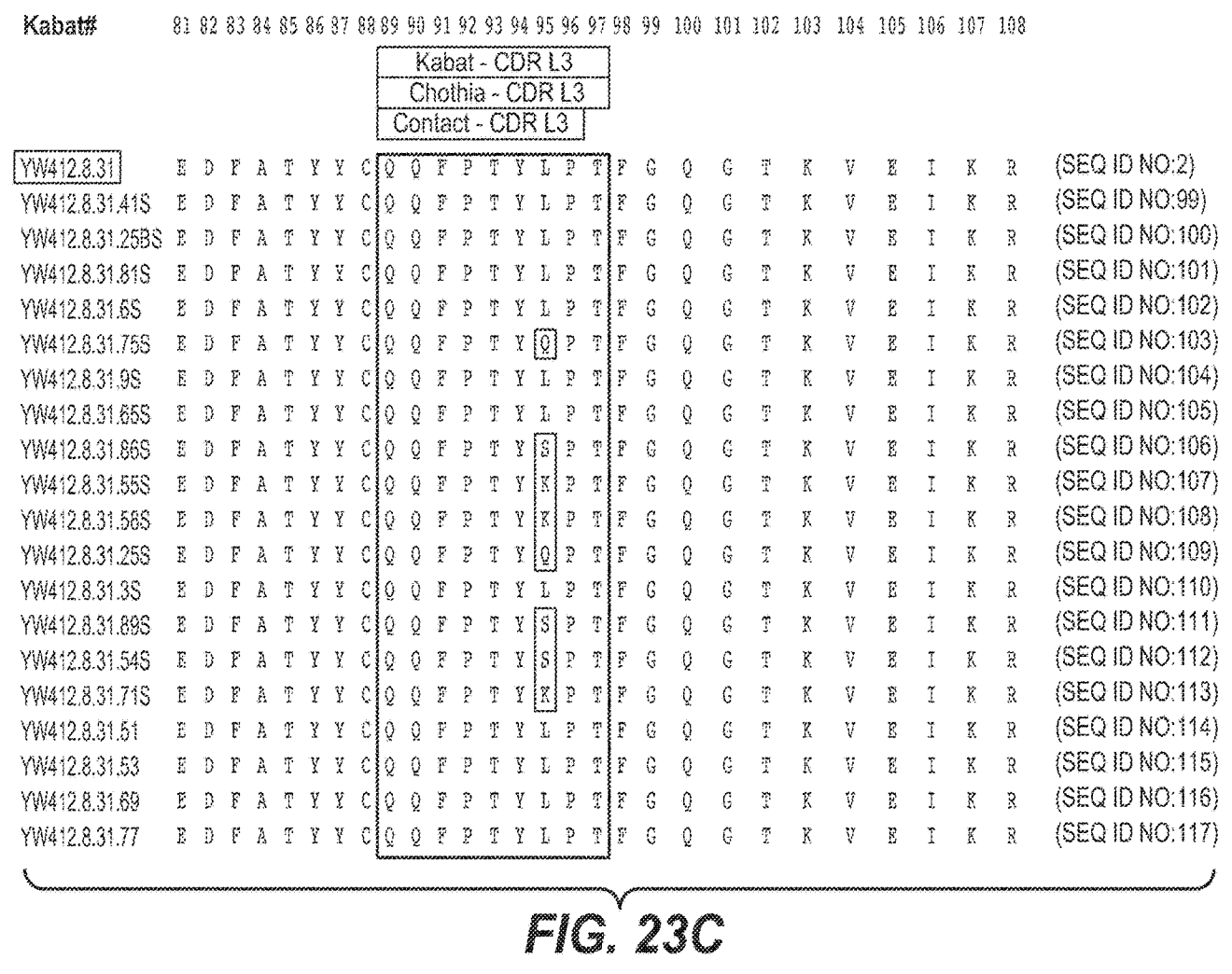
Figure 24A:
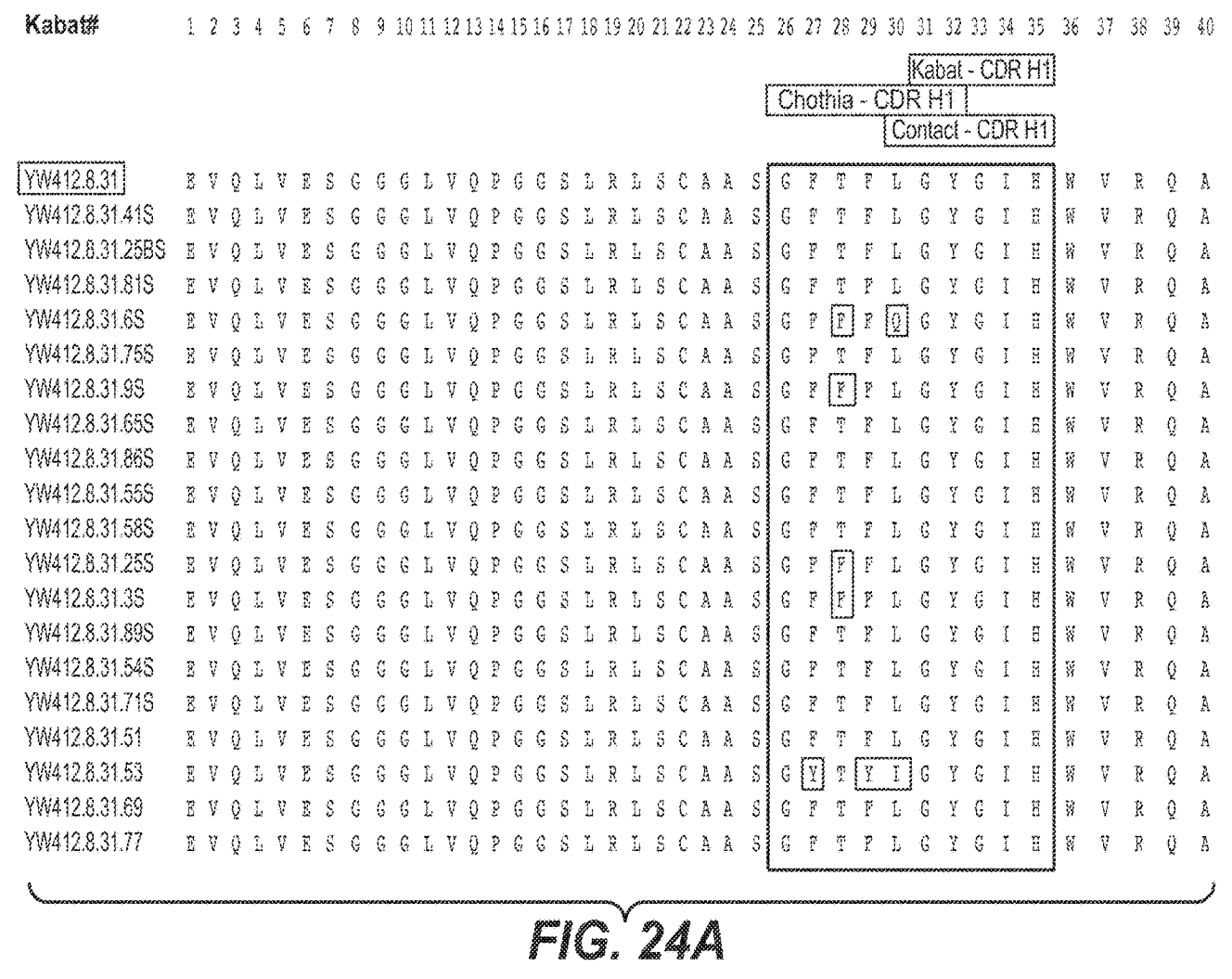
Figure 24B:
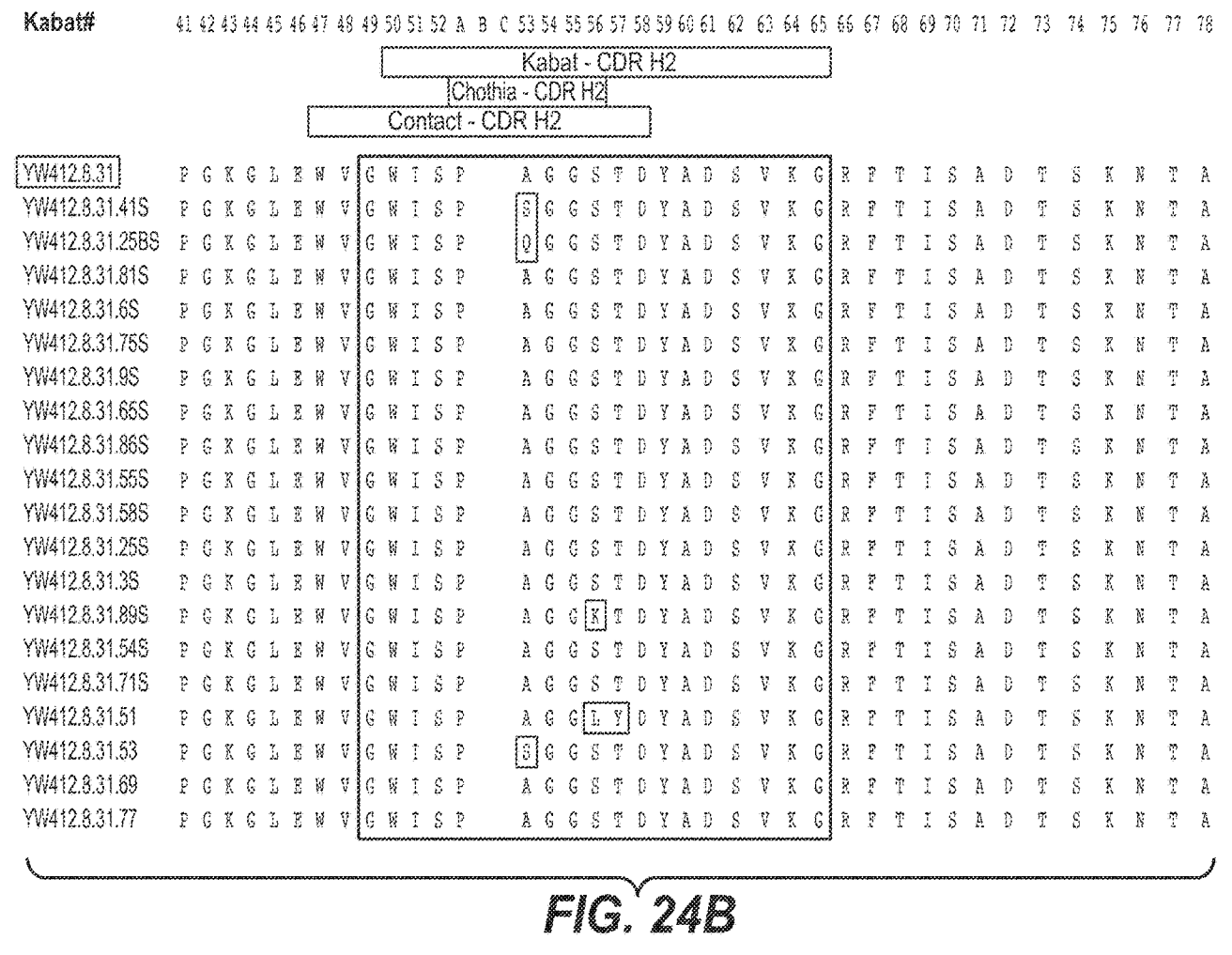
Figure 9A:
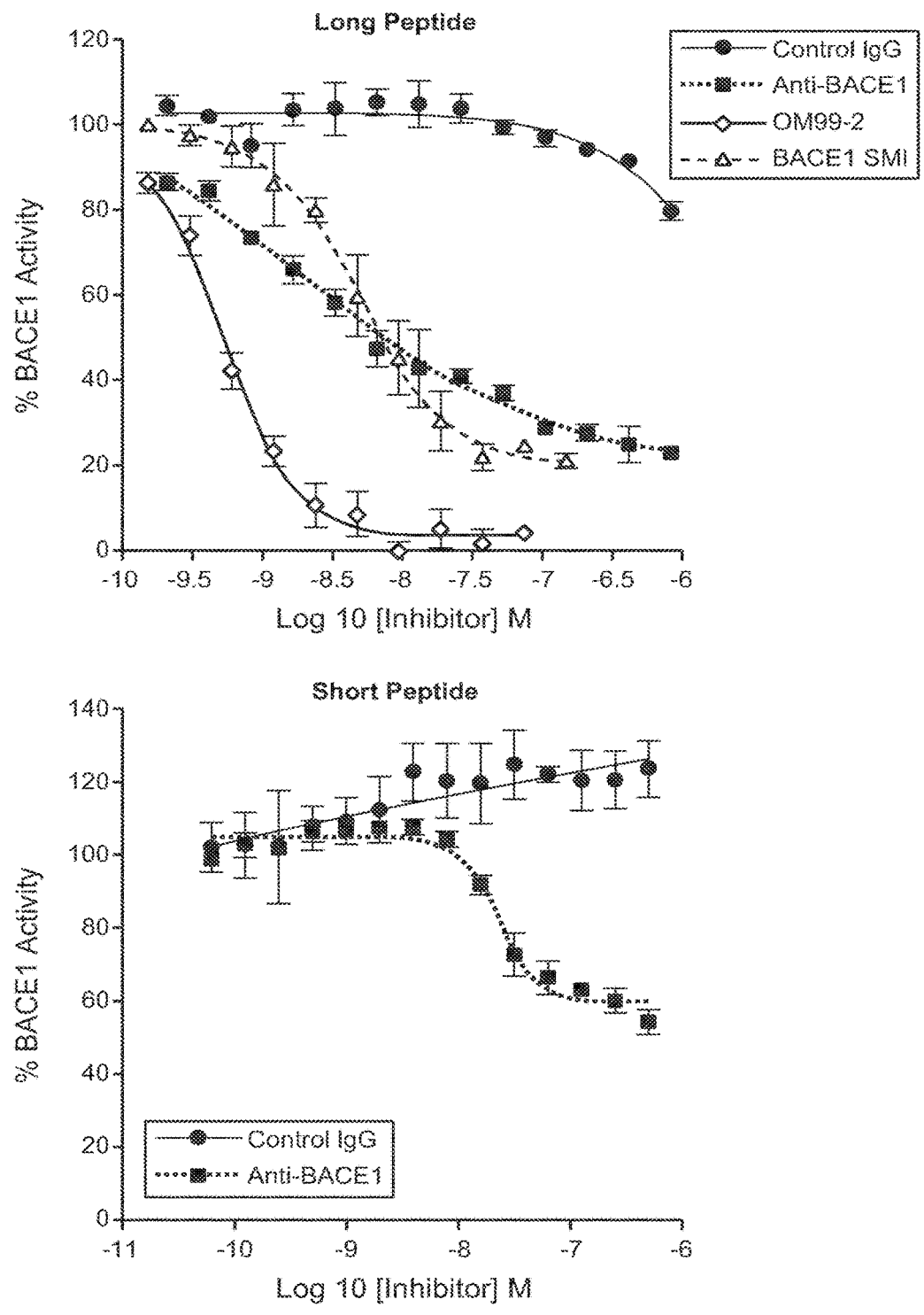
FIG. 9A provides a graph showing the impact of the affinity matured YW412.8.31 anti-BACE1 antibody on the in vitro enzymatic activity of human recombinant BACE1 using either a long peptide substrate with enhanced susceptibility to BACE1 in an HTRF assay (left panel) or a short peptide substrate with enhanced susceptibility to BACE1 in a FRET assay (right panel), as described in Example 2(B). OM99-2 (CalBiochem®, catalog #496000), a synthetic peptide inhibitor of BACE1, β-Secretase inhibitor IV (CalBiochem®, catalog #565788), a small molecule inhibitor of BACE1 (BACE1 SMI) and an IgG antibody which does not bind BACE1 were used as controls.
Figures 1, 9B:
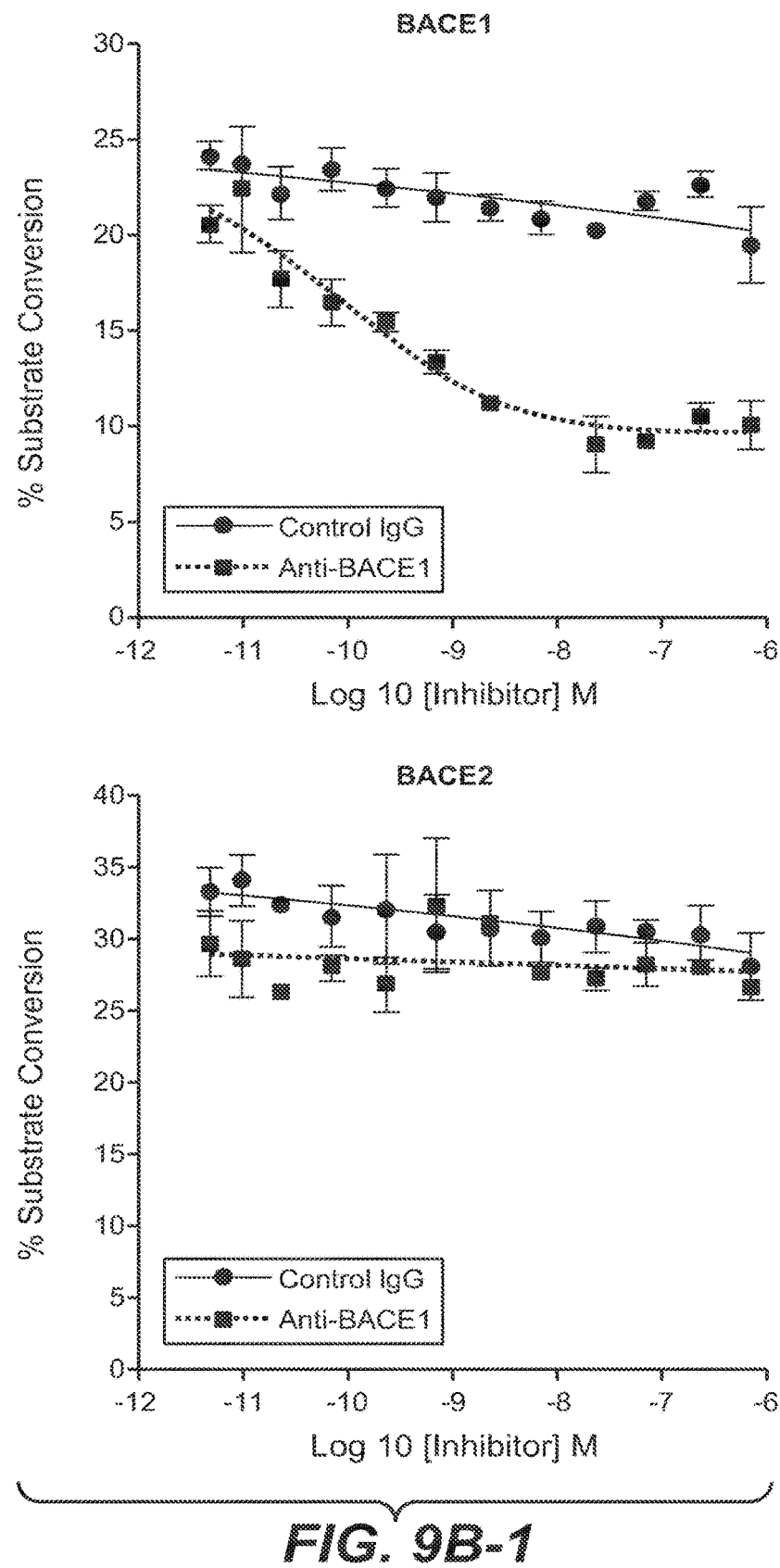
FIGS. 9B-1 and 9B-2 also provide graphs showing the in vitro enzymatic activity of human recombinant BACE1 extracellular domain, human recombinant BACE2 extracellular domain, or the cathepsin D extracellular domain on a short peptide substrate with enhanced susceptibility to BACE1 in the presence of YW412.8.31, or a control IgG antibody as described in Example 2(B).
Figures 2, 9B:
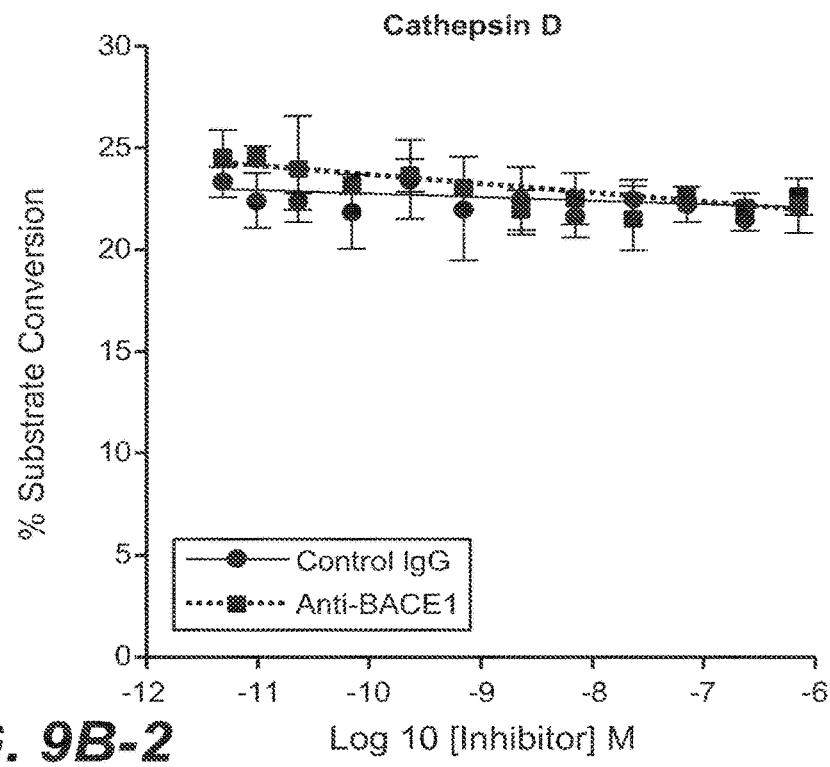

In one aspect, the invention provides an anti-BACE1 antibody comprising at least one, two, three, four, five, or six HVRs selected from the (a) HVR-H1 comprising an amino acid sequence in FIGS. 1(B), 2(B) and 24(A); (b) HVR-H2 comprising an amino acid sequence in FIGS. 1(B), 2(B) and 24(B); (c) HVR-H3 comprising an amino acid sequence in FIGS. 1(B), 2(B) and 24(C); (d) HVR-L1 comprising an amino acid sequence in FIGS. 1(A), 2(A) and 23(A); (e) HVR-L2 comprising an amino acid sequence in FIGS. 1(A), 2(A) and 23(B); and (f) HVR-L3 comprising an amino acid sequence in FIGS. 1(A) and 2(A) and 23(C).

In another aspect, an anti-BACE1 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence selected from SEQ ID NO:1-6, 31-34 and 99-117. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-BACE1 antibody comprising that sequence retains the ability to bind to BACE1 and/or inhibit or reduce BACE1 activity. In certain embodiments, a total of 1 to 10 amino acids have been substituted, inserted and/or deleted in SEQ ID NO:1-6, 31-34 and 99-117. In certain embodiments, the substitutions, insertions, or deletions occur in regions outside the HVRs (i.e., in the FRs). Optionally, the anti-BACE1 antibody comprises the VL sequence in SEQ ID NO:1-6, 31-34 or 99-117, including post-translational modifications of that sequence. In a particular embodiment, the VL comprises one, two or three HVRs selected from (a) HVR-L1 comprising the amino acid sequence of SEQ ID NO:7, 8, 17, 35 or 42; (b) HVR-L2 comprising the amino acid sequence of SEQ ID NO:9, 10, 18, 36-39, 41, 43 and 56, 58-64 or 118; and (c) HVR-L3 comprising the amino acid sequence of SEQ ID NO:11-16, 19, 40, 44, 57, 65, 66, 67 or 119.

In another aspect, an anti-BACE1 antibody is provided, wherein the antibody comprises a VH as in any of the embodiments provided above, and a VL as in any of the embodiments provided above. In one embodiment, the antibody comprises the VH and VL sequences in SEQ ID NO:21 and SEQ ID NO:2, respectively, including post-translational modifications of those sequences.

In a further aspect, the invention provides an antibody that binds to the same epitope as an anti-BACE1 antibody provided herein. For example, in certain embodiments, an antibody is provided that binds to the same epitope as an anti-BACE1 antibody comprising a VH sequence selected from SEQ ID NO: 20, 21, 27 and 80-98 and a VL sequence selected from SEQ ID NO: 1-6, 31-34 and 99-117. In certain embodiments, an antibody is provided that binds to the same epitope as an anti-BACE1 antibody comprising the VH and VL sequences in SEQ ID NO: 21 and SEQ ID NO:2, respectively.

In certain embodiments, an antibody is provided that binds to an epitope within BACE1 comprising at least one, at least two, at least three, at least four, at least five, at least six, at least seven, at least eight, at least nine amino acid(s) which corresponds to the amino acids 314 SER, 316 GLU, 317 LYS, 318 PHE, 319 PRO, 327 GLN, 328 LEU, 329 VAL, 330 CYS, 331 TRP, 332 GLN, 333 ALA, 335 THR, 337 PRO, 340 ILE, 375 THR, 378 ASP, 380 CYS, 426 PHE of SEQ ID NO:49.

In certain embodiments, an antibody is provided that binds to an epitope within BACE1 comprising at least one, at least two, at least three, at least four, at least five, at least six, at least seven, at least eight, at least nine amino acid(s) which corresponds to the amino acids 314 SER; 316 GLU; 317 LYS; 327 GLN; 330 CYS; 331 TRP; 332 GLN; 335 THR; and 378 ASP of SEQ ID NO:49. In other embodiments the conformational epitope comprises amino acids which correspond to 314 SER; 316 GLU; 317 LYS; 327 GLN; 330 CYS; 331 TRP; 332 GLN; 335 THR; and 378 ASP of SEQ ID NO:49. It will be appreciated that the amino acids identified in the BACE1 epitope correspond to the sequence of human BACE1 isoform A. However, the described BACE1 conformational epitope also encompasses corresponding amino acids in other variants and isoforms of BACE1 and the epitope may include amino acids other than the residues specified.

In certain embodiments, an antibody is provided that binds to an epitope within BACE1 comprising at least one, at least two or at least three amino acid region(s) of BACE1 which correspond to amino acids 315-318 of SEQ ID NO:49; amino acids 331-335 of SEQ ID NO:49; amino acids 370-381 of SEQ ID NO:49; or any combination thereof. In one embodiment, the antibody binds to an epitope of BACE1 comprising amino acids 315-318, 331-335 and 370-381 of SEQ ID NO:49.

In another embodiment an antibody is provided that binds to an epitope within BACE1 which results in a conformational change in the P6 and/or P7 sites (Turner et al., *Biochemistry* 44:105-112 (2005)) of BACE1 upon binding relative to BACE1 without the antibody bound. In an additional embodiment, an antibody is provided that binds to an epitope of BACE1 which induces amino acids 218-231 of SEQ ID NO:49 of BACE1 to adopt a random loop structure. Amino acids 218-231 of SEQ ID NO:49 of BACE1 exist in an α-helical structure in the substrate bound complex.

Figure 14:
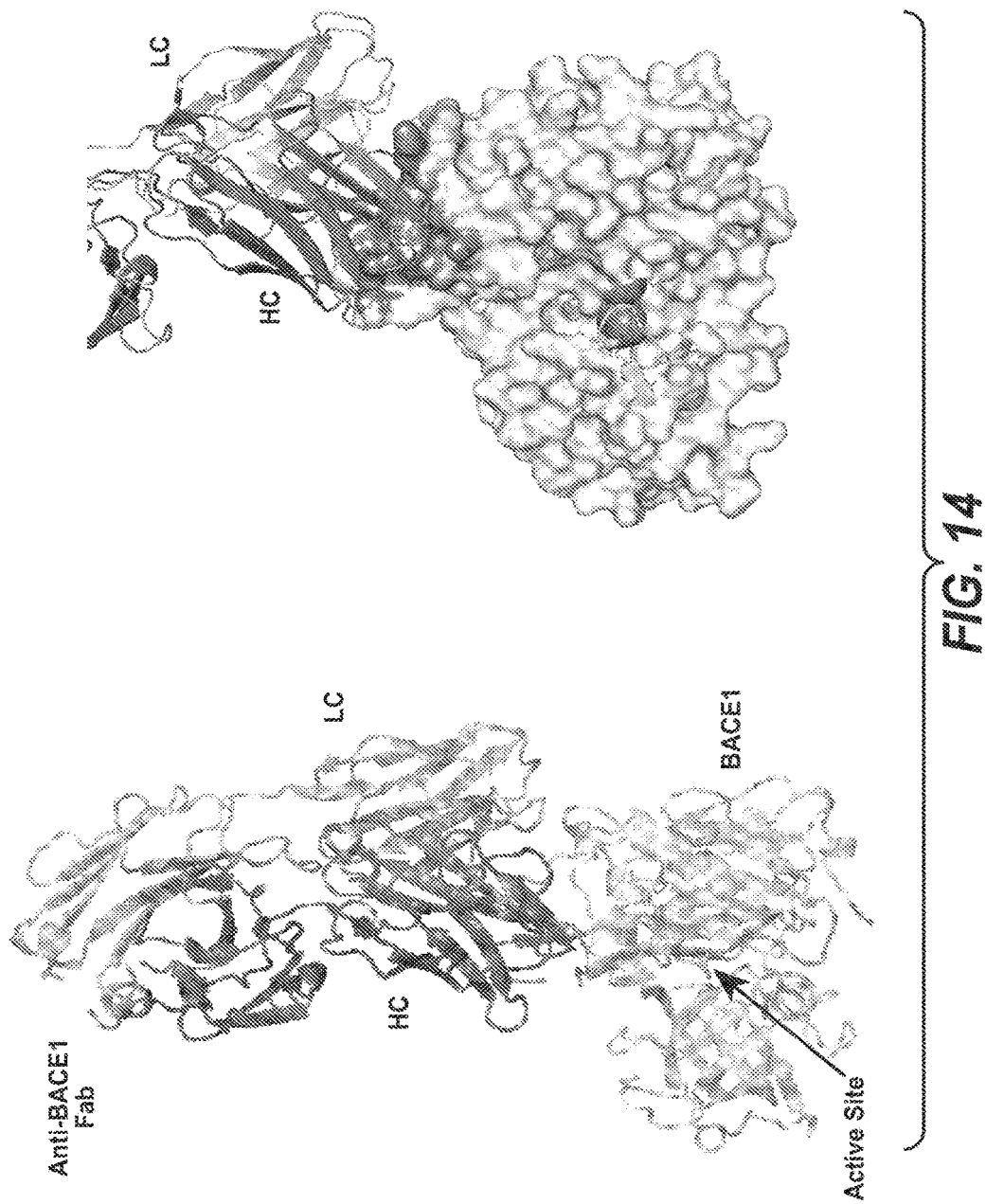
FIG. 14 shows different views of the 2.8 Å structure of the Fab YW412.8.31 co-crystallized with the human BACE1 extracellular domain as described in Example 3(B). The Fab binds to a BACE1 exosite distal to the secretase active site, partially overlapping with another exosite known to interact with certain peptides having BACE1-inhibitory properties.
Figure 15:
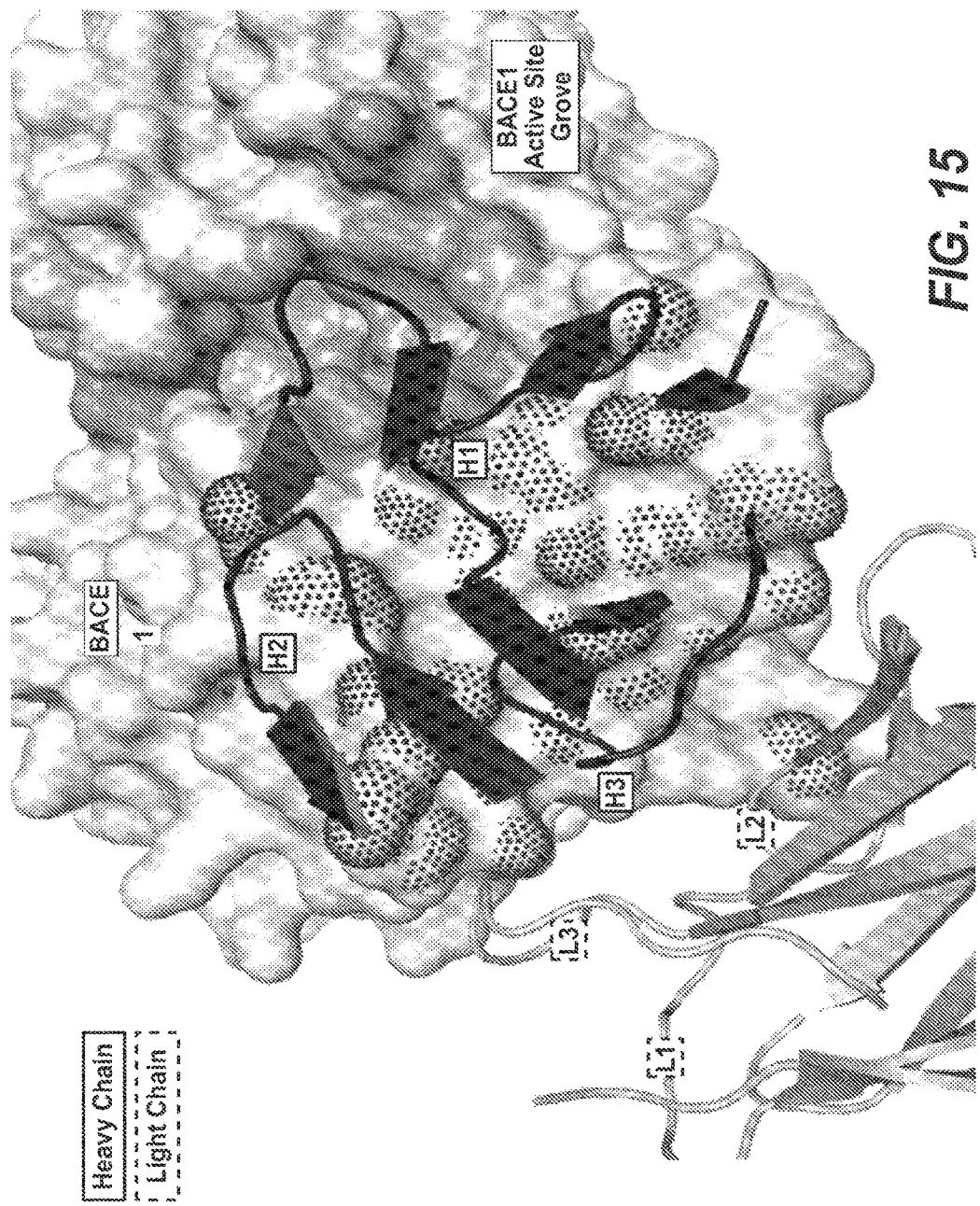
FIG. 15 provides a close-up view of the interaction of the Fab YW412.8.31 with the human BACE1 extracellular domain. BACE1 is shown in surface representation and the Fab is shown as ribbons. The dotted surface indicates the BACE1 epitope.

In another embodiment, an antibody is provided that binds to a site within BACE1 as indicated in FIGS. 14 and 15 and described in the crystal structure of BACE1 and the anti-BACE1 antibody, YW412.8.31 (Example 3(B)).

In other embodiments, an antibody is provided that binds to an exosite within BACE1. In one embodiment, the exosite within BACE1 is the same exosite as that identified by Kornacker et al., *Biochem.* 44:11567-11573 (2005). In one embodiment an antibody is provided that competes with the peptides identified in Kornacker et al., *Biochem.* 44:11567-11573 (2005), which is incorporated herein by reference in its entirety, (i.e., Peptides 1, 2, 3, 1-11, 1-10, 1-9, 1-8, 1-7, 1-6, 2-12, 3-12, 4-12, 5-12, 6-12, 7-12, 8-12, 9-12, 10-12, 4, 5, 6, 5-10, 5-9, Y5A, P6A, Y7A, F8A, I9A, P10A and L11A) for binding to BACE1.

In another embodiment, an antibody is provided that competes for binding (e.g., binds to the same epitope) as any anti-BACE1 antibody described herein.

In a further aspect of the invention, an anti-BACE1 antibody according to any of the above embodiments is a monoclonal antibody, including a chimeric, humanized or human antibody. In one embodiment, an anti-BACE1 antibody is an antibody fragment, e.g., a Fv, Fab, Fab', scFv, diabody, or F(ab')$_2$ fragment. In another embodiment, the antibody is a full length antibody, e.g., an intact IgG1 antibody or other antibody class or isotype as defined herein.

In a further aspect, an anti-BACE1 antibody according to any of the above embodiments may incorporate any of the features, singly or in combination, as described in Sections 1-7 below:

1. Antibody Affinity

In certain embodiments, an antibody provided herein has a dissociation constant (Kd) of ≤1 μM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ M$^{-1}$s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Natl. Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VelociMouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications*, pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, *Histology and Histopathology*, 20(3):927-937 (2005) and Vollmers and Brandlein, *Methods and Findings in Experimental and Clinical Pharmacology*, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for BACE1 and the other is for any other antigen. In certain embodiments, bispecific antibodies may bind to two different epitopes of BACE1. Bispecific antibodies may also be used to localize cytotoxic agents to cells which express BACE1. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see, e.g. Gruber et al., *J. Immunol.*, 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to BACE1 as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |

TABLE 1-continued

| Original Residue | Exemplary Substitutions | Preferred Substitutions |
|---|---|---|
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Natl. Acad. Sci. USA* 83:7059-7063 (1986)) and Hellstrom, I et al., *Proc. Natl. Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Natl. Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Intl. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-BACE1 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-BACE1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-BACE1 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

C. Assays

Anti-BACE1 antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes with any of the antibodies or Fabs descried herein, for example, YW412.8, YW412.8.31, YW412.8.30, YW412.8.2, YW412.8.29, YW412.8.51, Fab12, LC6, LC9, LC10 for binding to BACE1. In certain embodiments, such a competing antibody binds to the same epitope (e.g., a linear or a conformational epitope) that is bound by any of the antibodies or Fabs descried herein, for example, YW412.8, YW412.8.31, YW412.8.30, YW412.8.2, YW412.8.29, YW412.8.51, Fab12, LC6, LC9, LC10. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized BACE1 is incubated in a solution comprising a first labeled antibody that binds to BACE1 (e.g., YW412.8, YW412.8.31, YW412.8.30, YW412.8.2, YW412.8.29, YW412.8.51, Fab12, LC6, LC9, LC10) and a second unlabeled antibody that is being tested for its ability to compete with the first antibody for binding to BACE1. The second antibody may be present in a hybridoma supernatant. As a control, immobilized BACE1 is incubated in a solution comprising the first labeled antibody but not the second unlabeled antibody. After incubation under conditions permissive for binding of the first antibody to BACE1, excess unbound antibody is removed, and the amount of label associated with immobilized BACE1 is measured. If the amount of label associated with immobilized BACE1 is substantially reduced in the test sample relative to the control sample, then that indicates that the second antibody is competing with the first antibody for binding to BACE1. See Harlow and Lane (1988) *Antibodies: A Laboratory Manual* ch. 14 (Cold Spring Harbor Laboratory, Cold Spring Harbor, N.Y.).

2. Activity Assays

In one aspect, assays are provided for identifying anti-BACE1 antibodies thereof having biological activity. Biological activity may include, e.g., inhibition or reduction of BACE1 aspartyl protease activity; or inhibition or reduction in APP cleavage by BACE1; or inhibition or reduction in Aβ production. Antibodies having such biological activity in vivo and/or in vitro are also provided.

In certain embodiments, an antibody of the invention is tested for such biological activity. For example, BACE1 protease activity can be tested in an homogeneous time-resolved fluorescence HTRF assay or a microfluidic capillary electrophoretic (MCE) assay, as described in detail in Example 1 and 2(B), using synthetic substrate peptides.

Briefly, a homogeneous time-resolved fluorescence (HTRF) assay can be used to measure BACE1 aspartyl protease activity with the use of an amyloid precursor protein BACE1 cleavage site peptide. For example, the Bi27 peptide (Biotin-KTEEISEVNLDAEFRHDSGYEVHHQKL (SEQ ID NO:53), American Peptide Company)), is combined with BACE1 pre-incubated with an anti-BACE antibody in BACE reaction buffer (50 mM sodium acetate pH 4.4 and 0.1% CHAPS) in a 384-well plate (Proxiplate™, Perkin-Elmer). The proteolytic reaction mixture is incubated at ambient temperature for 75 minutes and was quenched by the addition of 5 μL HTRF detection mixture containing 2 nM Streptavidin-D2 and 150 nM of an anti-amyloid beta antibody labeled with Europium cryptate in detection buffer (200 mM Tris pH 8.0, 20 mM EDTA, 0.1% BSA, and 0.8M KF). The final reaction mixture is incubated at ambient temperature for 60 minutes and the TR-FRET signal is measured using an EnVision Multilabel Plate Reader™ (Perkin-Elmer) at an excitation wavelength of 320 nm and emission wavelengths of 615 and 665 nm.

An MCE assay reactions can be carried out in a standard enzymatic reaction, initiated by the addition of substrate to enzyme and 4× compound, containing human BACE1 (extracellular domain), amyloid precursor protein beta secretase active site peptide (FAM-KTEEISEVNLDAEFRWKK-$CONH_2$ (SEQ ID NO:55)), 50 mM NaOAc pH 4.4 and 0.1% CHAPS. After incubation for 60 minutes at ambient temperature, the product and substrate in each reaction is separated using a 12-sipper microfluidic chip analyzed on an LC3000® (both, Caliper Life Sciences). The separation of product and substrate is optimized by choosing voltages and pressure using the manufacturer's optimization software. Substrate conversion is calculated from the electrophoregram using HTS Well Analyzer software (Caliper Life Sciences).

In addition, BACE1 protease activity can be tested in vivo in cell lines which express BACE1 substrates such as APP, or in transgenic mice which express BACE1 substrates, such as human APP, as described in Examples 2(C) and 4.

Additionally, BACE1 protease activity can be tested with anti-BACE1 antibodies in animal models. For example, animal models of various neurological diseases and disorders, and associated techniques for examining the pathological processes associated with these models, are readily available in the art. Animal models of various neurological disorders include both non-recombinant and recombinant (transgenic) animals. Non-recombinant animal models include, for example, rodent, e.g., murine models. Such models can be generated by introducing cells into syngeneic mice using standard techniques, e.g. subcutaneous injection, tail vein injection, spleen implantation, intraperitoneal implantation, and implantation under the renal capsule. In vivo models include models of stroke/cerebral ischemia, in vivo models of neurodegenerative diseases, such as mouse models of Parkinson's disease; mouse models of Alzheimer's disease; mouse models of amyotrophic lateral sclerosis; mouse models of spinal muscular atrophy; mouse/rat models of focal and global cerebral ischemia, for instance, common carotid artery occlusion or middle cerebral artery occlusion models; or in ex vivo whole embryo cultures. As one nonlimiting example, there are a number of art-known mouse models for Alzheimer's disease ((see, e.g. Rakover et al., *Neurodegener. Dis*. (2007); 4(5): 392-402; Mouri et al., *FASEB J*. (2007) July; 21 (9): 2135-48; Minkeviciene et al., *J. Pharmacol. Exp. Ther*. (2004) November; 311 (2):677-82 and Yuede et al., *Behav Pharmacol*. (2007) September; 18 (5-6): 347-63). The various assays may be conducted in known in vitro or in vivo assay formats, as known in the art and described in the literature. Various such animal models are also available from commercial vendors such as the Jackson Laboratory. Additional animal model assays are described in Examples 4 and 5.

D. Immunoconjugates

The invention also provides immunoconjugates comprising an anti-BACE1 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)); an anthracycline such as daunomycin or doxorubicin (see Kratz et al., Current Med. Chem. 13:477-523 (2006); Jeffrey et al., Bioorganic & Med. Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med. Chem. Letters 12:1529-1532 (2002); King et al., J. Med. Chem. 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC 1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2, 4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the anti-BACE1 antibodies provided herein is useful for detecting the presence of BACE1 in a biological sample. The term "detecting" as used herein encompasses quantitative or qualitative detection. In certain embodiments, a biological sample comprises a cell or tissue, such as serum, plasma, saliva, gastric secretions, mucus, cerebrospinal fluid, lymphatic fluid, neuronal tissue, brain tissue, cardiac tissue or vascular tissue.

In one embodiment, an anti-BACE1 antibody for use in a method of diagnosis or detection is provided. In a further aspect, a method of detecting the presence of BACE1 in a biological sample is provided. In certain embodiments, the method comprises contacting the biological sample with an anti-BACE1 antibody as described herein under conditions permissive for binding of the anti-BACE1 antibody to BACE1, and detecting whether a complex is formed between the anti-BACE1 antibody and BACE1. Such method may be an in vitro or in vivo method. In one embodiment, an anti-BACE1 antibody is used to select subjects eligible for therapy with an anti-BACE1 antibody, e.g. where BACE1 is a biomarker for selection of patients.

Exemplary disorders that may be diagnosed using an antibody of the invention include neurodegenerative diseases (including, but not limited to, Lewy body disease, postpoliomyelitis syndrome, Shy-Draeger syndrome, olivopontocerebellar atrophy, Parkinson's disease, multiple system atrophy, striatonigral degeneration, tauopathies (including, but not limited to, Alzheimer disease and supranuclear palsy), prion diseases (including, but not limited to, bovine spongiform encephalopathy, scrapie, Creutzfeldt-Jakob syndrome, kuru, Gerstmann-Straussler-Scheinker disease, chronic wasting disease, and fatal familial insomnia), stroke, muscular dystrophy, multiple sclerosis, Amyotrophic lateral sclerosis (ALS), Angelman's syndrome, Liddle syndrome, Paget's syndrome, traumatic brain injury, bulbar palsy, motor neuron disease, and nervous system heterodegenerative disorders (including, but not limited to, Canavan disease, Huntington's disease, neuronal ceroid-lipofuscinosis, Alexander's disease, Tourette's syndrome, Menkes kinky hair syndrome, Cockayne syndrome, Halervorden-Spatz syndrome, lafora disease, Rett syndrome, hepatolenticular degeneration, Lesch-Nyhan syndrome, and Unverricht-Lundborg syndrome), dementia (including, but not limited to, Pick's disease, and spinocerebellar ataxia).

In certain embodiments, labeled anti-BACE1 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-BACE1 antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-BACE1 antibodies provided herein may be used in therapeutic methods.

In one aspect, an anti-BACE1 antibody for use as a medicament is provided. In further aspects, an anti-BACE1 antibody for use in treating a neurological disease or disorder is provided (e.g., AD). In certain embodiments, an anti-BACE1 antibody for use in a method of treatment is provided. In certain embodiments, the invention provides an anti-BACE1 antibody for use in a method of treating an individual having a neurological disease or disorder comprising administering to the individual an effective amount of the anti-BACE1 antibody. In one such embodiment, the method further comprises administering to the individual an effective amount of at least one additional therapeutic agent. In further embodiments, the invention provides an anti-BACE1 antibody for use in reducing or inhibiting amyloid plaque formation in a patient at risk or suffering from a neurological disease or disorder (e.g., AD). In certain embodiments, the invention provides an anti-BACE1 antibody for use in a method of reducing or inhibiting Aβ production in an individual comprising administering to the individual an effective of the anti-BACE1 antibody. An "individual" according to any of the above embodiments is preferably a human. In certain aspect, the anti-BACE antibody for use in the methods of the invention reduces or inhibits BACE1 activity. For example, the anti-BACE1 antibody reduces or inhibits the ability of BACE1 to cleave APP.

In a further aspect, the invention provides for the use of an anti-BACE1 antibody in the manufacture or preparation of a medicament. In one embodiment, the medicament is for treatment of neurological disease or disorder. In a further embodiment, the medicament is for use in a method of treating neurological disease or disorder comprising administering to an individual having neurological disease or disorder an effective amount of the medicament. In one such embodiment, the method further comprises administering to the individual an effective amount of at least one additional therapeutic agent, e.g., as described below. In a further embodiment, the medicament is for inhibiting BACE1 activity. In a further embodiment, the medicament is for use in a method of inhibiting Aβ production or plaque formation in an individual comprising administering to the individual an amount effective of the medicament to inhibit Aβ production or plaque formation. An "individual" according to any of the above embodiments may be a human.

In a further aspect, the invention provides a method for treating Alzheimer's disease. In one embodiment, the method comprises administering to an individual having AD an effective amount of an anti-BACE1 antibody. In one such embodiment, the method further comprises administering to the individual an effective amount of at least one additional therapeutic agent. An "individual" according to any of the above embodiments may be a human.

In a further aspect, the invention provides pharmaceutical formulations comprising any of the anti-BACE1 antibodies provided herein, e.g., for use in any of the above therapeutic methods. In one embodiment, a pharmaceutical formulation comprises any of the anti-BACE1 antibodies provided herein and a pharmaceutically acceptable carrier. In another embodiment, a pharmaceutical formulation comprises any of the anti-BACE1 antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies of the invention can also be used in combination with radiation therapy.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Certain embodiments of the invention provide for the antibody or fragment thereof to traverse the blood-brain barrier. Certain neurodegenerative diseases are associated with an increase in permeability of the blood-brain barrier, such that the antibody or active fragment thereof can be readily introduced to the brain. When the blood-brain barrier remains intact, several art-known approaches exist for transporting molecules across it, including, but not limited to, physical methods, lipid-based methods, and receptor and channel-based methods.

Physical methods of transporting the antibody or fragment thereof across the blood-brain barrier include, but are not limited to, circumventing the blood-brain barrier entirely, or by creating openings in the blood-brain barrier. Circumvention methods include, but are not limited to, direct injection into the brain (see e.g., Papanastassiou et al., *Gene Therapy* 9: 398-406 (2002)) and implanting a delivery device in the brain (see e.g., Gill et al., *Nature Med.* 9: 589-595 (2003); and Gliadel Wafers™, Guildford Pharmaceutical). Methods of creating openings in the barrier include, but are not limited to, ultrasound (see e.g., U.S. Patent Publication No. 2002/0038086), osmotic pressure (e.g., by administration of hypertonic mannitol (Neuwelt, E. A., *Implication of the Blood-Brain Barrier and its Manipulation*, Vols 1 & 2, Plenum Press, N.Y. (1989))), permeabilization by, e.g., bradykinin or permeabilizer A-7 (see e.g., U.S. Pat. Nos. 5,112,596, 5,268,164, 5,506,206, and 5,686,416), and transfection of neurons that straddle the blood-brain barrier with vectors containing genes encoding the antibody or fragment thereof (see e.g., U.S. Patent Publication No. 2003/0083299).

Lipid-based methods of transporting the antibody or fragment thereof across the blood-brain barrier include, but are not limited to, encapsulating the antibody or fragment thereof in liposomes that are coupled to antibody binding fragments that bind to receptors on the vascular endothelium of the blood-brain barrier (see e.g., U.S. Patent Application Publication No. 20020025313), and coating the antibody or active fragment thereof in low-density lipoprotein particles (see e.g., U.S. Patent Application Publication No. 20040204354) or apolipoprotein E (see e.g., U.S. Patent Application Publication No. 20040131692).

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-BACE1 antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-BACE1 antibody.

III. Examples

The following are examples of methods and compositions of the invention. It is understood that various other embodiments may be practiced, given the general description provided above.

Example 1: Generation and Characterization of Anti-BACE1 Antibodies

Antibodies specifically binding to BACE1 were generated by panning two different types of phage display antibody libraries (one with natural diversity (VH and VH/VL), the other with diversity in certain CDR regions artificially restricted to particular amino acid sets (YSGX)) against the human BACE1 extracellular domain, amino acids 1-457 of SEQ ID NO:49.

A. Natural Diversity Library Sorting and Screening to Identify Anti-BACE-1 Antibodies Selection of Phage Displayed Anti-BACE1 Clones Biotinylated human BACE-1 (1-457 of SEQ ID NO:49) was used as an antigen for library sorting. The natural diversity phage libraries were sorted five rounds against biotinylated BACE-1 pre-captured on alternating neutravidin/streptavidin plates. For the first round of sorting, NUNC 96 well Maxisorp immunoplates were first coated with 10 µg/mL neutravidin (Fisher Scientific, #21125) and blocked with phage blocking buffer PBST (phosphate-buffered saline (PBS) and 1% (w/v) bovine serum albumin (BSA) and 0.05% (v/v) Tween 20) overnight. First, 10 µg/mL biotinylated BACE-1 was captured on the immunoplates for 30 minutes. Antibody phage libraries VH (see e.g., Lee et al., *J. Immunol. Meth.* 284:119-132 (2004)) and VH/VL (see Liang et al., *J. Mol. Biol.* 366: 815-829 (2007)), pre-blocked with phage blocking buffer PBST, were subsequently added to the plates and incubated overnight at room temperature. The plates were washed 10× the following day with PBT (PBS with 0.05% Tween 20), and bound phage were eluted with 1 mL 50 mM HCl and 500 mM NaCl for 30 min and neutralized with 600 µL of 1 M Tris base (pH 8.0). Recovered phage were amplified in *E. coli* XL-1 Blue cells. During the subsequent selection rounds, propagated phage libraries were first pre-absorbed with 50 µl of Dynabeads® MyOne™ Streptavidin T1 (Invitrogen, #65601) in PBST/BSA and incubated for 30 minutes at room temperature. Phage particles that bound to neutravidin were subtracted from the phage stock with the removal of the Dynabeads®. The unbound phage were then added to BACE-1 antigen displayed on streptavidin plates and the incubation time was reduced to 2-3 hours. The stringency of plate washing was gradually increased.

After 5 rounds of panning, significant enrichment was observed. 96 clones were picked from the VH and VH/VL library sorting to determine whether they specifically bound to human BACE-1. The variable regions of these clones were PCR sequenced to identify unique sequence clones. 42 unique phage antibodies that bound human BACE-1 with at least 5× above background were chosen and reformatted to full length IgGs for evaluation in in vitro cell assays.

Clones of interest were reformatted into IgGs by cloning $V_L$ and $V_H$ regions of individual clones into the LPG3 and LPG4 vectors, respectively, and transiently expressed in mammalian CHO cells, and purified using protein A column chromatography.

Selection of Anti-BACE1 Inhibitory Clones

BACE1 is an aspartyl protease that normally cleaves amyloid precursor protein at a point near its transmembrane domain, close to the surface of the cell. Accordingly, the ability of antibodies identified above to modulate BACE1 proteolytic activity on certain BACE1 substrates, was assessed in vitro using a homogeneous time-resolved fluorescence (HTRF) assay.

The HTRF assay was performed as follows. Two microliters of 375 nM Bi27 (Biotin-KTEEISEVNLDAEFRHDS-GYEVHHQKL (SEQ ID NO:53), American Peptide Company)), an amyloid precursor protein BACE1 cleavage site peptide bearing a substitution to increase sensitivity to BACE1 cleavage, was combined with 3 µL of 125 nM BACE1 pre-incubated with an anti-BACE antibody in BACE reaction buffer (50 mM sodium acetate pH 4.4 and 0.1% CHAPS) in a 384-well plate (Proxiplate™, Perkin-Elmer). The proteolytic reaction mixture was incubated at ambient temperature for 75 minutes and was quenched by the addition of 5 µL HTRF detection mixture containing 2 nM Streptavidin-D2 and 150 nM of 6E10 anti-amyloid beta antibody (Covance, Emoryville, Calif.) labeled with Europium cryptate in detection buffer (200 mM Tris pH 8.0, 20 mM EDTA, 0.1% BSA, and 0.8M KF). The final reaction mixture was incubated at ambient temperature for 60 minutes and the TR-FRET signal was measured using an EnVision Multilabel Plate Reader™ (Perkin-Elmer) at an excitation wavelength of 320 nm and emission wavelengths of 615 and 665 nm. Reactions lacking BACE1 enzyme (0 BACE) and reactions containing lacking anti-BACE1 antibodies (PBS (100% BACE1 Activity) were used as controls.

Of the 42 antibodies tested which were identified from the natural diversity library, the best inhibitor of BACE1, YW412.8, was chosen for affinity maturation. See FIG. 4.

Affinity Maturation of Anti-BACE1 Inhibitory Clones

Libraries were constructed to affinity mature the YW412.8 antibody as follows. Phagemid pW0703 (derived from phagemid pV0350-2b (Lee et al., *J. Mol. Biol.* 340, 1073-1093 (2004)), containing a stop codon (TAA) in all CDR-L3 positions and displaying monovalent Fab on the surface of M13 bacteriophage) served as the library template for grafting heavy chain variable domains (VH) of clones of interest from the natural diversity library for affinity maturation. Both hard and soft randomization strategies were used for affinity maturation. For hard randomization, one light chain library with selected positions of the three light chain CDRs was randomized using amino acids designed to mimic natural human antibodies and the designed DNA degeneracy was as described in Lee et al. (*J. Mol. Biol.* 340, 1073-1093 (2004)). For soft randomization, residues at positions 91-94, and 96 of CDR-L3, 28-31 and 34-35 of CDR-H1, 50, 52, and 53-58 of CDR-H2, 95-99 and 100 A of CDR-H3, were targeted; and two different combinations of CDR loops, L3/H1/H2 and L3/H3, were selected for randomization. To achieve the soft randomization conditions, which introduced the mutation rate of approximately 50% at the selected positions, the mutagenic DNA was synthesized with 70-10-10-10 mixtures of bases favoring the wild type nucleotides (Gallop et al., *J. Med. Chem.* 37:1233-1251 (1994)).

Selection of affinity improved Fabs was performed as follows. Affinity improvement phage libraries were subjected to plate sorting for the first round, followed by four or five rounds of solution sorting. For the first round of plate sorting, the libraries were sorted against 10 µg/ml biotinylated target (BACE1) captured by neutravidin coated plate (NUNC Maxisorp plate) with phage input about 2 OD/ml in 1% BSA and 0.05% Tween 20 for 2 hours at room temperature. After the first round of plate sorting, solution sorting was performed to increase the stringency of selection. For solution sorting, 1 OD/ml phage propagated from the first round of plate sorting were incubated with 100 nM biotinylated target protein (the concentration was based on parental clone phage $IC_{50}$ values) in 100 µl buffer containing 1% Superblock (Pierce Biotechnology) and 0.05% Tween 20 for 30 minutes at room temperature. The mixture was further diluted 10× with 1% Superblock, and 100 µl/well was applied to neutravidin-coated wells (5 µg/ml) for 15 minutes at room temperature with gentle shaking such that biotinylated target bound phage. The wells were washed with PBS and 0.05% Tween 20 ten times. To determine background binding, control wells containing phage with targets that were not biotinylated were captured on neutravidin-coated plates. Bound phage were eluted with 0.1 N HCl for 20 minutes, neutralized by 1/10 volume of 1 M Tris pH 11, titered, and propagated for the next round. Next, two more rounds of solution sorting were carried out together with increasing selection stringency. The first round was for on-rate selection by decreasing biotinylated target protein concentration from 100 nM to 5 nM. The second round was for off-rate selection by adding excess amounts of non-biotinylated target protein (100-fold more) to compete off weaker binders at room temperature. Also, the phage input was decreased (0.1~0.5 OD/ml) to lower background phage binding.

Colonies were picked from the fourth round screens and were grown overnight at 37° C. in 150 µl/well of 2YT media with 50 µg/ml carbenicillin and 1E10/ml KO7 phage in 96-well plates (Falcon). From the same plate, a colony of XL-1 infected parental phage was picked as a control. 96-well Nunc Maxisorp plates were coated with 100 µl/well neutravidin (2 µg/ml) in PBS at 4° C. overnight or room temperature for 2 hours. The plates were blocked with 65 µl of 1% BSA for 30 min and 40 µl of 1% Tween 20 for another 30 minutes before biotinylated target protein (2 µg/ml) was added and incubated for 15 min at room temperature.

The phage supernatant was diluted 1:10 in ELISA (enzyme linked immunosorbent assay) buffer (PBS with 0.5% BSA, 0.05% Tween20) with or without 10 nM target protein in 100 µl total volume and incubated at least 1 hour at room temperature in an F plate (NUNC) for use in a single spot competition assay. 75 µl of mixture with or without target protein was transferred side by side to the target protein captured by neutravidin-coated plates. The plate was gently shaken for 15 min to allow the capture of unbound phage to the neutravidin-captured target protein. The plate was washed at least five times with PBS-0.05% Tween 20. The binding was quantified by adding horseradish peroxidase (HRP)-conjugated anti-M13 antibody in ELISA buffer (1:5000) and incubated for 30 minutes at room temperature. The plates were washed with PBS-0.05% Tween 20 at least five times. Next, 100 µl/well of a 1:1 ratio of 3,3',5,5'-tetramethylbenzidine (TMB) Peroxidase substrate and Peroxidase Solution B ($H_2O_2$) (Kirkegaard-Perry Laboratories (Gaithersburg, Md.)) was added to the well and incubated for 5 minutes at room temperature. The reaction was stopped by adding 100 µl 1 M phosphoric acid ($H_3PO_4$) to each well and allowed to incubate for 5 minutes at room temperature. The OD (optical density) of the yellow color in each well was determined using a standard ELISA plate reader at 450 nm. The OD reduction (%) was calculated by the following equation:

$$OD_{450nm} \text{ reduction } (\%) = [(OD_{450nm} \text{ of wells with competitor})/(OD_{450nm} \text{ of well with no competitor})]*100.$$

In comparison to the $OD_{450nm}$ reduction (%) of the well of parental phage (100%), clones that had the $OD_{450nm}$ reduction (%) lower than 50% for both the human and murine target were picked for sequence analysis. Unique clones were selected for phage preparation to determine binding affinity (phage $IC_{50}$) against target by comparison with parental clones. The most affinity-improved clones were reformatted into human IgG1 for antibody production and further binding kinetic analysis by surface plasmon resonance using BIAcore and other in vitro or in vivo assays.

The sequence of the light chain and heavy chain HVR region of YW412.8, chosen from the natural diversity phage library, is shown in FIGS. 1(A) and 1(B). Additionally, five antibodies obtained from affinity maturation of the YW412.8 antibody were also sequenced and the light chain and heavy chain HVR sequences are also shown in FIGS. 1(A) and 1(B). The consensus amino acid sequences of the light chain HVR regions that displayed variability in these antibodies were: HVR-L1: Arg Ala Ser Gln $X_1$ Val $X_2$ $X_3$ $X_4$ $X_5$ Ala (SEQ ID NO: 17), wherein $X_1$ is selected from aspartic acid and valine, $X_2$ is selected from serine and alanine, $X_3$ is selected from threonine and asparagine, $X_4$ is selected from alanine and serine, and $X_5$ is selected from valine and leucine; HVR-L2: $X_6$ Ala Ser Phe Leu Tyr Ser (SEQ ID NO: 18), wherein $X_6$ is selected from serine and leucine; and HVR-L3: Gln Gln $X_7$ $X_8$ $X_9$ $X_{10}$ $X_{11}$ $X_{12}$ Thr (SEQ ID NO: 19), wherein $X_7$ is selected from serine, phenylalanine, glycine, aspartic acid and tyrosine, $X_8$ is selected from tyrosine, proline, serine and alanine, $X_9$ is selected from threonine and asparagine, $X_{10}$ is selected from threonine, tyrosine, aspartic acid and serine, $X_{11}$ is selected from proline and leucine and $X_{12}$ is selected from proline and threonine. Only the heavy chain hypervariable region H1 displayed variability amongst these antibodies, and the consensus sequence for that region was: HVR-H1: Gly Phe Thr Phe $X_{13}$ Gly Tyr $X_{14}$ Ile His (SEQ ID NO: 26), wherein $X_{13}$ is selected from serine and leucine and $X_{14}$ is selected from alanine and glycine.

B. Synthetic Diversity Library Sorting and Screening to Identify Anti-BACE-1 Antibodies Minimalist synthetic antibody libraries with restricted chemical diversity at the complementary determining regions (CDRs) have been constructed and shown to be effective in obtaining high affinity antibody binders against a variety of proteins as previously described in Fellouse, F. A. et al. *J. Mol. Biol.* 373: 924-940 (2007). A synthetic diversity library, designated as the YSGX library, was used to search for an inhibitory antibody against BACE1 by solution sorting. Panning for binding was carried out for five rounds as described below.

The library for primary sorting, designated as YSGX library, was constructed as previously described using a phagemid for Fab-phage display (pF1359) (Library D in Fellouse, F. A. et al., *J. Mol. Biol.* 373: 924-940 (2007)). The diversity of the library was about $2 \times 10^{10}$.

For affinity maturation, all three CDRL were randomized with fixed CDRH for selected clones derived from the primary sorting. Three types of oligonucleotides were used for randomization. Type I uses the degenerate codon TMC that encodes only Tyr and Ser. Type II uses a custom trimer phosphoramidite mix containing codons for Tyr, Ser, Gly and Trp at equimolar ratios. Type III uses a trimer phosphoramidite mix encoding for 10 amino acid residues in the following molar ratios: Tyr (30%), Ser (15%), Gly (15%), Trp (10%) and Phe, Leu, His, Asp, Pro, Ala, 5% each. A mutation was introduced into the oligonucleotides used for CDR-L3 so that the KpnI site on the original template was silenced upon mutagenesis. The length variation was from 3 to 10 amino acids for CDR-L1, 7 amino acids for CDR-L2, and from 2-10 amino acids for CDR-L3. The oligonucleotides were pooled together properly to make the final set of oligonucleotides, i.e. mix all L1, L2 and L3 oligonucleotides with different length within one type and then mix all three types together as the oligonucleotide set for CDR-L1, CDR-L2 and CDR-L3, respectively. Kunkel mutagenesis was used to replace all CDR-LC positions. After Kunkel mutagenesis (Kunkel, T. A. et al., *Methods Enzymol.* 154: 367-382 (1987)), the DNA was purified and treated with KpnI at 37° C. for 3 h to digest the template DNA. The purified DNA was then subjected to electroporation for library construction.

Selection of Phage Displayed Anti-BACE1 Clones

Biotinylated human BACE-1 (1-457 of SEQ ID NO:49) was used as an antigen for library sorting. For the first round of panning, 20 ng of biotinylated BACE1 was incubated with 1 ml of the library at a concentration of $1 \times 10^{13}$ pfu/ml at 4° C. for 1.5 h. Phage that bound to the target were captured for 15 min with 200 nl Dynabeads® MyOne Streptavidin that had been previously blocked with Blocking buffer (PBS, 0.5% (w/v) bovine serum albumin). Bound phage were eluted with 0.1 M HCl and neutralized immediately with 1 M Tris base. Eluted phage were amplified following the standard protocol as described previously (Sidhu, S. S. et al. *Methods Enzymol.* 328: 333-363 (2000)). The second round was carried out the same as the first round using 10 ng of biotinylated BACE1 incubated with 400 µl of amplified phage. For all subsequent rounds, 2 ng biotinylated BACE1 was incubated with 400 µl of amplified phage. Phage that bound to biotinylated BACE1 were captured for 15 min using Maxisorp Immunoplates (NUNC) that had been previously coated with Neutravidin or Streptavidin (alternatively between rounds) and blocked with Blocking buffer.

After five rounds of selection, phage were produced from individual clones grown in a 96-well format and the culture supernatants were diluted threefold in phosphate-buffered saline (PBS), 0.5% (w/v) bovine serum albumin (BSA) (Sigma-Aldrich, St Louis, Mo.), 0.1% (v/v) Tween 20 (Sigma-Aldrich) (PBT buffer) for use in a phage spot ELISA. The diluted phage supernatants were incubated for 1 h with biotinylated BACE1 that was immobilized on Neutravidin-coated 384-well Maxisorp Immunoplates (NUNC). The plates were washed six times with PBS, 0.05% (v/v) Tween 20 (PT buffer) and incubated 30 min with horseradish peroxidase/anti-M13 antibody conjugate (1:5000 dilution in PBT buffer) (GE Healthcare). The plates were washed six times with PT buffer and twice with PBS, developed for 15 min with 3,3',5,5'-tetramethylbenzidine/ $H_2O_2$ peroxidase substrate (Kirkegaard-Perry Laboratories), quenched with 1.0 M $H_3PO_4$ and the absorbance was read spectrophotometrically at 450 nm.

Figure 3A:
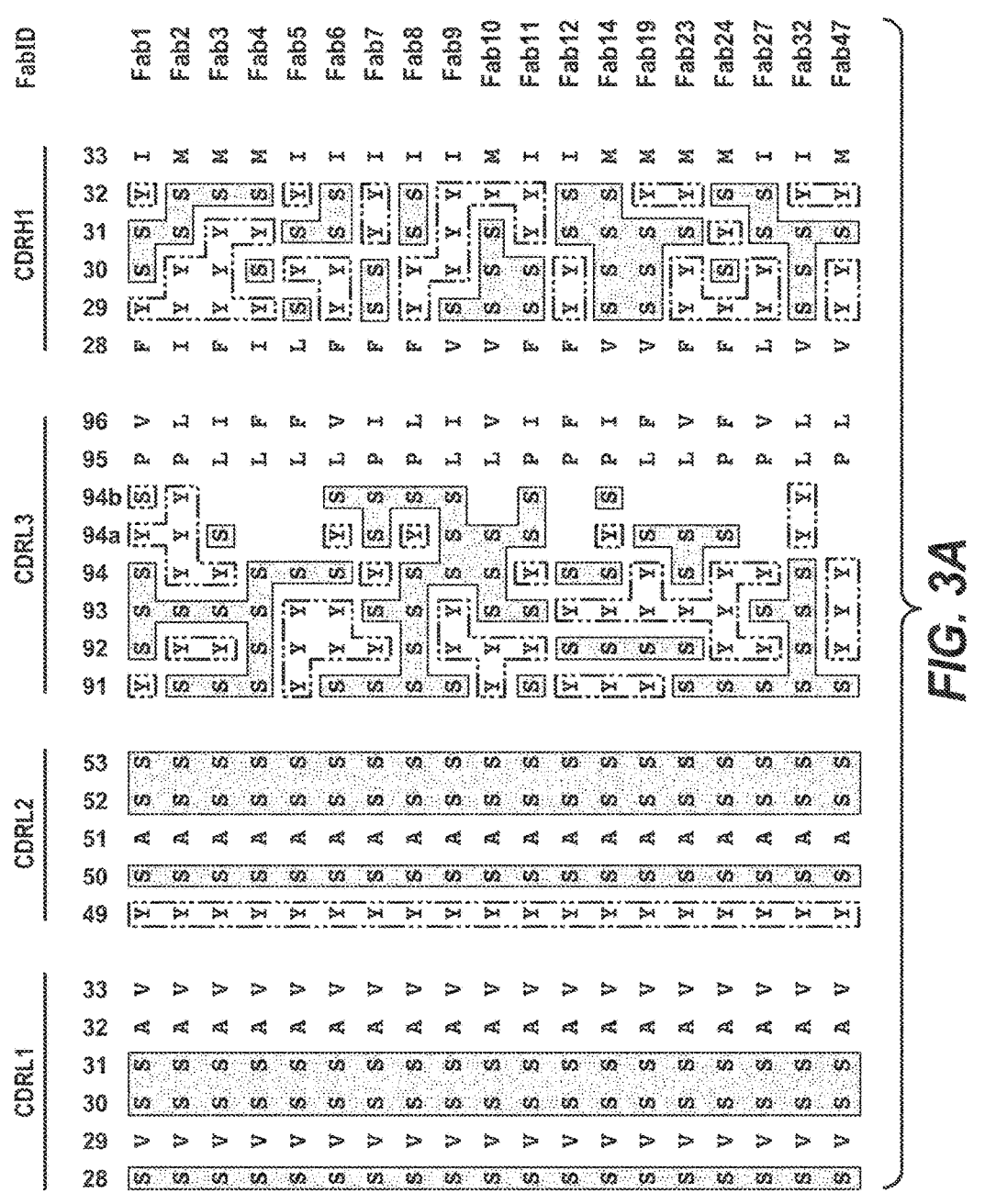
Figure 3B:
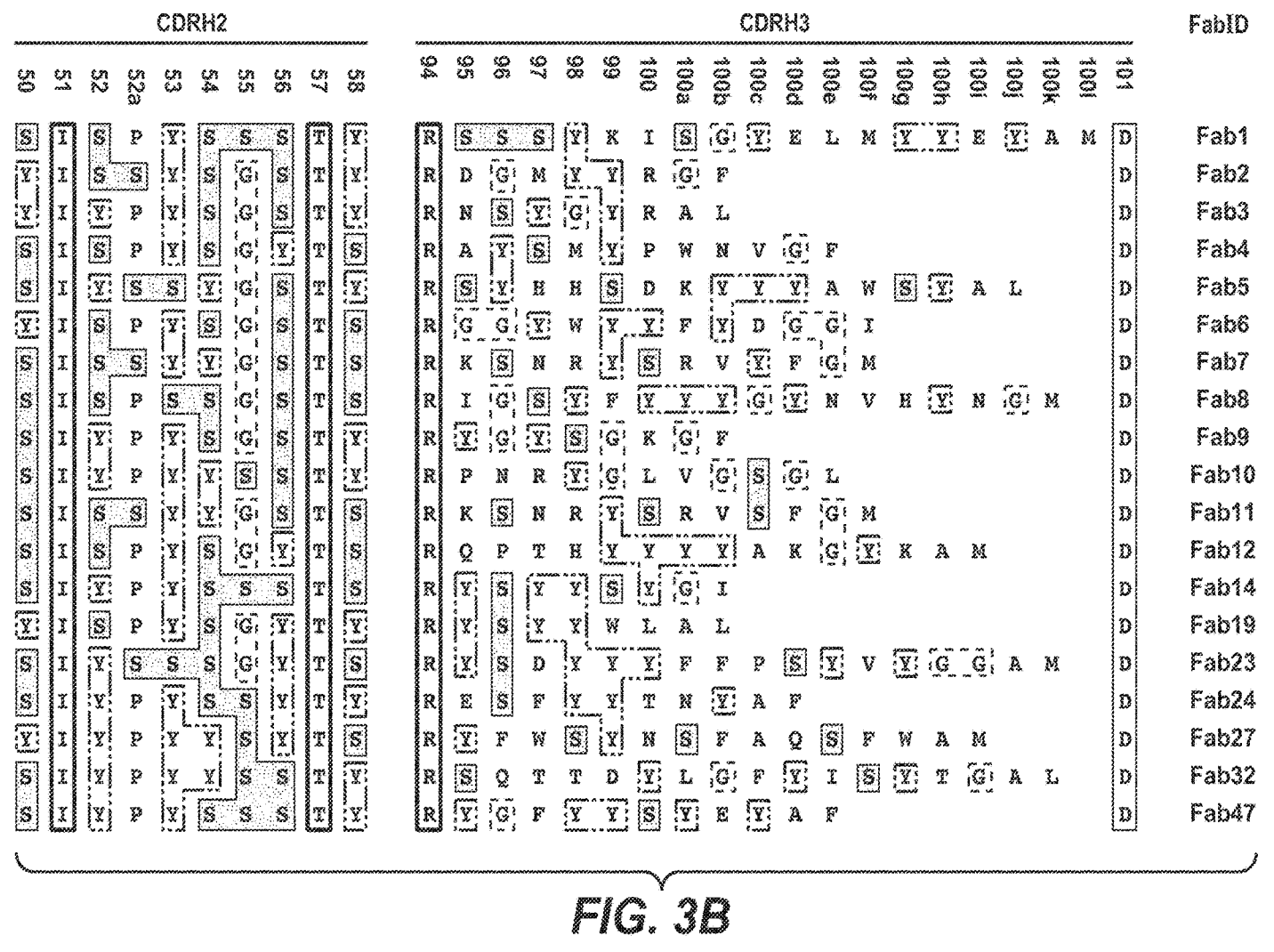

Selection of anti-BACE1 inhibitory clones Panning of the YSGX library resulted in the identification of 18 unique clones which bound BACE1. See FIG. 3. The Fab proteins corresponding to these clones were purified as follows. A stop codon was introduced between the heavy chain and gene 3 on the phagemid encoding the Fab. The resulting phagemid was transformed into *E. coli* strain 34B8. A single colony was grown overnight at 37° C. in 30 ml LB medium supplemented with 50 µg/ml of carbenicilin. The overnight culture (5 ml) was inoculated into 500 ml of complete C.R.A.P. medium supplemented with carbenicilin (50 µg/ml) and grown at 30° C. for 24 h. Fab proteins were purified using protein A agarose beads by standard methods.

Figure 5:
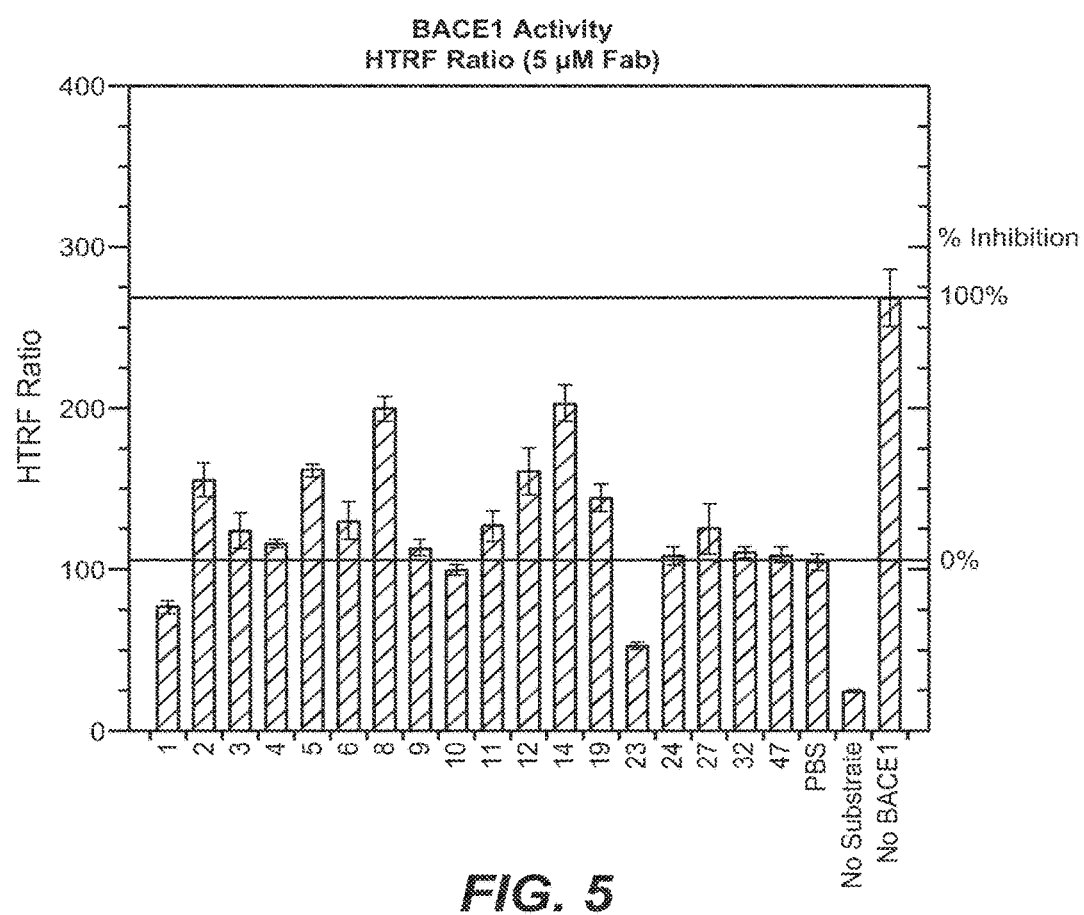
FIG. 5 is a graph showing the activity of BACE1 in an HTRF assay in the presence of anti-BACE1 Fabs identified from the synthetic diversity phage display library, as described in Example 1(B). Lines correspond to 100% activity (0% inhibition) in the presence of BACE1 and substrate (PBS Control) and 100% inhibition in the absence of BACE1.

The purified Fabs were screened for inhibitory activity against BACE1 using an HTRF enzyme activity assay as described above. Fabs 2, 5, 8, 12, 14 and 19 were identified as inhibitors of BACE1 and Fab 23 identified as an activator. See FIG. 5.

Fabs 2, 5, 8, 12, 14 and 19 were further characterized to determine their binding epitope. The panel of purified Fabs for all 6 antibodies was used to compete with the individual Fab-displaying phage bound to plate-captured BACE1 in a phage competition ELISA as described below.

Single colonies (in XL1 blue cells) of the selected clones were picked up and grown in 1 ml 2YT broth supplemented with 50 µg/ml carbenicillin, 10 µg/ml tetracycline and M13KO7 at 37° C. for 2 h. Kanamycin (25 µg/ml) was added to the culture, which continued to grow for 6 h. The culture was transferred to 30 ml 2YT broth supplemented with 50 µg/ml carbenicillin and 25 µg/ml kanamycin and grown at 37° C. overnight. Phage were harvested and purified as previously described (Sidhu, S. S. et al. *Methods Enzymol.* 328: 333-363 (2000)). The purified Fab-displaying phage were serially diluted in PBT buffer and tested for binding to BACE1 immobilized on a plate. A fixed phage concentration that gives 80% of saturation signals was selected for the subsequent competition ELISA. The competition was conducted by incubating the fixed, sub-saturating Fab-displaying phage with serial dilutions of BACE1 for 1 h and then transferred to the BACE1-immobulized plate for 15 min to capture unbound phage. The plate was then washed for 8 times and bound phage were detected by anti-M13-HRP.

Purified Fab 5 was competitive with the binding of BACE1 to phage-displayed Fabs 8 and 12, but not to Fabs 2, 14 and 19. Consistent with this data, purified Fab 8 was competitive with phage-displayed Fabs 5 and 12. Taken together, these data indicate that Fabs 5, 8 and 12 bind to the same or overlapping epitopes on BACE1. Fabs 14 and 19 were also competitive with each other based on the fact that either of these purified Fabs were competitive with either Fab 14- and 19-displaying phage. This suggested that these two antibodies bind to the same or overlapping epitope, which differs from the one(s) for Fabs 5, 8 and 12. In the phage ELISA assay, Fab 2-displaying phage could not be competed off by any of the purified Fab proteins, including Fab 2 itself, suggesting that the binding between Fab 2 and BACE1 was non-specific. Therefore, Fab 2 was excluded as a candidate for affinity maturation.

Affinity Maturation of Anti-BACE1 Inhibitory Clones

To improve the binding affinity of the parent inhibitory antibodies obtained by the initial panning process, new phage libraries were designed that randomized all three CDR-LC of Fabs 5, 8, 12, 14 and 19. These five antibodies were divided into two subgroups based on their different epitopes—Fabs 5, 8 and 12 as group 1 and Fabs 14 and 19 as group 2. Single stranded DNA (ssDNA) for individual clones was purified as templates for library construction. The ssDNA templates of group 1 were pooled together for affinity maturation library 1 (designed as LC-lib1), and group 2 pooled for library 2 (LC-lib2). The chemical diversity was restricted within the randomized CDRs based on the functional capacity of the natural amino acids for molecular recognition. See Birtalan, S. et al. *Mol Biosyst.* 6:1186-1194 (2010). Minimalist diversity (Tyr and Ser binary codon), semi-minimalist diversity (Tyr, Ser, Gly and Trp ternary codon) and additional diversity with 10 amino acids involved were mixed in order to achieve high affinity. Two affinity maturation libraries, LC-lib1 and LC-lib2, were constructed using the same set of oligonucleotide pools to randomize all three CDR-LC simultaneously as described above. For affinity maturation, all three CDR-LC (Complementarity Determining Region—Light Chain) were randomized with fixed CDR-HC (Complementarity Determining Region—Heavy Chain) for selected clones derived from the primary sorting.

Screening of the libraries for affinity maturation of initially obtained antibodies was carried out similarly as described above. The libraries were sorted with biotinylated BACE1 in solution for 3 rounds, which resulted in greater than 100-fold enrichment in binding. For round 1, 2 µg of biotin-BACE1 was incubated with the phage-displayed Fab library. For rounds 2 and 3, 20 nM and 5 nM biotinylated BACE1 was incubated with amplified phage, respectively. Clones (96) from each of the two libraries were screened in a one-point competition ELISA, where 20 nM of BACE1 was used in solution to compete the phage particle from binding to plate-immobilized BACE1 as described below.

A plate immobilized with BACE1 was prepared by capturing 2 µg/ml biotinylated BACE1 for 15 min using a 384-well Maxisorp Immunoplate that was previously coated with 2 µg/ml of Neutravidin at 4° C. for overnight and blocked with Blocking Buffer. The culture supernatants from individual clones grown in a 96-well format were diluted 20-fold in PBT buffer and was incubated with or without 20 nM BACE1 at room temperature for 1 h. The mixture was transferred to the plate with immobilized BACE1 and incubated for 15 min. The plate was washed six times by PT buffer and the bound phage was detected by anti-M13-HRP as described above. The ratio between the ELISA signal from the well in the absence and the presence of BACE1 in solution indicates the affinity of the clone, where higher ratios indicate the higher affinities.

Five clones from LC lib1 had a ratio of >4 between the ELISA signal from the well in the absence of BACE1 to the ELISA signal from the well in the presence of BACE1 and one clone from LC lib2 with ratio >3. Two clones, designated as LC4 and 11, were derived from Fab5; three clones, LC6, LC9 and LC10, from Fab 12, and LC40 from Fab14 (FIG. 6).

Figure 7A:
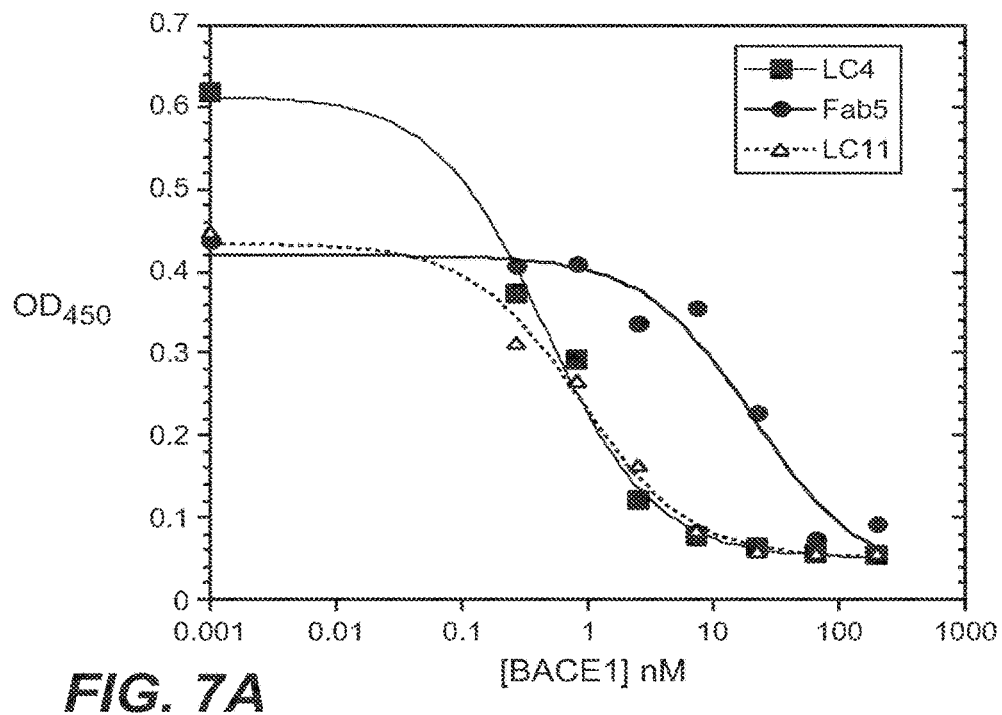
FIGS. 7A-7C contain graphs displaying data from competitive ELISA assays with affinity matured anti-BACE clones as described in Example 1(B). The binding between Fab-displaying phage and BACE1-immobilized on plates was competed with serial dilution of BACE1 in solution.
Figure 7B:
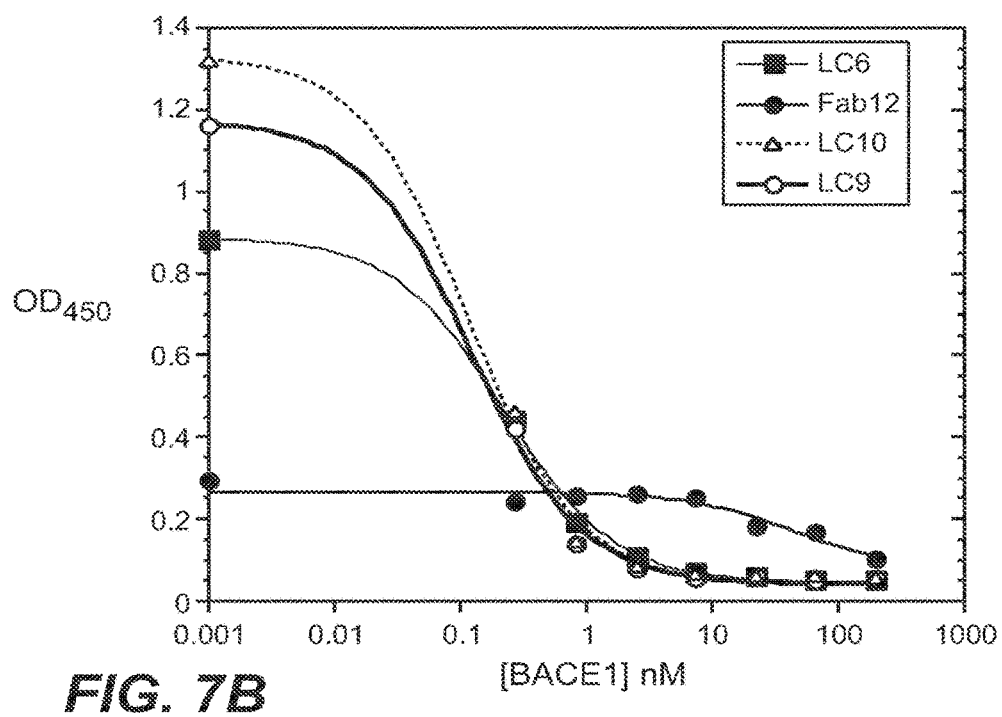
Figure 7C:
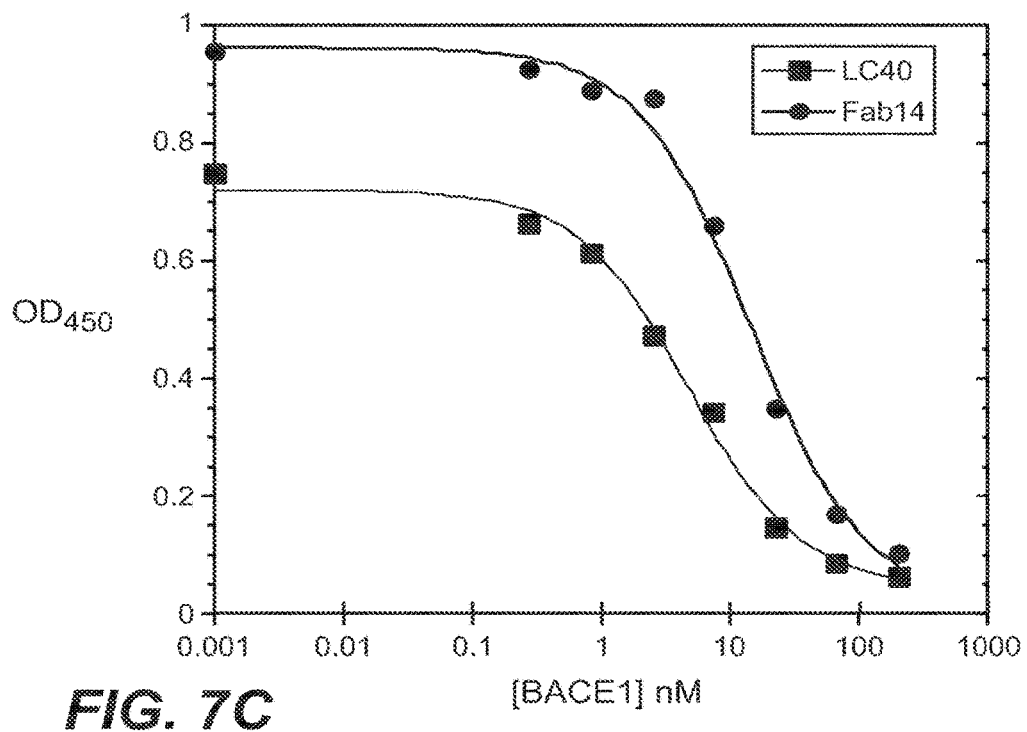

To estimate the affinity of these 6 clones, phage competition ELISAs were performed, as described above, and $IC_{50}$ values were determined (FIG. 7). The $IC_{50}$ values were determined by fitting the data to a four-parameter logistic equation developed by Marquardt (Marquardt, D. W. *SIAM Appl. Math.* 11: 431-441 (1963)) using Kaleidagraph (Synergy Software) and are shown below in Table 2.

TABLE 2

| FabID | IC50 nM | Fold affinity improvement |
|---|---|---|
| Fab5* | 20.7 ± 9.5 | 1 |
| LC4 | 0.46 ± 0.07 | 45 |
| LC11 | 0.88 ± 0.14 | 24 |
| Fab12* | 45.3 ± 31 | 1 |
| LC9 | 0.12 ± 0.02 | 378 |
| LC10 | 0.12 ± 0.01 | 378 |
| LC6 | 0.12 ± 0.02 | 156 |
| Fab14* | 14.3 ± 2.5 | 1 |
| LC40 | 4.7 ± 0.7 | 3 |

*parent

All LC clones indeed showed improved affinity compared to their respective parents. Notably, the introduction of two Trp residues into CDR-L2, improved the affinity of Fab 12 derivatives over 100-fold from the parent.

Figure 8A:
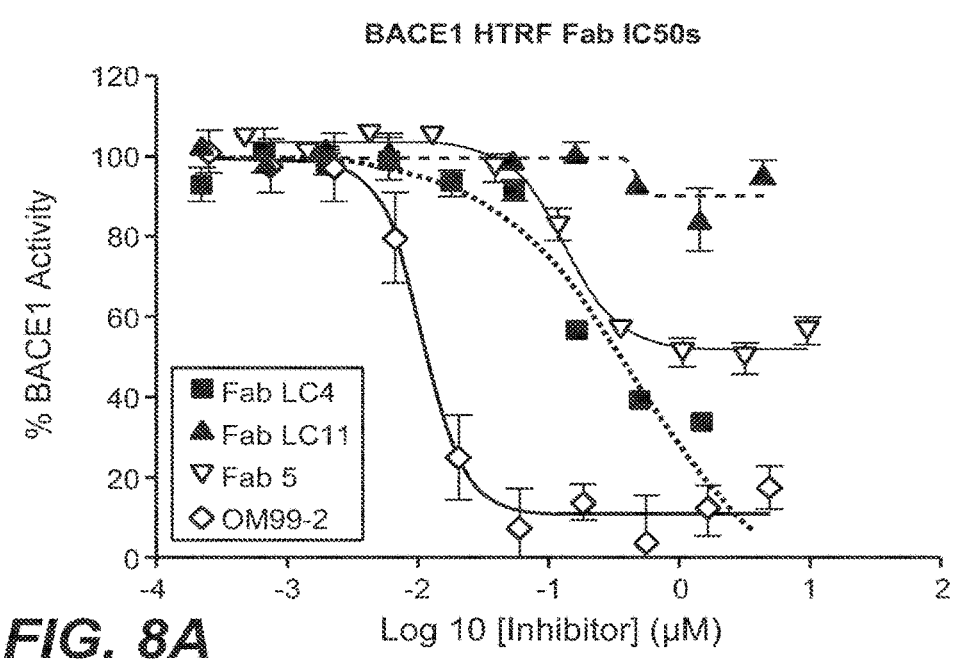
FIGS. 8A-8C depict graphs showing the inhibition of BACE1 with anti-BACE1 Fabs in an HTRF enzyme assay as described in Example 1(B). The inhibition activity of purified Fabs for individual anti-BACE1 clones were measured in an HTRF enzyme assay. OM99-2 (CalBiochem®, catalog #496000), is a synthetic peptide inhibitor for BACE1 and was used as a positive control.
Figure 8B:
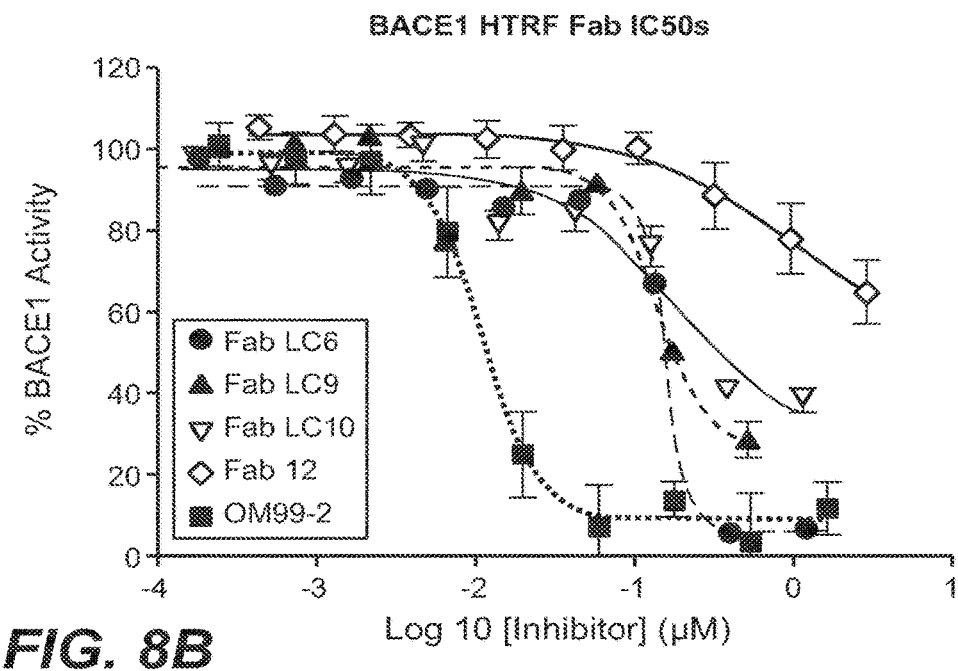
Figure 8C:
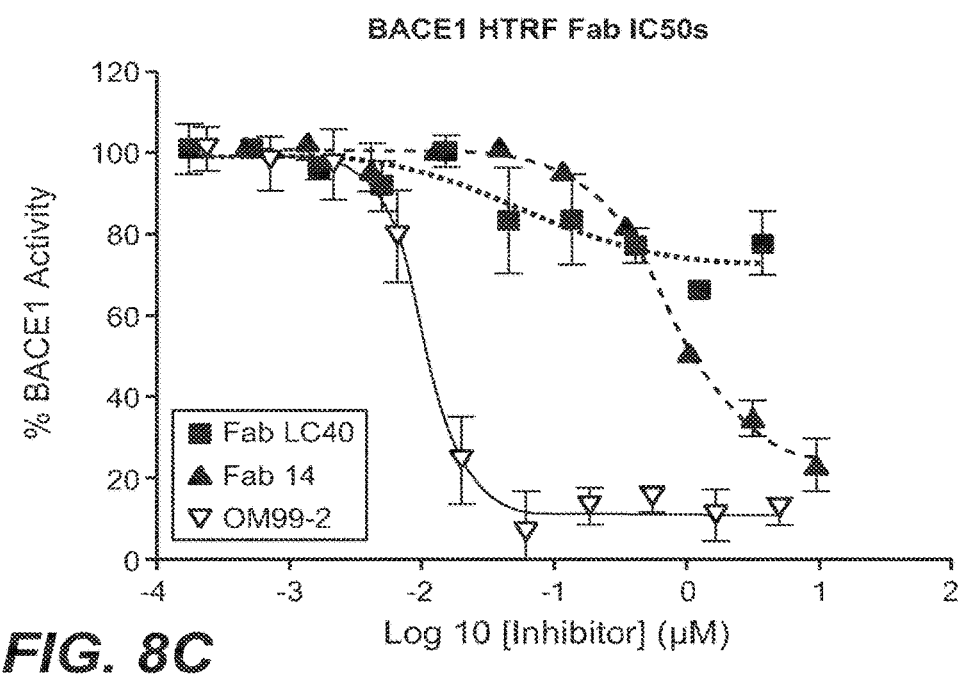

Fab proteins of 6 clones were purified and subjected for HTRF enzyme activity assay, as described above. OM99-2 (CalBiochem®, catalog #496000), a peptide inhibitor of BACE1, was used as a control. For the antibodies with Fab 5 as parent, Fab LC 4 showed significant improved inhibition, whereas LC11 lost inhibition activity. LC 40, derivative from Fab14, also lost its inhibition activity. The affinity improved derivatives of Fab 12, Fabs LC 6, LC 9 and LC10, generally showed approximately 20-fold improvement in their inhibition activity (FIG. 8). Based on this assay, Fab LC 6 was the best inhibitor and showed almost 100% inhibition of the enzyme activity, whereas other Fabs were partial inhibitors, having an extent of inhibition of approximately 60-70% (FIG. 8). The $IC_{50}$ values for the various Fabs tested are shown below in Table 3. The $IC_{50}$ OM99-2 was 11 nM in this assay.

TABLE 3

| Fab ID | IC50 (nM) |
| --- | --- |
| Fab5* | 130 |
| LC4 | 480 |
| LC11 | n.d. |
| Fab12* | n.d. |
| LC9 | 140 |
| LC10 | 180 |
| LC6 | 160 |
| Fab14* | 740 |
| LC40 | n.d. |

*parent

The sequence of the light and heavy chain HVR regions of Fab12 is shown in FIGS. 2(A) and 2(B). The light and heavy chain HVR sequence of three antibodies produced by affinity maturation of Fab 12 are also shown in FIGS. 2(A) and 2(B). Only light chain HVR-L2 displayed variability in these antibodies: HVR-L2: $X_{15}$ Ala Ser $X_{16}$ Leu Tyr Ser (SEQ ID NO: 41), wherein $X_{15}$ is selected from serine, tryptophan and tyrosine and $X_{16}$ is selected from serine and tryptophan. Each of the three heavy chain HVR regions were identical in the four antibodies.

Fabs were cloned as IgG antibodies for use in other applications as follows. The variable domains of light chain and heavy chain of the selected Fabs were cloned into a pRK5-based plasmid with human light chain or heavy chain (human IgG1) constant domain for transient IgG expression in 293T cell or Chinese hamster ovary (CHO) cells. IgG proteins were purified using protein A agarose beads by standard methods.

Example 2: Further Characterization of Anti-BACE1 Antibodies

As described above antibodies were identified in terms of function and epitope binding on BACE1. The parent and affinity matured antibodies were further characterized using the assays described below.

A. Binding Kinetics

The binding kinetics of YW412.8.31 was assessed. Briefly, binding affinities of anti-BACE1 IgGs were measured by surface plasmon resonance (SPR) using a BIAcore™-3000 instrument. YW412.8.31 anti-BACE1 human IgG was captured by mouse anti-human Fc antibody (GE Healthcare, cat# BR-1008-39) coated on CM5 biosensor chips to achieve approximately 100 response units (RU). For kinetics measurements, two-fold serial dilutions (0.98 nM to 125 nM) of human BACE1 ECD or murine BACE1 ECD (amino acids 1-457) was injected in PBT buffer (PBS with 0.05% Tween 20) at 25° C. with a flow rate of 30 μl/min. Association rates ($k_{on}$) and dissociation rates ($k_{off}$) were calculated using a simple one-to-one Langmuir binding model (BIAcore™ Evaluation Software version 3.2). The equilibrium dissociation constant ($K_D$) was calculated as the ratio $k_{off}/k_{on}$. The results of YW412.8.31 binding at pH 7.0 are shown in Table 4.

TABLE 4

Binding kinetics values for anti-BACE1 antibodies as measured by BIAcore™

| ANTIBODY | TYPE OF BACE1 | $K_{ON} (M^{-1}S^{-1})$ | $K_{OFF} (S^{-1})$ | $K_D (M)$ |
| --- | --- | --- | --- | --- |
| YW412.8.31 | Human | $1.1 \times 10^5$ | $3.1 \times 10^{-4}$ | $2.9 \times 10^{-9}$ |
| | | $1.05 \times 10^5$ | $1.39 \times 10^{-4}$ | $1.32 \times 10^{-9}$ |
| YW412.8.31 | Mouse | $1.4 \times 10^5$ | $2.9 \times 10^{-4}$ | $2.1 \times 10^{-9}$ |
| | | $1.01 \times 10^5$ | $1.41 \times 10^{-4}$ | $1.4 \times 10^{-9}$ |
| YW412.8.31 | Guinea pig | $1.0 \times 10^5$ | $2.7 \times 10^{-4}$ | $2.6 \times 10^{-9}$ |

Binding of YW412.8.31 to BACE1 was confirmed at both pH 7.0 and 5.0. This is important as BACE1 is optimally active at acidic pH, presumably in endocytic vesicles and/or the trans-Golgi network.

B. In Vitro Inhibition Assays

Additionally, the ability of antibodies to modulate BACE1 proteolytic activity on certain BACE substrates was assessed in vitro using two activity assays: the HTRF assay and a microfluidic capillary electrophoretic (MCE) assay with the human recombinant extracellular domain of BACE1.

The affinity matured YW412.8.31 anti-BACE1 antibody was tested in a HTRF assay as described in Example 1. A synthetic peptide inhibitor of BACE1, 0M99-2 (CalBiochem®, Catalog #496000), a small molecule inhibitor of BACE1 (β-Secretase inhibitor IV, CalBiochem®, Catalog #5657688) and an IgG antibody which does not bind to BACE1 were used as controls. See FIG. 9 (Panel A) (long peptide). Additionally, reactions using a short FRET peptide (Rh-EVNLDAEFK-quencher (SEQ ID NO:54), Invitrogen) were also performed identically to the HTRF reactions. The resulting fluorogenic products from the control reactions were measured as above, but at an excitation wavelength of 545 nm and an emission wavelength of 585 nm. Obtained data were analyzed using GraphPad Prism 5™ (LaJolla, Calif.). See FIG. 9 (Panel A) (short peptide).

The MCE assay reactions were carried out in a final volume of 20 μL per well in a 384-well microplate. A standard enzymatic reaction, initiated by the addition of 10 μL 2× substrate to 5 μL of 4× enzyme and 5 mL of 4× compound, containing 12 nM human BACE1 extracellular domain, 1 mM amyloid precursor protein beta secretase active site peptide (FAM-KTEEISEVNLDAEFRWKK-CONH$_2$ (SEQ ID NO:55)), 50 mM NaOAc pH 4.4 and 0.1% CHAPS. The same reaction conditions were used for the extracellular domain of human BACE2 enzyme (5 nM) and the extracellular domain of Cathepsin D (6 nM, Calbiochem®). After incubation for 60 minutes at ambient temperature, the product and substrate in each reaction were separated using a 12-sipper microfluidic chip analyzed on an LC3000® (both, Caliper Life Sciences). The separation of product and substrate was optimized by choosing voltages and pressure using the manufacturer's optimization software. The separate buffer contained 100 mM HEPES pH 7.2, 0.015% Brij-35, 0.1% coating reagent #3, 10 mM EDTA and 5% DMSO. The separation conditions used a downstream voltage of −500V, an upstream voltage of −2250V and a screening pressure of −1.2 psi. The product and substrate fluorescence was excited at a wavelength of 488 nm and detected at a wavelength of 530 nm. Substrate conversion was calculated from the electropherogram using HTS Well Analyzer software (Caliper Life Sciences).

The results from the HTRF and MCE assays, using the YW412.8.31 antibody, are shown in FIG. 9. The observed $IC_{50}$ of this antibody in the long peptide assay was 1.7 nM, with a maximal inhibition reaching 77%. Additionally, the YW412.8.31 antibody had an $IC_{50}$ in the short peptide assay of 17 nM. Further, the YW412.8.31 anti-BACE1 antibody inhibited BACE1 activity with an $IC_{50}$ of 80 pM in the microfluidic capillary electrophoresis assay, and did not inhibit human BACE2 or cathepsin D, a lysosomal aspartyl protease. SPR analysis of the YW412.8.31 antibody also confirmed that the antibody does not bind BACE2, the most highly related protease to BACE1. These data together indicate that the YW412.8.31 antibody is a potent and selective BACE1 antagonist. Further characterization of this antibody was performed to better understand its function.

C. Cell-Based Inhibition Assays

To determine whether the observed in vitro inhibitory action of the anti-BACE1 antibodies on APP processing was also present in a cellular context, in vivo studies were performed. The ability of the antibodies to inhibit $A\beta_{1-40}$ production in 293-HEK cells stably expressing wild-type human amyloid precursor protein was assessed as follows. 293-APP$^{WT}$ cells were seeded overnight at a density of $3\times10^4$ cells/well in a 96-well plate. 50 nl of fresh media (DMEM+10% FBS) containing an anti-BACE1 antibody or a control IgG1 antibody was incubated with the cells for 24 hours at 37° C. A tricyclic small molecule BACE1 inhibitor (BACE1 SMI) was also used as a control ((Compound 8e—Charrier, N. et al. *J. Med. Chem.* 51:3313-3317 (2008)). The cellular media was harvested and assayed for the presence of $A\beta_{1-40}$ using a $A\beta_{1-40}$ HTRF® assay (CisBio) according to the manufacturer's instructions. $A\beta_{1-40}$ values were normalized for cell viability, as determined using the CellTiter-Glo Luminescent Cell Viability Assay (Promega). Experiments were performed at least three times, and each point in each experiment was repeated in duplicate. Data was plotted using a four-parameter non-linear regression curve-fitting program (Kaleidagraph, Synergy Software).

Similar studies were also performed in dorsal root ganglia, cortical neurons and hippocampal neurons isolated from mice. Briefly, dissociated neuronal cultures were prepared from E13.5 dorsal root ganglia (DRG), E16.5 cortical neurons and E16.5 hippocampal neurons. Neurons were grown for five days in vitro. Fresh media containing YW412.8.31 anti-BACE antibody or control IgG1 was incubated with the neurons for 24 hours. Media was harvested and assayed for the presence of $A\beta_{40}$ using the MSD® Rodent/Human (4G8) A1340 Ultrasensitive kit according to the Manufacturer's instructions. $A\beta_{40}$ values were normalized for cell viability, as determined using the CellTiter-Glo Luminescent Cell Viability Assay (Promega). The experiment was performed at least three times, and each point was repeated in duplicate. Data was plotted using a four-parameter non-linear regression curve-fitting program (Kaleidagraph, Synergy Software).

Figure 10:
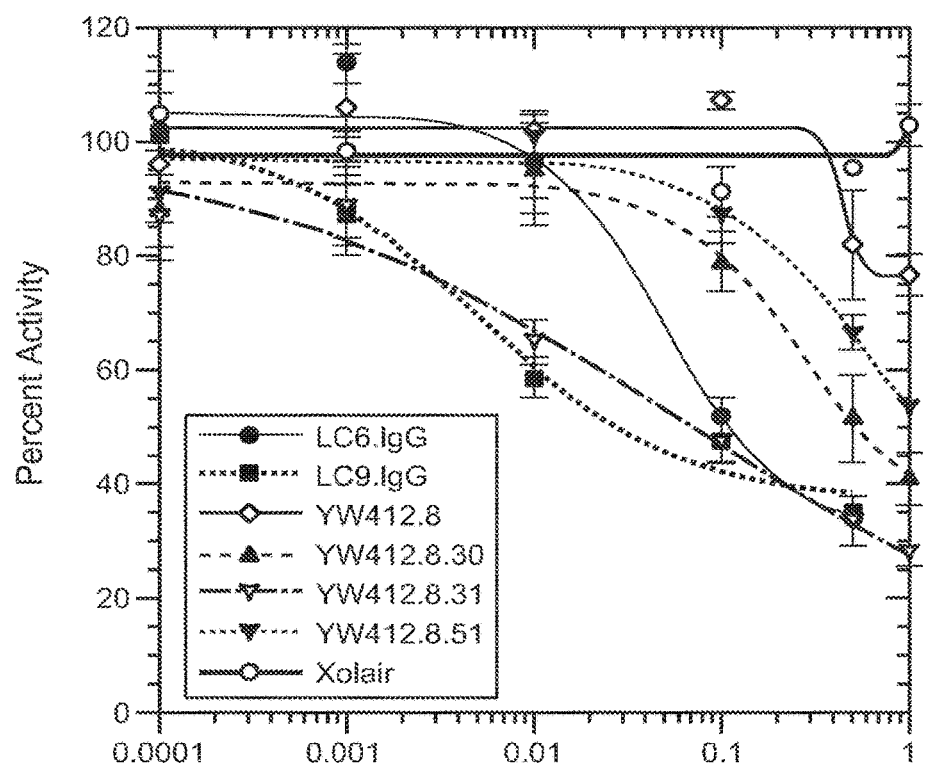
FIG. 10 depicts the results of experiments performed with various anti-BACE1 antibodies (LC6, LC9, YW412.8, YW412.8.30, YW412.8.31 and YW412.8.51) on the processing of recombinant amyloid precursor protein (APP) in 293-HEK cells, as described in Example 2(C). An IgG antibody which does not bind BACE1 (Xolair®) was used as a control.
Figure 11A:
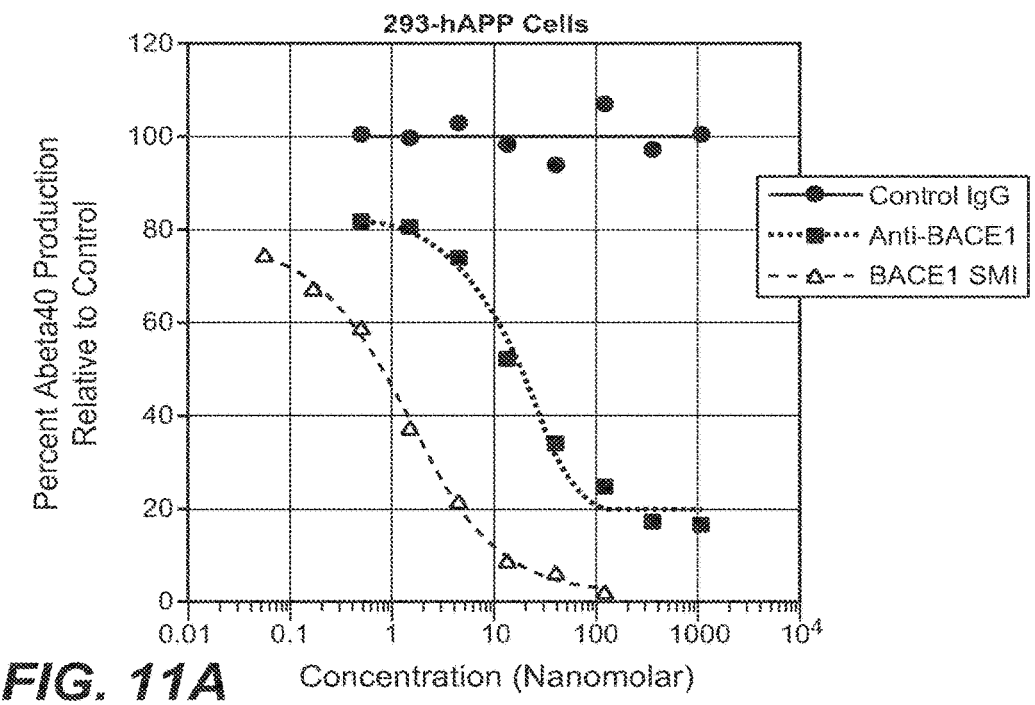
FIGS. 11A-11D provide graphs illustrating the effects of the YW412.8.31 anti-BACE1 antibody on processing of recombinant or endogenous amyloid precursor protein (APP), as described in Example 2(C).
Figure 11B:
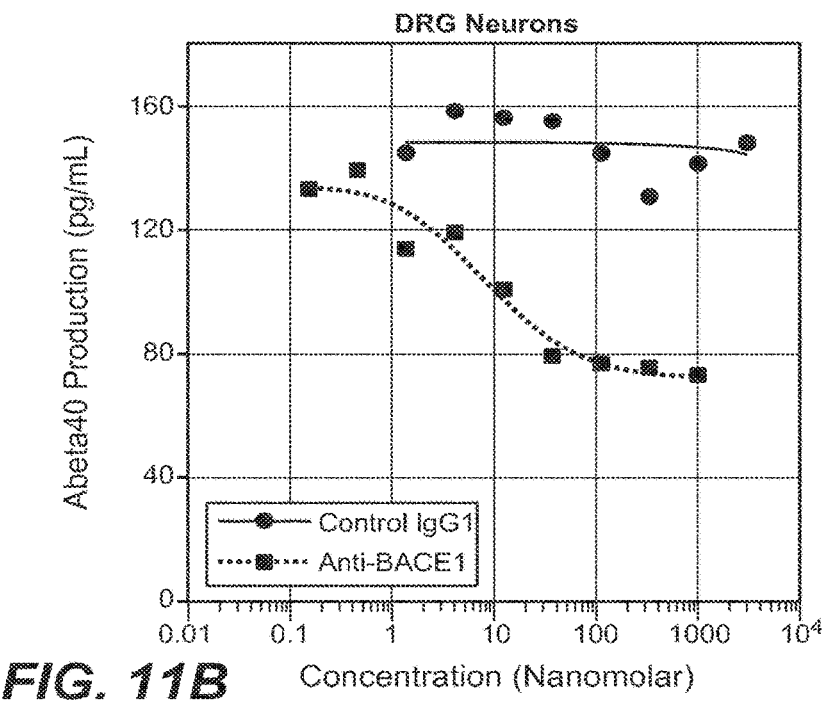
Figure 11C:
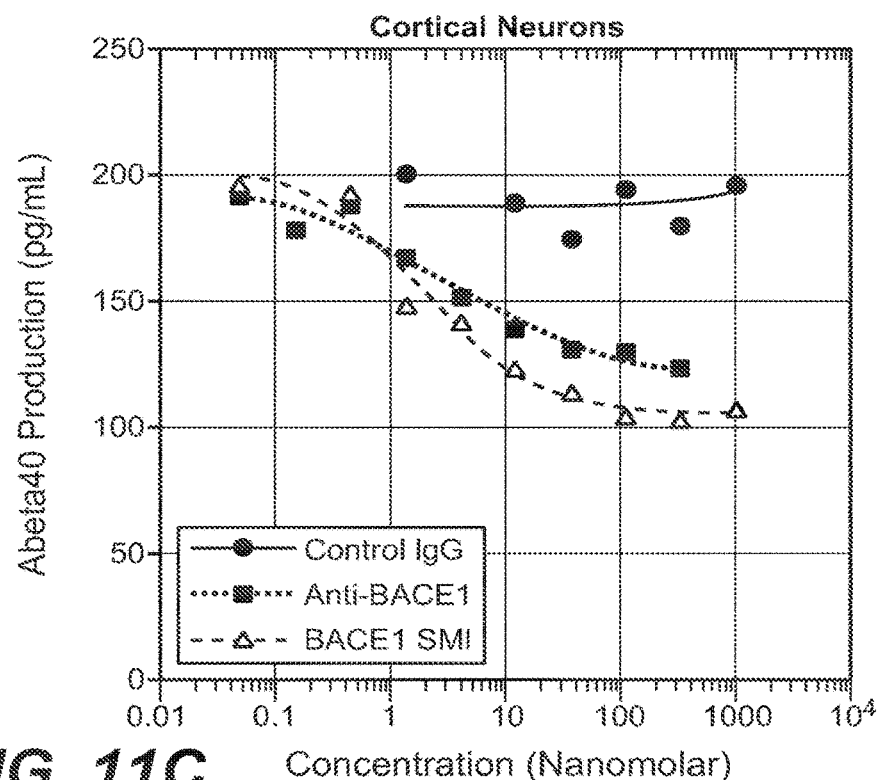
Figure 11D:
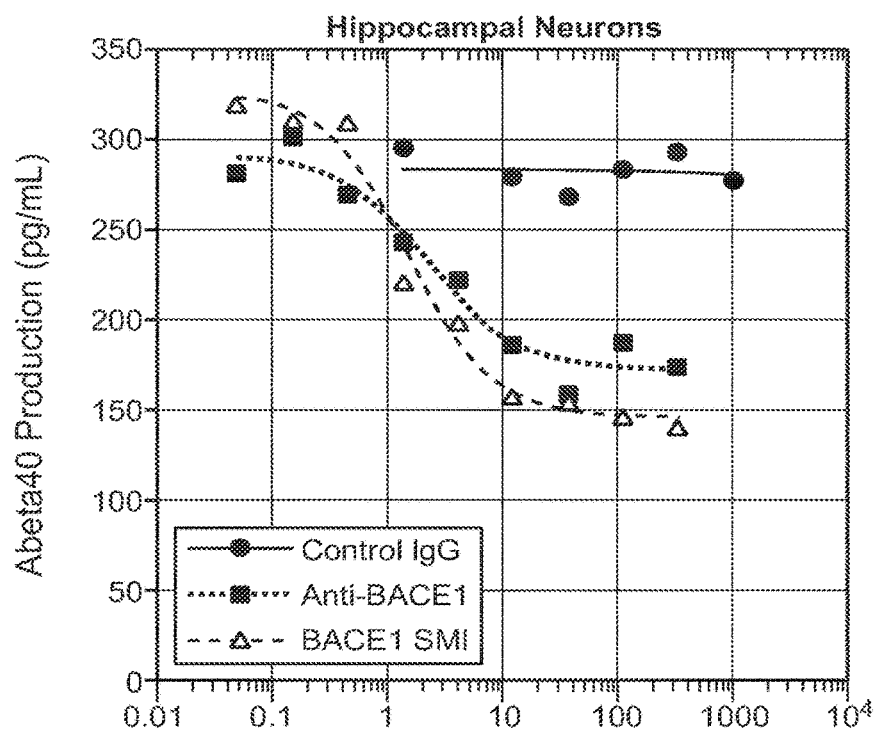

All anti-BACE1 antibodies tested (LC6, LC9, YW412.8, YW412.8.30, YW412.8.31 and YW412.8.51) inhibited $A\beta_{1-40}$ production in APP-expressing 293 cells as compared to a non-BACE1 IgG antibody inhibitor (Xolair®). See FIG. 10.

As shown in FIG. 11, the YW412.8.31 anti-BACE1 antibody inhibited $A\beta_{1-40}$ production in APP-expressing 293 cells to a similar extent as the BACE1 SMI control, with an $IC_{50}$ of 17 nM and a maximum reduction of ~90%. A similar result was obtained in DRG neurons, with about a 50% reduction in $A\beta_{40}$ production at the highest concentrations of YW412.8.31, and an $IC_{50}$ of 8.4 nM. The YW412.8.31 anti-BACE1 antibody also inhibited $A\beta_{40}$ production in cortical and hippocampal neurons with an $IC_{50}$ of 2.3-2.6 nM. These findings indicate that the anti-BACE1 antibodies functioned similarly on cells as previously observed in vitro. Furthermore, the YW412.8.31 antibody appears to show the best potency in neurons of the CNS.

D. Intracellular Localization of Anti-BACE1 Antibody

BACE1 is known to be expressed intracellularly, particularly in the Golgi. To ascertain whether or not YW412.8.31 interacts with BACE1 in an intracellular environment, internalization studies were performed. One set of neuronal cultures was prepared from E13.5 dorsal root ganglia (DRG) explants, and a second set of neuronal cultures was prepared from E16.5 dissociated cortical neurons from BACE1+/+ or BACE1−/− mice and cultured for 24 or 72 hours, respectively, at 37° C. Media containing 0.5 μM YW412.8.31 anti-BACE1 antibody was added to the cultures for time periods varying from 30 minutes to 2 hours, and incubated at either 4° C. or 37° C. Unbound antibody was washed out thoroughly with PBS after treatment. Cultures were fixed with 4% paraformaldehyde for 20 minutes at room temperature, and selected samples were also permeabilized with 0.1% Triton X-100. Bound antibody was detected using a secondary Alexa 568-conjugated anti-Human IgG1 antibody (Molecular Probes) according to the manufacturer's directions.

Figure 12A:
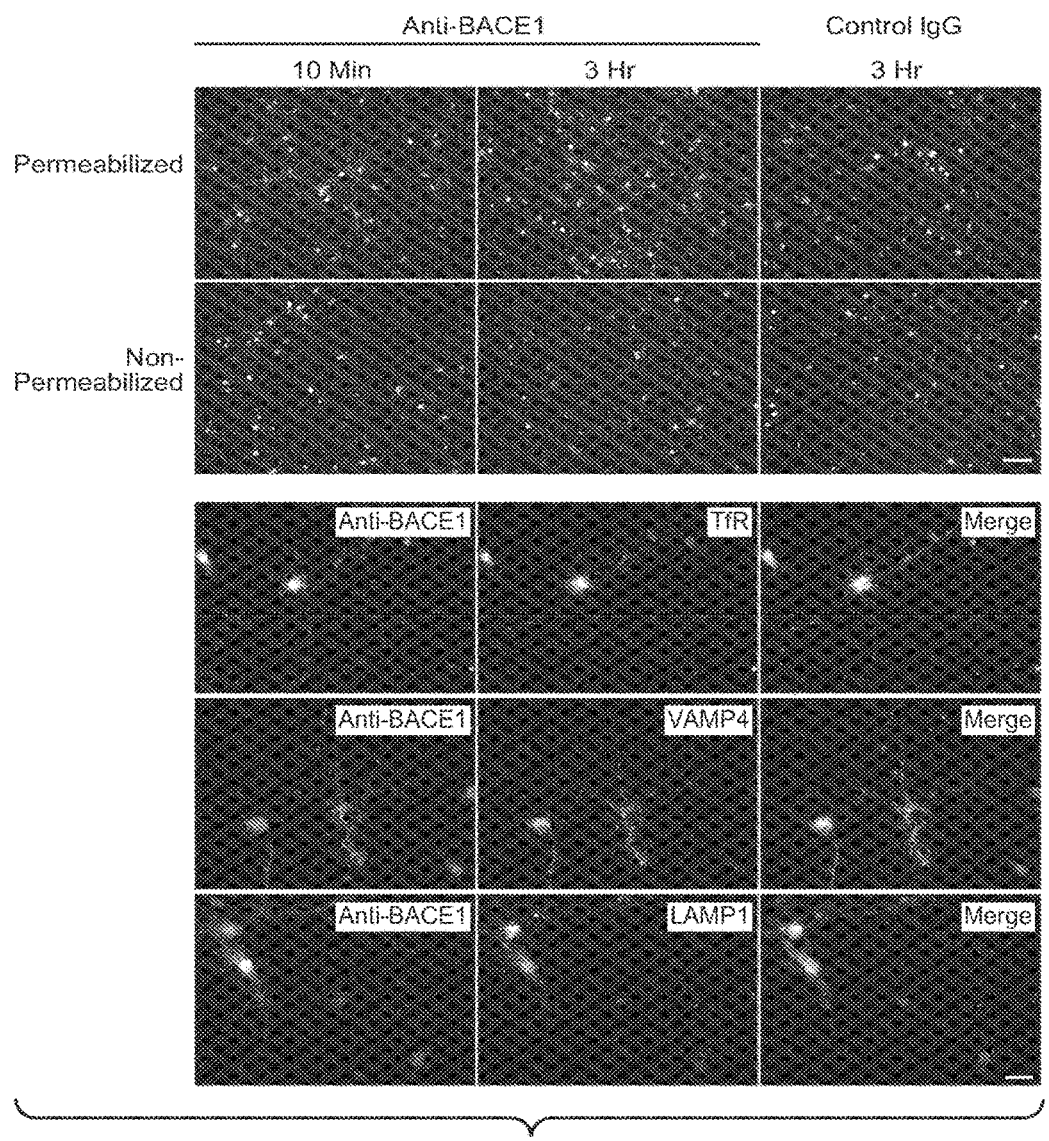
FIGS. 12A-12C provide images of YW412.8.31 anti-BACE1 antibody uptake into primary mouse neurons, as described in Example 2(D).
Figure 12B:
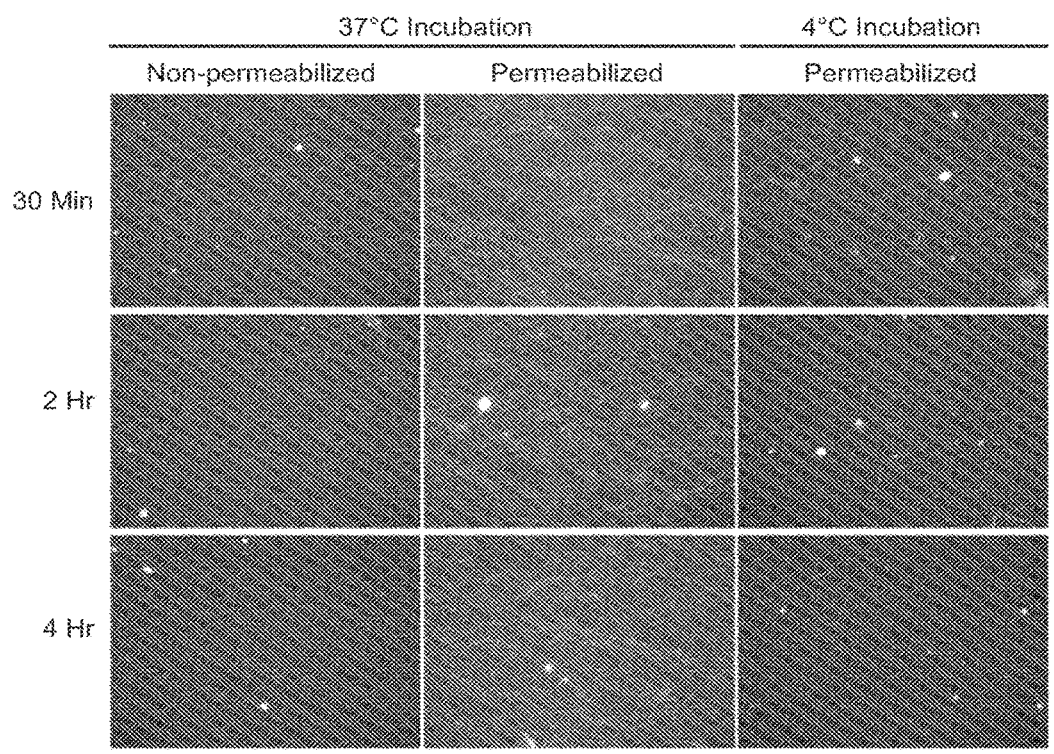
Figure 12C:
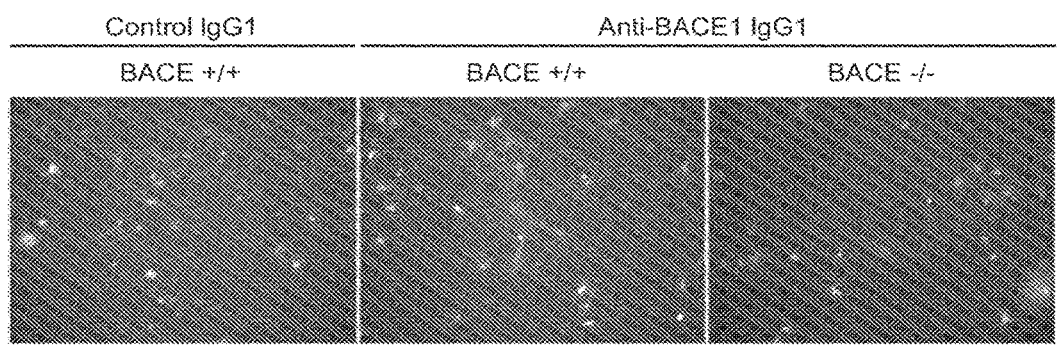

The majority of antibody signal was found to be internalized in the high temperature samples. As can be seen FIG. 12(B), BACE1 can be detected intracellularly in DRG axons at 37° C. when the cells are permeabilized to allow for detection of YW412.8.31 anti-BACE1 antibody with the secondary antibody. Conversely, when DRGs are cold incubated at 4° C. to prevent internalization, or when the cells are not permeabilized to allow for intracellular detection of YW412.8.31, very little BACE1 is detected at the cell surface. Internalization of the antibody into neurons was dependent on BACE1 binding, because it was detectable only in cortical neurons from BACE1+/+ animals, but not neurons from BACE1−/− animals (compare center and right panels of FIG. 12(C)).

Additionally, mouse cortical neurons were cultured in the presence of YW412.8.31 anti-BACE1 antibody or a control IgG for 10 minutes or 3 hours, after which the antibody was detected by immunostaining Neuronal cultures were prepared from E15.5 dissociated cortical neurons, and cultured for 14 DIV. Media containing 1 μM YW412.8.31 was added to cultures for 10 minutes to 3 hours, and incubated at 37° C. Unbound antibody was washed out thoroughly with HBSS after treatment. Cultures were fixed with 2% paraformaldehyde for 10 minutes at RT, and then either permeabilized with 0.1% Triton X-100, or not. Bound antibody was detected using an Alexa 568-conjugated anti-Human IgG1 secondary antibody (Molecular Probes). YW412.8.31 localization was analyzed in non-permeabilized cells, to see how much was bound on the surface of cells, as well as in permeabilized cells to see how much antibody was internalized. The majority of antibody signal detected was localized intracellularly, with little antibody staining observed on the cell surface (FIG. 12(A)). Internalization was evident following only 10 minutes of YW412.8.31 treatment, suggesting that the antibody is actively taken up by early endosomes. Much of the YW412.8.31 signal was punctate indicating it was likely contained within vesicles.

To better identify the subcellular compartments to which YW412.8.31 was localized, we co-stained with markers of different vesicular compartments: early endosomes (transferrin receptor, TfR), trans-golgi network (TGN) (VAMP4), and lysosome (LAMP1). Cells were co-stained with anti-TfR (Novus, Cat#NB100-64979), anti-VAMP4 (Novus, Cat#NB300-533) or anti-LAMP1 (BD Pharmingen, Cat#553792). YW412.8.31 immunoreactivity co-localized with markers for early endosomes and TGN, but not lysosomes (FIG. 12(A)). This pattern is consistent with antibody localizing to compartments where BACE1 is active.

Example 3: Anti-BACE1 Antibody Binding Site Characterization

Further studies were performed to identify the binding site of certain anti-BACE1 antibodies to human BACE1. In one set of experiments, the binding of the antibodies to BACE1 (hBACE1) was assessed in the presence or absence of known active site or exosite BACE1 binding peptides to determine which antibodies demonstrated competitive binding. In a second set of experiments, an anti-BACE1 Fab was co-crystallized with the human BACE1 extracellular domain to determine the three-dimensional binding site.

A. Competitive Binding

As an indirect method of determining the binding site on BACE1 of the anti-BACE1 antibodies of the invention, a competitive ELISA was performed. Briefly, antibody YW412.8 IgG (1 µg/ml) was coated onto NUNC 96 well Maxisorp immunoplates overnight at 4° C. and blocked at room temperature for 1 hour with blocking buffer PBST (PBS and 1% BSA and 0.05% Tween 20). Serial dilutions of anti-BACE1 antibody YW412.8 or an hBACE1 binding peptide were incubated with a predetermined amount of biotinylated hBACE1 and incubated at room temperature for 60 minutes. The serial dilutions were then added to a YW412.8-coated plate and incubated at room temperature for 30 minutes. Subsequently, the plates were washed with wash buffer (PBS with 0.05% T-20) and developed by the addition of streptavidin labeled with horseradish peroxidase (HRP) for 30 minutes at room temperature. The plates were then washed and developed with tetramethylbenzidine (TMB) substrate. HRP-conjugated streptavidin binding to captured biotinylated hBACE1 was measured at a wavelength of 630 nm using standard techniques.

To determine the optimal concentration of biotinylated target protein used for the above competition ELISA assay, NUNC 96 well Maxisorp immunoplates were coated and blocked as described above. Serial dilutions of biotinylated target were incubated with antibody-coated plates for 30 min at room temperature. The plates were then washed with PBST, followed by incubation with horseradish peroxidase conjugated strepavidin for 30 minutes at room temperature. Detection of binding signal was as described as above. Data was plotted using a four-parameter non-linear regression curve-fitting program (Kaleidagraph, Synergy Software). The sub-saturating concentration of biotinylated hBACE1 was determined from the curve fitting and applied to the competition ELISA from above.

Figure 13:
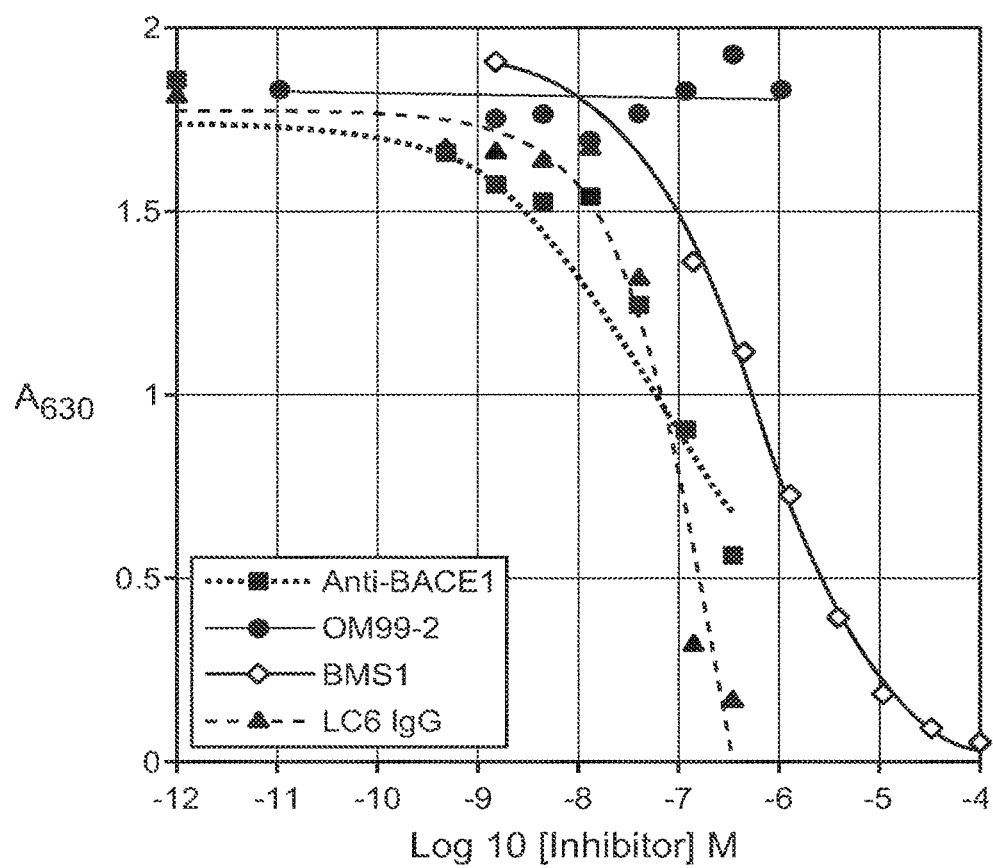
FIG. 13 provides a graphical representation of ELISA results from Example 3(A), comparing the competitive binding of YW412.8 anti-BACE1 antibody, with itself, another anti-BACE1 antibody (LC6), an active-site BACE1 binding peptide (OM99-2 (CalBiochem®, catalog #496000)) and an exosite BACE1 binding peptide (BMS1) (Peptide 1 in Kornacker et al., *Biochemistry* 44:11567-11572 (2005)).

As expected, YW412.8 competed with itself for binding to hBACE1 (FIG. 13). No competition was observed between YW412.8 and an active site inhibitor peptide OM99-2 (CalBiochem®, catalog #496000). Competition was observed between the LC6 and YW412.8 anti-BACE1 antibodies and a known exosite binding peptide, BMS1 (Peptide 1 from Kornacker et al., *Biochemistry* 44:11567-11572 (2005)). Combined, these results suggest that YW412.8 binds at a BACE1 exosite different from the BACE1 active site for APP cleavage. The shape of the curves in FIG. 13 suggests that YW412.8, LC6 and BMS1 may have overlapping binding sites on BACE1.

B. Crystal Structure

To better understand the interaction of the YW412.8 antibody with BACE1, the YW412.8.31 Fab was co-crystallized with the extracellular domain of human recombinant BACE1 extracellular domain.

Protein Expression and Purification

Protein expression and purification of BACE1 (amino acids 57-453 of SEQ ID NO:49) DNA with C-terminal His6 tag (SEQ ID NO: 210) was synthesized by Blue Heron, cloned into pET29a(+) vector (Novagen), and transformed into BL21(DE3) cells (Invitrogen). Expression was performed at 37° C. for 4 hours with 1 mM isopropyl β-D-1-thiogalactopyranoside (IPTG) induction. Cells were lysed with microfluidizer and inclusion bodies (containing BACE1) were isolated and washed two times with TE (10 mM Tris pH8.0 and 1 mM ethylenediaminetetraacetic acid (EDTA)) buffer. Protein solubilization was performed using 7.5 M urea, 100 mM AMPSO pH 10.8 and 100 mM β-mercaptoethanol (BME) at room temperature for 2 hours before centrifugation at 12,000 rpm for 30 min. The supernatant was then diluted with 7.5 M urea, 100 mM AMPSO pH 10.8 to achieve an $OD_{280}$ of about 1.5-2.0. Protein refolding was performed by first diluting the solubilized BACE1 1:20 in cold water, then gently stirring the sample at 4° C. for 3 weeks to allow refolding to take place. Purification of refolded BACE1 involved 3 column chromatography steps. First, BACE1 was loaded onto a 50 ml Q sepharose Fast Flow (GE Healthcare) column pre-equilibrated with 20 mM Tris pH 8.0 and 0.4 M urea, and was eluted with a salt gradient of 0-0.5 M NaCl. Peak fractions were pooled, diluted 5 fold with 20 mM Tris pH 8.0 buffer, and loaded onto a Source™ 15Q column (GE Healthcare). A gradient of 0-0.3 M NaCl was used to elute BACE1. Fractions containing BACE1 protein were pooled, concentrated and purified further on a Superdex™ S75 column (GE Healthcare) in 25 mM Hepes pH 7.5, 150 mM NaCl.

The YW412.8.31 Fab was expressed in *E. coli* and the cell paste was thawed in PBS, 25 mM EDTA and 1 mM PMSF. The mixture was homogenized, passed twice through a microfluidizer, and centrifuged at 12,000 rpm for 60 min. The supernatant was then loaded onto a Protein G column at 5 ml/min. The column was washed with PBS to base line and the protein was eluted with 0.58% acetic acid. Fractions containing the YW412.8.31 Fab were pooled and loaded onto a SP-sepharose column equilibrated with 20 mM MES, pH 5.5, and the Fab was eluted with a salt gradient of 0 to 0.25 M NaCl. The Fab was further purified on a Superdex™ S75 column in 25 mM Hepes pH 7.5 and 150 mM NaCl.

Crystallization

Purified BACE1 protein (amino acids 57 to 453 of SEQ ID NO:49) was mixed with purified YW412.8.31 Fab at a 1:1.5 molar ratio (excess of Fab). The complex was incubated for 1 hour on ice and purified on a S200 26/60 gel filtration column (GE Healthcare) to separate it from the excess Fab. The complex was then concentrated to 15 mg/ml. Crystallization was done by the sitting drop vapor diffusion method with 1 µl of the BACE1/Fab complex solution mixed with 1 µl of well solution containing 20% PEG 4000, 0.1M Tris pH 8.5 and 0.2M sodium acetate. The crystallization drops were then incubated at 19° C. Crystals appeared after 4 days and continued to grow for 2 more days. The crystals were then harvested and flash frozen in a cryo-protective solution containing mother liquor and 20% glycerol.

Data Collection and Structure Determination

The diffraction data were collected using a monochromatic X-ray beam (12658.4 eV) at the Stanford Synchrotron Radiation Facility (SSRL) beam line 7-1. The X-ray detection device was an ADSC quantum-315 CCD detector placed 430 mm away from the crystal. Rotation method was applied to a single crystal for collection of the complete data set, with 0.5° oscillation per frame and total wedge size of 180°. The data was then indexed, integrated, and scaled using program HKL2000® (HLK Research, Inc.).

The structure was solved using the molecular replacement (MR) method with the program Phaser (Read, R. J., *Acta Cryst. D*57:1373-1382 (2000)). Matthews' coefficient calculation results indicated each asymmetric unit was composed of one BACE1/Fab complex and 48% solvent. Therefore the MR calculation was directed to search for one set of three subunits including the N- and C-domains of the Fab, and the BACE1 extracellular domain. The N- and C-terminal Fab domains were searched separately to allow flexible elbow angle. The search models of Fab subunits were derived from the crystal structure of HGFA/Fab complex (PDB code: 2ROL, Wu, Y. et al. *Proc. Natl. Acad. Sci. USA* 104:19784-19789 (2007)). The search model of BACE1 is from the published BACE1 structure PDB code: 1FKN (Hong, L. et al. *Science* 290:150-153 (2000)). Significant conformational changes take place at the BACE1/Fab interface. Manual rebuilding was done with the program COOT (Crystallographic Object-Orientation Toolkit) (Emsley & Cowtan, *Acta. Cryst. D* 60:2126-2132 (2004)). Structure refinement was carried out iteratively with the program REFMAC5 (Murshudov, G. N., et al., *Acta Cryst. D* 53:240-255 (1997)) and PHENIX (Python-based Hierarchical Environment for Integrated Xtallography) (Adams, P. D. et al. *Acta. Cryst. D* 66:213-221 (2010)) using the maximum likelihood target functions, to achieve a final R factor of 0.221 and an $R_{free}$ of 0.274. Structure refinement statistics are shown in Table 5.

TABLE 5

Crystallography Data Statistics

| Data collection | |
| --- | --- |
| Space group | $P2_1$ |
| Unit cell | a = 46.1 Å, b = 75.5 Å, c = 112.0 Å, a = 90° b = 99.8° g = 90° |
| Resolution | 30-2.8 Å |
| Total number of reflections | 64939 |
| Completeness | 97.9% (84.4%)[2] |
| Redundancy | 3.5 (2.5) |
| I/σ | 10.8 (2.0) |
| Rsym[1] | 0.112 (0.366) |
| Refinement | |
| Resolution range | 30-2.8 Å |
| Rcryst[3]/Rfree[4] | 0.221/0.274 |
| Free R test set size | 5% of observed reflections |
| Non-hydrogen atoms | 6324 |
| Water molecules | 94 |
| Average B, Overall | 37.3 |
| Protein | 37.6 |
| Water | 29.7 |
| r.m.s.d bond lengths | 0.003 Å |
| r.m.s.d..angles | 0.705° |

[1]Rsym = Σ|I$_{hi}$ − I$_h$|/ΣI$_{hi}$, where I$_{hi}$ is the scaled intensity of the ith symmetry-related observation of reflection h and I$_h$ is the mean value.
[2]Values in parentheses are of the highest resolution shell which is (1.97-1.90 Å).
[3]Rcryst = Σ$_h$|F$_{oh}$ − F$_{ch}$|/Σ$_h$F$_{oh}$, where F$_{oh}$ and F$_{ch}$ are the observed and calculated structure factor amplitudes for reflection h.
[4]Value of Rfree is calculated for 5% randomly chosen reflections not included in the refinement.

The crystal diffracted and the structure was refined at 2.8 Å resolution. The overall structure of the BACE1 in the complex largely resembles its free form (Hong et al., *Science* 290:150-153 (2000)) which can be aligned with 0.63 Å RMSD at the Ca atom positions of 96% (373/385) of the residues. The YW412.8.31 Fab covers a surface area of ~840 Å$^2$ on the BACE1 molecular surface and does not bind in the vicinity of the active site. The epitope comprises structural elements denoted by Hong et al. (*Science* 290:150-153 (2000)) as loop C (amino acids 315-318 of full-length BACE1), D (amino acids 331-335 of full-length BACE1), and F (amino acids 370-381 of full-length BACE1), which are closely located in three-dimensional space. Additionally, the part of BACE1 at and in the vicinity of the YW412.8.31 binding site adopted conformational change, and resulted in a shape complementary score of 0.71, consistent with strong binding. The antibody induced conformational change is thought to contribute to allosteric inhibition of the secretase activity.

The Fab bound to an exosite distal to the active site of BACE1 for amyloid precursor protein, partially overlapping an exosite previously identified as the binding site for a panel of BACE1 binding peptides (Kornacker et al., *Biochemistry* 44:11567-11572 (2005) (FIG. 14). Both the heavy and light chains are involved in the interaction (FIG. 15). Unlike the free form, where the BACE1 epitope region is more dynamic as indicated by high temperature factors, the antibody-bound structure is stabilized in a unique confirmation, which deforms the P6 and P7 sites (Turner et al., *Biochemistry* 44:105-112 (2005)) of the secretase. Adjacent to those sites, amino acids 218-231 (AGFPLNQSEVLASV (SEQ ID NO:126) of SEQ ID NO:49 (residues 157-170 in Lin et al., *Proc. Natl. Acad. Sci. USA* 97:1456-1460 (2000) (amino acid numbering starts at the mature protease domain of BACE1)), which adopt an α-helical structure in the substrate-bound complex, become a random loop in the antibody complex, which adversely impacts APP proteolytic cleavage, perhaps by preventing APP from reaching into the BACE1 catalytic cleft in a catalytic competent manner. The structural epitope includes the amino acid residues of BACE1 that contain one or more atoms located within 4 angstroms distance from any part of the YW412.8.31 Fab in the crystal structure. Fab light chain residues belong to chain L, and Fab heavy chain residues belong to chain H in Table 6 below. Residue numbering for BACE1 amino acids is based on the full-length sequence of BACE1 (SEQ ID NO:49). Residue numbering for the Fab amino acids is based on the Kabat numbering scheme (Kabat et al., *Sequences of Proteins of ImmunologicalInterest*, 5th Ed. Public Health Service, National Institutes of Health, Bethesda, Md., 1991).

TABLE 6

Residues located in the YW412.8.31-BACE1 binding interface

| BACE1 Residues | Fab Residues |
| --- | --- |
| 314 SER | H 26 GLY |
| 316 GLU | H 27 PHE |
| 317 LYS | H 28 THR |
| 318 PHE | H 30 LEU |
| 319 PRO | H 31 GLY |
| 327 GLN | H 32 TYR |
| 328 LEU | H 53 ALA |
| 329 VAL | H 58 ASP |
| 330 CYS | H 94 ARG |
| 331 TRP | H 96 PRO |
| 332 GLN | H 97 PHE |
| 333 ALA | H 98 SER |
| 335 THR | H 99 PRO |
| 337 PRO | H 100 TRP |
| 340 ILE | |

TABLE 6-continued

Residues located in the YW412.8.31-BACE1 binding interface

| BACE1 Residues | Fab Residues |
|---|---|
| 375 THR | L 49 TYR |
| 378 ASP | L 53 PHE |
| 380 CYS | L 55 TYR |
| 426 PHE | L 56 SER |
|  | L 94 TYR |

The detailed atomic interactions are in the form of van der Waals contacts of polar interactions. Polar interactions include hydrogen bonds and salt bridges. Table 7 below includes a list of the pairwise polar interactions between BACE1 and the YW412.8.31 Fab. Fab light chain residues belong to chain L, and Fab heavy chain residues belong to chain H. Residue numbering for BACE1 amino acids is based on the full-length sequence of BACE1 (SEQ ID NO:49). Residue numbering for the Fab amino acids is based on the Kabat numbering scheme.

TABLE 7

Pairwise polar interactions between BACE1 and the YW412.8.31 Fab
BACE1 Residues---Fab Residues

| |
|---|
| 314 SER---H 98 SER |
| 317 LYS---H 58 ASP |
| 327 GLN---H 53 ALA |
| 330 CYS---H 31 GLY |
| 331 TRP---H 98 SER |
| 331 TRP---H 32 TYR |
| 332 GLN---H 32 TYR |
| 378 ASP---H 32 TYR |
| 316 GLU---L 94 TYR |
| 332 GLN---L 55 TYR |
| 335 THR---L 49 TYR |

As shown below, the amino acid composition in the YW412.8.31 antibody BACE1 epitope is poorly conserved among the corresponding regions in BACE2 and Cathepsin D. This amino acid difference in the epitope for the YW412.8.31 antibody is consistent with the observation that the antibody is highly selective toward BACE1. Numbering is based on the full-length sequence of BACE1 (SEQ ID NO:49). Sequences of BACE2 and Cathepsin D are aligned to BACE1 based on their respective crystal structures. Residues in the YW412.8.31 BACE1 epitope are boxed.

```
         312        322       332            372
BACE1 . . ASSIEKFPDG FWLGEQLVCW QAGCIIPWNIF . . . DVATSCDLCY . . . SEQ ID NOS 123 & 130

BACE2 . . ASLIPEFSDG FWTGSQLACW TNSETPWSYF . . . MGAGLNYECY . . . SEQ ID NOS 124 & 131

CatD  . . ----VPLTQG EYM---IPCE KVST-----L . . . SQAG-KTLCL . . . SEQ ID NOS 125 & 132
```

Example 4: In Vivo Characterization—Mice

Figure 16A:
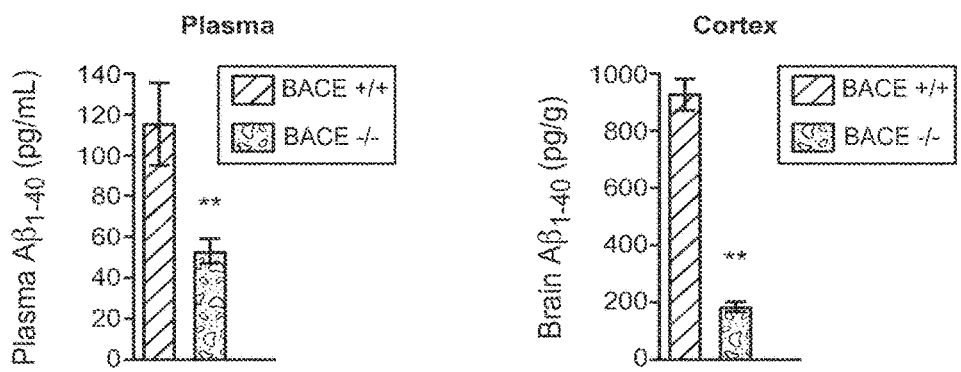
FIGS. 16A and 16B show the results of experiments to examine the contribution of BACE1 to $A\beta_{1-40}$ levels in wild-type mice. $A\beta_{1-40}$ levels in BACE1+/+vs. BACE1−/− mice were examined. Mice were dosed with a single dose of control IgG antibody or anti-BACE YW412.8.31 antibody as described in Example 4.
Figure 16B:
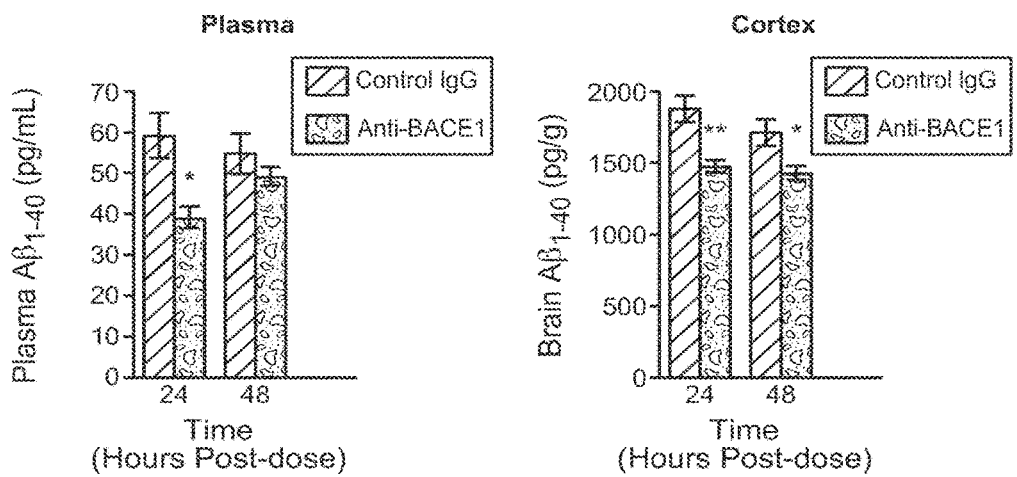

The effect of YW412.8.31 in vivo was assessed. To establish the maximal $A\beta_{1-40}$ reduction that a BACE1-specific inhibitor could achieve, the contribution of BACE1 to $A\beta_{1-40}$ production in plasma and forebrain of BACE1−/− mice compared to BACE1+/+ controls was examined. Plasma $A\beta_{1-40}$ signal was reduced by 45%, and brain $A\beta_{1-40}$ signal by 80% in BACE1−/− mice (FIG. 16, panel A). These results imply that BACE1 is indeed the major β-secretase in the forebrain, but that in the periphery, BACE1 accounts for only partial $A\beta_{1-40}$ production, with the remainder coming from another β-secretase.

With an understanding of the contribution of BACE1 to Aβ production, the ability of the anti-BACE1 antibody YW412.8.31 to modulate amyloidogenic processing in hAPP transgenic and wild-type mice was assessed.

hAPP Transgenic Mice

Briefly, 5-month old human APP-expressing mice were treated with 30 mg/kg or 100 mg/kg YW412.8.31 antibody or vehicle by intra-peritoneal injection every four days for a total of three doses (i.e., at days 1, 5, and 9). Animals were euthanized two hours post the final dose. Serum, plasma, and brains were harvested and processed. Plasma, cortex and hippocampus were analyzed for levels of soluble $A\beta_{1-40}$ and $A\beta_{1-42}$ using an Amyloid beta (Aβ) ELISA test kit per manufacture's instructions (The Genetics Company). Pharmacokinetic analysis was performed on serum and brain homogenates.

Figure 17A:
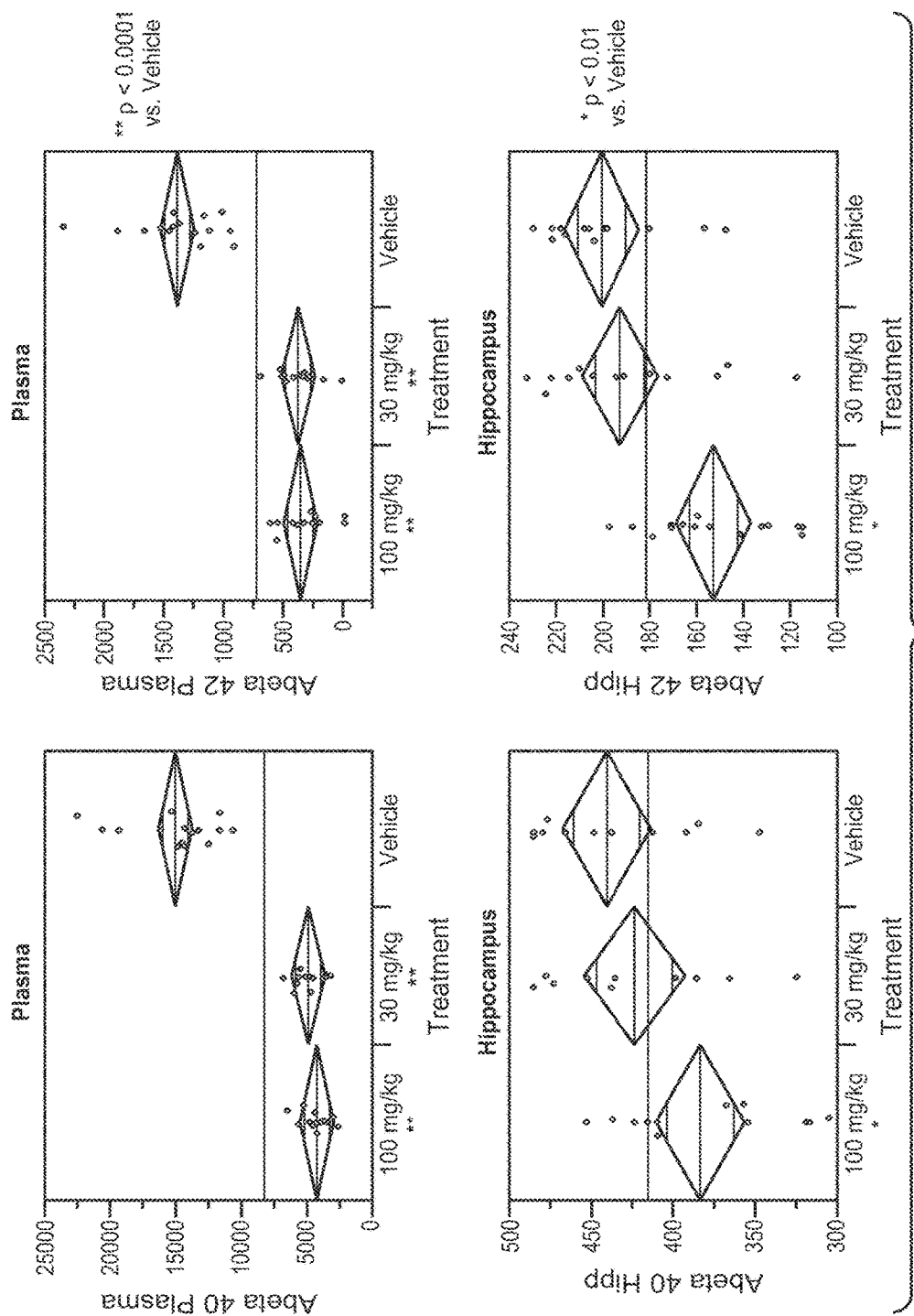
FIGS. 17A-17B provide results of the in vivo YW412.8.31 anti-BACE1 antibody experiments described in Example 4.
Figure 17B:
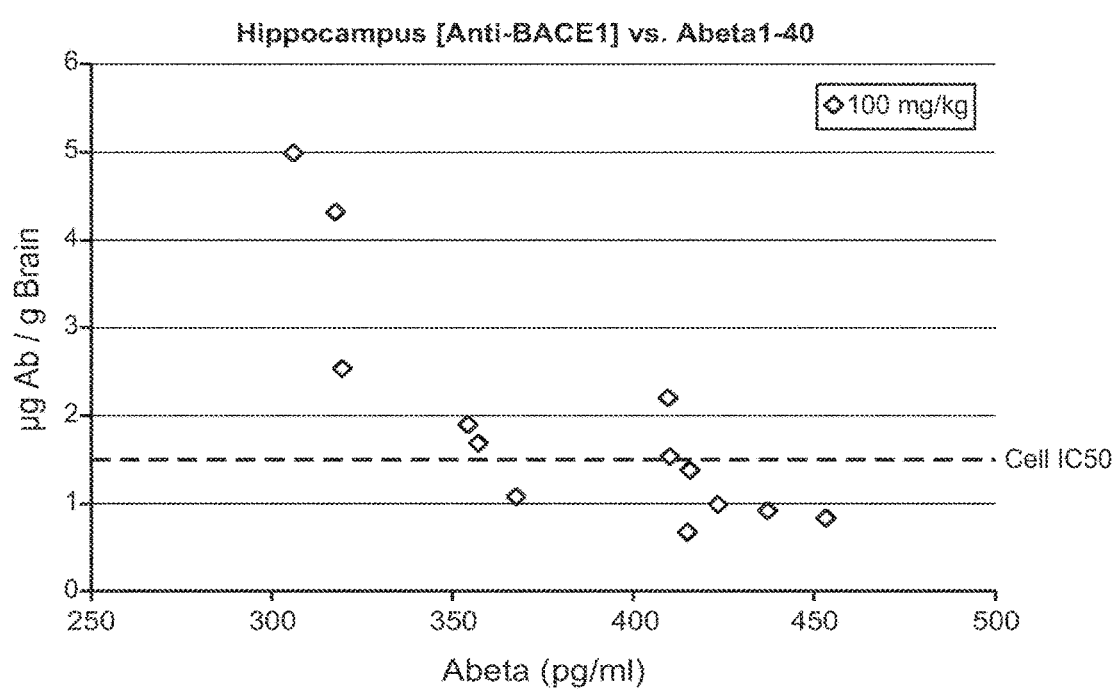
Figure 18A:
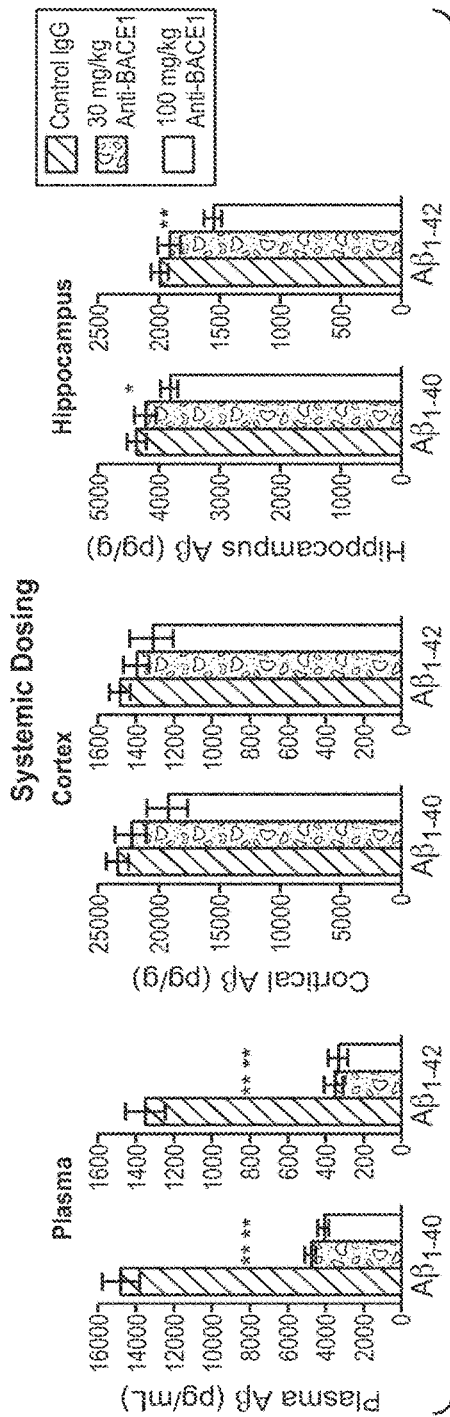
FIGS. 18A and 18B show a comparison from experiments in which hAPP-transgenic mice were dosed with the YW412.8.31 anti-BACE1 antibody systemically (Panel A, same experiment as described in FIG. 17A regraphed for comparison) or by continuous ICV infusion (Panel B).
Figure 18B:
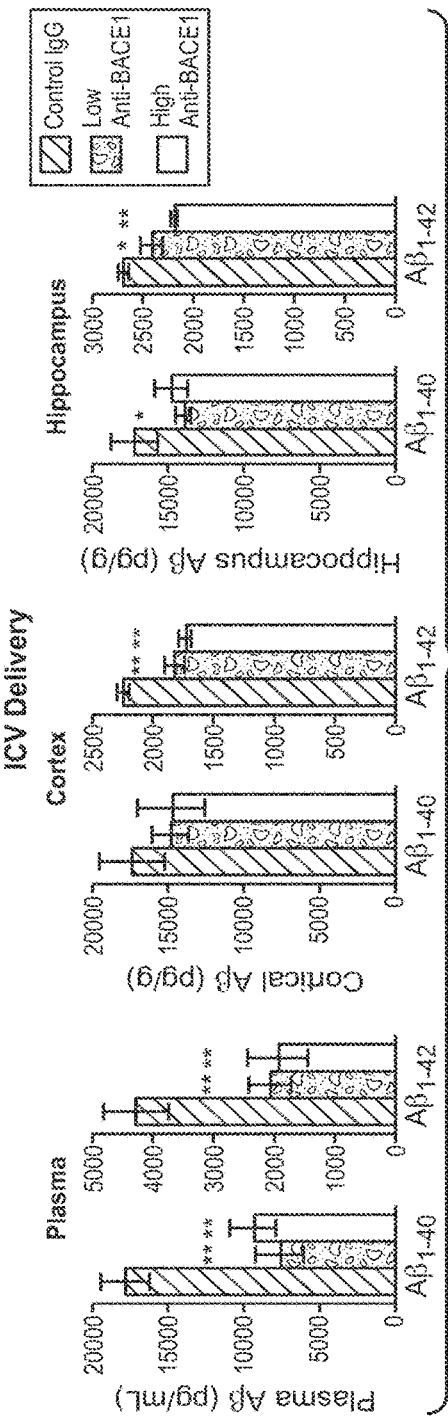

The results showed that plasma $A\beta_{1-40}$ and $A\beta_{1-42}$ levels were reduced to approximately 30% of control levels at both the 30 mg/kg and the 100 mg/kg YW412.8.31 antibody dose levels (FIG. 17(A), top panels and FIG. 18, panel A). However, in contrast to what was observed in wild-type mice, discussed below, levels of $A\beta_{1-40}$ and $A\beta_{1-42}$ in the brain were reduced by only 15-22% at the 100 mg/kg dose level of the YW412.8.31 antibody (FIG. 17(A), bottom panels and FIG. 18, panel A). The concentration of YW412.8.31 antibody in the brain of treated animals increased in a dose-dependent manner, with an observed concentration of antibody in the brain in 30 mg/kg-treated animals of 4.8±3.6 nM and an observed concentration of antibody in the brain in 100 mg/kg-treated animals of 14.0±9.3 nM, confirming that a higher intraperitoneally-administered dose of antibody indeed translated into a higher dose of antibody observed in the brain. Plotting of individual pharmacokinetic versus pharmacodynamic readouts suggested that a PK/PD relationship exists for this antibody in this model (FIG. 17(B)).

Similar experiments were also performed in which YW412.8.31 anti-BACE1 antibody was delivered systemically or directly into hAPP transgenic mice brains by continuous ICV infusion. For ICV delivery, antibody was delivered continuously for 7 days via an Alzet osmotic minipump (model 2001) implanted unilaterally. The amount of YW412.8.31 antibody delivered was 0.041 mg/day (low dose) or 0.41 mg/day (high dose); 0.33 mg/day Control IgG was delivered to the control group. At euthanasia, plasma, cortex, and hippocampus were harvested and analyzed for levels of soluble $A\beta_{1-40}$ and $A\beta_{1-42}$ by ELISA (The Genetics Company) following manufacturer's instructions.

Table 8 below shows the concentrations of YW412.8.31 antibody in the brain of mice dosed with 30 mg/kg or 100 mg/kg by systemic delivery or 0.041 mg/day and 0.41 mg/day by ICV delivery.

TABLE 8

| DOSE | | ANTIBODY CONCENTRATION IN BRAIN (µG/G) | ANTIBODY CONCENTRATION IN BRAIN (NM) |
|---|---|---|---|
| Systemic Delivery | 30 mg/kg | 0.7 | 4.8 |
| | 100 mg/kg | 2.1 | 14 |
| ICV Delivery | Low (0.041 mg/day) | 13-25 | 87-167 |
| | High (0.41 mg/day) | 110-305 | 733-2003 |

However, despite high levels of antibody in the brain following infusion, Aβ reduction was modest at 15-23% and was similar to the reduction observed with systemic delivery (FIG. 18, panel B). This observation suggests that high dose systemic injection may be able to reduce Aβ levels in hAPP transgenic mice, however the reduction is modest. The reduced efficacy in the hAPP transgenic mice is believed to be a consequence of the animal model, since high concentrations in the brain, equivalent to the concentration in serum following systemic delivery, did not further reduce Aβ production. Furthermore, the reduction in the brain in the hAPP transgenic mice is modest compared to what was observed in wild-type mice and described below. Thus, the transgenic hAPP mice may not be ideal for studying anti-BACE1 effects in vivo. Wild-type mice, are a more appropriate model for antibody efficacy from a disease viewpoint as well, as the overwhelming majority of the Alzheimer's patient population carries a wild-type APP allele.

Wild-Type Mice

The ability of anti-BACE1 antibodies YW412.8.31 to modulate amyloidogenic processing was also assessed in wild-type mice. Briefly, experiments were performed as described above. A single dose of control IgG antibody or YW412.8.31 anti-BACE1 antibody (50 mg/kg) was delivered systemically by intravenous (IV) injection to wild-type mice. After 24 or 48 hours, plasma and brain samples were harvested and $A\beta_{1-40}$ levels were analyzed. The concentrations of total mouse $A\beta_{1-40}$ in plasma and brain were determined using a sandwich ELISA following similar procedures described below for measuring total anti-BACE1 antibody concentrations. Briefly, rabbit polyclonal antibody specific for the C terminus of $A\beta_{1-40}$ (Millipore, Bedford, Mass.) was coated onto plates, and biotinylated anti-mouse Aβ monoclonal antibody M3.2 (Covance, Dedham, Mass.) was used for detection. The assay had lower limit of quantification values of 1.96 pg/ml in plasma and 39.1 pg/g in brain. As is shown in FIG. 16, panel B, Plasma $A\beta_{1-40}$ was reduced by 35% and cortical $A\beta_{1-40}$ was reduced by 20%.

Additional experiments with wild-type C57Bl/6J mice were performed in which 100 mg/kg of YW412.8.31, or a control IgG, was administered systemically. Levels of $A\beta_{1-40}$ in both the plasma and forebrain of treated animals four hours after a single intraperitoneal (IP) injection were determined. Blood was collected from animals by cardiac puncture to isolate plasma.

Following PBS perfusion, the brain was harvested and forebrain from one hemibrain was prepared in PK buffer (1% NP-40 in PBS, with Roche complete protease inhibitors) whereas forebrain from the other hemibrain was homogenized in 5M GuHCL, 50 mM Tris pH 8.0, and further diluted in Casein Blocking Buffer (0.25% casein/ 0.05% sodium azide, 20 µg/ml aprotinin/5 mM EDTA, pH 8.0/10 µg/ml leupeptin in PBS) for $A\beta_{1-40}$ analysis.

Figure 22A:
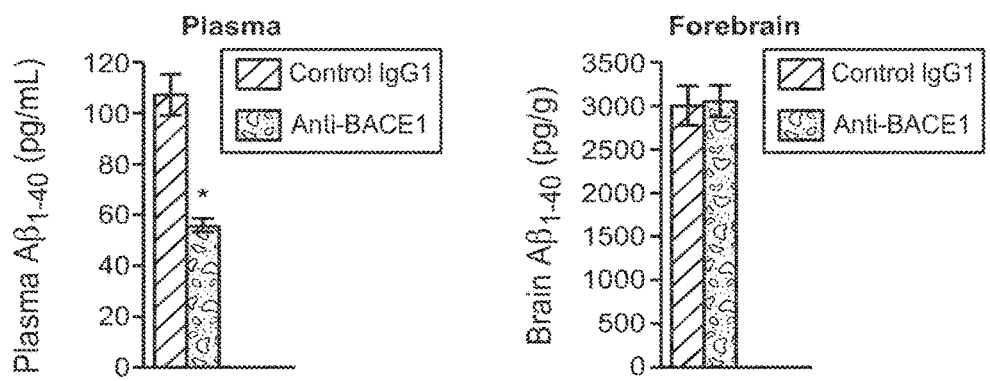
FIGS. 22A and 22B depict Aβ production following systemic dosing of YW412.8.31 in wild-type mice.
Figure 22B:
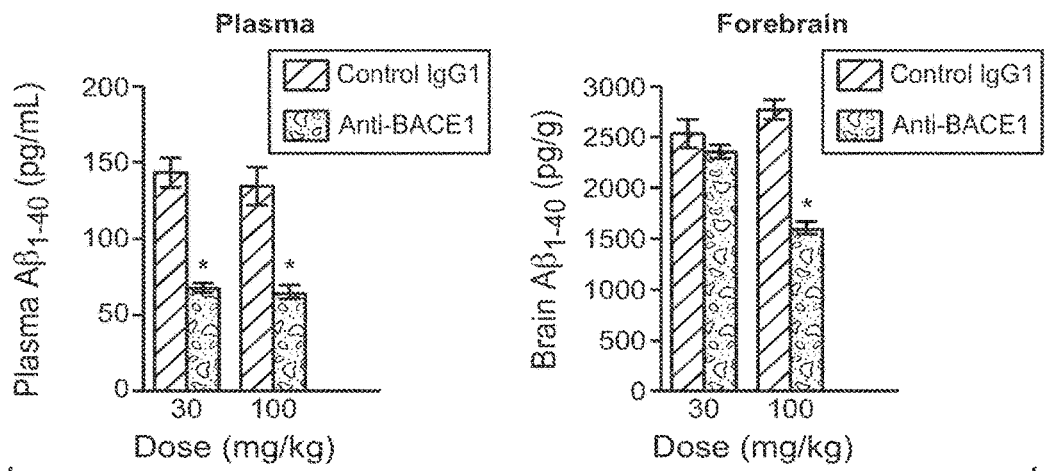

As shown in FIG. 22, panel A, the 100 mg/kg dose was able to reduce plasma $A\beta_{1-40}$ by ~50% of control levels and similar to BACE1 knockout levels described previously. However, no change was detected in forebrain $A\beta_{1-40}$ at 4 hours after administration. This early time point may be too soon after administration of YW412.8.31 to see an effect in the brain. A longer time period post administration may be required to observe reduced Aβ in the brain, especially since reduction of Aβ is observed in wild-type mice at a lower dose (50 mg/kg) at 24 hours, described above. YW412.8.31 concentrations in serum were very high, 1040±140 µg/mL (6.9±0.9 µM) by 4 hours post administration. YW412.8.31 concentrations in brain were much lower at 0.7±0.4 µg/g (4.7±2.7 nM), which represented ~0.07% of concentration in serum, closely approximating the predicted 0.1% steady state penetration of antibodies into the CNS (Reiber and Felgenhauer, *Clin. Chim. Acta.* 163:319-328 (1987). Importantly, the antibody concentration achieved in brain, 4.7±2.7 nM, is near the cellular $IC_{50}$ that was previously observed (FIG. 11). Thus the anti-BACE1 antibody is highly effective in vivo, as demonstrated by reduction of plasma $A\beta_{1-40}$ down to levels seen in BACE1 knockout mice. However, a single systemic dose did not result in brain reduction by 4 hours post administration to mice, mostly likely because the time point was too early to observe any effect.

Additional experiments were performed in order to determine the effect of elevated brain antibody levels through repeated dosing. YW412.8.31 antibody, or control IgG, was administered at 30 or 100 mg/kg IP every 4 days for a total of 3 doses. In this study the levels of $A\beta_{1-40}$ in both the plasma and forebrain of treated animals 4 hours post last dose were measured. Again, ~50% reduction in plasma $A\beta_{1-40}$ levels following multi-dosing at both 30 and 100 mg/kg was observed (FIG. 22, panel B). Remarkably, a 42% reduction in forebrain $A\beta_{1-40}$ at the high dose of anti-BACE1 was observed, although no reduction was observed at the low dose. YW412.8.31 antibody concentrations in serum were 480±210 and 1500±440 µg/mL, and concentrations in brain were 0.9±0.6 µg/g (5.9±4.3 nM) and 3.0±1.6 µg/g (20±10 nM) following administration at 30 and 100 mg/kg given every 4 days, respectively. Thus, as predicted, higher antibody levels in brain resulted in robust reductions in Aβ levels. Notably, there was no difference in peripheral Aβ levels at the 30 mg/kg dose compared to the 100 mg/kg dose, suggesting that a maximal peripheral inhibition at 30 mg/kg was achieved and, thus, simply reducing peripheral Aβ levels is not sufficient to reduce brain levels.

Figure 19A:
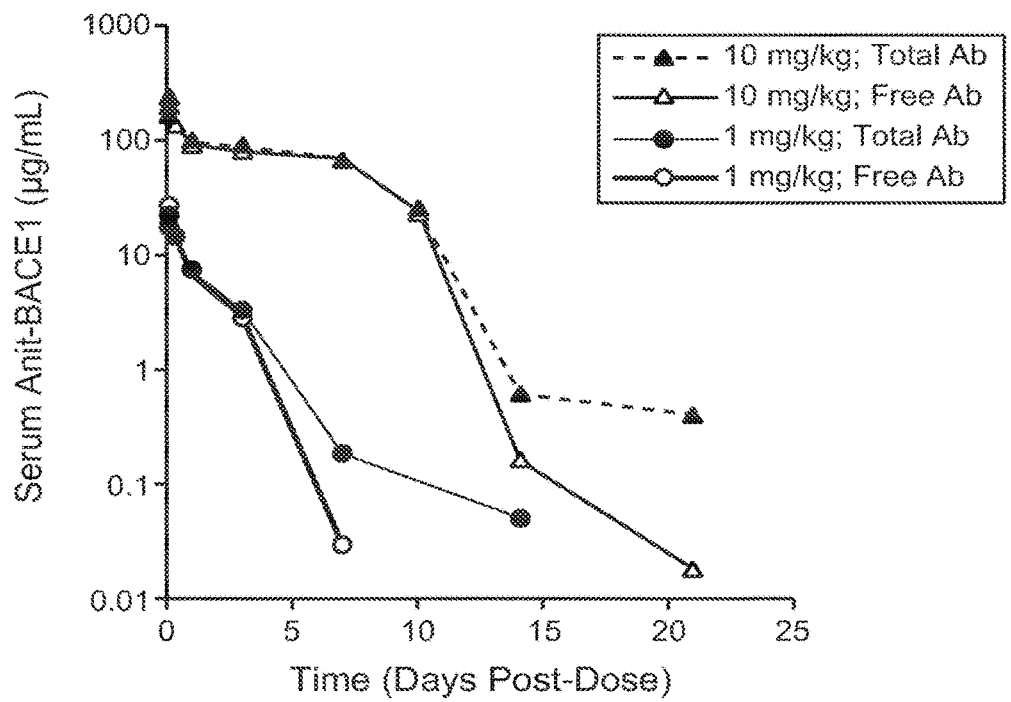
FIGS. 19A and 19B show the PK analysis of a single dose of YW412.8.31 anti-BACE1 (1 or 10 mg/kg) delivered via IV injection to BALB/C mice (FIG. 19A). Serum PK was analyzed out to 21 days post-dose. Two separate PK assays were used: an assay to detect all anti-BACE1 in serum (total mAb), and an assay to detect only unbound anti-BACE1 in serum (free mAb). Single dose PK analysis in BACE1+/+, BACE1+/−, and BACE1−/− mice confirms the non-linearity observed in the initial study, and indicates that the enhanced clearance is indeed target-mediated (FIG. 19B).
Figure 19B:
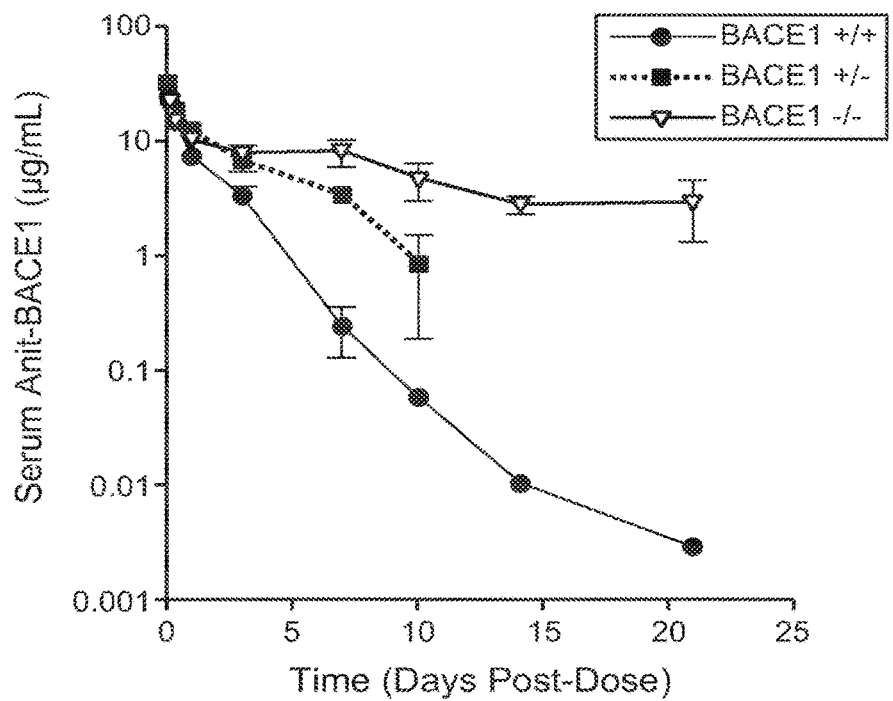

Additionally, PK data was obtained after dosing with YW412.8.31 anti-BACE1 antibody in wild-type and BACE1 knock-out mice. See FIG. 19. A single dose of anti-BACE1 (1 or 10 mg/kg) was delivered via IV injection to BALB/C mice. Serum PK was analyzed out to 21 days post-dose.

Total anti-BACE1 antibody concentrations in mouse serum and brain samples were measured as follows. Antibody concentrations in mouse serum and brain samples were measured using an enzyme-linked immunosorbent assay (ELISA). NUNC 384 well Maxisorp immunoplates (Neptune, N.J.) were coated with F(ab')$_2$ fragment of donkey anti-human IgG, Fc fragment specific polyclonal antibody (Jackson ImmunoResearch, West Grove, Pa.) overnight at 4° C. Plates were blocked with phosphate-buffered saline (PBS) containing 0.5% bovine serum albumin (BSA) for 1 hour at room temperature the next day. Each antibody (Control IgG and anti-BACE1) was used as a standard to quantify the respective antibody concentrations. After washing plates with PBS containing 0.05% Tween 20 using a microplate washer (Bio-Tek Instruments, Inc., Winooski, Vt.), standards and samples diluted in PBS containing 0.5% BSA, 0.35 M NaCl, 0.25% CHAPS, 5 mM EDTA, 0.05% Tween 20 and 15 ppm Proclin were incubated on plates for 2 hours at room temperature with mild agitation. Bound antibody was detected with horseradish peroxidase conjugated F(ab')$_2$ goat anti-human IgG, Fc specific polyclonal antibody (Jackson ImmunoResearch). Finally, plates were developed using the substrate 3,3',5,5'-tetramethyl benzidine (TMB) (KPL, Inc., Gaithersburg, Md.). Absorbance was measured at a wavelength of 450 nm with a reference of 630 nm on a Multiskan Ascent reader (Thermo Scientific, Hudson, N.H.). Concentrations were determined from the standard curve using a four-parameter non-linear regression program. The assay had lower limit of quantitation (LLOQ) values of 3.12 ng/ml in serum and 15.6 ng/g in brain.

Free YW412.8.31 antibody concentrations in mice were detected following similar procedures described above using BACE1 ECD as coat and an anti-human IgG, Fc specific antibody (Jackson ImmunoResearch) for detection. The free anti-BACE1 mouse ELISA had LLOQ values of 0.626 ng/ml in serum and 3.13 ng/g in brain Two separate PK assays were used: an assay to detect all YW412.8.31 in serum (total mAb), and an assay to detect only unbound YW412.8.31 in serum (free mAb). Observed PK kinetics were non-linear, and the difference in total versus free mAb values for samples where YW412.8.31 concentration is <10 μg/mL is suggestive of target-mediated clearance. See FIG. 19, panel A. Furthermore, the difference between total mAb and unbound mAb indicates that some of the YW412.8.31 in serum was likely bound to soluble BACE1. Single dose PK analysis in BACE1+/+, BACE1+/-, and BACE1-/- mice confirms the non-linearity observed in the initial study, and indicates that the enhanced clearance is indeed target-mediated. BACE1-/- mice show linear PK. See FIG. 19 (Panel B).

Example 5: In Vivo Characterization—Monkey

Figure 20A:
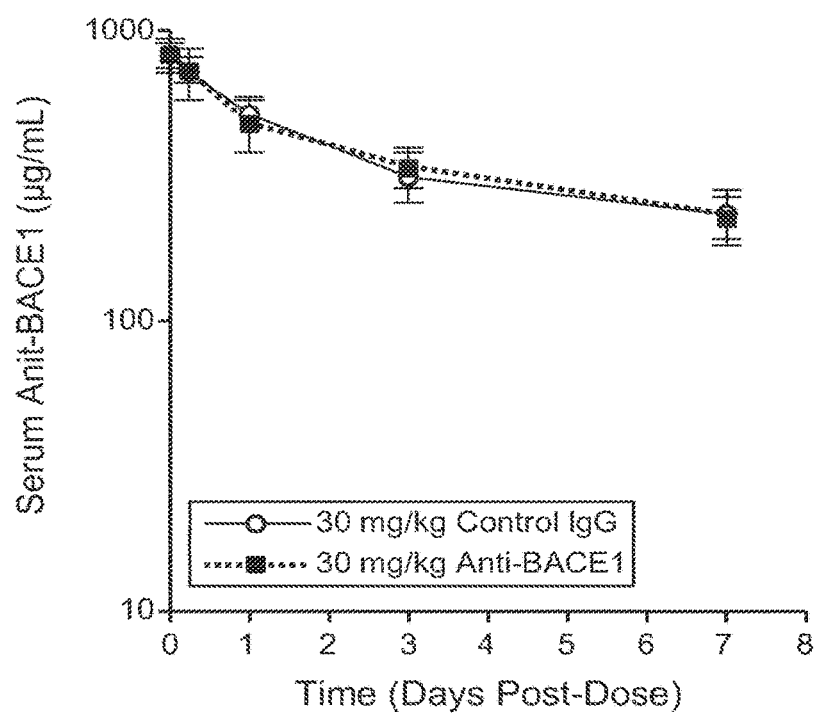
FIGS. 20A and 20B show the PK analysis of Cynomolgus monkeys dosed with control IgG or YW412.8.31 anti-BACE1 antibody (30 mg/kg) by IV delivery. Total anti-BACE1 or control antibody concentrations in monkey serum (FIG. 20A) and CSF samples (FIG. 20B) were measured using monkey-adsorbed goat anti-human IgG polyclonal antibody (Bethyl, Montgomery, Tex.) as described in Example 5.
Figure 20B:
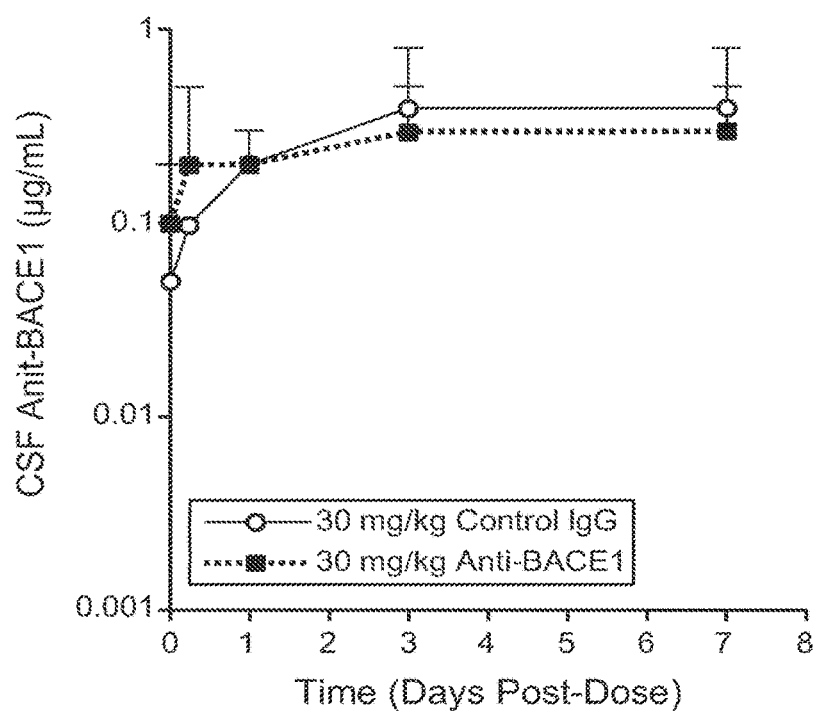
Figure 21A:
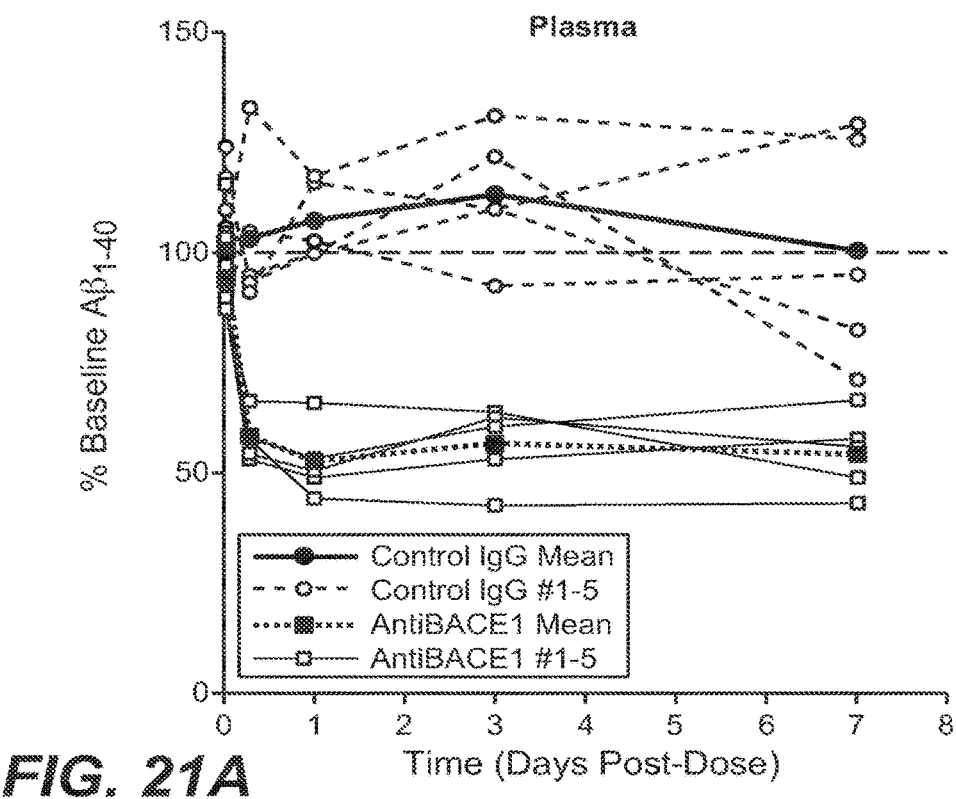
FIGS. 21A-21D are the results of experiments as described in Example 5 in which Cynomolgus monkeys were dosed with control IgG or anti-BACE1 antibody YW412.8.31 by IV delivery. Hatched lines show data for individual animals, and solid lines show group means. Plasma and CSF were sampled 7 days, 2 days and just prior to dosing to set a mean value for $A\beta_{1-40}$ baseline levels in each individual monkey. Plasma $A\beta_{1-40}$ (FIG. 21A) and CSF $A\beta_{1-40}$ (FIG. 21B) was measured at various times. The variability across animals in baseline plasma (FIG. 21C) and CSF (FIG. 21D) $A\beta_{1-40}$ is also shown.
Figure 21B:
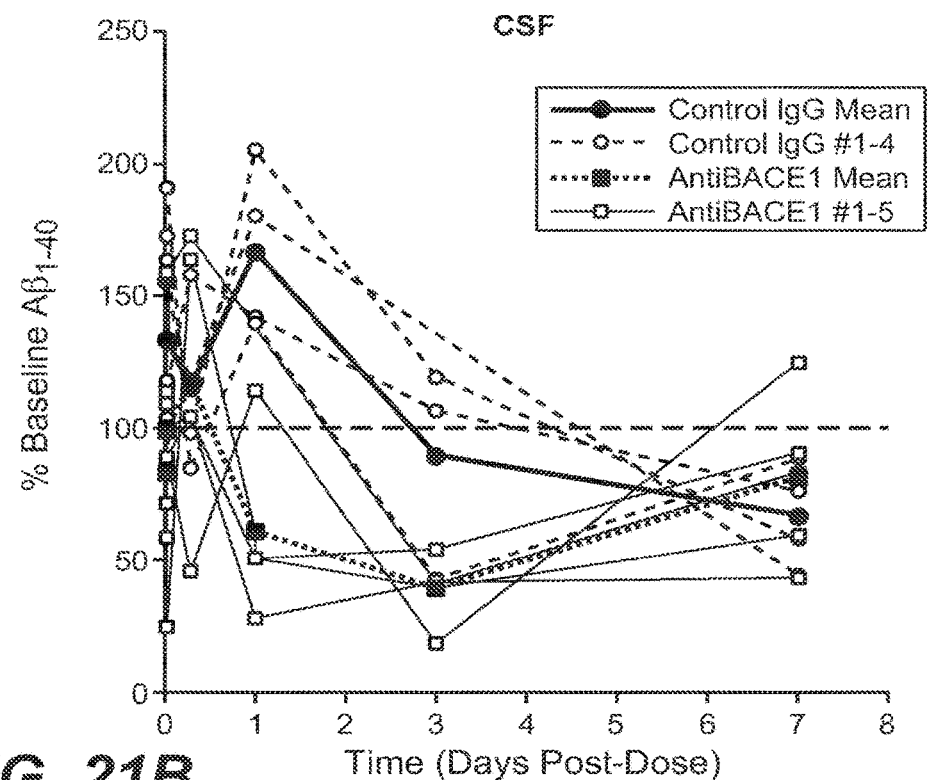
Figure 21C:
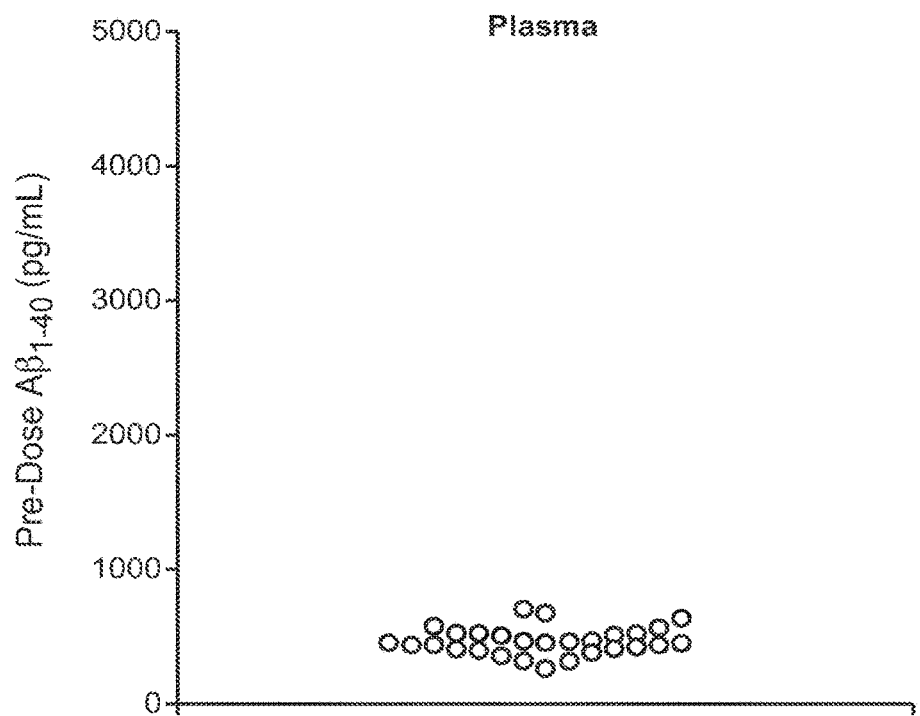
Figure 21D:
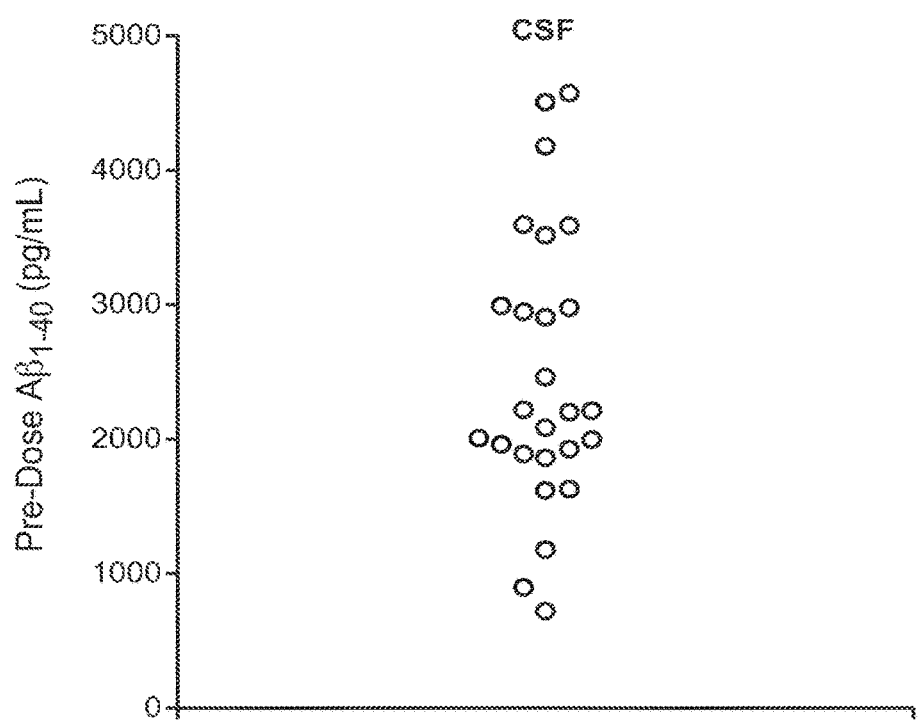

Cynomolgus monkeys were dosed with control IgG or YW412.8.31 anti-BACE1 antibody (30 mg/kg) by IV delivery. Plasma and CSF were sampled up to 7 days prior to dosing to set mean baseline Aβ$_{1-40}$ levels in each in individual animal, and then at various times after dosing. Total anti-BACE1 or control antibody concentrations in monkey serum and CSF samples were measured using monkey-adsorbed goat anti-human IgG polyclonal antibody (Bethyl, Montgomery, Tex.) as both coat and detection (FIG. 20). Free anti-BACE1 antibody concentrations in monkeys were determined using BACE1 ECD as coat and the monkey-adsorbed goat anti-human IgG antibody (Bethyl) for detection. Both total and free anti-BACE1 monkey assays had a LLOQ value of 6.25 ng/ml in serum or CSF. PK is as expected for IgG1 dosed in monkey and shows predicted exposure.

Aβ$_{1-40}$ levels in plasma and CSF from Cynomolgus monkeys tested was also determined. Briefly, the concentrations of total cyno Aβ$_{1-40}$ in plasma were determined using MSD MA6000 Human (6E10) Abeta Kit (Cat#K111BVE-2, Meso Scale Diagnostics) according to the Manufacturer's instructions. The capture antibody, specific for the C terminus of Aβ$_{1-40}$, was pre-coated on the plates, and Sulfo-Tag anti-Aβ monoclonal antibody 6E10 was used for detection. The assay had lower limit of quantification values of 49.4 pg/ml in plasma. The concentrations of total cyno Aβ$_{1-40}$ in CSF were determined using a sandwich ELISA. Rabbit polyclonal antibody specific for the C terminus of Aβ$_{1-40}$ (cat#AB5737, Millipore, Bedford, Mass.) was coated onto plates, and biotinylated anti-Aβ monoclonal antibody 6E10 (Cat#SIG-39340, Covance, Dedham, Mass.) was used for detection. The assay had a lower limit of quantification values of 15.6 pg/ml in CSF.

As shown in FIG. 21 (Panel A), plasma Aβ$_{1-40}$ levels were reduced ~50% of baseline across all individuals. 50% maximal plasma reductions in Aβ were sustained throughout the 7 day observation period. The serum concentration-time profile for YW412.8.31 anti-BACE1 antibody appeared similar to that observed for the control IgG antibody, suggesting kinetics similar to that of a typical IgG1 dosed in the linear range (FIG. 20, panel A). Peak serum antibody concentrations of ~800 μg/mL were observed at the time of first sample collection at 15 minutes post administration and fell to 232 μg/mL by 7 days post-dose. Notably, at all time points measured after dosing, the serum concentrations of YW412.8.31 exceeded the cellular IC$_{50}$ (~2.5 nM, see FIG. 11).

CSF Aβ$_{1-40}$ levels, as shown in FIG. 21 (Panel B), although variable, showed a reduction up to 50% at 1 and 3 days following dosing followed by a trend back toward baseline Aβ at day 7 post dose. The variability in baseline plasma and CSF levels is shown in FIG. 21 (Panels C and D). Baseline plasma levels were fairly uniform across animals, whereas CSF Aβ$_{1-40}$ levels were highly variable. Thus, all Aβ$_{1-40}$ measurements were normalized to baseline for each individual monkey.

These data show that a single dose of YW412.8.31 in monkey significantly reduces plasma and CSF Aβ levels. In the CSF, YW412.8.31 concentrations of 0.2-0.3 μg/ml were observed over this time period, which translates to ~2 nM (FIG. 20, panel B). From this data, it is inferred that the brain concentrations of YW412.8.31 are in a similar range. Comparing the PK and PD data, these results show that drug exposure in plasma is sufficient to maximally inhibit Aβ production over a 7 day window, while drug concentrations in CSF near the cellular IC$_{50}$ and reduce Aβ levels in brain transiently at the dose level tested (30 mg/kg). In summary, these data provide strong evidence that systemically administered anti-BACE1 can reduce BACE1 activity in brain, as determined by CSF Aβ measurements, in a non-human primate.

Example 6: Affinity Maturation of the YW412.8.31 Antibody

The YW412.8.31 antibody was affinity matured guided by the structure data provided by the previously described crystal structure. The antibody residues in contact with BACE1 were mutated in order to enhance affinity of the YW412.8.31 antibody. Affinity matured clones produced by this strategy have the nomenclature YW412.8.31xS. YW412.8.31 affinity matured clones were also produced via soft randomization targeting of all CDRs, as described previously, and have the nomenclature YW412.8.31x. Heavy chain variable sequences and light chain variable sequences for clones which bound BACE1 are depicted in FIGS. 23 (A)-(C) and 24 (A)-(C).

Figure 25A:
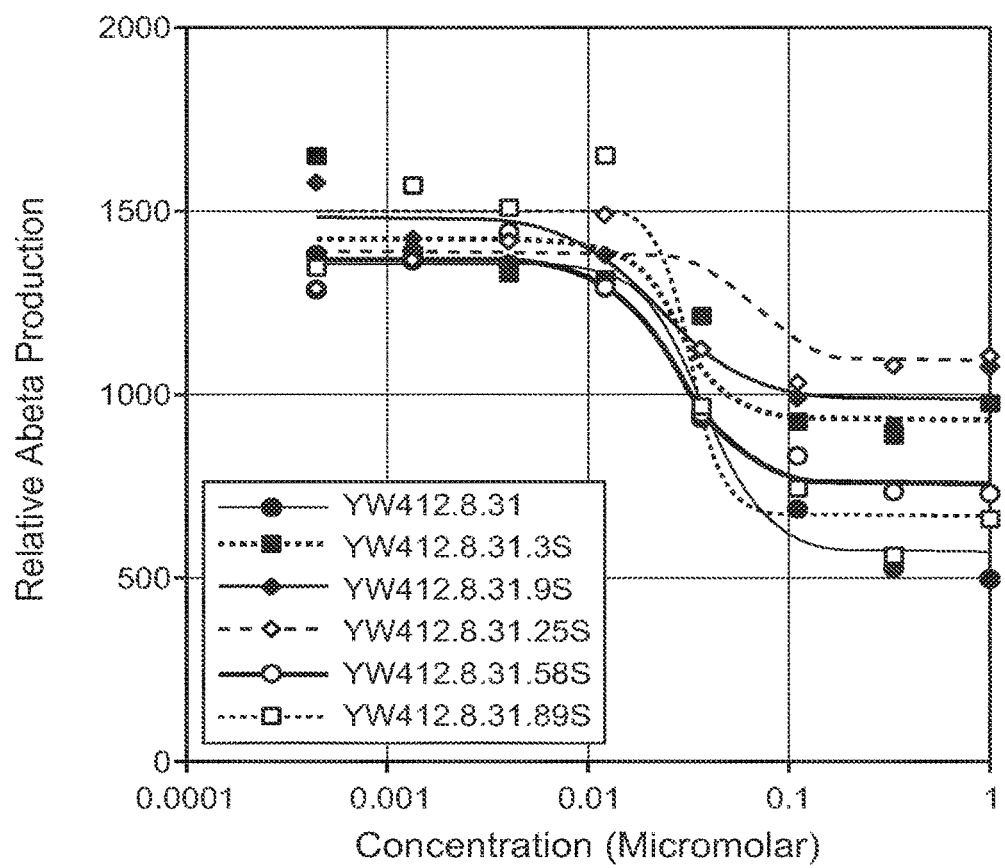
FIGS. 25A and B depict graphs showing the inhibition of BACE1 with YW412.8.31 and affinity matured clones in an HTRF assay as described in Example 6. The ability of clones YW412.8.31.35; YW412.8.31.95; YW412.8.31.255; YW412.8.31.585; YW412.8.31.53; YW412.8.31.69; YW412.8.31.77; YW412.8.31.81S and YW412.8.31.895 to inhibit the protease activity of BACE1 was tested.
Figure 25B:
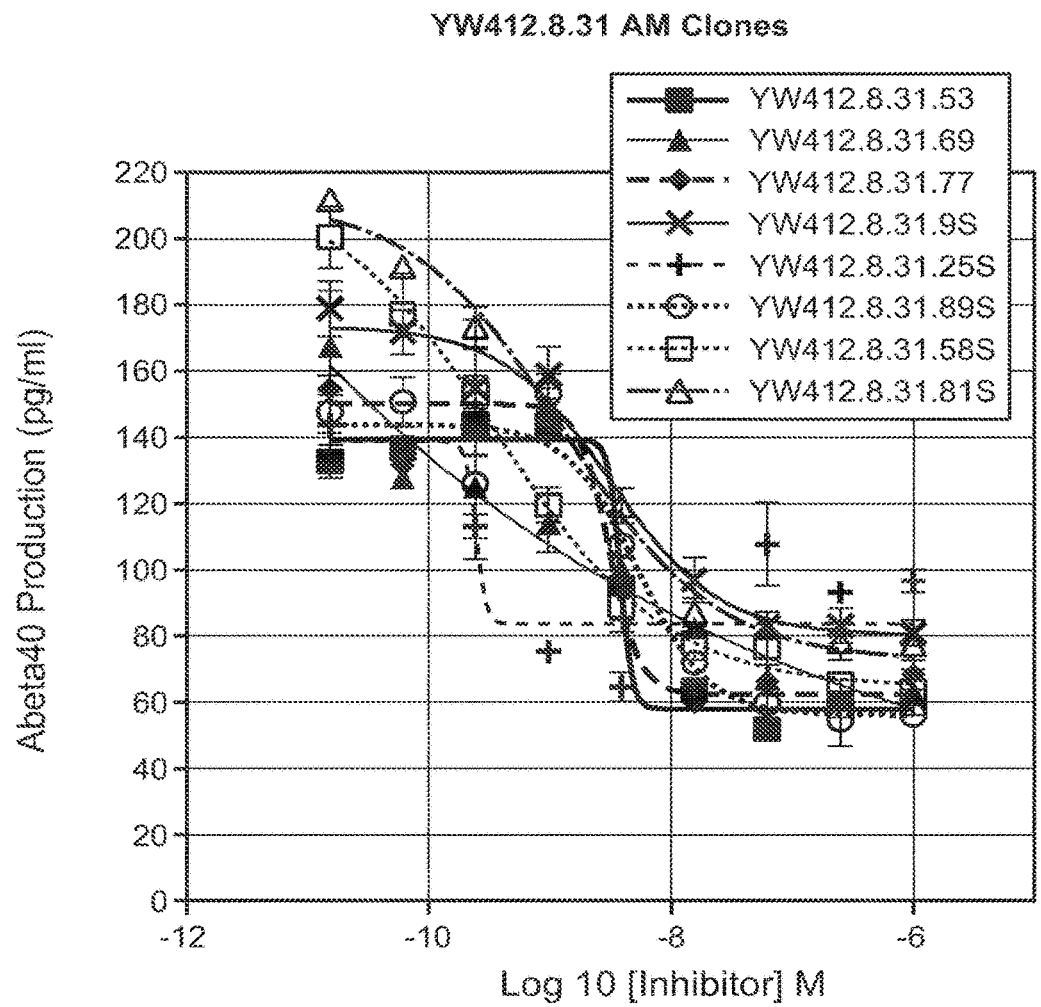

Clones which bound BACE1 were tested for BACE1 protease inhibition in a cell-based HTRF assay as described previously in Example 2C. Results of the assay are depicted in FIGS. 25A and 25B FIG. 25B shows the results of Aβ$_{1-40}$ production (pg/ml) from primary cortical neurons treated for 24 hours with various affinity matured anti-BACE1 antibodies at the indicated concentrations. Several of the antibodies tested inhibited BACE1 at a level similar to that observed with YW412.8.31.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A nucleic acid encoding a heavy chain, or both a heavy chain and a light chain, of an antibody or fragment thereof that binds to β-site amyloid precursor protein cleaving enzyme 1 (BACE1), wherein the antibody or fragment thereof comprises:
   a) a hypervariable region (HVR)-H1 comprising the amino acid sequence GFTFX$_{13}$GYX$_{14}$IH (SEQ ID NO:26), wherein X$_{13}$=S or L and X$_{14}$=A or G;
   b) an HVR-H2 comprising the amino acid sequence GWISPAGGSTDYADSVKG (SEQ ID NO: 24);
   c) an HVR-H3 comprising the amino acid sequence of GPFSPWVMDY (SEQ ID NO: 25),
   d) an HVR-L1 comprising the amino acid sequence of RASQX$_1$VX$_2$X$_3$X$_4$X$_5$A (SEQ ID NO:17), wherein X$_1$=D or V; X$_2$=S or A; X$_3$=T or N; X$_4$=S or A; X$_5$=V or L;
   e) an HVR-L2 comprising the amino acid sequence of X$_6$ASFLYS (SEQ ID NO:18) wherein X$_6$=S or L; and
   f) an HVR-L3 comprising the amino acid sequence of QQX$_7$X$_8$X$_9$X$_{10}$X$_{11}$X$_{12}$T (SEQ ID NO:19), wherein X$_7$=S, F, G, D or Y; X$_8$=Y, P, S, or A; X$_9$=T or N; X$_{10}$=T, Y, D or S; X$_{11}$=P or L; X$_{12}$=P or T;
wherein the antibody reduces or inhibits the activity of BACE1.

2. The nucleic acid of claim 1, wherein the nucleic acid encodes a heavy chain of the antibody.

3. The nucleic acid of claim 1, wherein the nucleic acid encodes the heavy chain and the light chain of the antibody.

4. The nucleic acid of claim 1, wherein the HVR-H1 comprises an amino acid sequence selected from SEQ ID NO:22 and SEQ ID NO:23.

5. The nucleic acid of claim 2, wherein the HVR-H1 comprises an amino acid sequence selected from SEQ ID NO:22 and SEQ ID NO:23.

6. The nucleic acid of claim 3, wherein the HVR-H1 comprises an amino acid sequence selected from SEQ ID NO:22 and SEQ ID NO:23.

7. The nucleic acid of claim 1, wherein the antibody comprises a VH chain having an amino acid sequence selected from SEQ ID NOs: 20 and 21.

8. The nucleic acid of claim 2, wherein the antibody comprises a VH chain having an amino acid sequence selected from SEQ ID NOs: 20 and 21.

9. The nucleic acid of claim 3, wherein the antibody comprises a VH chain having an amino acid sequence selected from SEQ ID NOs: 20 and 21.

10. The nucleic acid of claim 3, wherein the HVR-L1 comprises the amino acid sequence of SEQ ID NO:7 or SEQ ID NO:8; the HVR-L2 comprises the amino acid sequence of SEQ ID NO:9 or SEQ ID NO:10; and the HVR-L3 comprises an amino acid sequence selected from SEQ ID NOs:11-16.

11. The nucleic acid of claim 3, wherein the antibody comprises a VL chain sequence having an amino acid sequence selected from SEQ ID NOs: 1-6.

12. The nucleic acid of claim 3, wherein the HVR-H1 comprises the amino acid sequence selected of SEQ ID NO:23, the HVR-L1 comprises the amino acid sequence of SEQ ID NO:7, the HVR-L2 comprises the amino acid sequence of SEQ ID NO:9 and the HVR-L3 comprises the amino acid sequence of SEQ ID NO:12.

13. The nucleic acid of claim 3, wherein the antibody comprises a VH chain having an amino acid sequence selected from SEQ ID NOs: 20 and 21, and a VL chain sequence having an amino acid sequence selected from SEQ ID NOs: 1-6.

14. The nucleic acid of claim 3, wherein the antibody comprises a VH chain having the amino acid sequence of SEQ ID NO: 21 and a VL chain sequence having the amino acid sequence of SEQ ID NO: 2.

15. A host cell comprising the nucleic acid of claim 1.

16. A host cell comprising the nucleic acid of claim 3.

17. A host cell comprising a first nucleic acid and a second nucleic acid, wherein the first nucleic acid encodes the heavy chain of an antibody or fragment thereof and the second nucleic acid encodes the light chain of an antibody or fragment thereof, wherein the antibody or fragment thereof binds to n-site amyloid precursor protein cleaving enzyme 1 (BACE1); and wherein the antibody or fragment thereof comprises:
   a) a hypervariable region (HVR)-H1 comprising the amino acid sequence GFTFX$_{13}$GYX$_{14}$IH (SEQ ID NO:26), wherein X$_{13}$=S or L and X$_{14}$=A or G;
   b) an HVR-H2 comprising the amino acid sequence GWISPAGGSTDYADSVKG (SEQ ID NO: 24);
   c) an HVR-H3 comprising the amino acid sequence of GPFSPWVMDY (SEQ ID NO: 25),
   d) an HVR-L1 comprising the amino acid sequence of RASQX$_1$VX$_2$X$_3$X$_4$X$_5$A (SEQ ID NO:17), wherein X$_1$=D or V; X$_2$=S or A; X$_3$=T or N; X$_4$=S or A; X$_5$=V or L;
   e) an HVR-L2 comprising the amino acid sequence of X$_6$ASFLYS (SEQ ID NO:18) wherein X$_6$=S or L; and
   f) an HVR-L3 comprising the amino acid sequence of QQX$_7$X$_8$X$_9$X$_{10}$X$_{11}$X$_{12}$T (SEQ ID NO:19), wherein X$_7$=S, F, G, D or Y; X$_8$=Y, P, S, or A; X$_9$=T or N; X$_{10}$=T, Y, D or S; X$_{11}$=P or L; X$_{12}$=P or T;

wherein the antibody reduces or inhibits the activity of BACE1.

18. The host cell of claim 16, wherein the HVR-H1 comprises the amino acid sequence selected of SEQ ID NO:23, the HVR-L1 comprises the amino acid sequence of SEQ ID NO:7, the HVR-L2 comprises the amino acid sequence of SEQ ID NO:9 and the HVR-L3 comprises the amino acid sequence of SEQ ID NO:12.

19. The host cell of claim 17, wherein the HVR-H1 comprises the amino acid sequence selected of SEQ ID NO:23, the HVR-L1 comprises the amino acid sequence of SEQ ID NO:7, the HVR-L2 comprises the amino acid sequence of SEQ ID NO:9 and the HVR-L3 comprises the amino acid sequence of SEQ ID NO:12.

20. The host cell of claim 16, wherein the antibody comprises a VH chain having an amino acid sequence selected from SEQ ID NOs: 20 and 21, and a VL chain sequence having an amino acid sequence selected from SEQ ID NOs: 1-6.

21. The host cell of claim 17, wherein the antibody comprises a VH chain having an amino acid sequence selected from SEQ ID NOs: 20 and 21, and a VL chain sequence having an amino acid sequence selected from SEQ ID NOs: 1-6.

22. The host cell of claim 16, wherein the antibody comprises a VH chain having the amino acid sequence of SEQ ID NO: 21 and a VL chain sequence having the amino acid sequence of SEQ ID NO: 2.

23. The host cell of claim 17, wherein the antibody comprises a VH chain having the amino acid sequence of SEQ ID NO: 21 and a VL chain sequence having the amino acid sequence of SEQ ID NO: 2.

24. A method of producing an antibody comprising culturing the host cell of claim 16 so that the antibody is produced.

25. A method of producing an antibody comprising culturing the host cell of claim 17 so that the antibody is produced.

26. A nucleic acid encoding a light chain of an antibody or fragment thereof that binds to β-site amyloid precursor protein cleaving enzyme 1 (BACE1), wherein the antibody or fragment thereof comprises:
   a) an HVR-L1 comprising an amino acid sequence of SEQ ID NO:7 or SEQ ID NO:8; and
   b) an HVR-L2 comprising an amino acid sequence of SEQ ID NO:9 or SEQ ID NO:10; and
   c) an HVR-L3 comprising an amino acid sequence selected from SEQ ID NOs:12-16.

27. The nucleic acid molecule of claim 26, wherein the antibody comprises a VL chain sequence having an amino acid sequence selected from SEQ ID NOs: 2-6.

* * * * *

UNITED STATES PATENT AND TRADEMARK OFFICE
CERTIFICATE OF CORRECTION

PATENT NO. : 9,879,094 B2
APPLICATION NO. : 15/234649
DATED : January 30, 2018
INVENTOR(S) : Jasvinder Atwal et al.

It is certified that error appears in the above-identified patent and that said Letters Patent is hereby corrected as shown below:

In the Claims

Claim 17, Column 191, Line 33, "n-site" should read --β-site--.

Signed and Sealed this
Seventeenth Day of April, 2018

Andrei Iancu
*Director of the United States Patent and Trademark Office*

SEQUENCE LISTING

```
<160> NUMBER OF SEQ ID NOS: 210

<210> SEQ ID NO 1
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg
            100                 105

<210> SEQ ID NO 2
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Pro Thr Tyr Leu Pro
                85                  90                  95

Thr Phe Gly Gln Gly Thr Lys Val Glu Ile Lys Arg
            100                 105

<210> SEQ ID NO 3
<211> LENGTH: 108
<212> TYPE: PRT
<213> ORGANISM: Artificial Sequence
<220> FEATURE:
<223> OTHER INFORMATION: Synthetic polypeptide
```

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Asn Asp Pro Pro
                85                  90                  95

Thr Phe Gly Gln Gly Thr Lys Val Glu Ile Lys Arg
            100                 105

<210> SEQ ID NO 4
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Thr Asp Pro Thr
                85                  90                  95

Thr Phe Gly Gln Gly Thr Lys Val Glu Ile Lys Arg
            100                 105

<210> SEQ ID NO 5
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Val Ala Asn Ser
            20                  25                  30

Leu Ala Trp Tyr Gln Gln Lys Pro Gly Lys Ala Pro Lys Leu Leu Ile
        35                  40                  45

Tyr Leu Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Asp Ala Thr Ser Pro Pro
                85                  90                  95

Thr Phe Gly Gln Gly Thr Lys Val Glu Ile Lys Arg
            100                 105

<210> SEQ ID NO 6
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ala Thr Asp Pro Pro
                85                  90                  95

Thr Phe Gly Gln Gly Thr Lys Val Glu Ile Lys Arg
            100                 105

<210> SEQ ID NO 7
<211> LENGTH: 11
<212> TYPE: PRT
<213> ORGANISM: Artificial Sequence
<220> FEATURE:
<223> OTHER INFORMATION: Synthetic peptide

<400> SEQUENCE: 7

Arg Ala Ser Gln Asp Val Ser Thr Ala Val Ala
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 8

Arg Ala Ser Gln Val Val Ala Asn Ser Leu Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide

<400> SEQUENCE: 9

Ser Ala Ser Phe Leu Tyr Ser
1               5

<210> SEQ ID NO 10
<211> LENGTH: 7
```

```
<212> TYPE: PRT
<213> ORGANISM: Artificial Sequence
<220> FEATURE:
<223> OTHER INFORMATION: Synthetic peptide

<400> SEQUENCE: 10

Leu Ala Ser Phe Leu Tyr Ser
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic peptide

<400> SEQUENCE: 11

Gln Gln Ser Tyr Thr Thr Pro Pro Thr
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic peptide

<400> SEQUENCE: 12

Gln Gln Phe Pro Thr Tyr Leu Pro Thr
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic peptide

<400> SEQUENCE: 13

Gln Gln Gly Tyr Asn Asp Pro Pro Thr
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic peptide

<400> SEQUENCE: 14

Gln Gln Ser Ser Thr Asp Pro Thr Thr
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic peptide

<400> SEQUENCE: 15

Gln Gln Asp Ala Thr Ser Pro Pro Thr
1               5

<210> SEQ ID NO 16
<211> LENGTH: 9
<212> TYPE: PRT
```

```
<213> ORGANISM: Artificial Sequence
<220> FEATURE:
<223> OTHER INFORMATION: Synthetic peptide

<400> SEQUENCE: 16

Gln Gln Tyr Ala Thr Asp Pro Pro Thr
1               5

<210> SEQ ID NO 17
<211> LENGTH: 11
<212> TYPE: PRT
<213> ORGANISM: Artificial Sequence
<220> FEATURE:
<223> OTHER INFORMATION: Synthetic consensus sequence
<220> FEATURE:
<221> NAME/KEY: VARIANT
<222> LOCATION: (5)..(5)
<223> OTHER INFORMATION: /replace="Val"
<220> FEATURE:
<221> NAME/KEY: misc_feature
<222> LOCATION: (5)..(5)
<223> OTHER INFORMATION: /note="Residue given in the sequence has no
      preference with respect to the annotations for said position"
<220> FEATURE:
<221> NAME/KEY: VARIANT
<222> LOCATION: (7)..(7)
<223> OTHER INFORMATION: /replace="Ala"
<220> FEATURE:
<221> NAME/KEY: misc_feature
<222> LOCATION: (7)..(10)
<223> OTHER INFORMATION: /note="Residues given in the sequence have no
      preference with respect to those in the annotations for said
      positions"
<220> FEATURE:
<221> NAME/KEY: VARIANT
<222> LOCATION: (8)..(8)
<223> OTHER INFORMATION: /replace="Asn"
<220> FEATURE:
<221> NAME/KEY: VARIANT
<222> LOCATION: (9)..(9)
<223> OTHER INFORMATION: /replace="Ala"
<220> FEATURE:
<221> NAME/KEY: VARIANT
<222> LOCATION: (10)..(10)
<223> OTHER INFORMATION: /replace="Leu"

<400> SEQUENCE: 17

Arg Ala Ser Gln Asp Val Ser Thr Ser Val Ala
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Synthetic consensus sequence
<220> FEATURE:
<221> NAME/KEY: VARIANT
<222> LOCATION: (1)..(1)
<223> OTHER INFORMATION: /replace="Leu"
<220> FEATURE:
<221> NAME/KEY: misc_feature
<222> LOCATION: (1)..(1)
<223> OTHER INFORMATION: /note="Residue given in the sequence has no
      preference with respect to the annotations for said position"

<400> SEQUENCE: 18

Ser Ala Ser Phe Leu Tyr Ser
1               5

<210> SEQ ID NO 19
<211> LENGTH: 9
<212> TYPE: PRT
```

<213> ORGANISM: Artificial Sequence
<220> FEATURE:
<223> OTHER INFORMATION: Synthetic consensus sequence
<220> FEATURE:
<221> NAME/KEY: VARIANT
<222> LOCATION: (3)..(3)
<223> OTHER INFORMATION: /replace="Phe" or "Gly" or "Asp" or "Tyr"
<220> FEATURE:
<221> NAME/KEY: misc_feature
<222> LOCATION: (3)..(8)
<223> OTHER INFORMATION: /note="Residues given in the sequence have no
    preference with respect to those in the annotations for said
    positions"
<220> FEATURE:
<221> NAME/KEY: VARIANT
<222> LOCATION: (4)..(4)
<223> OTHER INFORMATION: /replace="Pro" or "Ser" or "Ala"
<220> FEATURE:
<221> NAME/KEY: VARIANT
<222> LOCATION: (5)..(5)
<223> OTHER INFORMATION: /replace="Asn"
<220> FEATURE:
<221> NAME/KEY: VARIANT
<222> LOCATION: (6)..(6)
<223> OTHER INFORMATION: /replace="Tyr" or "Asp" or "Ser"
<220> FEATURE:
<221> NAME/KEY: VARIANT
<222> LOCATION: (7)..(7)
<223> OTHER INFORMATION: /replace="Leu"
<220> FEATURE:
<221> NAME/KEY: VARIANT
<222> LOCATION: (8)..(8)
<223> OTHER INFORMATION: /replace="Thr"

<400> SEQUENCE: 19

Gln Gln Ser Tyr Thr Thr Pro Pro Thr
1               5

<210> SEQ ID NO 20
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ala Ile His Trp Val Arg Gln Ala Pro Gly Lys Gly Leu Glu Trp Val
        35                  40                  45

Gly Trp Ile Ser Pro Ala Gly Gly Ser Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Pro Phe Ser Pro Trp Val Met Asp Tyr Trp Gly Gln Gly
            100                 105                 110

Thr Leu Val Thr Val Ser Ser
        115

<210> SEQ ID NO 21
<211> LENGTH: 119
<212> TYPE: PRT
<213> ORGANISM: Artificial Sequence
<220> FEATURE:

<223> OTHER INFORMATION: Synthetic polypeptide

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Leu Gly Tyr
            20                  25                  30

Gly Ile His Trp Val Arg Gln Ala Pro Gly Lys Gly Leu Glu Trp Val
        35                  40                  45

Gly Trp Ile Ser Pro Ala Gly Gly Ser Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Pro Phe Ser Pro Trp Val Met Asp Tyr Trp Gly Gln Gly
            100                 105                 110

Thr Leu Val Thr Val Ser Ser
        115

<210> SEQ ID NO 22
<211> LENGTH: 10
<212> TYPE: PRT
<213> ORGANISM: Artificial Sequence
<220> FEATURE:
<223> OTHER INFORMATION: Synthetic peptide

<400> SEQUENCE: 22

Gly Phe Thr Phe Ser Gly Tyr Ala Ile His
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic peptide

<400> SEQUENCE: 23

Gly Phe Thr Phe Leu Gly Tyr Gly Ile His
1               5                   10

<210> SEQ ID NO 24
<211> LENGTH: 18
<212> TYPE: PRT
<213> ORGANISM: Artificial Sequence
<220> FEATURE:
<223> OTHER INFORMATION: Synthetic peptide

<400> SEQUENCE: 24

Gly Trp Ile Ser Pro Ala Gly Gly Ser Thr Asp Tyr Ala Asp Ser Val
1               5                   10                  15

Lys Gly

<210> SEQ ID NO 25
<211> LENGTH: 10
<212> TYPE: PRT
<213> ORGANISM: Artificial Sequence
<220> FEATURE:
<223> OTHER INFORMATION: Synthetic peptide

<400> SEQUENCE: 25

```
Gly Pro Phe Ser Pro Trp Val Met Asp Tyr
1               5                   10
```

<210> SEQ ID NO 26
<211> LENGTH: 10
<212> TYPE: PRT
<213> ORGANISM: Artificial Sequence
<220> FEATURE:
<223> OTHER INFORMATION: Synthetic consensus sequence
<220> FEATURE:
<221> NAME/KEY: VARIANT
<222> LOCATION: (5)..(5)
<223> OTHER INFORMATION: /replace="Leu"
<220> FEATURE:
<221> NAME/KEY: misc_feature
<222> LOCATION: (5)..(5)
<223> OTHER INFORMATION: /note="Residue given in the sequence has no
      preference with respect to the annotations for said position"
<220> FEATURE:
<221> NAME/KEY: VARIANT
<222> LOCATION: (8)..(8)
<223> OTHER INFORMATION: /replace="Gly"
<220> FEATURE:
<221> NAME/KEY: misc_feature
<222> LOCATION: (8)..(8)
<223> OTHER INFORMATION: /note="Residue given in the sequence has no
      preference with respect to the annotations for said position"

<400> SEQUENCE: 26

```
Gly Phe Thr Phe Ser Gly Tyr Ala Ile His
1               5                   10
```

<210> SEQ ID NO 27
<211> LENGTH: 129
<212> TYPE: PRT
<213> ORGANISM: Artificial Sequence
<220> FEATURE:
<223> OTHER INFORMATION: Synthetic polypeptide

<400> SEQUENCE: 27

```
Glu Ile Ser Glu Val Gln Leu Val Glu Ser Gly Gly Gly Leu Val Gln
1               5                   10                  15

Pro Gly Gly Ser Leu Arg Leu Ser Cys Ala Ala Ser Gly Phe Asn Phe
            20                  25                  30

Tyr Tyr Ser Ser Ile His Trp Val Arg Gln Ala Pro Gly Lys Gly Leu
        35                  40                  45

Glu Trp Val Ala Ser Ile Ser Pro Tyr Ser Gly Tyr Thr Ser Tyr Ala
    50                  55                  60

Asp Ser Val Lys Gly Arg Phe Thr Ile Ser Ala Asp Thr Ser Lys Asn
65                  70                  75                  80

Thr Ala Tyr Leu Gln Met Asn Ser Leu Arg Ala Glu Asp Thr Ala Val
                85                  90                  95

Tyr Tyr Cys Ala Arg Gln Pro Thr His Tyr Tyr Tyr Ala Lys Gly
            100                 105                 110

Tyr Lys Ala Met Asp Tyr Trp Gly Gln Gly Thr Leu Val Thr Val Ser
        115                 120                 125

Ser
```

<210> SEQ ID NO 28
<211> LENGTH: 10
<212> TYPE: PRT
<213> ORGANISM: Artificial Sequence
<220> FEATURE:
<223> OTHER INFORMATION: Synthetic peptide

<400> SEQUENCE: 28

```
Gly Phe Asn Phe Tyr Tyr Ser Ser Ile His
1               5                   10
```

```
<210> SEQ ID NO 29
<211> LENGTH: 18
<212> TYPE: PRT
<213> ORGANISM: Artificial Sequence
<220> FEATURE:
<223> OTHER INFORMATION: Synthetic peptide

<400> SEQUENCE: 29

Ala Ser Ile Ser Pro Tyr Ser Gly Tyr Thr Ser Tyr Ala Asp Ser Val
1               5                   10                  15

Lys Gly
```

```
<210> SEQ ID NO 30
<211> LENGTH: 17
<212> TYPE: PRT
<213> ORGANISM: Artificial Sequence
<220> FEATURE:
<223> OTHER INFORMATION: Synthetic peptide

<400> SEQUENCE: 30

Gln Pro Thr His Tyr Tyr Tyr Ala Lys Gly Tyr Lys Ala Met Asp
1               5                   10                  15

Tyr
```

```
<210> SEQ ID NO 31
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Tyr Ser Pro Phe
                85                  90                  95

Thr Phe Gly Gln Gly Thr Lys Val Glu Ile Lys Arg
            100                 105
```

```
<210> SEQ ID NO 32
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
```

```
                    20                  25                  30

Val Ala Trp Tyr Gln Gln Lys Pro Gly Lys Ala Pro Lys Leu Leu Ile
            35                  40                  45

Ser Trp Ala Ser Trp Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Tyr Ser Pro Phe
                    85                  90                  95

Thr Phe Gly Gln Gly Thr Lys Val Glu Ile Lys Arg
                100                 105

<210> SEQ ID NO 33
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 33

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
                    20                  25                  30

Val Ala Trp Tyr Gln Gln Lys Pro Gly Lys Ala Pro Lys Leu Leu Ile
            35                  40                  45

Trp Tyr Ala Ser Trp Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Tyr Ser Pro Phe
                    85                  90                  95

Thr Phe Gly Gln Gly Thr Lys Val Glu Ile Lys Arg
                100                 105

<210> SEQ ID NO 34
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 34

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ser Ala
                    20                  25                  30

Val Ala Trp Tyr Gln Gln Lys Pro Gly Lys Ala Pro Lys Leu Leu Ile
            35                  40                  45

Trp Trp Ala Ser Ser Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Tyr Ser Pro Phe
                    85                  90                  95

Thr Phe Gly Gln Gly Thr Lys Val Glu Ile Lys Arg
                100                 105
```

```
<210> SEQ ID NO 35
<211> LENGTH: 11
<212> TYPE: PRT
<213> ORGANISM: Artificial Sequence
<220> FEATURE:
<223> OTHER INFORMATION: Synthetic peptide

<400> SEQUENCE: 35

Arg Ala Ser Gln Ser Val Ser Ser Ala Val Ala
1               5                   10

<210> SEQ ID NO 36
<211> LENGTH: 7
<212> TYPE: PRT
<213> ORGANISM: Artificial Sequence
<220> FEATURE:
<223> OTHER INFORMATION: Synthetic peptide

<400> SEQUENCE: 36

Ser Ala Ser Ser Leu Tyr Ser
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic peptide

<400> SEQUENCE: 37

Trp Ala Ser Trp Leu Tyr Ser
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic peptide

<400> SEQUENCE: 38

Tyr Ala Ser Trp Leu Tyr Ser
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic peptide

<400> SEQUENCE: 39

Trp Ala Ser Ser Leu Tyr Ser
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic peptide

<400> SEQUENCE: 40

Gln Gln Tyr Ser Tyr Ser Pro Phe Thr
1               5
```

```
<210> SEQ ID NO 41
<211> LENGTH: 7
<212> TYPE: PRT
<213> ORGANISM: Artificial Sequence
<220> FEATURE:
<223> OTHER INFORMATION: Synthetic consensus sequence
<220> FEATURE:
<221> NAME/KEY: VARIANT
<222> LOCATION: (1)..(1)
<223> OTHER INFORMATION: /replace="Trp" or "Tyr"
<220> FEATURE:
<221> NAME/KEY: misc_feature
<222> LOCATION: (1)..(1)
<223> OTHER INFORMATION: /note="Residue given in the sequence has no
      preference with respect to the annotations for said position"
<220> FEATURE:
<221> NAME/KEY: VARIANT
<222> LOCATION: (4)..(4)
<223> OTHER INFORMATION: /replace="Trp"
<220> FEATURE:
<221> NAME/KEY: misc_feature
<222> LOCATION: (4)..(4)
<223> OTHER INFORMATION: /note="Residue given in the sequence has no
      preference with respect to the annotations for said position"

<400> SEQUENCE: 41

Ser Ala Ser Ser Leu Tyr Ser
1               5

<210> SEQ ID NO 42
<211> LENGTH: 11
<212> TYPE: PRT
<213> ORGANISM: Artificial Sequence
<220> FEATURE:
<223> OTHER INFORMATION: Synthetic consensus sequence
<220> FEATURE:
<221> NAME/KEY: VARIANT
<222> LOCATION: (5)..(5)
<223> OTHER INFORMATION: /replace="Asp" or "Val"
<220> FEATURE:
<221> NAME/KEY: misc_feature
<222> LOCATION: (5)..(5)
<223> OTHER INFORMATION: /note="Residue given in the sequence has no
      preference with respect to the annotations for said position"
<220> FEATURE:
<221> NAME/KEY: VARIANT
<222> LOCATION: (7)..(7)
<223> OTHER INFORMATION: /replace="Ala"
<220> FEATURE:
<221> NAME/KEY: misc_feature
<222> LOCATION: (7)..(10)
<223> OTHER INFORMATION: /note="Residues given in the sequence have no
      preference with respect to those in the annotations for said
      positions"
<220> FEATURE:
<221> NAME/KEY: VARIANT
<222> LOCATION: (8)..(8)
<223> OTHER INFORMATION: /replace="Thr" or "Asn"
<220> FEATURE:
<221> NAME/KEY: VARIANT
<222> LOCATION: (9)..(9)
<223> OTHER INFORMATION: /replace="Ser"
<220> FEATURE:
<221> NAME/KEY: VARIANT
<222> LOCATION: (10)..(10)
<223> OTHER INFORMATION: /replace="Leu"

<400> SEQUENCE: 42

Arg Ala Ser Gln Ser Val Ser Ser Ala Val Ala
1               5                   10

<210> SEQ ID NO 43
<211> LENGTH: 7
<212> TYPE: PRT
<213> ORGANISM: Artificial Sequence
```

```
<220> FEATURE:
<223> OTHER INFORMATION: Synthetic consensus sequence
<220> FEATURE:
<221> NAME/KEY: VARIANT
<222> LOCATION: (1)..(1)
<223> OTHER INFORMATION: /replace="Trp" or "Tyr" or "Leu"
<220> FEATURE:
<221> NAME/KEY: misc_feature
<222> LOCATION: (1)..(1)
<223> OTHER INFORMATION: /note="Residue given in the sequence has no
      preference with respect to the annotations for said position"
<220> FEATURE:
<221> NAME/KEY: VARIANT
<222> LOCATION: (4)..(4)
<223> OTHER INFORMATION: /replace="Ser" or "Trp"
<220> FEATURE:
<221> NAME/KEY: misc_feature
<222> LOCATION: (4)..(4)
<223> OTHER INFORMATION: /note="Residue given in the sequence has no
      preference with respect to the annotations for said position"

<400> SEQUENCE: 43

Ser Ala Ser Phe Leu Tyr Ser
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic consensus sequence
<220> FEATURE:
<221> NAME/KEY: VARIANT
<222> LOCATION: (3)..(3)
<223> OTHER INFORMATION: /replace="Phe" or "Gly" or "Asp" or "Tyr"
<220> FEATURE:
<221> NAME/KEY: misc_feature
<222> LOCATION: (3)..(8)
<223> OTHER INFORMATION: /note="Residues given in the sequence have no
      preference with respect to those in the annotations for said
      positions"
<220> FEATURE:
<221> NAME/KEY: VARIANT
<222> LOCATION: (4)..(4)
<223> OTHER INFORMATION: /replace="Pro" or "Ser" or "Ala"
<220> FEATURE:
<221> NAME/KEY: VARIANT
<222> LOCATION: (5)..(5)
<223> OTHER INFORMATION: /replace="Thr" or "Asn"
<220> FEATURE:
<221> NAME/KEY: VARIANT
<222> LOCATION: (6)..(6)
<223> OTHER INFORMATION: /replace="Tyr" or "Asp" or "Ser"
<220> FEATURE:
<221> NAME/KEY: VARIANT
<222> LOCATION: (7)..(7)
<223> OTHER INFORMATION: /replace="Leu"
<220> FEATURE:
<221> NAME/KEY: VARIANT
<222> LOCATION: (8)..(8)
<223> OTHER INFORMATION: /replace="Pro" or "Thr"

<400> SEQUENCE: 44

Gln Gln Ser Tyr Tyr Thr Pro Phe Thr
1               5

<210> SEQ ID NO 45
<211> LENGTH: 10
<212> TYPE: PRT
<213> ORGANISM: Artificial Sequence
<220> FEATURE:
<223> OTHER INFORMATION: Synthetic consensus sequence
<220> FEATURE:
<221> NAME/KEY: VARIANT
<222> LOCATION: (3)..(3)
```

```
<223> OTHER INFORMATION: /replace="Thr"
<220> FEATURE:
<221> NAME/KEY: misc_feature
<222> LOCATION: (3)..(3)
<223> OTHER INFORMATION: /note="Residue given in the sequence has no
      preference with respect to the annotations for said position"
<220> FEATURE:
<221> NAME/KEY: VARIANT
<222> LOCATION: (5)..(5)
<223> OTHER INFORMATION: /replace="Leu" or "Tyr"
<220> FEATURE:
<221> NAME/KEY: misc_feature
<222> LOCATION: (5)..(8)
<223> OTHER INFORMATION: /note="Residues given in the sequence have no
      preference with respect to those in the annotations for said
      positions"
<220> FEATURE:
<221> NAME/KEY: VARIANT
<222> LOCATION: (6)..(6)
<223> OTHER INFORMATION: /replace="Tyr"
<220> FEATURE:
<221> NAME/KEY: VARIANT
<222> LOCATION: (7)..(7)
<223> OTHER INFORMATION: /replace="Ser"
<220> FEATURE:
<221> NAME/KEY: VARIANT
<222> LOCATION: (8)..(8)
<223> OTHER INFORMATION: /replace="Gly" or "Ser"

<400> SEQUENCE: 45

Gly Phe Asn Phe Ser Gly Tyr Ala Ile His
1               5                   10

<210> SEQ ID NO 46
<211> LENGTH: 18
<212> TYPE: PRT
<213> ORGANISM: Artificial Sequence
<220> FEATURE:
<223> OTHER INFORMATION: Synthetic consensus sequence
<220> FEATURE:
<221> NAME/KEY: VARIANT
<222> LOCATION: (1)..(1)
<223> OTHER INFORMATION: /replace="Gly"
<220> FEATURE:
<221> NAME/KEY: misc_feature
<222> LOCATION: (1)..(2)
<223> OTHER INFORMATION: /note="Residues given in the sequence have no
      preference with respect to those in the annotations for said
      positions"
<220> FEATURE:
<221> NAME/KEY: VARIANT
<222> LOCATION: (2)..(2)
<223> OTHER INFORMATION: /replace="Ser"
<220> FEATURE:
<221> NAME/KEY: VARIANT
<222> LOCATION: (6)..(6)
<223> OTHER INFORMATION: /replace="Tyr"
<220> FEATURE:
<221> NAME/KEY: misc_feature
<222> LOCATION: (6)..(7)
<223> OTHER INFORMATION: /note="Residues given in the sequence have no
      preference with respect to those in the annotations for said
      positions"
<220> FEATURE:
<221> NAME/KEY: VARIANT
<222> LOCATION: (7)..(7)
<223> OTHER INFORMATION: /replace="Ser"
<220> FEATURE:
<221> NAME/KEY: VARIANT
<222> LOCATION: (9)..(9)
<223> OTHER INFORMATION: /replace="Tyr"
<220> FEATURE:
<221> NAME/KEY: misc_feature
<222> LOCATION: (9)..(9)
<223> OTHER INFORMATION: /note="Residue given in the sequence has no
      preference with respect to the annotations for said position"
<220> FEATURE:
```

```
<221> NAME/KEY: VARIANT
<222> LOCATION: (11)..(11)
<223> OTHER INFORMATION: /replace="Ser"
<220> FEATURE:
<221> NAME/KEY: misc_feature
<222> LOCATION: (11)..(11)
<223> OTHER INFORMATION: /note="Residue given in the sequence has no
      preference with respect to the annotations for said position"

<400> SEQUENCE: 46

Ala Trp Ile Ser Pro Ala Gly Gly Ser Thr Asp Tyr Ala Asp Ser Val
1               5                   10                  15

Lys Gly

<210> SEQ ID NO 47
<211> LENGTH: 17
<212> TYPE: PRT
<213> ORGANISM: Artificial Sequence
<220> FEATURE:
<223> OTHER INFORMATION: Synthetic consensus sequence
<220> FEATURE:
<221> NAME/KEY: VARIANT
<222> LOCATION: (1)..(1)
<223> OTHER INFORMATION: /replace="Gly"
<220> FEATURE:
<221> NAME/KEY: misc_feature
<222> LOCATION: (1)..(1)
<223> OTHER INFORMATION: /note="Residue given in the sequence has no
      preference with respect to the annotations for said position"
<220> FEATURE:
<221> NAME/KEY: VARIANT
<222> LOCATION: (3)..(3)
<223> OTHER INFORMATION: /replace="Phe"
<220> FEATURE:
<221> NAME/KEY: misc_feature
<222> LOCATION: (3)..(14)
<223> OTHER INFORMATION: /note="Residues given in the sequence have no
      preference with respect to those in the annotations for said
      positions"
<220> FEATURE:
<221> NAME/KEY: VARIANT
<222> LOCATION: (4)..(4)
<223> OTHER INFORMATION: /replace="Ser"
<220> FEATURE:
<221> NAME/KEY: VARIANT
<222> LOCATION: (5)..(5)
<223> OTHER INFORMATION: /replace="Pro"
<220> FEATURE:
<221> NAME/KEY: VARIANT
<222> LOCATION: (6)..(6)
<223> OTHER INFORMATION: /replace="Trp"
<220> FEATURE:
<221> NAME/KEY: VARIANT
<222> LOCATION: (7)..(7)
<223> OTHER INFORMATION: /replace="Val"
<220> FEATURE:
<221> NAME/KEY: VARIANT
<222> LOCATION: (8)..(14)
<223> OTHER INFORMATION: /replace=" "
<220> FEATURE:
<221> NAME/KEY: misc_feature
<222> LOCATION: (8)..(14)
<223> OTHER INFORMATION: /note="When present, this region is present in
      its entirety"

<400> SEQUENCE: 47

Gln Pro Thr His Tyr Tyr Tyr Tyr Ala Lys Gly Tyr Lys Ala Met Asp
1               5                   10                  15

Tyr

<210> SEQ ID NO 48
<211> LENGTH: 7
<212> TYPE: PRT
```

```
<213> ORGANISM: Artificial Sequence
<220> FEATURE:
<223> OTHER INFORMATION: Synthetic peptide

<400> SEQUENCE: 48

Tyr Ala Lys Gly Tyr Lys Ala
1               5

<210> SEQ ID NO 49
<211> LENGTH: 501
<212> TYPE: PRT
<213> ORGANISM: Homo sapiens

<400> SEQUENCE: 49

Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
                20                  25                  30

Gly Leu Gly Gly Ala Pro Leu Gly Leu Arg Leu Pro Arg Glu Thr Asp
            35                  40                  45

Glu Glu Pro Glu Glu Pro Gly Arg Arg Gly Ser Phe Val Glu Met Val
    50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
    130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
            180                 185                 190

Ser Leu Glu Pro Phe Phe Asp Ser Leu Val Lys Gln Thr His Val Pro
        195                 200                 205

Asn Leu Phe Ser Leu Gln Leu Cys Gly Ala Gly Phe Pro Leu Asn Gln
    210                 215                 220

Ser Glu Val Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
            260                 265                 270

Asp Leu Lys Met Asp Cys Lys Glu Tyr Asn Tyr Asp Lys Ser Ile Val
        275                 280                 285

Asp Ser Gly Thr Thr Asn Leu Arg Leu Pro Lys Lys Val Phe Glu Ala
    290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335
```

```
Pro Trp Asn Ile Phe Pro Val Ile Ser Leu Tyr Leu Met Gly Glu Val
            340                 345                 350

Thr Asn Gln Ser Phe Arg Ile Thr Ile Leu Pro Gln Gln Tyr Leu Arg
        355                 360                 365

Pro Val Glu Asp Val Ala Thr Ser Gln Asp Asp Cys Tyr Lys Phe Ala
    370                 375                 380

Ile Ser Gln Ser Ser Thr Gly Thr Val Met Gly Ala Val Ile Met Glu
385                 390                 395                 400

Gly Phe Tyr Val Val Phe Asp Arg Ala Arg Lys Arg Ile Gly Phe Ala
                405                 410                 415

Val Ser Ala Cys His Val His Asp Glu Phe Arg Thr Ala Ala Val Glu
                420                 425                 430

Gly Pro Phe Val Thr Leu Asp Met Glu Asp Cys Gly Tyr Asn Ile Pro
            435                 440                 445

Gln Thr Asp Glu Ser Thr Leu Met Thr Ile Ala Tyr Val Met Ala Ala
        450                 455                 460

Ile Cys Ala Leu Phe Met Leu Pro Leu Cys Leu Met Val Cys Gln Trp
465                 470                 475                 480

Cys Cys Leu Arg Cys Leu Arg Gln Gln His Asp Asp Phe Ala Asp Asp
                485                 490                 495

Ile Ser Leu Leu Lys
            500

<210> SEQ ID NO 50
<211> LENGTH: 476
<212> TYPE: PRT
<213> ORGANISM: Homo sapiens

<400> SEQUENCE: 50

Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
            20                  25                  30

Gly Leu Gly Gly Ala Pro Leu Gly Leu Arg Leu Pro Arg Glu Thr Asp
        35                  40                  45

Glu Glu Pro Glu Glu Pro Gly Arg Arg Gly Ser Phe Val Glu Met Val
    50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
    130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Leu Cys Gly
            180                 185                 190

Ala Gly Phe Pro Leu Asn Gln Ser Glu Val Leu Ala Ser Val Gly Gly
```

195                 200                 205
Ser Met Ile Gly Gly Ile Asp His Ser Leu Tyr Thr Gly Ser Leu
    210                 215                 220

Trp Tyr Thr Pro Ile Arg Arg Glu Trp Tyr Tyr Glu Val Ile Val
225                 230                 235                 240

Arg Val Glu Ile Asn Gly Gln Asp Leu Lys Met Asp Cys Lys Glu Tyr
                245                 250                 255

Asn Tyr Asp Lys Ser Ile Val Asp Ser Gly Thr Thr Asn Leu Arg Leu
            260                 265                 270

Pro Lys Lys Val Phe Glu Ala Ala Val Lys Ser Ile Lys Ala Ala Ser
            275                 280                 285

Ser Thr Glu Lys Phe Pro Asp Gly Phe Trp Leu Gly Glu Gln Leu Val
    290                 295                 300

Cys Trp Gln Ala Gly Thr Thr Pro Trp Asn Ile Phe Pro Val Ile Ser
305                 310                 315                 320

Leu Tyr Leu Met Gly Glu Val Thr Asn Gln Ser Phe Arg Ile Thr Ile
                325                 330                 335

Leu Pro Gln Gln Tyr Leu Arg Pro Val Glu Asp Val Ala Thr Ser Gln
            340                 345                 350

Asp Asp Cys Tyr Lys Phe Ala Ile Ser Gln Ser Ser Thr Gly Thr Val
        355                 360                 365

Met Gly Ala Val Ile Met Glu Gly Phe Tyr Val Val Phe Asp Arg Ala
    370                 375                 380

Arg Lys Arg Ile Gly Phe Ala Val Ser Ala Cys His Val His Asp Glu
385                 390                 395                 400

Phe Arg Thr Ala Ala Val Glu Gly Pro Phe Val Thr Leu Asp Met Glu
                405                 410                 415

Asp Cys Gly Tyr Asn Ile Pro Gln Thr Asp Glu Ser Thr Leu Met Thr
            420                 425                 430

Ile Ala Tyr Val Met Ala Ala Ile Cys Ala Leu Phe Met Leu Pro Leu
        435                 440                 445

Cys Leu Met Val Cys Gln Trp Cys Cys Leu Arg Cys Leu Arg Gln Gln
    450                 455                 460

His Asp Asp Phe Ala Asp Asp Ile Ser Leu Leu Lys
465                 470                 475

<210> SEQ ID NO 51
<211> LENGTH: 457
<212> TYPE: PRT
<213> ORGANISM: Homo sapiens

<400> SEQUENCE: 51

Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
                20                  25                  30

Gly Leu Gly Gly Ala Pro Leu Gly Leu Arg Leu Pro Arg Glu Thr Asp
            35                  40                  45

Glu Glu Pro Glu Glu Pro Gly Arg Arg Gly Ser Phe Val Glu Met Val
        50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

```
Ser Asn Phe Ala Val Gly Ala Ala Pro His Pro Phe Leu His Arg Tyr
                100                 105                 110

Tyr Gln Arg Gln Leu Ser Ser Thr Tyr Arg Asp Leu Arg Lys Gly Val
            115                 120                 125

Tyr Val Pro Tyr Thr Gln Gly Lys Trp Glu Gly Glu Leu Gly Thr Asp
        130                 135                 140

Leu Pro Asp Asp Ser Leu Glu Pro Phe Phe Asp Ser Leu Val Lys Gln
145                 150                 155                 160

Thr His Val Pro Asn Leu Phe Ser Leu Gln Leu Cys Gly Ala Gly Phe
                165                 170                 175

Pro Leu Asn Gln Ser Glu Val Leu Ala Ser Val Gly Gly Ser Met Ile
            180                 185                 190

Ile Gly Gly Ile Asp His Ser Leu Tyr Thr Gly Ser Leu Trp Tyr Thr
        195                 200                 205

Pro Ile Arg Arg Glu Trp Tyr Tyr Glu Val Ile Ile Val Arg Val Glu
    210                 215                 220

Ile Asn Gly Gln Asp Leu Lys Met Asp Cys Lys Glu Tyr Asn Tyr Asp
225                 230                 235                 240

Lys Ser Ile Val Asp Ser Gly Thr Thr Asn Leu Arg Leu Pro Lys Lys
                245                 250                 255

Val Phe Glu Ala Ala Val Lys Ser Ile Lys Ala Ala Ser Ser Thr Glu
            260                 265                 270

Lys Phe Pro Asp Gly Phe Trp Leu Gly Glu Gln Leu Val Cys Trp Gln
        275                 280                 285

Ala Gly Thr Thr Pro Trp Asn Ile Phe Pro Val Ile Ser Leu Tyr Leu
    290                 295                 300

Met Gly Glu Val Thr Asn Gln Ser Phe Arg Ile Thr Ile Leu Pro Gln
305                 310                 315                 320

Gln Tyr Leu Arg Pro Val Glu Asp Val Ala Thr Ser Gln Asp Asp Cys
                325                 330                 335

Tyr Lys Phe Ala Ile Ser Gln Ser Ser Thr Gly Thr Val Met Gly Ala
            340                 345                 350

Val Ile Met Glu Gly Phe Tyr Val Val Phe Asp Arg Ala Arg Lys Arg
        355                 360                 365

Ile Gly Phe Ala Val Ser Ala Cys His Val His Asp Glu Phe Arg Thr
    370                 375                 380

Ala Ala Val Glu Gly Pro Phe Val Thr Leu Asp Met Glu Asp Cys Gly
385                 390                 395                 400

Tyr Asn Ile Pro Gln Thr Asp Glu Ser Thr Leu Met Thr Ile Ala Tyr
                405                 410                 415

Val Met Ala Ala Ile Cys Ala Leu Phe Met Leu Pro Leu Cys Leu Met
            420                 425                 430

Val Cys Gln Trp Cys Cys Leu Arg Cys Leu Arg Gln Gln His Asp Asp
        435                 440                 445

Phe Ala Asp Asp Ile Ser Leu Leu Lys
    450                 455

<210> SEQ ID NO 52
<211> LENGTH: 432
<212> TYPE: PRT
<213> ORGANISM: Homo sapiens

<400> SEQUENCE: 52

Met Ala Gln Ala Leu Pro Trp Leu Leu Leu Trp Met Gly Ala Gly Val
1               5                   10                  15
```

-continued

Leu Pro Ala His Gly Thr Gln His Gly Ile Arg Leu Pro Leu Arg Ser
            20                  25                  30

Gly Leu Gly Gly Ala Pro Leu Gly Leu Arg Leu Pro Arg Glu Thr Asp
            35                  40                  45

Glu Glu Pro Glu Glu Pro Gly Arg Arg Gly Ser Phe Val Glu Met Val
50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
            115                 120                 125

Tyr Val Pro Tyr Thr Gln Gly Lys Trp Glu Gly Glu Leu Gly Thr Asp
130                 135                 140

Leu Leu Cys Gly Ala Gly Phe Pro Leu Asn Gln Ser Glu Val Leu Ala
145                 150                 155                 160

Ser Val Gly Gly Ser Met Ile Ile Gly Gly Ile Asp His Ser Leu Tyr
                165                 170                 175

Thr Gly Ser Leu Trp Tyr Thr Pro Ile Arg Arg Glu Trp Tyr Tyr Glu
            180                 185                 190

Val Ile Ile Val Arg Val Glu Ile Asn Gly Gln Asp Leu Lys Met Asp
            195                 200                 205

Cys Lys Glu Tyr Asn Tyr Asp Lys Ser Ile Val Asp Ser Gly Thr Thr
210                 215                 220

Asn Leu Arg Leu Pro Lys Lys Val Phe Glu Ala Ala Val Lys Ser Ile
225                 230                 235                 240

Lys Ala Ala Ser Ser Thr Glu Lys Phe Pro Asp Gly Phe Trp Leu Gly
                245                 250                 255

Glu Gln Leu Val Cys Trp Gln Ala Gly Thr Thr Pro Trp Asn Ile Phe
            260                 265                 270

Pro Val Ile Ser Leu Tyr Leu Met Gly Glu Val Thr Asn Gln Ser Phe
            275                 280                 285

Arg Ile Thr Ile Leu Pro Gln Gln Tyr Leu Arg Pro Val Glu Asp Val
290                 295                 300

Ala Thr Ser Gln Asp Asp Cys Tyr Lys Phe Ala Ile Ser Gln Ser Ser
305                 310                 315                 320

Thr Gly Thr Val Met Gly Ala Val Ile Met Glu Gly Phe Tyr Val Val
                325                 330                 335

Phe Asp Arg Ala Arg Lys Arg Ile Gly Phe Ala Val Ser Ala Cys His
            340                 345                 350

Val His Asp Glu Phe Arg Thr Ala Ala Val Glu Gly Pro Phe Val Thr
            355                 360                 365

Leu Asp Met Glu Asp Cys Gly Tyr Asn Ile Pro Gln Thr Asp Glu Ser
370                 375                 380

Thr Leu Met Thr Ile Ala Tyr Val Met Ala Ala Ile Cys Ala Leu Phe
385                 390                 395                 400

Met Leu Pro Leu Cys Leu Met Val Cys Gln Trp Cys Cys Leu Arg Cys
                405                 410                 415

Leu Arg Gln Gln His Asp Asp Phe Ala Asp Asp Ile Ser Leu Leu Lys
            420                 425                 430

```
<210> SEQ ID NO 53
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(27)
<223> OTHER INFORMATION: /note="N-term biotin"

<400> SEQUENCE: 53

Lys Thr Glu Glu Ile Ser Glu Val Asn Leu Asp Ala Glu Phe Arg His
1               5                   10                  15

Asp Ser Gly Tyr Glu Val His His Gln Lys Leu
            20                  25

<210> SEQ ID NO 54
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(9)
<223> OTHER INFORMATION: /note="N-term Rh"
<220> FEATURE:
<221> NAME/KEY: misc_feature
<222> LOCATION: (1)..(9)
<223> OTHER INFORMATION: /note="C-term quencher"

<400> SEQUENCE: 54

Glu Val Asn Leu Asp Ala Glu Phe Lys
1               5

<210> SEQ ID NO 55
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(18)
<223> OTHER INFORMATION: /note="N-term FAM"
<220> FEATURE:
<221> NAME/KEY: misc_feature
<222> LOCATION: (1)..(18)
<223> OTHER INFORMATION: /note="C-term CONH2"

<400> SEQUENCE: 55

Lys Thr Glu Glu Ile Ser Glu Val Asn Leu Asp Ala Glu Phe Arg Trp
1               5                   10                  15

Lys Lys

<210> SEQ ID NO 56
<211> LENGTH: 7
<212> TYPE: PRT
<213> ORGANISM: Artificial Sequence
<220> FEATURE:
<223> OTHER INFORMATION: Synthetic consensus sequence
<220> FEATURE:
<221> NAME/KEY: VARIANT
<222> LOCATION: (1)..(1)
<223> OTHER INFORMATION: /replace="Phe"
<220> FEATURE:
<221> NAME/KEY: misc_feature
<222> LOCATION: (1)..(1)
<223> OTHER INFORMATION: /note="Residue given in the sequence has no
```

```
      preference with respect to the annotations for said position"
<220> FEATURE:
<221> NAME/KEY: VARIANT
<222> LOCATION: (4)..(4)
<223> OTHER INFORMATION: /replace="Tyr"
<220> FEATURE:
<221> NAME/KEY: misc_feature
<222> LOCATION: (4)..(5)
<223> OTHER INFORMATION: /note="Residues given in the sequence have no
      preference with respect to those in the annotations for said
      positions"
<220> FEATURE:
<221> NAME/KEY: VARIANT
<222> LOCATION: (5)..(5)
<223> OTHER INFORMATION: /replace="Arg"
<220> FEATURE:
<221> NAME/KEY: VARIANT
<222> LOCATION: (7)..(7)
<223> OTHER INFORMATION: /replace="Pro" or "Arg" or "Lys" or "Trp"
<220> FEATURE:
<221> NAME/KEY: misc_feature
<222> LOCATION: (7)..(7)
<223> OTHER INFORMATION: /note="Residue given in the sequence has no
      preference with respect to the annotations for said position"

<400> SEQUENCE: 56

Ser Ala Ser Phe Leu Tyr Ser
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic consensus sequence
<220> FEATURE:
<221> NAME/KEY: VARIANT
<222> LOCATION: (7)..(7)
<223> OTHER INFORMATION: /replace="Gln" or "Ser" or "Lys"
<220> FEATURE:
<221> NAME/KEY: misc_feature
<222> LOCATION: (7)..(7)
<223> OTHER INFORMATION: /note="Residue given in the sequence has no
      preference with respect to the annotations for said position"

<400> SEQUENCE: 57

Gln Gln Phe Pro Thr Tyr Leu Pro Thr
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic peptide

<400> SEQUENCE: 58

Ser Ala Ser Tyr Leu Tyr Ser
1               5

<210> SEQ ID NO 59
<211> LENGTH: 7
<212> TYPE: PRT
<213> ORGANISM: Artificial Sequence
<220> FEATURE:
<223> OTHER INFORMATION: Synthetic peptide

<400> SEQUENCE: 59

Ser Ala Ser Phe Leu Tyr Pro
1               5
```

```
<210> SEQ ID NO 60
<211> LENGTH: 7
<212> TYPE: PRT
<213> ORGANISM: Artificial Sequence
<220> FEATURE:
<223> OTHER INFORMATION: Synthetic peptide

<400> SEQUENCE: 60

Ser Ala Ser Phe Leu Tyr Arg
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic peptide

<400> SEQUENCE: 61

Ser Ala Ser Tyr Leu Tyr Lys
1               5

<210> SEQ ID NO 62
<211> LENGTH: 7
<212> TYPE: PRT
<213> ORGANISM: Artificial Sequence
<220> FEATURE:
<223> OTHER INFORMATION: Synthetic peptide

<400> SEQUENCE: 62

Ser Ala Ser Tyr Leu Tyr Trp
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic peptide

<400> SEQUENCE: 63

Phe Ala Ser Phe Leu Tyr Ser
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic peptide

<400> SEQUENCE: 64

Phe Ala Ser Phe Arg Tyr Ser
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic peptide

<400> SEQUENCE: 65

Gln Gln Phe Pro Thr Tyr Gln Pro Thr
1               5

<210> SEQ ID NO 66
```

```
<211> LENGTH: 9
<212> TYPE: PRT
<213> ORGANISM: Artificial Sequence
<220> FEATURE:
<223> OTHER INFORMATION: Synthetic peptide

<400> SEQUENCE: 66

Gln Gln Phe Pro Thr Tyr Ser Pro Thr
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic peptide

<400> SEQUENCE: 67

Gln Gln Phe Pro Thr Tyr Lys Pro Thr
1               5

<210> SEQ ID NO 68
<211> LENGTH: 10
<212> TYPE: PRT
<213> ORGANISM: Artificial Sequence
<220> FEATURE:
<223> OTHER INFORMATION: Synthetic consensus sequence
<220> FEATURE:
<221> NAME/KEY: VARIANT
<222> LOCATION: (2)..(2)
<223> OTHER INFORMATION: /replace="Tyr"
<220> FEATURE:
<221> NAME/KEY: misc_feature
<222> LOCATION: (2)..(5)
<223> OTHER INFORMATION: /note="Residues given in the sequence have no
      preference with respect to those in the annotations for said
      positions"
<220> FEATURE:
<221> NAME/KEY: VARIANT
<222> LOCATION: (3)..(3)
<223> OTHER INFORMATION: /replace="Phe"
<220> FEATURE:
<221> NAME/KEY: VARIANT
<222> LOCATION: (4)..(4)
<223> OTHER INFORMATION: /replace="Tyr"
<220> FEATURE:
<221> NAME/KEY: VARIANT
<222> LOCATION: (5)..(5)
<223> OTHER INFORMATION: /replace="Gln" or "Ile"

<400> SEQUENCE: 68

Gly Phe Thr Phe Leu Gly Tyr Gly Ile His
1               5                   10

<210> SEQ ID NO 69
<211> LENGTH: 18
<212> TYPE: PRT
<213> ORGANISM: Artificial Sequence
<220> FEATURE:
<223> OTHER INFORMATION: Synthetic consensus sequence
<220> FEATURE:
<221> NAME/KEY: VARIANT
<222> LOCATION: (6)..(6)
<223> OTHER INFORMATION: /replace="Ser" or "Gln"
<220> FEATURE:
<221> NAME/KEY: misc_feature
<222> LOCATION: (6)..(7)
<223> OTHER INFORMATION: /note="Residues given in the sequence have no
      preference with respect to those in the annotations for said
      positions"
<220> FEATURE:
<221> NAME/KEY: VARIANT
<222> LOCATION: (7)..(7)
```

```
<223> OTHER INFORMATION: /replace="Ser"
<220> FEATURE:
<221> NAME/KEY: VARIANT
<222> LOCATION: (9)..(9)
<223> OTHER INFORMATION: /replace="Lys" or "Leu"
<220> FEATURE:
<221> NAME/KEY: misc_feature
<222> LOCATION: (9)..(10)
<223> OTHER INFORMATION: /note="Residues given in the sequence have no
      preference with respect to those in the annotations for said
      positions"
<220> FEATURE:
<221> NAME/KEY: VARIANT
<222> LOCATION: (10)..(10)
<223> OTHER INFORMATION: /replace="Tyr"

<400> SEQUENCE: 69

Gly Trp Ile Ser Pro Ala Gly Gly Ser Thr Asp Tyr Ala Asp Ser Val
1               5                   10                  15
Lys Gly

<210> SEQ ID NO 70
<211> LENGTH: 10
<212> TYPE: PRT
<213> ORGANISM: Artificial Sequence
<220> FEATURE:
<223> OTHER INFORMATION: Synthetic consensus sequence
<220> FEATURE:
<221> NAME/KEY: VARIANT
<222> LOCATION: (4)..(4)
<223> OTHER INFORMATION: /replace="Tyr"
<220> FEATURE:
<221> NAME/KEY: misc_feature
<222> LOCATION: (4)..(4)
<223> OTHER INFORMATION: /note="Residue given in the sequence has no
      preference with respect to the annotations for said position"

<400> SEQUENCE: 70

Gly Pro Phe Ser Pro Trp Val Met Asp Tyr
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Synthetic peptide

<400> SEQUENCE: 71

Gly Phe Phe Phe Gln Gly Tyr Gly Ile His
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Synthetic peptide

<400> SEQUENCE: 72

Gly Phe Phe Phe Leu Gly Tyr Gly Ile His
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Synthetic peptide
```

```
<400> SEQUENCE: 73

Gly Tyr Thr Tyr Ile Gly Tyr Gly Ile His
1               5                   10

<210> SEQ ID NO 74
<211> LENGTH: 18
<212> TYPE: PRT
<213> ORGANISM: Artificial Sequence
<220> FEATURE:
<223> OTHER INFORMATION: Synthetic peptide

<400> SEQUENCE: 74

Gly Trp Ile Ser Pro Ser Gly Gly Ser Thr Asp Tyr Ala Asp Ser Val
1               5                   10                  15

Lys Gly

<210> SEQ ID NO 75
<211> LENGTH: 18
<212> TYPE: PRT
<213> ORGANISM: Artificial Sequence
<220> FEATURE:
<223> OTHER INFORMATION: Synthetic peptide

<400> SEQUENCE: 75

Gly Trp Ile Ser Pro Gln Gly Gly Ser Thr Asp Tyr Ala Asp Ser Val
1               5                   10                  15

Lys Gly

<210> SEQ ID NO 76
<211> LENGTH: 18
<212> TYPE: PRT
<213> ORGANISM: Artificial Sequence
<220> FEATURE:
<223> OTHER INFORMATION: Synthetic peptide

<400> SEQUENCE: 76

Gly Trp Ile Ser Pro Ala Gly Gly Lys Thr Asp Tyr Ala Asp Ser Val
1               5                   10                  15

Lys Gly

<210> SEQ ID NO 77
<211> LENGTH: 18
<212> TYPE: PRT
<213> ORGANISM: Artificial Sequence
<220> FEATURE:
<223> OTHER INFORMATION: Synthetic peptide

<400> SEQUENCE: 77

Gly Trp Ile Ser Pro Ala Gly Gly Leu Tyr Asp Tyr Ala Asp Ser Val
1               5                   10                  15

Lys Gly

<210> SEQ ID NO 78
<211> LENGTH: 18
<212> TYPE: PRT
<213> ORGANISM: Artificial Sequence
<220> FEATURE:
<223> OTHER INFORMATION: Synthetic peptide

<400> SEQUENCE: 78

Gly Trp Ile Ser Pro Ser Gly Gly Ser Thr Asp Tyr Ala Asp Ser Val
1               5                   10                  15

Lys Gly
```

```
<210> SEQ ID NO 79
<211> LENGTH: 10
<212> TYPE: PRT
<213> ORGANISM: Artificial Sequence
<220> FEATURE:
<223> OTHER INFORMATION: Synthetic peptide

<400> SEQUENCE: 79

Gly Pro Phe Tyr Pro Trp Val Met Asp Tyr
1               5                   10

<210> SEQ ID NO 80
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Leu Gly Tyr
            20                  25                  30

Gly Ile His Trp Val Arg Gln Ala Pro Gly Lys Gly Leu Glu Trp Val
        35                  40                  45

Gly Trp Ile Ser Pro Ser Gly Ser Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Pro Phe Ser Pro Trp Val Met Asp Tyr Trp Gly Gln Gly
            100                 105                 110

Thr Leu Val Thr Val Ser Ser
        115

<210> SEQ ID NO 81
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Leu Gly Tyr
            20                  25                  30

Gly Ile His Trp Val Arg Gln Ala Pro Gly Lys Gly Leu Glu Trp Val
        35                  40                  45

Gly Trp Ile Ser Pro Gln Gly Gly Ser Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Pro Phe Ser Pro Trp Val Met Asp Tyr Trp Gly Gln Gly
            100                 105                 110
```

```
Thr Leu Val Thr Val Ser Ser
        115

<210> SEQ ID NO 82
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Leu Gly Tyr
            20                  25                  30

Gly Ile His Trp Val Arg Gln Ala Pro Gly Lys Gly Leu Glu Trp Val
        35                  40                  45

Gly Trp Ile Ser Pro Ala Gly Gly Ser Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Pro Phe Ser Pro Trp Val Met Asp Tyr Trp Gly Gln Gly
            100                 105                 110

Thr Leu Val Thr Val Ser Ser
        115

<210> SEQ ID NO 83
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Phe Phe Gln Gly Tyr
            20                  25                  30

Gly Ile His Trp Val Arg Gln Ala Pro Gly Lys Gly Leu Glu Trp Val
        35                  40                  45

Gly Trp Ile Ser Pro Ala Gly Gly Ser Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Pro Phe Ser Pro Trp Val Met Asp Tyr Trp Gly Gln Gly
            100                 105                 110

Thr Leu Val Thr Val Ser Ser
        115

<210> SEQ ID NO 84
<211> LENGTH: 119
<212> TYPE: PRT
<213> ORGANISM: Artificial Sequence
<220> FEATURE:
<223> OTHER INFORMATION: Synthetic polypeptide
```

```
<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Leu Gly Tyr
            20                  25                  30

Gly Ile His Trp Val Arg Gln Ala Pro Gly Lys Gly Leu Glu Trp Val
        35                  40                  45

Gly Trp Ile Ser Pro Ala Gly Gly Ser Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Pro Phe Ser Pro Trp Val Met Asp Tyr Trp Gly Gln Gly
            100                 105                 110

Thr Leu Val Thr Val Ser Ser
        115

<210> SEQ ID NO 85
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Phe Phe Leu Gly Tyr
            20                  25                  30

Gly Ile His Trp Val Arg Gln Ala Pro Gly Lys Gly Leu Glu Trp Val
        35                  40                  45

Gly Trp Ile Ser Pro Ala Gly Gly Ser Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Pro Phe Ser Pro Trp Val Met Asp Tyr Trp Gly Gln Gly
            100                 105                 110

Thr Leu Val Thr Val Ser Ser
        115

<210> SEQ ID NO 86
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Leu Gly Tyr
            20                  25                  30

Gly Ile His Trp Val Arg Gln Ala Pro Gly Lys Gly Leu Glu Trp Val
        35                  40                  45
```

Gly Trp Ile Ser Pro Ala Gly Gly Ser Thr Asp Tyr Ala Asp Ser Val
            50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly Pro Phe Ser Pro Trp Val Met Asp Tyr Trp Gly Gln Gly
            100                 105                 110

Thr Leu Val Thr Val Ser Ser
            115

<210> SEQ ID NO 87
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 87

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Leu Gly Tyr
             20                  25                  30

Gly Ile His Trp Val Arg Gln Ala Pro Gly Lys Gly Leu Glu Trp Val
         35                  40                  45

Gly Trp Ile Ser Pro Ala Gly Gly Ser Thr Asp Tyr Ala Asp Ser Val
            50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly Pro Phe Ser Pro Trp Val Met Asp Tyr Trp Gly Gln Gly
            100                 105                 110

Thr Leu Val Thr Val Ser Ser
            115

<210> SEQ ID NO 88
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 88

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Leu Gly Tyr
             20                  25                  30

Gly Ile His Trp Val Arg Gln Ala Pro Gly Lys Gly Leu Glu Trp Val
         35                  40                  45

Gly Trp Ile Ser Pro Ala Gly Gly Ser Thr Asp Tyr Ala Asp Ser Val
            50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly Pro Phe Ser Pro Trp Val Met Asp Tyr Trp Gly Gln Gly
            100                 105                 110

Thr Leu Val Thr Val Ser Ser
        115

<210> SEQ ID NO 89
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Leu Gly Tyr
            20                  25                  30

Gly Ile His Trp Val Arg Gln Ala Pro Gly Lys Gly Leu Glu Trp Val
        35                  40                  45

Gly Trp Ile Ser Pro Ala Gly Gly Ser Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Pro Phe Ser Pro Trp Val Met Asp Tyr Trp Gly Gln Gly
            100                 105                 110

Thr Leu Val Thr Val Ser Ser
        115

<210> SEQ ID NO 90
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Phe Phe Leu Gly Tyr
            20                  25                  30

Gly Ile His Trp Val Arg Gln Ala Pro Gly Lys Gly Leu Glu Trp Val
        35                  40                  45

Gly Trp Ile Ser Pro Ala Gly Gly Ser Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Pro Phe Ser Pro Trp Val Met Asp Tyr Trp Gly Gln Gly
            100                 105                 110

Thr Leu Val Thr Val Ser Ser
        115

<210> SEQ ID NO 91
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 91

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Phe Phe Leu Gly Tyr
            20                  25                  30

Gly Ile His Trp Val Arg Gln Ala Pro Gly Lys Gly Leu Glu Trp Val
        35                  40                  45

Gly Trp Ile Ser Pro Ala Gly Gly Ser Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Pro Phe Ser Pro Trp Val Met Asp Tyr Trp Gly Gln Gly
            100                 105                 110

Thr Leu Val Thr Val Ser Ser
            115
```

<210> SEQ ID NO 92
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 92

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Leu Gly Tyr
            20                  25                  30

Gly Ile His Trp Val Arg Gln Ala Pro Gly Lys Gly Leu Glu Trp Val
        35                  40                  45

Gly Trp Ile Ser Pro Ala Gly Gly Lys Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Pro Phe Ser Pro Trp Val Met Asp Tyr Trp Gly Gln Gly
            100                 105                 110

Thr Leu Val Thr Val Ser Ser
            115
```

<210> SEQ ID NO 93
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 93

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Leu Gly Tyr
            20                  25                  30

Gly Ile His Trp Val Arg Gln Ala Pro Gly Lys Gly Leu Glu Trp Val
        35                  40                  45
```

Gly Trp Ile Ser Pro Ala Gly Gly Ser Thr Asp Tyr Ala Asp Ser Val
            50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly Pro Phe Ser Pro Trp Val Met Asp Tyr Trp Gly Gln Gly
                100                 105                 110

Thr Leu Val Thr Val Ser Ser
            115

<210> SEQ ID NO 94
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 94

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Leu Gly Tyr
                 20                  25                  30

Gly Ile His Trp Val Arg Gln Ala Pro Gly Lys Gly Leu Glu Trp Val
             35                  40                  45

Gly Trp Ile Ser Pro Ala Gly Gly Ser Thr Asp Tyr Ala Asp Ser Val
            50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly Pro Phe Ser Pro Trp Val Met Asp Tyr Trp Gly Gln Gly
                100                 105                 110

Thr Leu Val Thr Val Ser Ser
            115

<210> SEQ ID NO 95
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 95

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Leu Gly Tyr
                 20                  25                  30

Gly Ile His Trp Val Arg Gln Ala Pro Gly Lys Gly Leu Glu Trp Val
             35                  40                  45

Gly Trp Ile Ser Pro Ala Gly Gly Leu Tyr Asp Tyr Ala Asp Ser Val
            50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly Pro Phe Tyr Pro Trp Val Met Asp Tyr Trp Gly Gln Gly

Thr Leu Val Thr Val Ser Ser
        115

<210> SEQ ID NO 96
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 96

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Tyr Ile Gly Tyr
            20                  25                  30

Gly Ile His Trp Val Arg Gln Ala Pro Gly Lys Gly Leu Glu Trp Val
        35                  40                  45

Gly Trp Ile Ser Pro Ser Gly Ser Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Pro Phe Ser Pro Trp Val Met Asp Tyr Trp Gly Gln Gly
            100                 105                 110

Thr Leu Val Thr Val Ser Ser
        115

<210> SEQ ID NO 97
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 97

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Leu Gly Tyr
            20                  25                  30

Gly Ile His Trp Val Arg Gln Ala Pro Gly Lys Gly Leu Glu Trp Val
        35                  40                  45

Gly Trp Ile Ser Pro Ala Gly Gly Ser Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Pro Phe Ser Pro Trp Val Met Asp Tyr Trp Gly Gln Gly
            100                 105                 110

Thr Leu Val Thr Val Ser Ser
        115

<210> SEQ ID NO 98
<211> LENGTH: 119
<212> TYPE: PRT
<213> ORGANISM: Artificial Sequence
<220> FEATURE:

<223> OTHER INFORMATION: Synthetic polypeptide

<400> SEQUENCE: 98

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Leu Gly Tyr
            20                  25                  30

Gly Ile His Trp Val Arg Gln Ala Pro Gly Lys Gly Leu Glu Trp Val
        35                  40                  45

Gly Trp Ile Ser Pro Ala Gly Gly Ser Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Pro Phe Ser Pro Trp Val Met Asp Tyr Trp Gly Gln Gly
            100                 105                 110

Thr Leu Val Thr Val Ser Ser
        115

<210> SEQ ID NO 99
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Pro Thr Tyr Leu Pro
                85                  90                  95

Thr Phe Gly Gln Gly Thr Lys Val Glu Ile Lys Arg
            100                 105

<210> SEQ ID NO 100
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly

```
                50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Pro Thr Tyr Leu Pro
                 85                  90                  95

Thr Phe Gly Gln Gly Thr Lys Val Glu Ile Lys Arg
                100                 105

<210> SEQ ID NO 101
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 101

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Ser Thr Ala
                 20                  25                  30

Val Ala Trp Tyr Gln Gln Lys Pro Gly Lys Ala Pro Lys Leu Leu Ile
                 35                  40                  45

Tyr Ser Ala Ser Tyr Leu Tyr Ser Gly Val Pro Ser Arg Phe Ser Gly
             50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Pro Thr Tyr Leu Pro
                 85                  90                  95

Thr Phe Gly Gln Gly Thr Lys Val Glu Ile Lys Arg
                100                 105

<210> SEQ ID NO 102
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 102

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Ser Thr Ala
                 20                  25                  30

Val Ala Trp Tyr Gln Gln Lys Pro Gly Lys Ala Pro Lys Leu Leu Ile
                 35                  40                  45

Tyr Ser Ala Ser Tyr Leu Tyr Ser Gly Val Pro Ser Arg Phe Ser Gly
             50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Pro Thr Tyr Leu Pro
                 85                  90                  95

Thr Phe Gly Gln Gly Thr Lys Val Glu Ile Lys Arg
                100                 105

<210> SEQ ID NO 103
<211> LENGTH: 108
<212> TYPE: PRT
<213> ORGANISM: Artificial Sequence
<220> FEATURE:
```

<223> OTHER INFORMATION: Synthetic polypeptide

<400> SEQUENCE: 103

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Ser Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Phe Pro Thr Tyr Gln Pro
                85                  90                  95
Thr Phe Gly Gln Gly Thr Lys Val Glu Ile Lys Arg
            100                 105
```

<210> SEQ ID NO 104
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 104

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Ser Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Phe Pro Thr Tyr Leu Pro
                85                  90                  95
Thr Phe Gly Gln Gly Thr Lys Val Glu Ile Lys Arg
            100                 105
```

<210> SEQ ID NO 105
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 105

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Ser Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Pro Gly Val Pro Ser Arg Phe Ser Gly
    50                  55                  60
Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Phe Pro Thr Tyr Leu Pro
                    85                  90                  95

Thr Phe Gly Gln Gly Thr Lys Val Glu Ile Lys Arg
            100                 105

<210> SEQ ID NO 106
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Pro Thr Tyr Ser Pro
                85                  90                  95

Thr Phe Gly Gln Gly Thr Lys Val Glu Ile Lys Arg
            100                 105

<210> SEQ ID NO 107
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Pro Thr Tyr Lys Pro
                85                  90                  95

Thr Phe Gly Gln Gly Thr Lys Val Glu Ile Lys Arg
            100                 105

<210> SEQ ID NO 108
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 108
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Arg Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Pro Thr Tyr Lys Pro
                85                  90                  95

Thr Phe Gly Gln Gly Thr Lys Val Glu Ile Lys Arg
            100                 105

<210> SEQ ID NO 109
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 109

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Leu Tyr Lys Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Pro Thr Tyr Gln Pro
                85                  90                  95

Thr Phe Gly Gln Gly Thr Lys Val Glu Ile Lys Arg
            100                 105

<210> SEQ ID NO 110
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 110

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Pro Thr Tyr Leu Pro 85                  90                  95

Thr Phe Gly Gln Gly Thr Lys Val Glu Ile Lys Arg
            100                 105

<210> SEQ ID NO 111
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Pro Thr Tyr Ser Pro
                85                  90                  95

Thr Phe Gly Gln Gly Thr Lys Val Glu Ile Lys Arg
            100                 105

<210> SEQ ID NO 112
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 112

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Pro Thr Tyr Ser Pro
                85                  90                  95

Thr Phe Gly Gln Gly Thr Lys Val Glu Ile Lys Arg
            100                 105

<210> SEQ ID NO 113
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 113

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Leu Tyr Trp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Pro Thr Tyr Lys Pro
                85                  90                  95

Thr Phe Gly Gln Gly Thr Lys Val Glu Ile Lys Arg
            100                 105

<210> SEQ ID NO 114
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 114

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Pro Thr Tyr Leu Pro
                85                  90                  95

Thr Phe Gly Gln Gly Thr Lys Val Glu Ile Lys Arg
            100                 105

<210> SEQ ID NO 115
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 115

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Pro Thr Tyr Leu Pro
                85                  90                  95

Thr Phe Gly Gln Gly Thr Lys Val Glu Ile Lys Arg
```

<210> SEQ ID NO 116
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 116

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Phe Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Pro Thr Tyr Leu Pro
                85                  90                  95

Thr Phe Gly Gln Gly Thr Lys Val Glu Ile Lys Arg
            100                 105

<210> SEQ ID NO 117
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 117

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Phe Ala Ser Phe Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Pro Thr Tyr Leu Pro
                85                  90                  95

Thr Phe Gly Gln Gly Thr Lys Val Glu Ile Lys Arg
            100                 105

<210> SEQ ID NO 118
<211> LENGTH: 7
<212> TYPE: PRT
<213> ORGANISM: Artificial Sequence
<220> FEATURE:
<223> OTHER INFORMATION: Synthetic consensus sequence
<220> FEATURE:
<221> NAME/KEY: VARIANT
<222> LOCATION: (1)..(1)
<223> OTHER INFORMATION: /replace="Trp" or "Tyr" or "Phe" or "Leu"
<220> FEATURE:
<221> NAME/KEY: misc_feature
<222> LOCATION: (1)..(1)
<223> OTHER INFORMATION: /note="Residue given in the sequence has no

```
      preference with respect to the annotations for said position"
<220> FEATURE:
<221> NAME/KEY: VARIANT
<222> LOCATION: (4)..(4)
<223> OTHER INFORMATION: /replace="Ser" or "Tyr" or "Trp"
<220> FEATURE:
<221> NAME/KEY: misc_feature
<222> LOCATION: (4)..(5)
<223> OTHER INFORMATION: /note="Residues given in the sequence have no
      preference with respect to those in the annotations for said
      positions"
<220> FEATURE:
<221> NAME/KEY: VARIANT
<222> LOCATION: (5)..(5)
<223> OTHER INFORMATION: /replace="Arg"
<220> FEATURE:
<221> NAME/KEY: VARIANT
<222> LOCATION: (7)..(7)
<223> OTHER INFORMATION: /replace="Pro" or "Arg" or "Lys" or "Trp"
<220> FEATURE:
<221> NAME/KEY: misc_feature
<222> LOCATION: (7)..(7)
<223> OTHER INFORMATION: /note="Residue given in the sequence has no
      preference with respect to the annotations for said position"

<400> SEQUENCE: 118

Ser Ala Ser Phe Leu Tyr Ser
1               5

<210> SEQ ID NO 119
<211> LENGTH: 9
<212> TYPE: PRT
<213> ORGANISM: Artificial Sequence
<220> FEATURE:
<223> OTHER INFORMATION: Synthetic consensus sequence
<220> FEATURE:
<221> NAME/KEY: VARIANT
<222> LOCATION: (3)..(3)
<223> OTHER INFORMATION: /replace="Phe" or "Gly" or "Asp" or "Tyr"
<220> FEATURE:
<221> NAME/KEY: misc_feature
<222> LOCATION: (3)..(8)
<223> OTHER INFORMATION: /note="Residues given in the sequence have no
      preference with respect to those in the annotations for said
      positions"
<220> FEATURE:
<221> NAME/KEY: VARIANT
<222> LOCATION: (4)..(4)
<223> OTHER INFORMATION: /replace="Pro" or "Ser" or "Ala"
<220> FEATURE:
<221> NAME/KEY: VARIANT
<222> LOCATION: (5)..(5)
<223> OTHER INFORMATION: /replace="Thr" or "Asn"
<220> FEATURE:
<221> NAME/KEY: VARIANT
<222> LOCATION: (6)..(6)
<223> OTHER INFORMATION: /replace="Tyr" or "Asp" or "Ser"
<220> FEATURE:
<221> NAME/KEY: VARIANT
<222> LOCATION: (7)..(7)
<223> OTHER INFORMATION: /replace="Gln" or "Ser" or "Lys" or "Leu"
<220> FEATURE:
<221> NAME/KEY: VARIANT
<222> LOCATION: (8)..(8)
<223> OTHER INFORMATION: /replace="Pro" or "Thr"

<400> SEQUENCE: 119

Gln Gln Ser Tyr Tyr Thr Pro Phe Thr
1               5

<210> SEQ ID NO 120
<211> LENGTH: 10
<212> TYPE: PRT
<213> ORGANISM: Artificial Sequence
<220> FEATURE:
```

```
<223> OTHER INFORMATION: Synthetic consensus sequence
<220> FEATURE:
<221> NAME/KEY: VARIANT
<222> LOCATION: (2)..(2)
<223> OTHER INFORMATION: /replace="Tyr"
<220> FEATURE:
<221> NAME/KEY: misc_feature
<222> LOCATION: (2)..(8)
<223> OTHER INFORMATION: /note="Residues given in the sequence have no
      preference with respect to those in the annotations for said
      positions"
<220> FEATURE:
<221> NAME/KEY: VARIANT
<222> LOCATION: (3)..(3)
<223> OTHER INFORMATION: /replace="Asn" or "Thr"
<220> FEATURE:
<221> NAME/KEY: VARIANT
<222> LOCATION: (4)..(4)
<223> OTHER INFORMATION: /replace="Tyr"
<220> FEATURE:
<221> NAME/KEY: VARIANT
<222> LOCATION: (5)..(5)
<223> OTHER INFORMATION: /replace="Gln" or "Ile" or "Ser" or "Tyr"
<220> FEATURE:
<221> NAME/KEY: VARIANT
<222> LOCATION: (6)..(6)
<223> OTHER INFORMATION: /replace="Tyr"
<220> FEATURE:
<221> NAME/KEY: VARIANT
<222> LOCATION: (7)..(7)
<223> OTHER INFORMATION: /replace="Ser"
<220> FEATURE:
<221> NAME/KEY: VARIANT
<222> LOCATION: (8)..(8)
<223> OTHER INFORMATION: /replace="Gly" or "Ser"

<400> SEQUENCE: 120

Gly Phe Phe Phe Leu Gly Tyr Ala Ile His
1               5                   10

<210> SEQ ID NO 121
<211> LENGTH: 18
<212> TYPE: PRT
<213> ORGANISM: Artificial Sequence
<220> FEATURE:
<223> OTHER INFORMATION: Synthetic consensus sequence
<220> FEATURE:
<221> NAME/KEY: VARIANT
<222> LOCATION: (1)..(1)
<223> OTHER INFORMATION: /replace="Gly"
<220> FEATURE:
<221> NAME/KEY: misc_feature
<222> LOCATION: (1)..(2)
<223> OTHER INFORMATION: /note="Residues given in the sequence have no
      preference with respect to those in the annotations for said
      positions"
<220> FEATURE:
<221> NAME/KEY: VARIANT
<222> LOCATION: (2)..(2)
<223> OTHER INFORMATION: /replace="Ser"
<220> FEATURE:
<221> NAME/KEY: VARIANT
<222> LOCATION: (6)..(6)
<223> OTHER INFORMATION: /replace="Ser" or "Gln" or "Tyr"
<220> FEATURE:
<221> NAME/KEY: misc_feature
<222> LOCATION: (6)..(7)
<223> OTHER INFORMATION: /note="Residues given in the sequence have no
      preference with respect to those in the annotations for said
      positions"
<220> FEATURE:
<221> NAME/KEY: VARIANT
<222> LOCATION: (7)..(7)
<223> OTHER INFORMATION: /replace="Ser"
<220> FEATURE:
<221> NAME/KEY: VARIANT
<222> LOCATION: (9)..(9)
```

```
<223> OTHER INFORMATION: /replace="Lys" or "Leu" or "Tyr"
<220> FEATURE:
<221> NAME/KEY: misc_feature
<222> LOCATION: (9)..(11)
<223> OTHER INFORMATION: /note="Residues given in the sequence have no
      preference with respect to those in the annotations for said
      positions"
<220> FEATURE:
<221> NAME/KEY: VARIANT
<222> LOCATION: (10)..(10)
<223> OTHER INFORMATION: /replace="Tyr"
<220> FEATURE:
<221> NAME/KEY: VARIANT
<222> LOCATION: (11)..(11)
<223> OTHER INFORMATION: /replace="Ser"

<400> SEQUENCE: 121

Ala Trp Ile Ser Pro Ala Gly Gly Ser Thr Asp Tyr Ala Asp Ser Val
1               5                   10                  15

Lys Gly

<210> SEQ ID NO 122
<211> LENGTH: 17
<212> TYPE: PRT
<213> ORGANISM: Artificial Sequence
<220> FEATURE:
<223> OTHER INFORMATION: Synthetic consensus sequence
<220> FEATURE:
<221> NAME/KEY: VARIANT
<222> LOCATION: (1)..(1)
<223> OTHER INFORMATION: /replace="Gly"
<220> FEATURE:
<221> NAME/KEY: misc_feature
<222> LOCATION: (1)..(1)
<223> OTHER INFORMATION: /note="Residue given in the sequence has no
      preference with respect to the annotations for said position"
<220> FEATURE:
<221> NAME/KEY: VARIANT
<222> LOCATION: (3)..(3)
<223> OTHER INFORMATION: /replace="Phe"
<220> FEATURE:
<221> NAME/KEY: misc_feature
<222> LOCATION: (3)..(14)
<223> OTHER INFORMATION: /note="Residues given in the sequence have no
      preference with respect to those in the annotations for said
      positions"
<220> FEATURE:
<221> NAME/KEY: VARIANT
<222> LOCATION: (4)..(4)
<223> OTHER INFORMATION: /replace="Tyr" or "Ser"
<220> FEATURE:
<221> NAME/KEY: VARIANT
<222> LOCATION: (5)..(5)
<223> OTHER INFORMATION: /replace="Pro"
<220> FEATURE:
<221> NAME/KEY: VARIANT
<222> LOCATION: (6)..(6)
<223> OTHER INFORMATION: /replace="Trp"
<220> FEATURE:
<221> NAME/KEY: VARIANT
<222> LOCATION: (7)..(7)
<223> OTHER INFORMATION: /replace="Val"
<220> FEATURE:
<221> NAME/KEY: VARIANT
<222> LOCATION: (8)..(14)
<223> OTHER INFORMATION: /replace=" "
<220> FEATURE:
<221> NAME/KEY: misc_feature
<222> LOCATION: (8)..(14)
<223> OTHER INFORMATION: /note="When present, this region is present in
      its entirety"

<400> SEQUENCE: 122

Gln Pro Thr His Tyr Tyr Tyr Tyr Ala Lys Gly Tyr Lys Ala Met Asp
1               5                   10                  15
```

Tyr

<210> SEQ ID NO 123
<211> LENGTH: 30
<212> TYPE: PRT
<213> ORGANISM: Homo sapiens

<400> SEQUENCE: 123

Ala Ser Ser Thr Glu Lys Phe Pro Asp Gly Phe Trp Leu Gly Glu Gln
1               5                   10                  15

Leu Val Cys Trp Gln Ala Gly Thr Thr Pro Trp Asn Ile Phe
            20                  25                  30

<210> SEQ ID NO 124
<211> LENGTH: 30
<212> TYPE: PRT
<213> ORGANISM: Homo sapiens

<400> SEQUENCE: 124

Ala Ser Leu Ile Pro Glu Phe Ser Asp Gly Phe Trp Thr Gly Ser Gln
1               5                   10                  15

Leu Ala Cys Trp Thr Asn Ser Glu Thr Pro Trp Ser Tyr Phe
            20                  25                  30

<210> SEQ ID NO 125
<211> LENGTH: 18
<212> TYPE: PRT
<213> ORGANISM: Homo sapiens

<400> SEQUENCE: 125

Val Pro Leu Thr Gln Gly Glu Tyr Met Ile Pro Cys Glu Lys Val Ser
1               5                   10                  15

Thr Leu

<210> SEQ ID NO 126
<211> LENGTH: 14
<212> TYPE: PRT
<213> ORGANISM: Homo sapiens

<400> SEQUENCE: 126

Ala Gly Phe Pro Leu Asn Gln Ser Glu Val Leu Ala Ser Val
1               5                   10

<210> SEQ ID NO 127
<211> LENGTH: 4
<212> TYPE: PRT
<213> ORGANISM: Artificial Sequence
<220> FEATURE:
<223> OTHER INFORMATION: Synthetic peptide

<400> SEQUENCE: 127

Glu Lys Phe Pro
1

<210> SEQ ID NO 128
<211> LENGTH: 7
<212> TYPE: PRT
<213> ORGANISM: Artificial Sequence
<220> FEATURE:
<223> OTHER INFORMATION: Synthetic peptide

<400> SEQUENCE: 128

Gln Leu Val Cys Trp Gln Ala

```
<210> SEQ ID NO 129
<211> LENGTH: 5
<212> TYPE: PRT
<213> ORGANISM: Artificial Sequence
<220> FEATURE:
<223> OTHER INFORMATION: Synthetic peptide

<400> SEQUENCE: 129

Pro Phe Ser Pro Trp
1               5

<210> SEQ ID NO 130
<211> LENGTH: 10
<212> TYPE: PRT
<213> ORGANISM: Homo sapiens

<400> SEQUENCE: 130

Asp Val Ala Thr Ser Gln Asp Asp Cys Tyr
1               5                   10

<210> SEQ ID NO 131
<211> LENGTH: 10
<212> TYPE: PRT
<213> ORGANISM: Homo sapiens

<400> SEQUENCE: 131

Met Gly Ala Gly Leu Asn Tyr Glu Cys Tyr
1               5                   10

<210> SEQ ID NO 132
<211> LENGTH: 9
<212> TYPE: PRT
<213> ORGANISM: Homo sapiens

<400> SEQUENCE: 132

Ser Gln Ala Gly Lys Thr Leu Cys Leu
1               5

<210> SEQ ID NO 133
<211> LENGTH: 6
<212> TYPE: PRT
<213> ORGANISM: Artificial Sequence
<220> FEATURE:
<223> OTHER INFORMATION: Synthetic peptide

<400> SEQUENCE: 133

Ser Val Ser Ser Ala Val
1               5

<210> SEQ ID NO 134
<211> LENGTH: 5
<212> TYPE: PRT
<213> ORGANISM: Artificial Sequence
<220> FEATURE:
<223> OTHER INFORMATION: Synthetic peptide

<400> SEQUENCE: 134

Tyr Ser Ala Ser Ser
1               5

<210> SEQ ID NO 135
<211> LENGTH: 8
<212> TYPE: PRT
<213> ORGANISM: Artificial Sequence
```

```
<220> FEATURE:
<223> OTHER INFORMATION: Synthetic peptide

<400> SEQUENCE: 135

Tyr Ser Ser Ser Tyr Ser Pro Val
1               5

<210> SEQ ID NO 136
<211> LENGTH: 8
<212> TYPE: PRT
<213> ORGANISM: Artificial Sequence
<220> FEATURE:
<223> OTHER INFORMATION: Synthetic peptide

<400> SEQUENCE: 136

Ser Tyr Ser Tyr Tyr Tyr Pro Leu
1               5

<210> SEQ ID NO 137
<211> LENGTH: 7
<212> TYPE: PRT
<213> ORGANISM: Artificial Sequence
<220> FEATURE:
<223> OTHER INFORMATION: Synthetic peptide

<400> SEQUENCE: 137

Ser Tyr Ser Tyr Ser Leu Ile
1               5

<210> SEQ ID NO 138
<211> LENGTH: 6
<212> TYPE: PRT
<213> ORGANISM: Artificial Sequence
<220> FEATURE:
<223> OTHER INFORMATION: Synthetic peptide

<400> SEQUENCE: 138

Ser Ser Ser Ser Leu Phe
1               5

<210> SEQ ID NO 139
<211> LENGTH: 6
<212> TYPE: PRT
<213> ORGANISM: Artificial Sequence
<220> FEATURE:
<223> OTHER INFORMATION: Synthetic peptide

<400> SEQUENCE: 139

Tyr Tyr Tyr Ser Leu Phe
1               5

<210> SEQ ID NO 140
<211> LENGTH: 8
<212> TYPE: PRT
<213> ORGANISM: Artificial Sequence
<220> FEATURE:
<223> OTHER INFORMATION: Synthetic peptide

<400> SEQUENCE: 140

Ser Tyr Tyr Ser Tyr Ser Leu Val
1               5

<210> SEQ ID NO 141
<211> LENGTH: 8
<212> TYPE: PRT
<213> ORGANISM: Artificial Sequence
<220> FEATURE:
```

```
<223> OTHER INFORMATION: Synthetic peptide

<400> SEQUENCE: 141

Ser Tyr Ser Tyr Ser Ser Pro Ile
1               5

<210> SEQ ID NO 142
<211> LENGTH: 8
<212> TYPE: PRT
<213> ORGANISM: Artificial Sequence
<220> FEATURE:
<223> OTHER INFORMATION: Synthetic peptide

<400> SEQUENCE: 142

Ser Ser Ser Ser Tyr Ser Pro Leu
1               5

<210> SEQ ID NO 143
<211> LENGTH: 8
<212> TYPE: PRT
<213> ORGANISM: Artificial Sequence
<220> FEATURE:
<223> OTHER INFORMATION: Synthetic peptide

<400> SEQUENCE: 143

Ser Tyr Tyr Ser Ser Ser Leu Ile
1               5

<210> SEQ ID NO 144
<211> LENGTH: 7
<212> TYPE: PRT
<213> ORGANISM: Artificial Sequence
<220> FEATURE:
<223> OTHER INFORMATION: Synthetic peptide

<400> SEQUENCE: 144

Tyr Tyr Ser Ser Ser Leu Val
1               5

<210> SEQ ID NO 145
<211> LENGTH: 6
<212> TYPE: PRT
<213> ORGANISM: Artificial Sequence
<220> FEATURE:
<223> OTHER INFORMATION: Synthetic peptide

<400> SEQUENCE: 145

Tyr Ser Tyr Ser Pro Phe
1               5

<210> SEQ ID NO 146
<211> LENGTH: 8
<212> TYPE: PRT
<213> ORGANISM: Artificial Sequence
<220> FEATURE:
<223> OTHER INFORMATION: Synthetic peptide

<400> SEQUENCE: 146

Tyr Ser Tyr Ser Tyr Ser Pro Ile
1               5

<210> SEQ ID NO 147
<211> LENGTH: 7
<212> TYPE: PRT
<213> ORGANISM: Artificial Sequence
<220> FEATURE:
<223> OTHER INFORMATION: Synthetic peptide
```

<400> SEQUENCE: 147

Tyr Ser Tyr Tyr Ser Leu Phe
1               5

<210> SEQ ID NO 148
<211> LENGTH: 7
<212> TYPE: PRT
<213> ORGANISM: Artificial Sequence
<220> FEATURE:
<223> OTHER INFORMATION: Synthetic peptide

<400> SEQUENCE: 148

Ser Ser Tyr Ser Ser Leu Val
1               5

<210> SEQ ID NO 149
<211> LENGTH: 7
<212> TYPE: PRT
<213> ORGANISM: Artificial Sequence
<220> FEATURE:
<223> OTHER INFORMATION: Synthetic peptide

<400> SEQUENCE: 149

Ser Tyr Tyr Tyr Ser Pro Phe
1               5

<210> SEQ ID NO 150
<211> LENGTH: 6
<212> TYPE: PRT
<213> ORGANISM: Artificial Sequence
<220> FEATURE:
<223> OTHER INFORMATION: Synthetic peptide

<400> SEQUENCE: 150

Ser Tyr Ser Tyr Pro Val
1               5

<210> SEQ ID NO 151
<211> LENGTH: 8
<212> TYPE: PRT
<213> ORGANISM: Artificial Sequence
<220> FEATURE:
<223> OTHER INFORMATION: Synthetic peptide

<400> SEQUENCE: 151

Ser Ser Ser Ser Tyr Tyr Leu Leu
1               5

<210> SEQ ID NO 152
<211> LENGTH: 6
<212> TYPE: PRT
<213> ORGANISM: Artificial Sequence
<220> FEATURE:
<223> OTHER INFORMATION: Synthetic peptide

<400> SEQUENCE: 152

Ser Tyr Tyr Tyr Pro Leu
1               5

<210> SEQ ID NO 153
<211> LENGTH: 6
<212> TYPE: PRT
<213> ORGANISM: Artificial Sequence
<220> FEATURE:
<223> OTHER INFORMATION: Synthetic peptide

```
<400> SEQUENCE: 153

Phe Tyr Ser Ser Tyr Ile
1               5

<210> SEQ ID NO 154
<211> LENGTH: 6
<212> TYPE: PRT
<213> ORGANISM: Artificial Sequence
<220> FEATURE:
<223> OTHER INFORMATION: Synthetic peptide

<400> SEQUENCE: 154

Ile Tyr Tyr Ser Ser Met
1               5

<210> SEQ ID NO 155
<211> LENGTH: 6
<212> TYPE: PRT
<213> ORGANISM: Artificial Sequence
<220> FEATURE:
<223> OTHER INFORMATION: Synthetic peptide

<400> SEQUENCE: 155

Phe Tyr Tyr Tyr Ser Met
1               5

<210> SEQ ID NO 156
<211> LENGTH: 6
<212> TYPE: PRT
<213> ORGANISM: Artificial Sequence
<220> FEATURE:
<223> OTHER INFORMATION: Synthetic peptide

<400> SEQUENCE: 156

Ile Tyr Ser Tyr Ser Met
1               5

<210> SEQ ID NO 157
<211> LENGTH: 6
<212> TYPE: PRT
<213> ORGANISM: Artificial Sequence
<220> FEATURE:
<223> OTHER INFORMATION: Synthetic peptide

<400> SEQUENCE: 157

Leu Ser Tyr Ser Tyr Ile
1               5

<210> SEQ ID NO 158
<211> LENGTH: 6
<212> TYPE: PRT
<213> ORGANISM: Artificial Sequence
<220> FEATURE:
<223> OTHER INFORMATION: Synthetic peptide

<400> SEQUENCE: 158

Phe Tyr Tyr Ser Ser Ile
1               5

<210> SEQ ID NO 159
<211> LENGTH: 6
<212> TYPE: PRT
<213> ORGANISM: Artificial Sequence
<220> FEATURE:
<223> OTHER INFORMATION: Synthetic peptide

<400> SEQUENCE: 159
```

Phe Ser Ser Tyr Tyr Ile
1               5

<210> SEQ ID NO 160
<211> LENGTH: 6
<212> TYPE: PRT
<213> ORGANISM: Artificial Sequence
<220> FEATURE:
<223> OTHER INFORMATION: Synthetic peptide

<400> SEQUENCE: 160

Val Ser Tyr Tyr Tyr Ile
1               5

<210> SEQ ID NO 161
<211> LENGTH: 6
<212> TYPE: PRT
<213> ORGANISM: Artificial Sequence
<220> FEATURE:
<223> OTHER INFORMATION: Synthetic peptide

<400> SEQUENCE: 161

Val Ser Ser Ser Tyr Met
1               5

<210> SEQ ID NO 162
<211> LENGTH: 6
<212> TYPE: PRT
<213> ORGANISM: Artificial Sequence
<220> FEATURE:
<223> OTHER INFORMATION: Synthetic peptide

<400> SEQUENCE: 162

Val Ser Ser Ser Ser Met
1               5

<210> SEQ ID NO 163
<211> LENGTH: 6
<212> TYPE: PRT
<213> ORGANISM: Artificial Sequence
<220> FEATURE:
<223> OTHER INFORMATION: Synthetic peptide

<400> SEQUENCE: 163

Phe Tyr Tyr Ser Tyr Met
1               5

<210> SEQ ID NO 164
<211> LENGTH: 6
<212> TYPE: PRT
<213> ORGANISM: Artificial Sequence
<220> FEATURE:
<223> OTHER INFORMATION: Synthetic peptide

<400> SEQUENCE: 164

Phe Tyr Ser Tyr Ser Met
1               5

<210> SEQ ID NO 165
<211> LENGTH: 6
<212> TYPE: PRT
<213> ORGANISM: Artificial Sequence
<220> FEATURE:
<223> OTHER INFORMATION: Synthetic peptide

<400> SEQUENCE: 165

```
Leu Tyr Tyr Ser Ser Ile
1               5

<210> SEQ ID NO 166
<211> LENGTH: 6
<212> TYPE: PRT
<213> ORGANISM: Artificial Sequence
<220> FEATURE:
<223> OTHER INFORMATION: Synthetic peptide

<400> SEQUENCE: 166

Val Ser Ser Ser Tyr Ile
1               5

<210> SEQ ID NO 167
<211> LENGTH: 6
<212> TYPE: PRT
<213> ORGANISM: Artificial Sequence
<220> FEATURE:
<223> OTHER INFORMATION: Synthetic peptide

<400> SEQUENCE: 167

Val Tyr Tyr Ser Tyr Met
1               5

<210> SEQ ID NO 168
<211> LENGTH: 10
<212> TYPE: PRT
<213> ORGANISM: Artificial Sequence
<220> FEATURE:
<223> OTHER INFORMATION: Synthetic peptide

<400> SEQUENCE: 168

Ser Ile Ser Pro Tyr Ser Ser Ser Thr Tyr
1               5                   10

<210> SEQ ID NO 169
<211> LENGTH: 10
<212> TYPE: PRT
<213> ORGANISM: Artificial Sequence
<220> FEATURE:
<223> OTHER INFORMATION: Synthetic peptide

<400> SEQUENCE: 169

Tyr Ile Ser Ser Tyr Ser Gly Ser Thr Tyr
1               5                   10

<210> SEQ ID NO 170
<211> LENGTH: 10
<212> TYPE: PRT
<213> ORGANISM: Artificial Sequence
<220> FEATURE:
<223> OTHER INFORMATION: Synthetic peptide

<400> SEQUENCE: 170

Tyr Ile Tyr Pro Tyr Ser Gly Ser Thr Tyr
1               5                   10

<210> SEQ ID NO 171
<211> LENGTH: 10
<212> TYPE: PRT
<213> ORGANISM: Artificial Sequence
<220> FEATURE:
<223> OTHER INFORMATION: Synthetic peptide

<400> SEQUENCE: 171

Ser Ile Ser Pro Tyr Ser Gly Tyr Thr Ser
```

<210> SEQ ID NO 172
<211> LENGTH: 10
<212> TYPE: PRT
<213> ORGANISM: Artificial Sequence
<220> FEATURE:
<223> OTHER INFORMATION: Synthetic peptide

<400> SEQUENCE: 172

Ser Ile Tyr Ser Ser Tyr Gly Ser Thr Tyr
1               5                   10

<210> SEQ ID NO 173
<211> LENGTH: 10
<212> TYPE: PRT
<213> ORGANISM: Artificial Sequence
<220> FEATURE:
<223> OTHER INFORMATION: Synthetic peptide

<400> SEQUENCE: 173

Tyr Ile Ser Pro Tyr Ser Gly Ser Thr Ser
1               5                   10

<210> SEQ ID NO 174
<211> LENGTH: 10
<212> TYPE: PRT
<213> ORGANISM: Artificial Sequence
<220> FEATURE:
<223> OTHER INFORMATION: Synthetic peptide

<400> SEQUENCE: 174

Ser Ile Ser Ser Tyr Tyr Gly Ser Thr Ser
1               5                   10

<210> SEQ ID NO 175
<211> LENGTH: 10
<212> TYPE: PRT
<213> ORGANISM: Artificial Sequence
<220> FEATURE:
<223> OTHER INFORMATION: Synthetic peptide

<400> SEQUENCE: 175

Ser Ile Ser Pro Ser Ser Gly Ser Thr Ser
1               5                   10

<210> SEQ ID NO 176
<211> LENGTH: 10
<212> TYPE: PRT
<213> ORGANISM: Artificial Sequence
<220> FEATURE:
<223> OTHER INFORMATION: Synthetic peptide

<400> SEQUENCE: 176

Ser Ile Tyr Pro Tyr Ser Gly Ser Thr Tyr
1               5                   10

<210> SEQ ID NO 177
<211> LENGTH: 10
<212> TYPE: PRT
<213> ORGANISM: Artificial Sequence
<220> FEATURE:
<223> OTHER INFORMATION: Synthetic peptide

<400> SEQUENCE: 177

Ser Ile Tyr Pro Tyr Tyr Ser Ser Thr Tyr
1               5                   10

<210> SEQ ID NO 178
<211> LENGTH: 10
<212> TYPE: PRT
<213> ORGANISM: Artificial Sequence
<220> FEATURE:
<223> OTHER INFORMATION: Synthetic peptide

<400> SEQUENCE: 178

Ser Ile Tyr Pro Tyr Ser Ser Ser Thr Ser
1               5                   10

<210> SEQ ID NO 179
<211> LENGTH: 10
<212> TYPE: PRT
<213> ORGANISM: Artificial Sequence
<220> FEATURE:
<223> OTHER INFORMATION: Synthetic peptide

<400> SEQUENCE: 179

Tyr Ile Ser Pro Tyr Ser Gly Tyr Thr Tyr
1               5                   10

<210> SEQ ID NO 180
<211> LENGTH: 10
<212> TYPE: PRT
<213> ORGANISM: Artificial Sequence
<220> FEATURE:
<223> OTHER INFORMATION: Synthetic peptide

<400> SEQUENCE: 180

Ser Ile Tyr Ser Ser Ser Gly Tyr Thr Ser
1               5                   10

<210> SEQ ID NO 181
<211> LENGTH: 10
<212> TYPE: PRT
<213> ORGANISM: Artificial Sequence
<220> FEATURE:
<223> OTHER INFORMATION: Synthetic peptide

<400> SEQUENCE: 181

Ser Ile Tyr Pro Tyr Ser Ser Tyr Thr Tyr
1               5                   10

<210> SEQ ID NO 182
<211> LENGTH: 10
<212> TYPE: PRT
<213> ORGANISM: Artificial Sequence
<220> FEATURE:
<223> OTHER INFORMATION: Synthetic peptide

<400> SEQUENCE: 182

Tyr Ile Tyr Pro Tyr Tyr Ser Tyr Thr Ser
1               5                   10

<210> SEQ ID NO 183
<211> LENGTH: 10
<212> TYPE: PRT
<213> ORGANISM: Artificial Sequence
<220> FEATURE:
<223> OTHER INFORMATION: Synthetic peptide

<400> SEQUENCE: 183

Ser Ile Tyr Pro Tyr Ser Ser Ser Thr Tyr
1               5                   10

<210> SEQ ID NO 184
<211> LENGTH: 20
<212> TYPE: PRT
<213> ORGANISM: Artificial Sequence
<220> FEATURE:
<223> OTHER INFORMATION: Synthetic peptide

<400> SEQUENCE: 184

Arg Ser Ser Tyr Lys Ile Ser Gly Tyr Glu Leu Met Tyr Tyr Glu
1               5                   10                  15

Tyr Ala Met Asp
            20

<210> SEQ ID NO 185
<211> LENGTH: 10
<212> TYPE: PRT
<213> ORGANISM: Artificial Sequence
<220> FEATURE:
<223> OTHER INFORMATION: Synthetic peptide

<400> SEQUENCE: 185

Arg Asp Gly Met Tyr Tyr Arg Gly Phe Asp
1               5                   10

<210> SEQ ID NO 186
<211> LENGTH: 10
<212> TYPE: PRT
<213> ORGANISM: Artificial Sequence
<220> FEATURE:
<223> OTHER INFORMATION: Synthetic peptide

<400> SEQUENCE: 186

Arg Asn Ser Tyr Gly Tyr Arg Ala Leu Asp
1               5                   10

<210> SEQ ID NO 187
<211> LENGTH: 13
<212> TYPE: PRT
<213> ORGANISM: Artificial Sequence
<220> FEATURE:
<223> OTHER INFORMATION: /Synthetic peptide

<400> SEQUENCE: 187

Arg Ala Tyr Ser Met Tyr Pro Trp Asn Val Gly Phe Asp
1               5                   10

<210> SEQ ID NO 188
<211> LENGTH: 18
<212> TYPE: PRT
<213> ORGANISM: Artificial Sequence
<220> FEATURE:
<223> OTHER INFORMATION: Synthetic peptide

<400> SEQUENCE: 188

Arg Ser Tyr His His Ser Asp Lys Tyr Tyr Tyr Ala Trp Ser Tyr Ala
1               5                   10                  15

Leu Asp

<210> SEQ ID NO 189
<211> LENGTH: 14
<212> TYPE: PRT
<213> ORGANISM: Artificial Sequence
<220> FEATURE:
<223> OTHER INFORMATION: Synthetic peptide

<400> SEQUENCE: 189

```
Arg Gly Gly Tyr Trp Tyr Tyr Phe Tyr Asp Gly Gly Ile Asp
1               5                   10
```

<210> SEQ ID NO 190
<211> LENGTH: 14
<212> TYPE: PRT
<213> ORGANISM: Artificial Sequence
<220> FEATURE:
<223> OTHER INFORMATION: Synthetic peptide

<400> SEQUENCE: 190

```
Arg Lys Ser Asn Arg Tyr Ser Arg Val Tyr Phe Gly Met Asp
1               5                   10
```

<210> SEQ ID NO 191
<211> LENGTH: 19
<212> TYPE: PRT
<213> ORGANISM: Artificial Sequence
<220> FEATURE:
<223> OTHER INFORMATION: Synthetic peptide

<400> SEQUENCE: 191

```
Arg Ile Gly Ser Tyr Phe Tyr Tyr Tyr Gly Tyr Asn Val His Tyr Asn
1               5                   10                  15

Gly Met Asp
```

<210> SEQ ID NO 192
<211> LENGTH: 10
<212> TYPE: PRT
<213> ORGANISM: Artificial Sequence
<220> FEATURE:
<223> OTHER INFORMATION: Synthetic peptide

<400> SEQUENCE: 192

```
Arg Tyr Gly Tyr Ser Gly Lys Gly Phe Asp
1               5                   10
```

<210> SEQ ID NO 193
<211> LENGTH: 13
<212> TYPE: PRT
<213> ORGANISM: Artificial Sequence
<220> FEATURE:
<223> OTHER INFORMATION: Synthetic peptide

<400> SEQUENCE: 193

```
Arg Pro Asn Arg Tyr Gly Leu Val Gly Ser Gly Leu Asp
1               5                   10
```

<210> SEQ ID NO 194
<211> LENGTH: 14
<212> TYPE: PRT
<213> ORGANISM: Artificial Sequence
<220> FEATURE:
<223> OTHER INFORMATION: Synthetic peptide

<400> SEQUENCE: 194

```
Arg Lys Ser Asn Arg Tyr Ser Arg Val Ser Phe Gly Met Asp
1               5                   10
```

<210> SEQ ID NO 195
<211> LENGTH: 17
<212> TYPE: PRT
<213> ORGANISM: Artificial Sequence
<220> FEATURE:
<223> OTHER INFORMATION: Synthetic peptide

```
<400> SEQUENCE: 195

Arg Gln Pro Thr His Tyr Tyr Tyr Ala Lys Gly Tyr Lys Ala Met
1               5                   10                  15

Asp

<210> SEQ ID NO 196
<211> LENGTH: 10
<212> TYPE: PRT
<213> ORGANISM: Artificial Sequence
<220> FEATURE:
<223> OTHER INFORMATION: Synthetic peptide

<400> SEQUENCE: 196

Arg Tyr Ser Tyr Tyr Ser Tyr Gly Ile Asp
1               5                   10

<210> SEQ ID NO 197
<211> LENGTH: 10
<212> TYPE: PRT
<213> ORGANISM: Artificial Sequence
<220> FEATURE:
<223> OTHER INFORMATION: Synthetic peptide

<400> SEQUENCE: 197

Arg Tyr Ser Tyr Tyr Trp Leu Ala Leu Asp
1               5                   10

<210> SEQ ID NO 198
<211> LENGTH: 19
<212> TYPE: PRT
<213> ORGANISM: Artificial Sequence
<220> FEATURE:
<223> OTHER INFORMATION: Synthetic peptide

<400> SEQUENCE: 198

Arg Tyr Ser Asp Tyr Tyr Phe Phe Pro Ser Tyr Val Tyr Gly Gly
1               5                   10                  15

Ala Met Asp

<210> SEQ ID NO 199
<211> LENGTH: 12
<212> TYPE: PRT
<213> ORGANISM: Artificial Sequence
<220> FEATURE:
<223> OTHER INFORMATION: Synthetic peptide

<400> SEQUENCE: 199

Arg Glu Ser Phe Tyr Tyr Thr Asn Tyr Ala Phe Asp
1               5                   10

<210> SEQ ID NO 200
<211> LENGTH: 17
<212> TYPE: PRT
<213> ORGANISM: Artificial Sequence
<220> FEATURE:
<223> OTHER INFORMATION: Synthetic peptide

<400> SEQUENCE: 200

Arg Tyr Phe Trp Ser Tyr Asn Ser Phe Ala Gln Ser Phe Trp Ala Met
1               5                   10                  15

Asp

<210> SEQ ID NO 201
<211> LENGTH: 19
```

```
<212> TYPE: PRT
<213> ORGANISM: Artificial Sequence
<220> FEATURE:
<223> OTHER INFORMATION: Synthetic peptide

<400> SEQUENCE: 201

Arg Ser Gln Thr Thr Asp Tyr Leu Gly Phe Tyr Ile Ser Tyr Thr Gly
1               5                   10                  15

Ala Leu Asp

<210> SEQ ID NO 202
<211> LENGTH: 13
<212> TYPE: PRT
<213> ORGANISM: Artificial Sequence
<220> FEATURE:
<223> OTHER INFORMATION: Synthetic peptide

<400> SEQUENCE: 202

Arg Tyr Gly Phe Tyr Tyr Ser Tyr Glu Tyr Ala Phe Asp
1               5                   10

<210> SEQ ID NO 203
<211> LENGTH: 7
<212> TYPE: PRT
<213> ORGANISM: Artificial Sequence
<220> FEATURE:
<223> OTHER INFORMATION: Synthetic peptide

<400> SEQUENCE: 203

Tyr Ser Tyr Ser Tyr Ser Val
1               5

<210> SEQ ID NO 204
<211> LENGTH: 5
<212> TYPE: PRT
<213> ORGANISM: Artificial Sequence
<220> FEATURE:
<223> OTHER INFORMATION: Synthetic peptide

<400> SEQUENCE: 204

Ser Trp Ala Ser Trp
1               5

<210> SEQ ID NO 205
<211> LENGTH: 5
<212> TYPE: PRT
<213> ORGANISM: Artificial Sequence
<220> FEATURE:
<223> OTHER INFORMATION: Synthetic peptide

<400> SEQUENCE: 205

Trp Tyr Ala Ser Trp
1               5

<210> SEQ ID NO 206
<211> LENGTH: 5
<212> TYPE: PRT
<213> ORGANISM: Artificial Sequence
<220> FEATURE:
<223> OTHER INFORMATION: Synthetic peptide

<400> SEQUENCE: 206

Trp Trp Ala Ser Ser
1               5

<210> SEQ ID NO 207
```

```
<211> LENGTH: 5
<212> TYPE: PRT
<213> ORGANISM: Artificial Sequence
<220> FEATURE:
<223> OTHER INFORMATION: Synthetic peptide

<400> SEQUENCE: 207

Ser Tyr Ala Ser Tyr
1               5

<210> SEQ ID NO 208
<211> LENGTH: 6
<212> TYPE: PRT
<213> ORGANISM: Artificial Sequence
<220> FEATURE:
<223> OTHER INFORMATION: Synthetic peptide

<400> SEQUENCE: 208

Tyr Ser Tyr Ser Leu Leu
1               5

<210> SEQ ID NO 209
<211> LENGTH: 4
<212> TYPE: PRT
<213> ORGANISM: Artificial Sequence
<220> FEATURE:
<223> OTHER INFORMATION: Synthetic peptide

<400> SEQUENCE: 209

Tyr Tyr Pro Leu
1

<210> SEQ ID NO 210
<211> LENGTH: 6
<212> TYPE: PRT
<213> ORGANISM: Artificial Sequence
<220> FEATURE:
<223> OTHER INFORMATION: Synthetic 6xHis tag

<400> SEQUENCE: 210

His His His His His His
1               5
```